United States Patent [19]

Baker et al.

[11] Patent Number: 5,231,102

[45] Date of Patent: Jul. 27, 1993

[54] TETRAHYDROQUINOLINE DERIVATIVES USEFUL FOR NEURODEGENERATIVE DISORDERS

[75] Inventors: Raymond Baker, Much Hadham; William R. Carling, Bishops Stortford; Paul D. Leeson, Cambridge; Julian D. Smith, Sawbridgeworth, all of England

[73] Assignee: Merck Sharp & Dohme, Ltd., Hoddesdon, England

[21] Appl. No.: 719,423

[22] Filed: Jun. 24, 1991

Related U.S. Application Data

[63] Continuation of Ser. No. 487,477, Mar. 2, 1990, abandoned.

[51] Int. Cl.⁵ ............... A61K 31/47; C07D 215/36
[52] U.S. Cl. .................. 514/312; 514/311; 514/313; 514/314; 546/153; 546/156; 546/159; 546/165
[58] Field of Search ............ 546/153, 156, 159, 165; 514/311, 312, 313, 314

[56] References Cited

FOREIGN PATENT DOCUMENTS 0203891 5/1986 European Pat. Off. .
0303387 8/1988 European Pat. Off. .

OTHER PUBLICATIONS

Journal of Org. Chem. vol. 55, No. 2, pp. 738–741, 1990.
Chem. Absts. vol. 110, No. 19, 1989 p. 61.
Chem. Absts. vol. 70, No. 5 1969, p. 1997.

Primary Examiner—Johann Richter
Attorney, Agent, or Firm—Robert J. North; Joseph F. DiPrima

[57] ABSTRACT

A class of 1,2,3,4-tetrahydroquinolines possessing at least one substituent, or a spirocyclic moiety, at the 4-position, and an acidic group or a group convertible thereto in vivo at the 2-position, are specific antagonists of N-methyl-D-aspartate (NMDA) receptors and are therefore useful in the treatment and/or prevention of neurodegenerative disorders.

9 Claims, No Drawings

TETRAHYDROQUINOLINE DERIVATIVES USEFUL FOR NEURODEGENERATIVE DISORDERS

This is a continuation of application Ser. No. 487,477, filed Mar. 2, 1990 now abandoned.

This invention relates to a class of 4-substituted 1,2,3,4-tetrahydroquinolines which are selective non-competitive antagonists of N-methyl-D-aspartate (NMDA) receptors and are therefore useful in the treatment and/or prevention of neurodegenerative disorders arising as a consequence of such pathological conditions as stroke, hypoglycaemia, cerebral ischaemia transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord and head injury and poisoning by exogenous NMDA receptor agonists and neurotoxins.

Various N-acyl-substituted derivatives of 1,2,3,4-tetrahydroquinoline-2-carboxylic acid, optionally substituted on the benzo moiety of the tetrahydroquinoline structure, are known to have angiotensin converting enzyme (ACE) inhibitory activity and are thus effective antihypertensive agents. Such compounds are described in, for example, DE-A-2937779, U.S. Pat. Nos. 4,273,927, 4,374,246, 4,390,700, 4,401,818, 4,461,896, EP-A-0029488, *J. Med. Chem.*, 1983, 26, 1267 and *J. Med. Chem.*, 1985, 28, 1606. The parent compound in this series, 1,2,3,4-tetrahydroquinoline-2-carboxylic acid, is known from *Chem. Ber.*, 1928, 61, 2377. None of the compounds specifically disclosed in any of the above-mentioned documents, however, possesses a substituent in the 4-position of the tetrahydroquinoline moiety. Moreover, there is no suggestion in any of these documents that the compounds described therein may be useful in the treatment and/or prevention of neurodegenerative disorders.

The compounds 4-oxo-1,2,3,4-tetrahydroquinoline-2-carboxylic acid and its methyl ester, and 8-hydroxy-4-oxo-1,2,3,4-tetrahydroquinoline-2-carboxylic acid, are described in *J. Am. Chem. Soc.*, 1967, 89, 1017. However, no therapeutic utility is disclosed therein for these compounds.

The preparation of 1,2,3,4-tetrahydroquinoline-2,4-dicarboxylic acid and its diethyl ester, by zinc/formic acid reduction of the corresponding quinolinedicarboxylic acid and subsequent esterification, is described in *Collect. Czech. Chem. Commun.*, 1978, 43, 1413. Again, however, no therapeutic utility for these compounds is disclosed.

We have now found that a class of 1,2,3,4-tetrahydroquinolines, substituted at the 4-position of the tetrahydroquinoline ring system, are potent and selective non-competitive NMDA antagonists. They therefore have useful neuroprotective activity. The compounds act by selectively inhibiting the glycine modulation of NMDA receptors.

EP-A-0203891 and U.S. Pat. No. 4,746,653 describe inter alia certain phosphonic acid derivatives of 1,2,3,4-tetrahydroquinoline-2-carboxylic acid. The compounds described in EP-A-0203891 and U.S. Pat. No. 4,746,653 are stated to be competitive antagonists of the NMDA-sensitive amino acid receptor.

Hence, the mechanism of action of the compounds described in EP-A-0203891 and U.S. Pat. No. 4,746,653 differs from that of the compounds according to the present invention in that the former compounds are competitive inhibitors of glutamate binding at the neurotransmitter recognition site whereas, as mentioned above, the latter compounds are non-competitive NMDA antagonists, acting as inhibitors at the glycine modulatory site on the NMDA receptor.

The present invention provides a compound of formula I or a salt thereof:

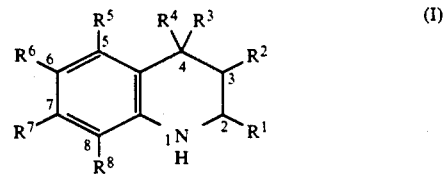

wherein $R^1$ represents an acidic group or a group which is convertible thereto in vivo;

$R^2$ represents hydrogen or hydrocarbon;

$R^3$ represents hydrogen, hydrocarbon, —$OR^a$, —$SR^a$, —$NR^aR^b$, —$NR^aCOR^b$, —$NR^aCO_2R^b$, —$NR^aSO_2R^b$, —$NR^iCXNR^aR^b$, —$CO_2R^a$, or —$CONR^aR^b$;

$R^4$ represents hydrocarbon, —$OR^a$, —$SR^a$, —$NR^aR^b$, —$NR^aCOR^b$, —$NR^aCO_2R^b$, —$NR^aSO_2R^b$, —$NR^iCXNR^aR^b$, —$CO_2R^a$ or —$CONR^aR^b$; or $R^3$ and $R^4$ together with the intervening carbon atom represent carbonyl (C=O), thiocarbonyl (C=S), imino (C=N.$R^a$), oximino (C=N.$OR^a$), or a 3- to 8-membered ring containing from zero to 4 heteroatoms selected from oxygen, nitrogen, sulphur and phosphorus;

$R^5$, $R^6$, $R^7$ and $R^8$ independently represent hydrogen, hydrocarbon, halogen, cyano, trifluoromethyl, nitro, —$OR^a$, —$SR^a$, —$NR^aR^b$ or —$CO_2R^a$;

$R^a$, $R^b$ and $R^i$ independently represent hydrogen or hydrocarbon;

X represents oxygen, sulphur or a group of formula =N.E; and

E represents hydrocarbon or an electron-withdrawing group;

provided that when $R^2$, $R^5$, $R^6$ and $R^7$ each represents hydrogen and $R^3$ and $R^4$ together with the intervening carbon atom represent carbonyl, then $R^8$ does not represent hydrogen if $R^1$ represents carboxy or methoxycarbonyl, and $R^8$ does not represent hydroxy if $R^1$ represents carboxy;

provided also that when $R^2$, $R^3$, $R^5$, $R^6$, $R^7$ and $R^8$ each represents hydrogen, then $R^1$ and $R^4$ do not simultaneously represent carboxy or ethoxycarbonyl.

U.S. Pat. Nos. 4,390,700 and 4,401,818 purport to describe a class of intermediates falling within formula I above wherein $R^1$ represents carboxy; $R^2$, $R^3$ and $R^4$ are hydrogen or $C_{1-7}$ alkyl; and one to three of $R^5$, $R^6$, $R^7$ and $R^8$ are independently selected from hydrogen, $C_{1-7}$ alkyl, $C_{1-7}$ alkoxy, $C_{1-7}$ alkylenedioxy, hydroxy, halogen and trifluoromethyl, the remaining group(s) $R^5$, $R^6$, $R^7$ and/or $R^8$ representing hydrogen. Neither document, however, specifically discloses any compound having at least one substituent in the 4-position, and hence no compound is disclosed which falls within the scope of the present invention.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include alkali metal salts, e.g. sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, ary or aryl($C_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, isobutyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl, naphthyl and fluorenyl groups.

A particular aryl($C_{1-6}$)alkyl group is benzyl.

Suitable heterocycloalkyl groups include piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, indolinyl, imidazolyl, oxadiazolyl, thiadiazolyl and tetrazolyl groups. Particular heteroaryl groups are pyridyl, furyl, thienyl, indolinyl and oxadiazolyl.

The hydrocarbon group may in turn be optionally substituted by one or more groups selected from $C_{1-6}$ alkyl, adamantyl, phenyl, halogen, $C_{1-6}$ haloalkyl, amino($C_{1-6}$)alkyl, mono- or di($C_{1-6}$)alkylamino($C_{1-6}$)alkyl, arylamino($C_{1-6}$)alkyl, amino($C_{2-6}$)alkenyl, amino($C_{2-6}$)alkynyl, trifluoromethyl, hydroxy, $C_{1-6}$ alkoxy, aryloxy, keto, $C_{1-3}$ alkylenedioxy, nitro, cyano, carboxy, $C_{1-6}$ alkoxycarbonyl, $C_{1-6}$ alkoxycarbonyl($C_{1-6}$)alkyl, $C_{1-6}$ alkylcarbonyloxy, optionally substituted arylcarbonyloxy, $C_{1-6}$ alkylcarbonyl, optionally substituted arylcarbonyl, $C_{1-6}$ alkylthio, $C_{1-6}$ alkylsulphinyl, $C_{1-6}$ alkylsulphonyl, amino, mono- or di($C_{1-6}$)alkylamino, arylamino, $C_{1-6}$ alkylcarbonylamino and $C_{1-6}$ alkoxycarbonylamino.

When the group E represents an electron-withdrawing group, this group is suitably cyano, nitro, —$COR^a$, —$CO_2R^a$ or —$SO_2R^a$, in which $R^a$ is as defined above.

The acidic group $R^1$ may represent carboxy, carboxyalkyl, or a group convertible thereto in vivo such as an in vivo hydrolysable ester or amido group. Such groups may be represented by the moiety —$(CH_2)_n COT$ wherein n is zero, 1 or 2, and T is Or or $NR^pR^q$, where R is hydrogen, hydrocarbon or an in vivo hydrolysable ester residue and $R^p$ and $R^q$ are independently hydrogen, hydrocarbon or in vivo hydrolysable amido residues.

Examples of suitable in vivo hydrolysable ester and amido groups for $R^1$ include those which break down readily in the human body to leave the parent acid or its salt. Suitable ester and amido groups $R^1$ of this type include those of part formulae (i)–(vi):

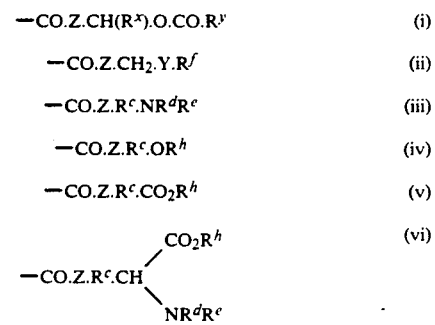

wherein Z is O or NH; $R^x$ is hydrogen, $C_{1-6}$ alkyl or phenyl; $R^y$ is $C_{1-6}$ alkyl, $C_{1-6}$ alkoxy or phenyl, any of which may be optionally substituted by a group of formula —$NR^dR^e$; or $R^x$ and $R^y$ together form a 1,2-phenylene group; $R^c$ represents $C_{1-6}$ alkylene optionally substituted by $C_{1-6}$ alkyl or by a carbonyl group; $R^d$ and $R^e$ independently represent hydrogen, $C_{1-6}$ alkyl, amino($C_{1-6}$)alkyl, mono- or di($C_{1-6}$)alkylamino($C_{1-6}$)alkyl, aryl or aryl($C_{1-6}$)alkyl, or $R^d$ and $R^e$ together with the intervening nitrogen atom represent a pyrrolidino, piperidino or morpholino group; Y represents oxygen or sulphur; $R^f$ represents $C_{1-6}$ alkyl, aryl or aryl ($C_{1-6}$)alkyl; and $R^h$ represents hydrogen or $C_{1-6}$ alkyl. Thus, suitable in vivo hydrolysable ester and amido residues include, for example, acyloxyalkyl groups such as acetoxymethyl, pivaloyloxymethyl, α-acetoxyethyl and α-pivaloyloxyethyl groups; alkoxycarbonyloxyalkyl groups such as ethoxycarbonyloxymethyl and α-ethoxycarbonyloxyethyl; dialkylaminoalkyl especially diloweralkylaminoalkyl groups such as dimethylaminomethyl, dimethylaminoethyl, dimethylaminopropyl, diethylaminomethyl or diethylaminoethyl; and heterocyclylalkyl groups such as pyrrolidinylethyl or morpholinoethyl.

Alternatively, the acidic group $R^1$ may represent any other group which can provide an anion. Such groups suitably include tetrazolyl or tetrazolyl($C_{1-3}$)alkyl; 5-pyrazolon-3-yl; groups of formula —$CONR^pOR^a$, —$CONR^pNR^aR^b$, —$CONR^pE^1$, or —$COCHR^aE^1$, in which $E^1$ represents an electron-withdrawing group as defined above for E, and $R^a$ and $R^p$ are as defined above; or a derivative of any of these groups which is hydrolysable thereto in vivo.

The benzo moiety of the tetrahydroquinoline ring system shown in formula I above may be substituted or unsubstituted. Particular substituents include halogen, cyano, trifluoromethyl, nitro, hydroxy, amino, carboxy, $C_{1-6}$ alkyl, $C_{1-6}$ alkoxy, $C_{1-6}$ alkylthio and $C_{1-6}$ alkoxycarbonyl. Suitably, $R^8$ represents hydrogen and $R^5$, $R^6$ and $R^7$ independently represent hydrogen, halogen or $C_{1-6}$ alkyl. Preferably, $R^6$ and $R^8$ each represents hydrogen and $R^5$ and $R^7$ independently represent methyl, ethyl or halogen, in particular chloro, bromo or iodo.

The compounds according to the invention have a number of asymmetric centres, and may accordingly exist both as enantiomers and as diastereoisomers. In particular, the relative orientation of the substituents at the 2- and 4-positions of the tetrahydroquinoline ring system may give rise to cis and trans isomers. It is to be understood that all such isomers and mixtures thereof are encompassed within the scope of the present invention.

A particular subgroup of compounds within the scope of the present invention is represented by the compounds of formula IIA and salts thereof:

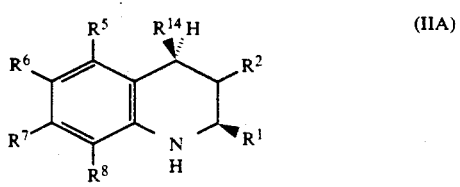
(IIA)

wherein $R^1$, $R^2$, $R^5$, $R^6$, $R^7$ and $R^8$ are as defined above; and $R^{14}$ represents hydrocarbon, $-NR^aR^b$, $-NR^aCOR^b$, $-NR^aCO_2R^b$, $-CO_2R^a$ or $-CONR^aR^b$ in which $R^a$ and $R^b$ are as defined above, in particular wherein $R^a$ and $R^b$ independently represent hydrogen, $C_{1-6}$ alkyl, phenyl or benzyl. Preferably, $R^{14}$ represents amino, benzoylamino, t-butoxycarbonylamino, amido, $C_{1-4}$ alkoxycarbonyl or benzyloxycarbonyl, or an optionally substituted heteroaryl group. When $R^{14}$ represents an optionally substituted heteroaryl group, this group is suitably 3-methyl-1,2,4-oxadiazol-5-yl.

Another subgroup of compounds within the scope of this invention is represented by the compounds of formula IIB and salts thereof:

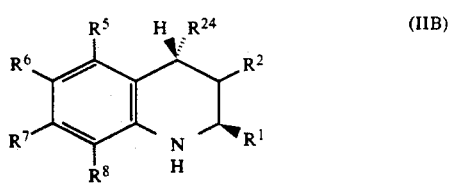
(IIB)

wherein $R^1$, $R^2$, $R^5$, $R^6$, $R^7$ and $R^8$ are as defined above; and $R^{24}$ represents $-NR^aR^b$, $-NR^aCO_2R^b$, $-NR^aSO_2R^b$, $-CO_2R^a$ or $-CONR^aR^b$ in which $R^a$ and $R^b$ are as defined above, in particular wherein $R^a$ and $R^b$ independently represent hydrogen, optionally substituted $C_{1-6}$ alkyl or optionally substituted benzyl. Suitably, $R^{24}$ represents amino, benzylamino, phenylaminocarbonylmethylamino, dichlorophenylamino, t-butoxycarbonylamino, methanesulphonylamino, $C_{1-4}$ alkoxycarbonyl, benzyloxycarbonyl or amido. A preferred value for the $R^{24}$ substituent is methoxycarbonyl.

A further subgroup of compounds within the scope of the invention is represented by the compounds of formula IIC and salts thereof:

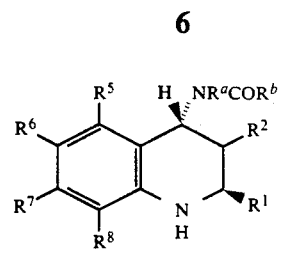
(IIC)

wherein $R^1$, $R^2$, $R^5$, $R^6$, $R^7$ and $R^8$ are as defined above; and $R^a$ and $R^b$ independently represent hydrogen, $C_{1-6}$ alkyl, $C_{2-6}$ alkenyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted. Suitable values of $R^a$ and $R^b$ include hydrogen, methyl, ethyl, n-propyl, isopropyl, n-butyl, isobutyl, ethenyl, cyclohexyl, cyclohexylmethyl, phenyl, naphthyl, fluorenyl, benzyl, phenethyl, phenylpropyl, naphthylmethyl, piperidylmethyl, 1,2,3,4-tetrahydroisoquinolyl, pyridyl, furyl, indolinyl and thienylmethyl. Suitable substituents on the $R^a$ and/or $R^b$ moiety include methyl, ethyl, phenyl, chloro, aminomethyl, aminoethyl, aminopropyl, aminobutyl, methylaminomethyl, dimethylaminomethyl, aminopropynyl, aminobutynyl, hydroxy, methoxy, phenoxy, nitro, cyano, carboxy, acetyl, amino and acetylamino groups. Preferably, $R^a$ is hydrogen and $R^b$ represents phenyl or benzyl, optionally substituted by an aminomethyl or aminoethyl group.

A further subgroup of compounds within the scope of the invention is represented by the compounds of formula IID and salts thereof:

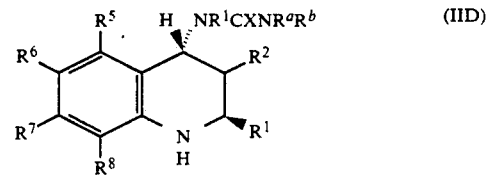
(IID)

wherein $R^1$, $R^2$, $R^5$, $R^6$, $R^7$ and $R^8$ are as defined above; $R^a$ and $R^i$ independently represent hydrogen, $C_{1-6}$ alkyl or aryl; $R^b$ represents $C_{3-7}$ cycloalkyl, aryl or aryl($C_{1-6}$)alkyl, any of which groups may be optionally substituted; and X represents oxygen or sulphur. Suitably, $R^a$ and $R^i$ independently represent hydrogen, methyl, ethyl or phenyl; and $R^b$ represents cyclohexyl, phenyl, naphthyl or benzyl. Preferably, $R^a$ and $R^i$ both represent hydrogen; and X represents oxygen. Suitable substituents on the moiety $R^b$ include methyl, ethyl, chloro, iodo, methoxy and nitro.

A further subgroup of compounds within the scope of the invention is represented by the compounds of formula IIE and salts thereof:

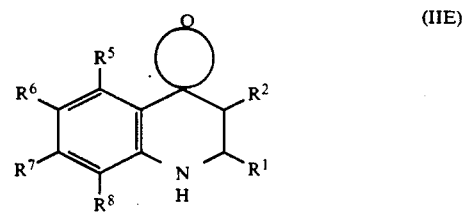
(IIE)

wherein $R^1$, $R^2$, $R^5$, $R^6$, $R^7$ and $R^8$ are as defined above; and Q represents the residue of a 3- to 8-membered ring containing from zero to 4 heteroatoms selected from oxygen, nitrogen, sulphur and phosphorus.

The 3- to 8-membered ring of which Q is the residue is an optionally substituted non-aromatic ring, which is selected from the group consisting of:

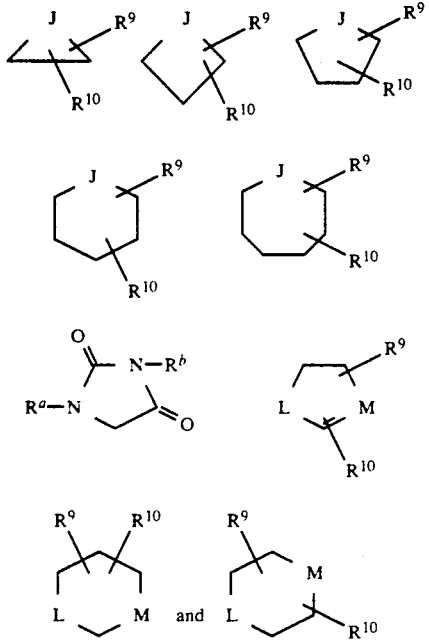

wherein
the broken line represents an optional chemical bond;
J, L and M independently represent $-CH_2-$, $-O-$, $-S(O)_m-$, $-CO-$, $-N(R^a)-$, $-PO(R^a)-$, $-PO(OR^a)-$, $-CO_2-$, $-CON(R^a)-$, $-SO_2N(R^a)-$ or $-C(=N.R^a)N(R^b)-$;
$R^9$ and $R^{10}$ independently represent hydrogen, hydrocarbon, halogen, $-OR^a$ or $-CO_2R^a$; or $R^9$ and $R^{10}$ together with a ring carbon atom represent carbonyl;
m is zero, 1 or 2; and
$R^a$ and $R^b$ are as defined above.

It will be appreciated that the $R^9$ and $R^{10}$ substituents may be present at any available position in the ring of which Q is the residue. It will further be appreciated that the point of spiro attachment of this ring to the tetrahydroquinoline ring system may be at any available position of the ring which Q completes.

Suitably, $R^9$ represents hydrogen or methyl; and $R^{10}$ represents hydrogen, hydroxy, $C_{1-4}$ alkyl or $C_{1-4}$ alkoxy, preferably hydroxy, methyl or methoxy. Preferably, one or both of $R^9$ and $R^{10}$ is hydrogen.

In formula IIE above, preferred rings of which Q is the residue are the hydantoin and dioxolane structures represented by formulae IIIA and IIIB respectively:

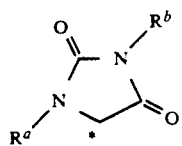

(IIIA)

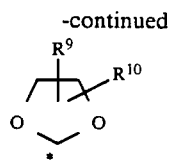

(IIIB)

wherein $R^a$, $R^b$, $R^9$ and $R^{10}$ are as defined above; and the asterisk denotes in each case the point of spiro attachment to the tetrahydroquinoline ring system. Preferably, $R^a$, $R^b$, $R^9$ and $R^{10}$ each represents hydrogen.

Specific compounds within the scope of the present invention include:

2-carboxy-5,7-dichloro-4-oxo-1,2,3,4-tetrahydroquinoline;
2-carboxy-5,7-dimethyl-4-oxo-1,2,3,4-tetrahydroquinoline;
2-carboxy-4-oxo-3,5,7-trimethyl-1,2,3,4-tetrahydroquinoline;
4-t-butoxycarbonylamino-2-carboxy-5,7-dichloro-1,2,3,4-tetrahydroquinoline;
4-amino-2-carboxy-5,7-dichloro-1,2,3,4-tetrahydroquinoline;
4-benzoylamino-2-carboxy-5,7-dichloro-1,2,3,4-tetrahydroquinoline;
4-acetylamino-2-carboxy-5,7-dichloro-1,2,3,4-tetrahydroquinoline;
5,7-dichloro-4-(1,3-dioxolan-2-yl)-2-(2-hydroxyethoxycarbonyl)-1,2,3,4-tetrahydroquinoline;
2-carboxy-5,7-dichloro-4-(2,4-imidazolidinedione-3-yl)-1,2,3,4-tetrahydroquinoline;
2,4-dicarboxy-5,7-dichloro-1,2,3,4-tetrahydroquinoline;
2-carboxy-5,7-dichloro-4-ethoxycarbonyl-1,2,3,4-tetrahydroquinoline;
2-carboxy-5,7-dichloro-4-(3,5-dichlorophenylamino)-4-ethoxycarbonyl-1,2,3,4-tetrahydroquinoline;
2-carboxy-5,7-dichloro-4-methoxycarbonyl-1,2,3,4-tetrahydroquinoline;
4-benzyloxycarbonyl-2-carboxy-5,7-dichloro-1,2,3,4-tetrahydroquinoline;
2-carboxy-5,7-dichloro-4-(3-methyl-1,2,4-oxadiazol-5-yl)-1,2,3,4-tetrahydroquinoline;
4-aminocarbonyl-2-carboxy-5,7-dichloro-1,2,3,4-tetrahydroquinoline;
2-carboxy-5,7-dimethyl-4-methoxycarbonyl-1,2,3,4-tetrahydroquinoline;
2-carboxy-4-methoxycarbonyl-5,6,7-trichloro-1,2,3,4-tetrahydroquinoline;
2-carboxy-7-chloro-5-iodo-4-methoxycarbonyl-1,2,3,4-tetrahydroquinoline;
2-carboxy-7-chloro-4-methoxycarbonyl-1,2,3,4-tetrahydroquinoline;
2-carboxy-5-chloro-4-methoxycarbonyl-1,2,3,4-tetrahydroquinoline;
2-carboxy-5,7-dibromo-4-methoxycarbonyl-1,2,3,4-tetrahydroquinoline;
2-carboxy-5,7-dichloro-4-methanesulphonylamino-1,2,3,4-tetrahydroquinoline;
2-carboxy-5,7-dichloro-4-cyclohexylcarbonylamino-1,2,3,4-tetrahydroquinoline;
4-benzylcarbonylamino-2-carboxy-5,7-dichloro-1,2,3,4-tetrahydroquinoline;
2-carboxy-5,7-dichloro-4-(1-naphthylcarbonylamino)-1,2,3,4-tetrahydroquinoline;
2-carboxy-4-(2-chlorophenylcarbonylamino)-5,7-dichloro-1,2,3,4-tetrahydroquinoline;

2-carboxy-4-(4-chlorophenylcarbonylamino)-5,7-dichloro-1,2,3,4-tetrahydroquinoline;
2-carboxy-5,7-dichloro-4-(4-pyridylcarbonylamino)-1,2,3,4-tetrahydroquinoline;
2-carboxy-5,7-dichloro-4-[2-(2-aminophenethyl)]carbonylamino-1,2,3,4-tetrahydroquinoline;
2-carboxy-5,7-dichloro-4-n-propylcarbonylamino-1,2,3,4-tetrahydroquinoline;
2-carboxy-5,7-dichloro-4-phenylaminocarbonylamino-1,2,3,4-tetrahydroquinoline;
2-carboxy-4-(4-chlorophenylcarbonylamino)-5,7-dichloro-1,2,3,4-tetrahydroquinoline;
2-carboxy-5,7-dichloro-4-(4-methoxyphenylcarbonylamino)-1,2,3,4-tetrahydroquinoline;
4-benzylaminocarbonylamino-2-carboxy-5,7-dichloro-1,2,3,4-tetrahydroquinoline;
2-carboxy-5,7-dichloro-4-(2-methoxybenzylcarbonylamino)-1,2,3,4-tetrahydroquinoline;
2-carboxy-5,7-dichloro-4-(2-methylbenzylcarbonylamino)-1,2,3,4-tetrahydroquinoline;
2-carboxy-5,7-dichloro-4-(α-methoxybenzylcarbonylamino)-1,2,3,4-tetrahydroquinoline;
2-carboxy-5,7-dichloro-4-(2-nitrobenzylcarbonylamino)-1,2,3,4-tetrahydroquinoline;
2-carboxy-5,7-dichloro-4-(2-nitrophenylaminocarbonylamino)-1,2,3,4-tetrahydroquinoline;
2-carboxy-5,7-dichloro-4-(2-methoxyphenylaminocarbonylamino)-1,2,3,4-tetrahydroquinoline;
2-carboxy-5,7-dichloro-4-(2-methylphenylaminocarbonylamino)-1,2,3,4-tetrahydroquinoline;
2-carboxy-4-(2-chlorophenylaminocarbonylamino)-5,7-dichloro-1,2,3,4-tetrahydroquinoline;
4-(4'-biphenylcarbonylamino)-2-carboxy-5,7-dichloro-1,2,3,4-tetrahydroquinoline;
2-carboxy-5,7-dichloro-4-isopropylcarbonylamino-1,2,3,4-tetrahydroquinoline;
2-carboxy-4-(2-chlorophenylcarbonylamino)-5,7-dichloro-1,2,3,4-tetrahydroquinoline;
2-carboxy-5,7-dichloro-4-(1-naphthylcarbonylamino)-1,2,3,4-tetrahydroquinoline;
2-carboxy-5,7-dichloro-4-(2-naphthylcarbonylamino)-1,2,3,4-tetrahydroquinoline;
2-carboxy-5,7-dichloro-4-(2-furylcarbonylamino)-1,2,3,4-tetrahydroquinoline;
2-carboxy-5,7-dichloro-4-(2-methylphenylcarbonylamino)-1,2,3,4-tetrahydroquinoline;
2-carboxy-5,7-dichloro-4-(2-phenethylcarbonylamino)-1,2,3,4-tetrahydroquinoline;
2-carboxy-5,7-dichloro-4-(2-phenylethenylcarbonylamino)-1,2,3,4-tetrahydroquinoline;
2-carboxy-5,7-dichloro-4-(2-thienylmethylcarbonylamino)-1,2,3,4-tetrahydroquinoline;
2-carboxy-4-(3-chlorophenylcarbonylamino)-5,7-dichloro-1,2,3,4-tetrahydroquinoline;
2-carboxy-5,7-dichloro-4-(3-phenylpropylcarbonylamino)-1,2,3,4-tetrahydroquinoline;
2-carboxy-5,7-dichloro-4-(9-fluorenylcarbonylamino)-1,2,3,4-tetrahydroquinoline;
2-carboxy-4-cyclohexylmethylcarbonylamino-5,7-dichloro-1,2,3,4-tetrahydroquinoline;
2-carboxy-4-(2-chlorobenzylcarbonylamino)-5,7-dichloro-1,2,3,4-tetrahydroquinoline;
2-carboxy-4-(3-chlorobenzylcarbonylamino)-5,7-dichloro-1,2,3,4-tetrahydroquinoline;
2-carboxy-4-(4-chlorobenzylcarbonylamino)-5,7-dichloro-1,2,3,4-tetrahydroquinoline;
2-carboxy-5,7-dichloro-4-(4-methylbenzylcarbonylamino)-1,2,3,4-tetrahydroquinoline;
2-carboxy-5,7-dichloro-4-(4-methoxybenzylcarbonylamino)-1,2,3,4-tetrahydroquinoline;
2-carboxy-5,7-dichloro-4-(4-nitrobenzylcarbonylamino)-1,2,3,4-tetrahydroquinoline;
2-carboxy-4-(3-cyanophenylcarbonylamino)-5,7-dichloro-1,2,3,4-tetrahydroquinoline;
2-carboxy-4-(4-chlorophenylaminocarbonylamino)-5,7-dichloro-1,2,3,4-tetrahydroquinoline;
2-carboxy-5,7-dichloro-4-(4-methylphenylaminocarbonylamino)-1,2,3,4-tetrahydroquinoline;
2-carboxy-5,7-dichloro-4-(4-methoxyphenylaminocarbonylamino)-1,2,3,4-tetrahydroquinoline;
2-carboxy-5,7-dichloro-4-(4-nitrophenylaminocarbonylamino)-1,2,3,4-tetrahydroquinoline;
2-carboxy-5,7-dichloro-4-(4-iodophenylaminocarbonylamino)-1,2,3,4-tetrahydroquinoline;
2-carboxy-5,7-dichloro-4-[phenylaminocarbonyl (N-methyl)amino]-1,2,3,4-tetrahydroquinoline;
2-carboxy-5,7-dichloro-4-[(N-methyl-N-phenyl)aminocarbonylamino]-1,2,3,4-tetrahydroquinoline;
2-carboxy-5,7-dichloro-4-(2,3-dihydroindol-1-ylcarbonylamino)-1,2,3,4-tetrahydroquinoline;
2-carboxy-4-[2-(carboxyethyl)carbonylamino]-5,7-dichloro-1,2,3,4-tetrahydroquinoline;
4-[3-(aminomethyl)phenylcarbonylamino]-2-carboxy-5,7-dichloro-1,2,3,4-tetrahydroquinoline;
4-[3-(aminomethyl)phenylcarbonylamino]-5,7-dichloro-2-methoxycarbonyl-1,2,3,4-tetrahydroquinoline;
4-[4-(aminomethyl)phenylcarbonylamino]-2-carboxy-5,7-dichloro-1,2,3,4-tetrahydroquinoline;
4-[4-(aminomethyl)phenylcarbonylamino]-5,7-dichloro-2-methoxycarbonyl-1,2,3,4-tetrahydroquinoline;
4-[4-(2-aminoethyl)phenylcarbonylamino]-2-carboxy-5,7-dichloro-1,2,3,4-tetrahydroquinoline;
4-[4-(2-aminoethyl)phenylcarbonylamino]-5,7-dichloro-2-methoxycarbonyl-1,2,3,4-tetrahydroquinoline;
2-carboxy-5,7-dichloro-4-(3-methylbenzylcarbonylamino)-1,2,3,4-tetrahydroquinoline;
2-carboxy-5,7-dichloro-4-(3-nitrobenzylcarbonylamino)-1,2,3,4-tetrahydroquinoline;
2-carboxy-5,7-dichloro-4-(3-methoxybenzylcarbonylamino)-1,2,3,4-tetrahydroquinoline;
2-carboxy-5,7-dichloro-4-(1-naphthylmethylcarbonylamino)-1,2,3,4-tetrahydroquinoline;
2-carboxy-5,7-dichloro-4-(2-naphthylmethylcarbonylamino)-1,2,3,4-tetrahydroquinoline;
2-carboxy-5,7-dichloro-4-(3-thienylmethylcarbonylamino)-1,2,3,4-tetrahydroquinoline;
2-carboxy-5,7-dichloro-4-(2,6-dichlorobenzylcarbonylamino)-1,2,3,4-tetrahydroquinoline;
2-carboxy-5,7-dichloro-4-phenylaminothiocarbonylamino-1,2,3,4-tetrahydroquinoline;
4-benzyloxycarbonylamino-2-carboxy-5,7-dichloro-1,2,3,4-tetrahydroquinoline;
2-carboxy-5,7-dichloro-4-(3-methoxyphenylaminocarbonylamino)-1,2,3,4-tetrahydroquinoline;
2-carboxy-5,7-dichloro-4-(3-methylphenylaminocarbonylamino)-1,2,3,4-tetrahydroquinoline;
2-carboxy-4-(3-chlorophenylaminocarbonylamino)-5,7-dichloro-1,2,3,4-tetrahydroquinoline;
2-carboxy-5,7-dichloro-4-(3-nitrophenylaminocarbonylamino)-1,2,3,4-tetrahydroquinoline;
4-(3-aminopropyl)carbonylamino-2-carboxy-5,7-dichloro-1,2,3,4-tetrahydroquinoline;
4-(2-aminoethyl)carbonylamino-2-carboxy-5,7-dichloro-1,2,3,4-tetrahydroquinoline;
4-(4-aminobutyl)carbonylamino-2-carboxy-5,7-dichloro-1,2,3,4-tetrahydroquinoline;

2-carboxy-5,7-dichloro-4-(4-piperidylmethylcarbonylamino)-1,2,3,4-tetrahydroquinoline;
4-[4-(aminomethyl)benzylcarbonylamino]-2-carboxy-5,7-dichloro-1,2,3,4-tetrahydroquinoline;
4-[4-(aminomethyl)benzylcarbonylamino]-5,7-dichloro-2-methoxycarbonyl-1,2,3,4-tetrahydroquinoline;
4-[4-(2-aminoethyl)benzylcarbonylamino]-2-carboxy-5,7-dichloro-1,2,3,4-tetrahydroquinoline;
4-[4-(2-aminoethyl)benzylcarbonylamino]-5,7-dichloro-2-methoxycarbonyl-1,2,3,4-tetrahydroquinoline;
2-carboxy-5,7-dichloro-4-[4-(N-methylaminomethyl)benzylcarbonylamino]-1,2,3,4-tetrahydroquinoline;
5,7-dichloro-2-methoxycarbonyl-4-[4-(N-methylaminomethyl)benzylcarbonylamino]-1,2,3,4-tetrahydroquinoline;
5,7-dichloro-4-[4-(N,N-dimethylaminomethyl)benzylcarbonylamino]-2-methoxycarbonyl-1,2,3,4-tetrahydroquinoline;
2-carboxy-5,7-dichloro-4-[4-(N,N-dimethylaminomethyl)benzylcarbonylamino]-1,2,3,4-tetrahydroquinoline;
4-[4-(3-aminoprop-2-ynyl)benzylcarbonylamino]-2-carboxy-5,7-dichloro-1,2,3,4-tetrahydroquinoline;
4-[4-(3-aminoprop-2-ynyl)benzylcarbonylamino]-5,7-dichloro-2-methoxycarbonyl-1,2,3,4-tetrahydroquinoline;
4-[4-(3-aminopropyl)benzylcarbonylamino]-2-carboxy-5,7-dichloro-1,2,3,4-tetrahydroquinoline;
4-[4-(3-aminopropyl)benzylcarbonylamino]-5,7-dichloro-2-methoxycarbonyl-1,2,3,4-tetrahydroquinoline;
4-[4-(4-aminobut-2-ynyl)benzylcarbonylamino]-2-carboxy-5,7-dichloro-1,2,3,4-tetrahydroquinoline;
4-[4-(4-aminobut-2-ynyl)benzylcarbonylamino]-5,7-dichloro-2-methoxycarbonyl-1,2,3,4-tetrahydroquinoline;
4-[4-(4-aminobutyl)benzylcarbonylamino]-2-carboxy-5,7-dichloro-1,2,3,4-tetrahydroquinoline;
4-[4-(4-aminobutyl)benzylcarbonylamino]-5,7-dichloro-2-methoxycarbonyl-1,2,3,4-tetrahydroquinoline;
4-[3-(aminomethyl)benzylcarbonylamino]-2-carboxy-5,7-dichloro-1,2,3,4-tetrahydroquinoline;
4-[3-(aminomethyl)benzylcarbonylamino]-5,7-dichloro-2-methoxycarbonyl-1,2,3,4-tetrahydroquinoline;
4-[2-(aminomethyl)benzylcarbonylamino]-2-carboxy-5,7-dichloro-1,2,3,4-tetrahydroquinoline;
4-[2-(aminomethyl)benzylcarbonylamino]-5,7-dichloro-2-methoxycarbonyl-1,2,3,4-tetrahydroquinoline;
4-[2-(4-aminomethyl)phenyl)ethylcarbonylamino]-2-carboxy-5,7-dichloro-1,2,3,4-tetrahydroquinoline;
4-[2-(4-(aminomethyl)phenyl)ethylcarbonylamino]-5,7-dichloro-2-methoxycarbonyl-1,2,3,4-tetrahydroquinoline;
4-(4-aminobenzylcarbonylamino)-2-carboxy-5,7-dichloro-1,2,3,4-tetrahydroquinoline;
2-carboxy-5,7-dichloro-4-(1,2,3,4-tetrahydroisoquinol-3-ylcarbonylamino)-1,2,3,4-tetrahydroquinoline;
2-carboxy-4-(2-carboxyphenylcarbonylamino)-5,7-dichloro-1,2,3,4-tetrahydroquinoline;
2-carboxy-4-(4-chloro-3-nitrobenzylcarbonylamino)-5,7-dichloro-1,2,3,4-tetrahydroquinoline;
2-carboxy-5,7-dichloro-4-(4-hydroxy-3-nitrobenzylcarbonylamino)-1,2,3,4-tetrahydroquinoline;
2-carboxy-5,7-dichloro-4-(diphenylmethylcarbonylamino)-1,2,3,4-tetrahydroquinoline;
2-carboxy-5,7-dichloro-4-(1-phenylethyl)carbonylamino-1,2,3,4-tetrahydroquinoline;
4-(4-acetylbenzylcarbonylamino)-2-carboxy-5,7-dichloro-1,2,3,4-tetrahydroquinoline;
2-carboxy-5,7-dichloro-4-phenoxymethylcarbonylamino-1,2,3,4-tetrahydroquinoline;
2-carboxy-5,7-dichloro-4-(4-ethylbenzylcarbonylamino)-1,2,3,4-tetrahydroquinoline;
2-carboxy-5,7-dichloro-4-(4-hydroxybenzylcarbonylamino)-1,2,3,4-tetrahydroquinoline;
4-(4-acetamidobenzylcarbonylamino)-2-carboxy-5,7-dichloro-1,2,3,4-tetrahydroquinoline;
2-carboxy-5,7-dichloro-4-(1-naphthylaminocarbonylamino)-1,2,3,4-tetrahydroquinoline;
2-carboxy-4-cyclohexylaminocarbonylamino-5,7-dichloro-1,2,3,4-tetrahydroquinoline;
2-carboxy-5,7-dichloro-4-[N-methyl-N-(4-methylphenyl)amino]carbonylamino-1,2,3,4-tetrahydroquinoline;
2-carboxy-5,7-dichloro-4-(N,N-diphenylamino)carbonylamino-1,2,3,4-tetrahydroquinoline;
2-carboxy-5,7-dichloro-4-(4-ethylphenyl)aminocarbonylamino-1,2,3,4-tetrahydroquinoline;
2-carboxy-5,7-dichloro-4-(N-ethyl-N-phenyl)aminocarbonylamino-1,2,3,4-tetrahydroquinoline;
4-benzylamino-2-carboxy-5,7-dichloro-1,2,3,4-tetrahydroquinoline;
2-carboxy-5,7-dichloro-4-(phenylaminocarbonylmethyl)amino-1,2,3,4-tetrahydroquinoline;
4-benzylcarbonylamino-2-(t-butylcarbonyloxy)methoxycarbonyl-5,7-dichloro-1,2,3,4-tetrahydroquinoline;
4-benzylcarbonylamino-5,7-dichloro-2-(methylaminocarbonyl)methoxycarbonyl-1,2,3,4-tetrahydroquinoline;
4-benzylcarbonylamino-5,7-dichloro-2-[2-(N,N-dimethylamino)ethylaminocarbonyl]methoxycarbonyl-1,2,3,4-tetrahydroquinoline;
4-benzylcarbonylamino-5,7-dichloro-2-[2-(N,N-dimethylamino)ethoxycarbonyl]-1,2,3,4-tetrahydroquinoline;
4-benzylcarbonylamino-5,7-dichloro-2-[3-(N,N-dimethylamino)propoxycarbonyl]-1,2,3,4-tetrahydroquinoline;
4-benzylcarbonylamino-5,7-dichloro-2-[2-N,N-dimethylamino)ethylaminocarbonyl]-1,2,3,4-tetrahydroquinoline;
5,7-dichloro-2-[2-(N,N-dimethylamino)ethylaminocarbonyl]-4-phenylaminocarbonylamino-1,2,3,4-tetrahydroquinoline;
4-[4-(aminomethyl)benzylcarbonylamino]-5,7-dichloro-2-(methylaminocarbonyl)methoxycarbonyl-1,2,3,4-tetrahydroquinoline;
4-[4-(aminomethyl)benzylcarbonylamino]-5,7-dichloro-2-hexyloxycarbonyl-1,2,3,4-tetrahydroquinoline;
2-carboxy-5,7-dichloro-4-methoxycarbonylmethyl-1,2,3,4-tetrahydroquinoline;
2-carboxy-4-carboxymethyl-5,7-dichloro-1,2,3,4-tetrahydroquinoline;
2-carboxy-5,7-dichloro-4-phenylaminocarbonylmethyl-1,2,3,4-tetrahydroquinoline;
and salts thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein $R^3$ represents hydrogen may be prepared by a process which comprises reducing a quinoline derivative of formula IV:

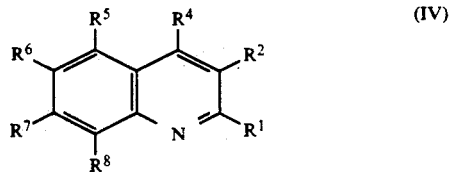

wherein $R^1$, $R^2$, $R^4$, $R^5$, $R^6$, $R^7$ and $R^8$ are as defined above.

A suitable reducing agent for carrying out the above transformation is sodium cyanoborohydride. The reaction is conveniently carried out in the presence of a suitable solvent, for example acetic acid, at an elevated temperature, e.g. a temperature in the region of 50° C.

An alternative method for reducing the intermediate of formula IV is catalytic hydrogenation. A suitable catalyst is platinum oxide, and the reaction is conveniently carried out in methanol as solvent. In view of the nature of the hydrogenation reaction, this method is particularly suitable for the preparation of products having an all-cis substitution pattern in the piperidine moiety of the tetrahydroquinoline ring system.

The compounds of the invention wherein $R^3$ is hydrogen and $R^4$ is a group of formula $-NR^aCOR^b$ may be prepared by reacting a compound of formula A—$COR^b$ with a compound of formula V:

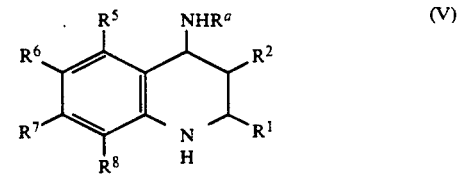

wherein $R^1$, $R^2$, $R^5$, $R^6$, $R^7$, $R^8$, $R^a$ and $R^b$ are as defined above; and A represents a leaving group. In this context, A suitably represents halogen, $C_{1-6}$ alkoxy or $-OCOR^b$.

The reaction is conveniently carried out by treating the compound of formula V with the appropriate acid chloride in the presence of triethylamine in an inert solvent, e.g. dichloromethane. Alternatively, the reaction may be effected by treating the compound of formula V with the appropriate carboxylic acid in the presence of a suitable condensing agent, e.g. 1,3-dicyclohexylcarbodiimide. Further methods for carrying out this transformation include standard amide bond-forming reactions used in peptide synthesis.

The compounds of the invention wherein $R^3$ is hydrogen and $R^4$ is a group of formula $-NR^aCO_2R^b$ may be prepared by reacting a compound of formula V as defined above with a compound of formula A-$CO_2R^b$ wherein A and $R^b$ are as defined above. In this context, A suitably represents halogen or $-OCO_2R^b$, and the reaction is conveniently carried out in an inert solvent, e.g. dichloromethane.

The compounds of the invention wherein $R^3$ is hydrogen and $R^4$ is a group of formula $-NR^aSO_2R^b$ may be prepared by reacting a compound of formula V as defined above with a compound of formula A—$SO_2R^b$ wherein A and $R^b$ are as defined above. In this context, A suitably represents halogen, particularly chlorine; and the reaction is conveniently carried out in the presence of triethylamine in an inert solvent, e.g. dichloromethane.

The compounds of formula V above wherein $R^a$ is hydrogen may be prepared by reducing a compound of formula VI:

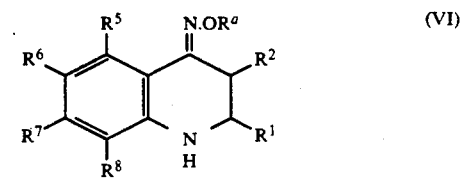

wherein $R^1$, $R^2$, $R^5$, $R^6$, $R^7$, $R^8$ and $R^a$ are as defined above.

A suitable reducing agent for this purpose is zinc in acetic acid, and the reaction is conveniently carried out at room temperature.

The compounds of formula VI above may be prepared by treating a compound of formula VII:

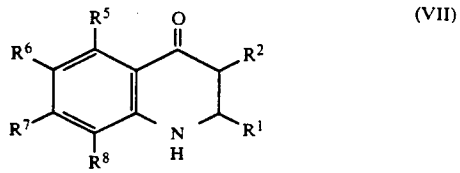
(VII)

wherein $R^1$, $R^2$, $R^5$, $R^6$, $R^7$ and $R^8$ are as defined above; with a hydroxylamine derivative of formula $H_2N.OR^a$ wherein $R^a$ is as defined above, or a salt thereof, particularly the hydrochloride salt.

The reaction is conveniently carried out in a suitable solvent, e.g. methanol, at reflux temperature, in the presence of a stoichiometric quantity of pyridine.

In an alternative procedure, the compounds of formula V may be prepared directly from the compounds of formula VII by reductive amination. This process comprises treating a compound of formula VII as defined above with an amine of formula $R^aNH_2$, in which $R^a$ is as defined above, in the presence of a reducing agent. Suitable reducing agents include sodium borohydride, sodium cyanoborohydride, and hydrogen in the presence of a catalyst such as palladium on charcoal, or platinum oxide.

The compounds of formula VII above may be prepared by a process which comprises cyclising a reactive derivative of a carboxylic acid of formula VIII:

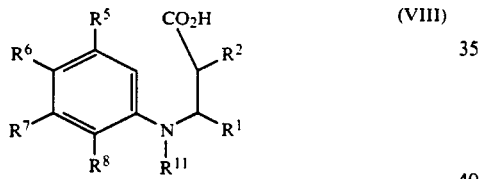
(VIII)

wherein $R^1$, $R^2$, $R^5$, $R^6$, $R^7$ and $R^8$ are as defined above and $R^{11}$ represents an amino-protecting group; and subsequently removing the amino-protecting group $R^{11}$.

The reactive derivatives of the carboxylic acid VIII suitably include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Suitable examples of amino-protecting groups for the substituent $R^{11}$ include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, trityl, o-nitrophenylsulphenyl or benzylidene.

A preferred amino-protecting group is acetyl.

The removal of the amino-protecting group present in the resultant compound may be effected by an appropriate procedure depending upon the nature of the protecting group. A typical procedure for the acetyl group involves heating at reflux temperature in the presence of 3N hydrochloric acid.

When $R^1$ in the compounds according to the invention represents carboxy, it is convenient to replace the carboxylic acid VIII in the above reaction with a cyclic anhydride of formula IX:

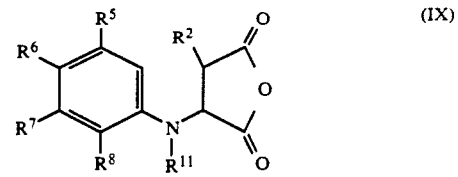
(IX)

wherein $R^2$, $R^5$, $R^6$, $R^7$, $R^8$ and $R^{11}$ are as defined above.

The reaction is suitably carried out in the presence of a Lewis acid catalyst such as aluminium chloride; and is conveniently effected at an elevated temperature, for example a temperature in the region of 160° C., suitably in the melt.

In an alternative process, the compounds according to the invention may be prepared by reacting a compound of formula X, or a protected derivative thereof, with a compound of formula XI, or a protected derivative thereof:

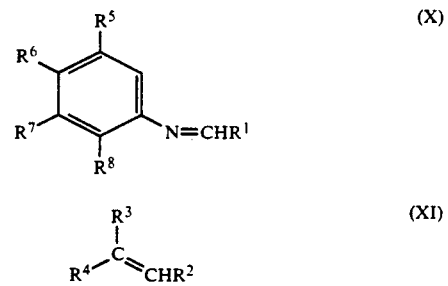
(X)

(XI)

wherein $R^1$ and $R^8$ are as defined above; followed, where necessary, by removal of the protecting groups.

The reaction is conveniently carried out at room temperature in an inert solvent, e.g. dichloromethane, in the presence of a Lewis acid catalyst such as boron trifluoride etherate. Illustrative experimental details for this reaction are described in J. Heterocycl. Chem., 1988, 25, 1831.

The compounds of the invention wherein $R^3$ is hydrogen and $R^4$ is a 3-methyl-1,2,4-oxadiazol-5-yl substituent may be prepared by a process which comprises reacting a reactive derivative of a carboxylic acid of formula XII with the compound of formula XIII, or a salt thereof:

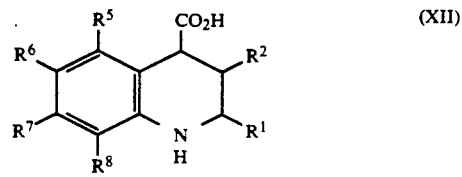
(XII)

(XIII)

wherein $R^1$, $R^2$, $R^5$, $R^6$, $R^7$ and $R^8$ are as defined above.

Suitable reactive derivatives of the carboxylic acid XII correspond to those of the carboxylic acid VIII above.

The reaction is conveniently carried out in tetrahydrofuran, dimethylformamide or a lower alkanol such as ethanol, propanol or ispropanol at a temperature of between 20° and 60° C. for 1 to 6 hours, suitably in the presence of a base such as sodium hydride.

It will be appreciated that the 3-substituent on the oxadiazole ring of the product can be varied by choosing an intermediate of formula XIII possessing an appropriate substituent in place of methyl.

The compounds of formula IIE wherein Q is the residue of a ring of formula IIIA in which $R^a$ and $R^b$ both represent hydrogen, i.e. the spirocyclic hydantoin derivatives of formula XIV:

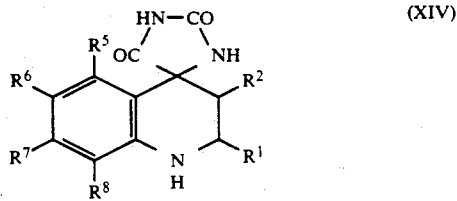

wherein $R^1$, $R^2$, $R^5$, $R^6$, $R^7$ and $R^8$ are as defined above; may be prepared by treating a compound of formula VII, as defined above, with sodium cyanide in the presence of ammonium carbonate. The reaction is conveniently carried out by heating the reagents together under reflux in water.

The compounds of formula IIE wherein Q is the residue of a ring of formula IIIB, i.e. the spirocyclic dioxolane derivatives of formula XV:

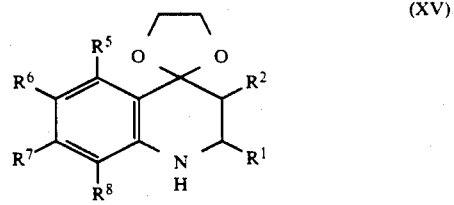

wherein $R^1$, $R^2$, $R^5$, $R^6$, $R^7$ and $R^8$ are as defined above; may be prepared by treating a compound of formula VII, as defined above, with ethylene glycol. The reaction is conveniently carried out at reflux temperature in a suitable solvent, e.g. toluene, preferably in the presence of a suitable catalyst, for example p-toluenesulphonic acid or, more particularly, pyridinium p-toluenesulphonate.

As will be appreciated, the compounds of formulae V, VI, VII and XII as defined above, used as intermediates in the preparation of compounds according to this invention, are themselves compounds of the present invention. Indeed, any compound of formula I initially obtained may, where appropriate, subsequently be elaborated into a further compound of formula I by techniques known from the art.

The intermediates of formulae IV, VIII and IX may conveniently be prepared by methods analogous to those described in the accompanying Examples.

Except where explicitly stated otherwise, the above-described processes for the preparation of the compounds according to the invention are likely to give rise to mixtures of stereoisomers. At an appropriate stage, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The compounds useful in this invention potently and selectively block responses to NMDA in a brain slice from rat cortex, and inhibit glycine binding to the strychnine-insensitive site present on the NMDA receptor.

CORTICAL SLICE STUDIES

The effects of compounds of the invention on responses to NMDA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA concentration-response curve produced by the compound under test. The compounds of the accompanying Examples were tested and each was found to possess a $K_b$ value below 100 μM.

INHIBITION OF GLYCINE BINDING

The ability of test compounds to displace $^3$H-glycine binding to the strychnine-insensitive site present on the NMDA receptor of rat forebrain membranes was determined by the method of Donald et al., *Proceedings of The British Pharmacological Society*, University of Nottingham, September 1988, Abstract P122. The concentration of the compounds of each of the accompanying Examples required to displace 50% of the specific binding (IC$_{50}$) is below 100 μM.

EXAMPLE 1

2-Carboxy-5,7-dichloro-4-oxo-1,2,3,4-tetrahydroquinoline a) Methyl-2-(3,5-dichlorophenylamino)-3-methoxycarbonylpropionate 3,5-Dichloroaniline (104 g) and dimethylacetylene dicarboxylate (79 ml) were dissolved in dry methanol (100 ml) and heated under reflux for 14 h. On cooling a yellow solid crystallised out and this was collected by filtration. The mother liquors were concentrated in vacuo to leave a residue from which a second crop of product was obtained by recrystallisation from diethyl ether/60-80 petrol. The combined crops of material weighed 167.5 g (after drying at 40° C. under a pressure of 20 mmHg for 18 h). A portion of this material (105 g) was dissolved in ethyl acetate (1000 ml) and hydrogenated at 50 psi over 10% palladium on carbon catalyst (4 g) for 40 h. The catalyst was removed by filtration and the solvent evaporated under vacuum to leave a residue which was recrystallised from diethyl ether/hexane to give the title compound as a white crystalline solid (84.8 g, m.p. 66°–67° C.); δ (360 MHz, CDCl$_3$) 2.88 (2H, m, CH$_B$H$_C$), 3.71 (3H, s, CH$_3$), 3.78 (3H, s, CH$_3$), 4.36 (1H, t, J=5.4 Hz, CH$_A$CH$_B$H$_C$), 4.71 (1H, br, s, NH), 6.51 (2H, d, J=1.8 Hz, 2-H and 6-H), 6.73 (1H, t, J=1.8 Hz, 4-H); m/e 305 (M$^+$), 246 (100%, M-CO$_2$CH$_2$); Found C, 47.14; H, 4.27; N, 4.56. C$_{12}$H$_{13}$Cl$_2$NO$_4$ requires C, 47.08; H, 4.28; N, 4.58%.

b) 3-Carboxy-2-(3,5-dichlorophenylamino)-propionic acid

Methyl-2-(3,5-Dichlorophenyl)amino-3-methoxycarboxylpropionate (131.4 g) was dissolved in methanol (800 ml) and sodium hydroxide (51.5 g in 600 ml of water) was added. The reaction mixture was stirred at room temperature for 5 h then the methanol was removed under vacuum and the residual solution was acidified to pH 1 by the cautious addition of concentrated hydrochloric acid. The aqueous solution was extracted with ethyl acetate (2×600 ml) and the combined organic layers were dried (MgSO$_4$), filtered and concentrated in vacuo to give the required compound as a white solid (11.6 g, m.p. 217° C. dec); δ (360 MHz), NaOD) 2.47 (1H, dd, J=15.1 and 10.1 Hz, CH$_A$CH$_B$H$_C$), 2.73 (1H, dd, J=15.1 and 3.8 Hz, CH$_A$CH$_B$H$_C$), 4.06 (1H, dd, J=10.1 and 3.8 Hz, CH$_A$CH$_B$H$_C$), 6.62 (2H, d, J=1.5 Hz, 2-H and 6-H), 6.79 (1H, t, J=1.5 Hz, 4-H); m/e 277 (M$^+$); Found: C, 43.29; H, 3.28; N, 5.02 C$_{10}$H$_9$Cl$_2$NO$_4$ requires C, 43.19; H, 3.26; N, 5.04%.

c) 2-[N-Acetyl-N-(3,5-dichlorophenylamino]-3-carboxy-propionic acid

3-Carboxy-2-(3,5-dichlorophenylamino-propionic acid (116 g) was suspended in acetic anhydride (1000 ml) and heated at 60°–70° C. under nitrogen for 6 h then cooled and concentrated in vacuo. The residue which was obtained was dissolved in methanol (500 ml) and sodium hydroxide solution (500 ml of 2.5N) was added. The reaction mixture was stirred at room temperature for 14 h then the methanol was removed by evaporation. The residual aqueous solution was washed with diethyl ether (2×200 ml) the acidified to pH 1 with concentrated hydrochloric acid and extracted into ethyl acetate (2×500 ml), dried (MgSO$_4$), filtered and concentrated under vacuum. The residue obtained was triturated with diethyl ether and collected by filtration to give the the title compound as a white solid (128.5 g, m.p. 181° C. dec); δ (360 MHz, DMSO) 1.79 (3H, s, CH$_3$), 2.72 (1H, dd, J=16.8 and 6.8 Hz, CH$_A$CH$_B$H$_C$). 2.90 (1H, dd, J=16.8 and 6.8 Hz, CH$_A$CH$_B$H$_C$), 4.78 (1H, t, J=6.8 Hz, CH$_A$CH$_B$H$_C$), 7.48 (2H, d, J=1.7 Hz, 2-H and 6-H), 7.69 (1H, t, J=1.7 Hz, 4-H); m/e (CI$^+$) 320 (M+1).

d) 1-Acetyl-2-carboxy-5,7-dichloro-4-oxo-1,2,3,4-tetrahydroquinoline

2[N-Acetyl-N-(3,5-dichlorophenyl)amino]-3-carboxy-propionic acid (128 g) was suspended in dichloromethane (1000 ml) and acetyl chloride (300 ml) was added. The reaction mixture was stirred overnight at room temperature under an inert atmosphere, filtered, then concentrated in vacuo and then dried under high vacuum to give as an off white solid the required substituted succinic anhydride (119.8 g); δ (360 MHz, CDCl$_3$) 1.97 (3H, s, CH$_3$), 3.27 (2H, m, CH$_A$CH$_B$H$_C$), 4.44 (1H, dd, J=9.4 and 7.0 Hz, CH$_A$CH$_B$H$_C$), 7.30 (2H, d, J=1.6 Hz, 2-H and 6-H), 7.46 (1H, t, J=1.6 Hz, 4-H). A portion of this material (60 g) and finely ground aluminium trichloride (168 g) were blended together and heated at 170° C. for 30 min. After this time the reaction mixture was allowed to cool and ice cold 1N hydrochloric acid was added cautiously until effervescence ceased. The aqueous layer was decanted and the residual solid retained and combined with the product from a second reaction carried out on the remaining anhydride (50.8 g). The solid was triturated with absolute ethanol and the title compound was collected by filtration (20.2 g, m.p. 212°–213° C.); δ (360 MHz, DMSO) 2.32 (3H, s, CH$_3$), 3.04 (1H, dd, J=17.4 and 1.7 Hz, CH$_A$CH$_B$H$_C$), 3.21 (1H, dd, J=17.4 and 6.6 Hz, CH$_A$CH$_B$H$_C$), 5.59 (1H, m, CH$_A$CH$_B$H$_C$), 7.54 (1H, d, J=2.0 Hz, 6-H or 8-H), 7.81 (1H, d, J=2.0 Hz, 6-H or 8-H); m/e 301 (M$^+$); Found: C, 47.48; H, 3.18; N, 4.49. C$_{12}$H$_9$Cl$_2$NO$_4$ requires C, 47.71; H, 3.00; N, 4.64%.

e) 2-Carboxy-5,7-dichloro-4-oxo-1,2,3,4-tetrahydroquinoline

1-Acetyl-2-carboxy-5,7-dichloro-4-oxo-1,2,3,4-tetrahydroquinoline (21.17 g) was suspended in 3N hydrochloric acid (500 ml) and heated at reflux overnight. After cooling, the aqueous solution was extracted with ethyl acetate (3×300 ml) and the combined organic layers were washed with brine (1×300 ml), dried (MgSO$_4$), filtered and evaporated in vacuo to give the title compound as a yellow solid (17.45 g, m.p. 218°–219° C.); δ (360 MHz, DMSO) 2.73 (1H, dd, J=15.7 and 6.8 Hz, CH$_A$CH$_B$H$_C$), 2.92 (1H, dd, J=15.7 and 6.2 Hz, CH$_A$CH$_B$H$_C$), 4.36 (1H, m, CH$_A$CH$_B$H$_C$), 6.67 (1H, d, J=2.0 Hz, 6-H or 8-H), 6.96 (1H, d, J=2.0 Hz, 6-H or 8-H), 7.62 (1H, br, s, NH); m/e (FAB) 260 (M+1); Found: C, 46.10; H, 2.85; N, 5.26. C$_{10}$H$_7$Cl$_2$NO$_3$ requires C, 46.18; H, 2.71; H, 5.39%.

EXAMPLE 2

2-Carboxy-5,7-dimethyl-4-oxo-1,2,3,4-tetrahydroquinoline

This compound was prepared by the route outlined in Example 1 starting with 3,5-dimethylaniline [m.p. 154°–155° C. (ethyl acetate/hexane)]; δ 2.14 (3H, s, CH$_3$), 2.40 (3H, s, CH$_3$), 2.65 (1H, dd, J=15.9 and 6.7 Hz, CH$_A$CH$_B$H$_C$), 2.79 (1H, dd, J=15.9 and 6.2 Hz, CH$_A$CH$_B$H$_C$), 4.18 (1H, ddd, J=6.7, 6.2 and 2.1 Hz, NHCH$_A$CH$_B$H$_C$), 6.21 (1H, s, 6-H or 8-H), 6.54 (1H, s, 6-H or 8-H), 6.83 (1H, br. s, NH); m/e FAB 220 (M+1); Found: C, 61.58; H, 6.26: N, 5.96. C$_{12}$H$_{13}$NO$_3$.0.8H$_2$O requires C, 61.69; H, 6.30; N, 5.99%.

EXAMPLES 3 AND 4

Trans and cis-2-carboxy-4-oxo-3,5,7-trimethyl-1,2,3,4-tetrahydroquinoline

These compounds were prepared by the route outlined in Example 1 using 3,5-dimethyl aniline and diethyloxalpropionate as the starting materials in the first step. The cis and the trans isomers were distinguished by X-ray crystallography. Trans isomer (Example 3) [m.p. 156°–157° C. (diethyl ether)]; δ (360 MHz, CDCl$_3$), 1.35 (3H, d, J=7.2 Hz, CH$_3$CH$_B$CH$_A$), 2.23 (3H, s, CH$_3$Ar), 2.54 (3H, s, CH$_3$Ar), 2.97 (1H, m, CH$_3$CH$_B$CH$_A$), 3.97 (1H, d, J=4.9 Hz, CH$_3$CH$_A$CH$_B$), 6.40 (2H, s, 6-H and 8-H); m/e 233 (M$^+$), 188 (100%, -CO$_2$H); Found: C, 66.73; H, 6.50; N, 5.95. C$_{13}$H$_{15}$NO$_3$ requires C, 66.94; H, 6.48; N, 6.00%. Cis-isomer (Example 4) (oil); δ (250 MHz, CDCl$_3$) 1.17 (3H, d, J=7.2 Hz, CH$_3$CH$_B$CH$_A$), 2.24 (3H, s, CH$_3$Ar), 2.57 (3H, s, CH$_3$Ar), 2.95 (1H, dq, J=7.2 and 4.0 Hz, CH$_3$CH$_B$CH$_A$), 4.43 (1H, d, J=4.0 Hz, CH$_3$CH$_B$CH$_A$), 4.90 (1H, br, s, NH), 6.40 (1H, s, 6-H or 8-H), 6.42 (1H, s, 6-H or 8-H); m/e 233 (M+), 188 (100%, M-CO$_2$H); Found: C, 64.97; H, 6.53; N, 5.72. C$_{13}$H$_{15}$NO$_3$.0.4 H$_2$O requires C, 64.93; H, 6.62; N, 5.82%.

EXAMPLE 5

Trans-4-tertiary-butyloxycarbonylamino-2-carboxy-5,7-dichloro-1,2,3,4-tetrahydroquinoline a) 5,7-Dichloro-4-hydroxyimino-2-methoxycarbonyl-1,2,3,4-tetrahydroquinoline To a solution of 2-carboxy-5,7-dichloro-4-oxo-1,2,3,4-tetrahydroquinoline (Example 1) (14.85 g, 57.1 mmol) in methanol (300 ml) was added hydroxylamine hydrochloride (4.17 g, 60.0 mmol) followed by dry pyridine (4.85 ml, 60.0 mmol) and the resulting mixture was heated at reflux under an atmosphere of nitrogen for 2 hours. The mixture was then cooled, and a solution of methanol saturated with hydrogen chloride (50 ml) was added and the reaction was stirred at room temperature under an atmosphere of nitrogen for 17 hours. The solvent was removed in vacuo and the residue was partitioned between water (300 ml) and diethyl ether (300 ml). The aqueous phase was further extracted with diethyl ether (2×300 ml) and the combined organic layers were washed with 0.5M aqueous citric acid solution (1×200 ml), saturated hydrogen sodium bicarbonate solution (2×200 ml), brine (1×200 ml), then dried (MgSO$_4$) and the solvent was removed under vacuum to give the title compound (15.1 g) as a brown solid (m.p. 216°-217° C.); δ (360 MHz, DMSO) 2.79 (1H, dd, J=15.4 and 6.1 Hz, CH$_A$H$_B$CH$_C$), 3.25 (1H, dd, J=15.4 and 5.8 Hz, CH$_A$H$_B$CH$_C$), 3.64 (3H, s, CO$_2$CH$_3$), 4.23 (1H, m, CH$_A$H$_B$CH$_C$), 6.70 (1H, d, J=2.1 Hz, 6-H or 8-H), 6.82 (1H, d, J=2.1 Hz, 6-H or 8-H), 7.01 (1H, br, s, NH), 11.41 (1H, s, NOH); m/e 288 (M+), 213 (100%); Found: C, 45.75; H, 3.50; N, 9.51; C$_{11}$H$_{10}$Cl$_2$N$_2$O$_3$ requires C, 45.70; H, 3.49; N, 9.69%.

b) Cis and trans-4-tertiary-butyloxcarbonylamino-5,7-dichloro-2-methoxycarbonyl-1,2,3,4-tetrahydroquinoline To a suspension of 5,7-dichloro-4-hydroxyimino-2-methoxycarbonyl-1,2,3,4-tetrahydroquinoline (8.0 g, 27.7 mmol) in glacial acetic acid (240 ml) was added zinc dust (12.0 g, 18 mmol) and the resulting mixture was heated at 60°-65° C., under an atmosphere of nitrogen, with stirring for 4 hours. The reaction mixture was allowed to cool, then filtered and the filtrate was evaporated in vacuo. The residue was redissolved in ethyl acetate (400 ml), washed with saturated sodium bicarbonate solution (2×200 ml) and saturated brine solution (1×200 ml) then dried (MgSO$_4$), filtered and concentrated under vacuum to give a brown foam (6.60 g). To a solution of this foam in dichloromethane (350 ml) was added di-tertiary-butyl-dicarbonate (12.0 g, 55 mmol) and the mixture was stirred at room temperature for 65 hours under an atmosphere of nitrogen. To the reaction mixture was added N,N-dimethylethylenediamine (6.6 ml, 60 mmol) and stirring was continued for a further 2 hours. The reaction mixture was washed successively with 0.5M citric acid solution (2×200 ml) and brine (1×200 ml), dried (MgSO$_4$), filtered and the solvent was removed under vacuum to give an oily solid (5.8 g). This was purified by flash chromatography using 20% ethyl acetate in petroleum ether (bp 60°-80° C.) as eluent to give a mixture of cis and trans isomers. Trituration of this mixture with diethyl ether gave a solid which was collected by filtration and was recrystallised from hot ethyl acetate/petroleum ether (bp 60°-80° C.) to give, as colourless needles, the less polar Trans-4-tertiarybutyloxycarbonylamino-5,7-dichloro-2-methoxycarbonyl-1,2,3,4-tetrahydroquinoline (1.33 g, m.p. 210°-211° C.). Purification of the mother liquors by normal phase Lobar chromatography using 15% ethyl acetate in petroleum ether (bp 60°-80° C.) followed by recrystallisation from hot ethyl acetate/petroleum ether (bp 60°-80° C.) gave the more polar cis-4-tertiary-butyloxycarbonylamino-5,7-dichloro-2-methoxycarbonyl-1,2,3,4-tetrahydroquinoline (0.43 g, m.p. 172°-173° C.). Data for trans: δ (360 MHz, CDCl$_3$) 1.66 (1H, ddd, J= 13.1, 12.7 and 3.6 Hz, CH$_A$CH$_B$H$_C$CH$_D$), 1.48 (9H, s, C(CH$_3$)$_3$), 2.61 (1H, dm, J=13.1 Hz, CH$_A$CH$_B$H$_C$CH$_D$), 4.00 (1H, dd, J=12.7 and 3.0 Hz, CH$_A$CH$_B$H$_C$CH$_D$), 4.52 (1H, m, CH$_A$CH$_B$H$_C$CH$_D$), 4.84 (1H, br, s, NH), 4.98 (1H, br, s, NH), 6.53 (1H, d, J=2.0 Hz, 6-H or 8-H), 6.72 (1H, d, J=2.0 Hz, 6-H or 8-H); m/e (Cl+) 375 (M+1); Found: C, 51.34; H, 5.43; N, 7.46; C$_{16}$H$_{20}$Cl$_2$N$_2$O$_4$ requires C, 51.21; H, 5.37; N, 7.47%. Data for cis δ (360 MHz, CDCl$_3$) 1.43 (9H, s, C(CH$_3$)$_3$, 2.05 (1H, m, CH$_A$CH$_B$H$_C$CH$_D$), 2.88 (1H, dm, J=14.2 Hz, CH$_A$CH$_B$H$_C$CH$_D$), 4.08 (1H, m, CH$_A$CH$_B$H$_C$CH$_D$), 4.34 (1H, m, CH$_A$CH$_B$H$_C$CH$_D$), 4.58 (1H, br, s, NH), 4.90 (1H, br, s, NH), 6.56 (1H, d, J=2.0 Hz, 6-H or 8-H), 6.75 (1H, d, J=2.0 Hz, 6-H or 8-H); m/e 374 (M+), 198 (100%, M-NHCO$_2$, tBu, CO$_2$CH$_3$ and H); Found: C, 51.37; H, 5.40; N, 7.55; C$_{16}$H$_{20}$Cl$_2$N$_2$O$_4$ requires C, 51.21; H, 5.37; N, 7.47%.

c) Trans-4-tertiary-butyloxycarbonylamino-2-carboxy-5,7-dichloro-1,2,3,4-tetrahydroquinoline To a solution of trans-4-tertiary-butyloxycarbonylamino-5,7-dichloro-2-methoxycarbonyl-1,2,3,4-tetrahydroquinoline (0.153 g, 0.408 mmol) in tetrahydrofuran (10 ml) was added aqueous lithium hydroxide (0.45 ml of a 1.0M solution, 0.45 mmol) followed by distilled water (3 ml) and the resulting mixture was stirred at room temperature for 4 hours. The mixture was then evaporated to dryness under vacuum and the residue was redissolved in water (40 ml). The solution was adjusted to pH 1 with dilute hydrochloric acid and the mixture was extracted with ethyl acetate (2×30 ml). The combined organic extracts were washed with brine then dried (MgSO$_4$), and concentrated in vacuo to give an oil from which two crops of crude product were obtained by recrystallisation from diethyl ether/petroleum ether (bp 60°-80° C.). The combined material was dissolved in methanol and evaporated under vacuum to give an oil which was recrystallised from diethyl ether to give the pure title compound as colourless crystals (0.071 g, m.p. 193°-195° C.); δ (360 MHz, DMSO) 1.40 (9H, s, C(CH$_3$)$_3$), 1.61 (1H, ddd, J=12.6, 11.9 and 4.0 Hz, CH$_A$CH$_B$H$_C$CH$_D$), 2.10 (1H, dm, J=12.6 Hz, CH$_A$CH$_B$H$_C$CH$_D$), 3.84 (1H, dm, J=11.9 Hz, CH$_A$CH$_B$H$_C$H$_D$), 4.75 (1H, m, CH$_A$CH$_B$H$_C$CH$_D$), 6.63 (1H, d, J=2.0 Hz, 6-H or 8-H), 6.68 (1H, s, NH), 6.83 (1H, d, J=2.0 Hz, 6-H or 8-H), 7.23 (1H, d, J=7.4 Hz, CONHCH); m/e (FAB) 361 (M+1); Found: C, 49.82; H, 5.10; N, 7.62; C$_{15}$H$_{18}$Cl$_2$N$_2$O$_4$ requires C, 49.88; H, 5.02; N, 7.76%.

EXAMPLE 6

Cis-4-tertiary-butyloxycarbonylamino-2-carboxy-5,7-dichloro-1,2,3,4-tetrahydroquinoline To a solution of cis-4-tertiary-butyloxy-carbonylamino-5,7-dichloro-2-methoxycarbonyl-1,2,3,4-tetrahydroquinoline (220 mg, 0.587 mmol) in tetrahydrofuran (10 ml) was added aqueous lithium hydroxide (0.65 ml of a 1.0M solution, 0.65 mmol) followed by distilled water (5 ml) and the resulting mixture was stirred at room temperature for 1.5 hours. The mixture was evaporated to dryness and the residue was redissolved in water (50 ml). The solution was washed with diethyl ether (20 ml) and the aqueous layer was acidified to pH 1 with dilute hydrochloric acid and extracted with ethyl acetate (2×30 ml). The combined organic layers were washed with water (30 ml) and brine (30 ml) then dried ($MgSO_4$) and evaporated to give a solid which was triturated with diethyl ether/petroleum ether bp 60°–80° C. (1:6) to give the title compound as a colourless solid (0.161 g, m.p. 186°–188° C.); δ (250 MHz, $CDCl_3$) 1.54 (9H, s, $C(CH_3)_3$), 1.76 (1H, m, $CH_ACH_BH_CCH_D$), 2.92 (1H, dm, J=14.0 Hz, $CH_ACH_BH_CCH_D$), 3.82 (1H, m, $CH_ACH_BH_CCH_D$), 4.86 (1H, m, $CH_ACH_BH_CCH_D$), 6.00 (1H, br,s, NH), 6.56 (1H, d, J=3.0 Hz, 6-H or 8-H), 6.63 (1H, br,s, 6-H or 8-H); m/e (FAB) 361 (M+); Found: C, 49.69; H, 5.03; N, 7.73. $C_{15}H_{18}Cl_2N_2O_4$ requires: C, 49.88; H, 5.02; N, 7.76%.

EXAMPLE 7

Trans-4-amino-2-carboxy-5,7-dichloro-1,2,3,4-tetrahydroquinoline hydrochloride

To a suspension of trans-4-tertiary-butyloxy-carbonylamino-2-carboxy-5,7-dichloro-1,2,3,4-tetrahydroquinoline (80 mg, 0.222 mmol) in ethyl acetate (3 ml) was added hydrogen chloride in ethyl acetate (3 ml of an approximately 5M solution) and the resulting mixture was stirred at room temperature for 5 hours. The solvent was removed under vacuum and the residue was triturated with ethyl acetate. The solid obtained was collected by filtration then washed with ethyl acetate and dried to give as a colourless solid, the title compound (0.054 g, m.p. 184°–188° C.); δ (360 MHz, $D_2O$) 2.10 (1H, ddd, J=14.8, 13.3 and 4.3 Hz, $CH_ACH_BH_CCH_D$), 2.62 (1H, ddd, J=14.8, 3.4 and 2.4 Hz, $CH_ACH_BH_CCH_D$), 4.09 (1H, dd, J=13.3 and 3.4 Hz, $CH_ACH_BH_CCH_D$), 4.91 (1H, dd, J=4.3 and 2.4 Hz, $CH_ACH_BH_CCH_D$), 6.80 (1H, d, J=2.0 Hz, 6-H or 8-H), 6.89 (1H, d, J=2.0 Hz, 6-H or 8-H); m/e (FAB) 261 (M+1); Found C, 39.11; H, 3.81; N, 9.20; $C_{10}H_{10}Cl_2N_2O_3.HCl.0.4H_2O$ requires C, 39.04; H, 3.90; N, 9.19%.

EXAMPLE 8

Cis-4-amino-2-carboxy-5,7-dichloro-1,2,3,4-tetrahydroquinoline hydrochloride

To a solution of cis-4-tertiary-butyloxycarbonylamino-2-carboxy-5,7-dichloro-1,2,3,4-tetrahydroquinoline (100 mg, 0.277 mmol) in ethyl acetate (5 ml) was added hydrogen chloride in ethyl acetate (5 ml of an approx. 5M solution) and the resulting mixture was stirred at room temperature for 2.5 h. The solvent was removed in vacuo and the residue was triturated with ethyl acetate. The solid was collected by filtration to give the title compound (0.073 g, m.p. 176°–178 g°C.); δ (360 MHz, $D_2O$) 2.42 (1H, m, $CH_ACH_BH_CCH_D$), 2.67 (1H, dm, J=15.6 Hz, $CH_ACH_BH_CCH_D$), 4.27 (1H, dd, J=6.6 and 1.7 Hz, $CH_ACH_BH_CCH_D$), 4.90 (1H, dd, J=5.6 and 1.4 Hz, $CH_ACH_BH_CCH_D$), 6.77 (1H, d, J=2.0 Hz, 6-H or 8-H), 6.88 (1H, d, J=2.0 Hz, 6-H or 8-H); m/e (FAB) 261 (M+1); Found: C, 40.17; H, 3.79; N, 9.23. $C_{10}H_{10}Cl_2N_2O_3.HCl$ requires C, 40.36; H, 3.73; N, 9.41%.

EXAMPLE 9

Trans-2-carboxy-5,7-dichloro-4-benzoylamino-1,2,3,4-tetrahydroquinoline a) Trans-4-amino-5,7-dichloro-2-methoxycarbonyl-1,2,3,4-tetrahydroquinoline hydrochloride To a suspension of trans-4-tertiary-butyloxy-carbonylamino-5,7-dichloro-2-methoxycarbonyl-1,2,3,4-tetrahydroquinoline (1.2 g) in ethyl acetate (25 ml) was added a solution of hydrogen chloride in ethyl acetate (25M of an approx 5M solution) and the resulting mixture was stirred at room temperature for 3 hours after which time the solvent was removed in vacuo. The residue was triturated with ethyl acetate and the solid was collected to give the title compound as a colourless solid (0.96 g, m.p. 192°–194° C. [sublimes]); δ (360 MHz, $D_2O$) 2.13 (1H, ddd, J=14.8, 13.2 and 4.4 Hz, $CH_ACH_BH_CCH_D$), 2.65 (1H, dm, J=14.8 Hz, $CH_ACH_BH_CCH_D$), 3.85 (3H, s, $CH_3$), 4.22 (1H, dd, J=13.2 and 3.4 Hz, $CH_ACH_BH_CCH_D$), 4.92 (1H, dd, J=4.4 and 2.4 Hz, $CH_ACH_BH_CCH_D$), 6.81 (1H, d, J=2.0 Hz, 6-H or 8-H), 6.92 (1H, d, J=2.0 Hz, 6-H or 8-H); m/e (FAB) 275 (M+1); Found: C, 42.14; H, 4.27; N, 8.92. $C_{11}H_{12}N_2O_2.HCl$ requires C, 42.40; H, 4.21; N, 8.99%.

b) Trans-5,7-dichloro-2-methoxycarbonyl-4-benzoylamino-1,2,3,4-tetrahydroquinoline To a suspension of trans-4-amino-5,7-dichloro-2-methoxycarbonyl-1,2,3,4-tetrahydroquinoline hydrochloride (0.2 g, 0.642 mmol) in anhydrous dichloromethane (15 ml) was added dry triethylamine (220 ml, 1.4 mmol) and the resulting mixture was stirred at room temperature under an atmosphere of nitrogen until dissolution was complete. To this solution was added benzoyl chloride (82 ml, 0.706 mmol) and stirring was continued for 17 hours. The solvent was removed in vacuo and the residue was partitioned between ethyl acetate (100 ml) and dilute citric acid (150 ml). The organic layer was washed successively with saturated sodium bicarbonate solution (2×50 ml) and brine (50 ml) then dried ($MgSO_4$) and evaporated to give the crude product (0.26 g) which was recrystallised from ethyl acetate/petroleum ether (bp 60°–80° C.) to give the pure title compound as colourless crystals (0.201 g, m.p. 258°–259° C.); δ (360 MHz, DMSO) 1.79 (1H, ddd, J=13.3, 12.6 and 4.1 Hz, $CH_ACH_BH_CCH_D$), 2.28 (1H, dm, J=13.3 Hz, $CH_ACH_BH_CCH_D$), 3.73 (3H, s, $-CO_2CH_3$), 4.09 (1H, dm, J=12.6 Hz, $CH_ACH_BH_CCH_D$), 5.28 (1H, m, $CH_ACH_BH_CCH_D$), 6.70 (1H, d, J=2.0 Hz, 6-H or 8-H), 6.91 (1H, d, J=2.0 Hz, 6-H or 8-H), 6.93 (1H, s, NH), 7.42–7.55 (3H, m, ArH), 7.89 (2H, d, J=7.1 Hz, ArH), 8.72 (1H, d, J=7.6 Hz, PhCONH-); m/e (CI+) 379 (M+1)+, 122 (100%); Found: C, 56.95; H, 4.30; N, 7.37; $C_{18}H_{16}Cl_2N_2O_3$ requires C, 57.01; H, 4.25; N, 7.39%.

c) Trans-2-carboxy-5,7-dichloro-4-benzoylamino-1,2,3,4-tetrahydroquinoline

To a solution of trans-5,7-dichloro-2-methoxy-carbonyl-4-benzoylamino-1,2,3,4-tetrahydroquinoline (0.189 g, 0.499 mmol) in tetrahydrofuran (10 ml) was added distilled water (5 ml) followed by aqueous lithium hydroxide (1.10 ml of a 0.50M solution, 0.549 mmol) and the resulting mixture was stirred at room temperature for 3 hours. The organic solvent was removed under vacuum and to the aqueous residue was added saturated sodium bicarbonate solution (20 ml) and deionised water (50 ml). The mixture was washed with ethyl acetate (2×50 ml), then acidified to pH 1 with dilute hydrochloric acid and extracted with ethyl acetate (2×50 ml). The combined organic extracts were washed with brine (50 ml) then dried ($Na_2SO_4$) and evaporated to give the crude product (0.16 g) which was triturated with diethyl ether to give two crops of the pure title compound as a colourless crystalline solid (0.11 g, m.p. 233°–236° C.); δ (360 MHz, methanol) 1.82 (1H, ddd, J=13.4, 12.7 and 4.1 Hz, $CH_ACH_BH_CCH_D$), 2.55 (1H, dm, J=13.4 Hz, $CH_ACH_BH_CCH_D$), 3.99 (1H, dd, J=12.7 and 2.7 Hz, $CH_ACH_BH_CCH_D$), 5.41(1H, m, $CH_ACH_BH_CCH_D$), 6.68 (1H, d, J=2.0 Hz, 6-H or 8-H), 6.74 (1H, d, J=2.0 Hz, 6-H or 8-H), 7.40–7.53 (3H, m, ArH), 7.80 (2H, m, ArH), 8.78 (1H, d, J=7 Hz, NHCO); m/e (FAB+) 365 (M+1); Found: C, 55.62; H, 3.90; N, 7.56. $C_{17}H_{14}Cl_2N_2O_3$ requires C, 55.91; H, 3.86; N, 7.67%.

EXAMPLE 10

Trans-2-carboxy-5,7-dichloro-4-acetylamino-1,2,3,4-tetrahydroquinoline a) Trans-5,7-dichloro-2-methoxycarbonyl-4-acetylamino-1,2,3,4-tetrahydroquinoline To a suspension of trans-4-amino-5,5-dichloro-2-methoxycarbonyl-1,2,3,4-tetrahydroquinoline hydrochloride (0.15 g, 0.481 mmol) in anhydrous dichloromethane (15 ml) was added dry triethylamine (0.141 ml, 1.01 mmol) and the resulting mixture was stirred at room temperature under an atmosphere of nitrogen until dissolution was complete. To this solution was added acetyl chloride (38 ml, 0.529 mmol) and the reaction mixture was stirred under an atmosphere of nitrogen for a further 5 hours at room temperature. The precipitate was collected by filtration and was washed with dichloromethane to give the title compound as a colourless crystalline solid (0.133 g, m.p. 280°–282° C.) (dec.). δ (360 MHZ, DMSO) 164 (1H, ddd, J=13.0, 12.6 and 3.9 Hz, $CH_ACH_BH_CCH_D$), 1.81 (3H, s, $COCH_3$), 2.15 (1H, dm, J=13.0 Hz, $CH_ACH_BH_CCH_D$), 3.73 (3H, s, $CO_2CH_3$), 3.93 (1H, dd, J=12.6 and 2.8 Hz, $CH_ACH_BH_CCH_D$), 5.00 (1H, m, $CH_ACH_BH_CCH_D$), 6.68 (1H, d, J=2.1 Hz, 6-H or 8-H), 6.86 (1H, d, J=2.1 Hz, 6-H or 8-H), 6.88 (1H, s, NH), 8.18 (1H, d, J=7.1 Hz, $CH_3CONH-CH$); m/e 316 (M+), 198 (100%, M-NHCOCH_3, CO_2Me and H); C, 48.86; H, 4.48; N, 8.73; $C_{13}H_{14}Cl_2N_2O_3.0.1H_2O$ requires C, 48.95; H, 4.49; N, 8.78%.

b) Trans-2-Carboxy-5,7-dichloro-4-acetylamino-1,2,3,4-tetrahydroquinoline

To a suspension of trans-5,7-dichloro-2-methoxy-carbonyl-4-acetylamino-1,2,3,4-tetrahydroquinoline (0.12 g, 0.379 mmol) in methanol (5 ml) was added aqueous lithium hydroxide (0.42 ml of a 1.0M solution, 0.42 mmol) and the resulting mixture was stirred at room temperaure for 7 hours. To this mixture was added additional aqueous lithium hydroxide (0.20 ml of a 1.0M solution, 0.20 mmol) and the mixture was stirred for a further 16 hours. The solution was evaporated to dryness in vacuo and the residue obtained was redissolved in water (50 ml). The solution was acidified to pH 1 with dilute hydrochloric acid and extracted with ethyl acetate (2×30 ml). The combined extracts were washed with brine (30 ml), dried ($Na_2SO_4$) and evaporated to give the pure title compound as colourless crystals (0.108 g, 223-225 pc); δ (360 MHz, methanol) 1.70 (1H, ddd, J=13.3, 12.8 and 4.0 Hz, $CH_ACH_BH_CCH_D$), 1.95 (3H, s, $COCH3$), 2.41 (1H, dm, J=13.3 Hz, $CH_ACH_BH_CCH_D$), 3.92 (1H, dd, J=12.8 and 3.0 Hz, $CH_ACH_BH_CCH_D$), 5.17 (1H, m, $CH_ACH_BH_CCH_D$), 6.66 (1H, d, J=2.0 Hz, 6-H or 8-H), 6.72 (1H, d, J=2.0 Hz, 6-H or 8-H); m/e 302 (M+), 198 (100%, m-NHCOCH_3, CO_2H, H); found: C, 47.65; H, 4.11; N, 9.07. $C_{12}H_{12}Cl_2N_2O_3$ requires C, 47.55; H, 3.99; N, 9.24%.

EXAMPLE 11

5,7-Dichloro-4-(1,3-dioxan-2-yl)-2-(2-hydroxyethoxycarbonyl)-1,2,3,4-tetrahydroquinoline To a suspension of 2-carboxy-5,7-dichloro-4-oxo-1,2,3,4-tetrahydroquinoline (1.0 g, 3.85 mmol) in dry toluene (100 ml) was added ethane-1,2-diol (2.1 ml, 3.85 mmol) and pyridinium toluene-4-sulphonate (0.19 g, 0.77 mmol) and the resulting mixture was heated at reflux for 18 h under an atmosphere of nitrogen. The mixture was cooled and diluted with ethyl acetate (100 ml). The solution was washed with water (2×70 ml), dried ($Na_2SO_4$) and the solvent was removed under vacuum to give an oil (1.28 g) which was purified by flash chromatography (using 5% isopropanol in dichloromethane as the eluent) to give impure product. This was further purified by flash chromatography (using 5% isopropanol in dichloromethane as the eluent) to give the crude product as an oil which was recrystalised from diethyl ether to give the title compound as colourless crystals (0.105 g, m.p. 118°–120° C.); δ (360 MHz, DMSO), 2.16 (1H, dd, J=13.6 and 4.5 Hz, $CH_AH_BCH_C$), 2.29 (1H, dd, J=13.6 and 7.0 Hz, $CH_AH_BCH_C$), 3.57–3.61 (1H, m, $-CO_2CH_2CH_2-OH$), 4.00–4.15 (7H, m, $CO_2CH_2CH_2OH$, $CH_AH_BCH_C$, $-O-CH_2CH-_2-O-$), 4.83 (1H, m, $CO_2CH_2CH_2OH$), 6.63 (1H, d, J=2.1 Hz, 6-H or 8-H), 6.78 (1H, d, J=2.1 Hz, 6-H or 8-H), 6.92 (1H, s, NH); m/e (FAB) 348 (M+1); Found: C, 48.32; H, 4.39; N, 3.95. $C_{14}H_{15}Cl_2NO_5$ requires C, 48.29; H, 4.34; N, 4.02%.

EXAMPLE 12

2-Carboxy-5,7-dichloro-4-(2,4-imidazolidindione-3-yl)-1,2,3,4-tetrahydroquinoline To a solution of ammonium carbonate monohydrate (2.64 g, 23.1 mmol) in distilled water (50 ml) was added 2-carboxy-5,7-dichloro-4-oxo-1,2,3,4-tetrahydroquinoline (Example 1), (1.0 g, 3.85 mmol) and potassium cyanide (0.5 g, 7.7 mmol) and the resulting solution was heated at reflux for 48 hours. The reaction mixture was allowed to stand at room temperature for 48 hours then brought to reflux for a further 24 hours. To this solution was added another portion of potassium cyanide (300 mg, 4.6 mmol) and ammonium carbonate monohydrate (1.6 g, 14.0 mmol) and the solution was heated at reflux for 48 hours. The reaction mixture was cooled, acidified to pH 1 with concentrated hydrochloric acid and stirred at room temperature for 80 hours. The mixture was extracted with ethyl acetate (2×50 ml) and the combined organic layers were washed with brine (50 ml), dried ($MgSO_4$) and evaporated in vacuo to give an oily solid (0.48 g). This solid was dissolved in dilute sodium hydroxide solution (50 ml) and the resulting solution was washed with diethyl ether (2×30 ml). The aqueous phase was acidified to pH 1 with dilute hydrochloric acid and the solid which was formed was removed by filtration. The filtrate was extracted with diethyl ether (3×30 ml) and ethyl acetate (2×30 ml) and the combined organic layers were dried over anhydrous sodium sulphate and evaporated in vacuo to give a mixture which was purified by flash chromatography (using 8% methanol/5% acetic acid in dichloromethane as the eluent) to give an oil which was recrystallised from diethyl ether/ethyl acetate. The solid was collected by filtration, redissolved in methanol and evaporated under vacuum to give a glassy solid which was suspended in distilled water and freeze dried to give the title compound (0.05 g, approx. 1:1 mixture of diastereoisomers) as an off-white solid (m.p.: decomposes above 240° C.); δ (360 MHz, DMSO) 1.89–2.35 (4H, m, 2×$CH_2$—CH), 3.90 (1H, m, 1×$CH_2$—CH), 4.18 (1H, m, 1×$CH_2$—CH), 6.67 (1H, d, J=2.1 Hz, 1×6-H or 8-H), 6.69 (1H, d, J=2.1 Hz, 1×6-H or 8-H), 6.88 (1H, d, J=2.1 Hz, 1×6-H or 8-H), 6.91 (1H, s, 1×NH), 6.95 (1H, d, J=2.1 Hz, 1×6-H or 8-H), 7.01 (1H, s, 1×NH), 8.00 (1H, s, 1×NH), 8.62 (1H, s, 1×NH), 10.94 (1H, s, 1×$CO_2$H), 10.98 (1H, s, 1×$CO_2$H); m/e (high T EI) 329 ($M^+$).

EXAMPLE 13

Cis-2-carboxy-5,7-dichloro-4-ethoxycarbonyl-1,2,3,4-tetrahydroquinoline a) 5,7-Dichloro-2,4-diethoxycarbonylquinoline and 5,7-dichloro-4-(3,5-dichloroanilo)-2,4-diethoxycarbonyl-1,2,3,4-tetrahydroquinoline 3.5-Dichloraniline (10.95 g) and diethylglutaconate (13.5 g) were dissolved in dry dichloromethane and heated at reflux for 14 h. Diethyl ether, saturated with hydrogen chloride (10 ml) was added and the reaction mixture was heated at reflux for a further 24 h. After this time the solution was filtered and the filtrate was washed with saturated sodium hydrogen carbonate solution, dried ($Na_2SO_4$), filtered and concentrated in vacuo to give an oily residue which was purified by silica gel chromatography using 15% ethyl acetate in hexane as the eluent to give as a colourless solid, 5,7-dichloro-2,4-diethoxycarbonylquinoline (2.4 g, m.p. 104°–106° C.); δ (360 MHz, $CDCl_3$), 1.44 (3H, t, J=7.2 Hz, $CH_3CH_2$), 1.49 (3H, t, J=7.2 Hz, $CH_3CH_2$), 4.51 (2H, q, J=7.2 Hz, $CH_3CH_2$), 4.56 (2H, q, J=7.2 Hz, $CH_3CH_2$), 7.77 (1H, d, J=1.9 Hz, 6-H or 8-H), 8.17 (1H, s, 3-H) and 8.32 (1H, d, J=1.9 Hz, 6-H or 8-H); m/z 342 (M+1), 269 (100%, M+1 -$CO_2Et$); Found: C, 52.58; H, 3.87; N, 4.04. $C_{15}H_{13}Cl_2NO_4$ requires C, 52.65; H, 3.83; N, 4.09% and 5,7-dichloro-4-(3,5-dichloroanilino)-2,4-diethoxycarbonyl-1,2,3,4-tetrahydro-quinoline (0.23 g, m.p. 153°–154° C.; δ (360 MHz, $CDCl_3$) 1.29 (6H, t, J=7.2 Hz, $CH_3CH_2$×2), 2.34 (1H, dd, J=14.4 and 2.9 Hz, $CH_AH_B$-$CH_C$), 2.65 (1H, dd, J=14.4 and 12.3 Hz, $CH_AH_B$-$CH_C$), 4.27 (5H, m, $CH_3CH_2$×2 and $H_C$), 4.91 (1H, br, NH), 5.54 (1H, br, NH), 6.28 (2H, d, J=1.8 Hz, ortho anilino protons), 6.60 (1H, t, J=1.8 Hz, para anilino proton), 6.64 (1H, d, J=2.1 Hz, 6-H or 8-H), 6.68 (1H, d, J=2.1 Hz, 6-H or 8-H); m/z 506 and 504 ($M^+$), 433 (100%, M-$CO_2Et$); Found: C, 49.95; H, 4.07; N, 5.51. $C_{21}H_{20}Cl_4N_2O_4$ requires C, 49.83; H, 3.98; N, 5.53%).

b) 2-Carboxy-5,7-dichloro-4-ethoxycarbonylquinoline 5,7-Dichloro-2,4-diethoxycarbonylquinoline (0.5 g) was dissolved in 60% aqueous methanol (70 ml) and sodium hydroxide (0.42 g, 5 molar equivalents) added. The reaction mixture was stirred at room temperature for 1 h then heated under reflux for 4 h and the methanol was removed by rotary evaporation. The residue was diluted to give a volume of 50 ml, acidified to pH 1 with concentrated hydrochloric acid, and extracted with diethyl ether (3×50 ml). The organic layers were combined, dried ($Na_2SO_4$), filtered and the solvent was removed by evaporation to give a residue which was purified by chromatography on silica gel with 10% methanol and 1% acetic acid in dichloromethane as eluent to give, as a colourless solid, 2-carboxy-5,7-dichloro-4-ethoxycarbonyl-quinoline (0.35 g, m.p. 152°–154° C.); δ (360 MHz, DMSO) 1.35 (3H, t, J=7.1 Hz, $CH_3CH_2$), 4.45 (2H, q, J=7.1 Hz, $CH_3CH_2$), 8.16 (1H, d, J=2.0 Hz, 6-H or 8-H), 8.18 (1H, s, 3-H), 8.34 (1H, d, J=2.0 Hz, 6-H or 8-H); m/e 313 ($M^+$), 196 (100%, M-$CO_2H$ and $CO_2Et$); Found: C, 49.55; H, 2.93; N, 4.44. $C_{13}H_9Cl_2NO_4$ requires C, 49.71; H, 2.89; N, 4.46%.

c) Cis-2-carboxy-5,7-dichloro-4-ethoxycarbonyl-1,2,3,4-tetrahydroquinoline

2-Carboxy-5,7-dichloro-4-ethoxycarbonylquinoline (1.6 g) was dissolved in ethanol (100 ml) and platinum oxide (0.16 g) was suspended in the solution. The reaction mixture was stirred under one atmosphere pressure of hydrogen for 1 h at ambient temperature, then filtered and concentrated in vacuo. Chromatography on $SiO_2$ with 2.5% methanol, 0.5% acetic acid and 97% dichloromethane gave, as a colourless solid, cis-2-carboxy-5,7-dichloro-4-ethoxycarbonyl-1,2,3,4-tetrahydroquinoline (0.9 g, m.p. 160°–162° C.); δ (360 MHz, DMSO), 1.15 (3H, t, J=7.1 Hz, $CH_3CH_2$), 2.17 (1H, m, $CH_ACH_BH_CCH_D$), 2.52 (1H, m, $CH_ACH_BH_CCH_D$), 3.85 (1H, dd, J=7.1 and 3.1 Hz, $CH_ACH_BH_CCH_D$), 3.98 (3H, m, $CH_3CH_2$ and $CH_ACH_BH_CCH_D$), 6.65 (1H, d, J=2.0 Hz, 6-H or 8-H), 6.70 (1H, d, J=2.0 Hz, 6-H or 8-H), 6.87 (1H, br, s, NH); m/z 317 ($M^+$), 198 (100%, M-$CO_2H$, $CO_2Et$ and H); Found: C, 49.12; H, 4.18; N, 4.27. $C_{13}H_{13}Cl_2NO_4$ requires C, 49.08; H, 4.22; N. 4.40%.

EXAMPLE 14

2-Carboxy-5,7-dichloro-4-(3,5-dichloroanilino)-4-ethoxycarbonyl-1,2,3,4-tetrahydroquinoline 5,7-Dichloro-4-(3,5-dichloroanilino)-2,4-diethoxycarbonyl-1,2,3,4-tetrahydroquinoline (0.22 g) was dissolved in aqueous methanol (10 ml), sodium hydroxide (0.087 g, 5 molar equivalents) was added and the reaction mixture was stirred for 14 h at room temperature. The solution was concentrated in vacuo, then diluted with water (30 ml) and washed with diethyl ether. The aqueous layer was acidified to pH 1 with concentrated hydrochloric acid and extracted with diethyl ether (2×30 ml). The combined organic layers were dried ($Na_2SO_4$), filtered and evaporated to give a residue which was triturated with diethyl ether/hexane and collected by filtration to give 2-carboxy-5,7-dichloro-4-(3,5-dichloro-anilino)-4-ethoxycarbonyl-1,2,3,4-tetrahydroquinoline as a colourless solid (0.15 g, m.p. 92°–94° C.); δ (360 MHz, $CDCl_3$) 1.28 (3H, t, J=7.1 Hz, $CH_3CH_2$), 2.37 (1H, dd, J=14.3 and 3.1 Hz, $CH_AH_BCH_C$), 2.72 (1H, dd, J=14.3 and 11.9 Hz, $CH_ACH_BCH_C$), 4.33 (2H, dq, J=7.1 and 2.1 Hz, $CH_3CH_2$), 4.41 (1H, dd, J=11.9 and 3.0 Hz, $CH_ACH_BCH_C$), 6.28 (2H, d, J=1.7 Hz, ortho aniline protons), 6.61 (1H, t, J=1.7 Hz, para aniline proton), 6.66 (1H, d, J=2.1 Hz, 6-H or 8-H), 6.69 (1H, d, J=2.1 Hz, 6-H or 8-H).

EXAMPLE 15

Cis-2-carboxy-5,7-dichloro-4-methoxycarbonyl-1,2,3,4-tetrahydroquinoline a) 5,7-Dichloro-2,4-dimethoxycarbonylquinoline 3,5-Dichloroaniline (75.35 g) and dimethyl gluataconate (100 g, 1.25 meq) were dissolved in dichloromethane (800 ml) and stirred at room temperature for 36 h after which time boron trifluoride etherate (100 ml) was added and the reaction mixture was stirred for a further 48 h. The reaction was quenched with saturated sodium hydrogen carbonate solution (100 ml) and the organic layer was separated, washed with brine (2×200 ml), dried (MgSO$_4$), filtered and concentrated in vacuo. The residue was purified by chromatography on silica gel, with 15% ethyl acetate in hexane as eluent, and recrystallisation from methanol gave as a colourless solid 5,7-dichloro-2,4-dimethoxycarbonylquinoline (28 g, m.p. 116°–118° C.); δ (360 MHz, CDCl$_3$) 4.04 (3H, s, CH$_3$), 4.10 (3H, s, CH$_3$), 7.77 (1H, d, J=2.2 Hz, 6-H or 8-H), 8.19 (1H, s, 3-H), 8.31 (1H, d, J=2.2 Hz, 6-H or 8-H); m/e 313 (M$^+$), 255 (100%, M+1-CO$_2$CH$_3$); Found: C, 49.43; H, 2.91; N, 4.42. C$_{13}$H$_9$NO$_4$Cl$_2$ requires C, 49.71; H, 2.89; N, 4.46%.

b) 2-Carboxy-5,7-dichloro-4-methoxycarbonylquinoline 5,7-Dichloro-2,4-dimethoxyquinoline (5 g) was dissolved in 50% aqueous methanol and sodium hydroxide (0.7 g, 1.1 molar equivalents) was added. After stirring at room temperature for 24 h the reaction mixture was evaporated under vacuum and the residue dissolved in water (5000 ml). The aqueous was washed with diethyl ether (250 ml) then acidified to pH 1 with concentrated hydrochloric acid and extracted with dichloromethane (3×200 ml). The combined dichloromethane layers were dried (Na$_2$SO$_4$), filtered, and concentrated in vacuo to give the title compound as a yellow solid (4.8 g, m.p. 169°–171° C.); δ (360 MHz, CDCl$_3$), 4.05 (3H, s, CH$_3$), 7.82 (1H, d, J=2.0 Hz, 6-H or 8-H), 8.20 (1H, d, J=2.0 Hz, 6-H or 8-H), 8.28 (1H, s, 3-H); m/e 299 (M$^+$) 264 (100%, M-Cl); Found: C, 46.92; H, 2.57; N, 4.59. C$_{12}$H$_7$Cl$_2$NO$_4$.0.4H$_2$O requires C, 46.90; H, 2.56; N, 4.56%.

c) Cis-2-carboxy-5,7-dichloro-4-methoxycarbonyl-1,2,3,4-tetrahydroquinoline

2-Carboxy-5,7-dichloro-4-methoxycarbonylquinoline (4.8 g) was dissolved in methanol (300 ml) and platinum oxide (0.48 g) was suspended in the solution. Rapid stirring under one atmosphere of hydrogen at room temperature for 75 minutes, followed by filtration and evaporation gave a crude product which was purified by chromatography on silica gel with 2.5% methanol, 0.5% acetic acid and 97% dichloromethane as eluent to give the title compound as a colourless solid (1.3 g, m.p. 154°–156° C.); δ (360 MHz, DMSO) 2.23 (1H, ddd, J=13.9, 7.1 and 5.3 Hz, $CH_ACH_BH_CCH_D$), 2.66 (1H, dt, J=13.9 and 4.0 Hz, $CH_ACH_BH_CCH_D$), 3.57 (3H, s, CH$_3$), 3.86 (1H, dd, J=7.1 and 4.0 Hz, $CH_ACH_BH_CCH_D$), 3.91 (1H, broad multiplet, $CH_ACH_BH_CCH_D$), 5.74 (1H, broad s, NH), 6.56 (1H, d, J=1.9 Hz, 6-H or 8-H), 6.58 (1H, d, J=1.9 Hz, 6-H or 8-H); m/e 303 (M$^+$) 198 (100%, M-H, CO$_2$H and CO$_2$Me); Found: C, 47.62; H, 3.60; N, 4.66. C$_{12}$H$_{11}$Cl$_2$NO$_4$ requires C, 47.39; H, 3.65; N, 4.61%.

Also isolated as a major by-product was the corresponding dimethyl ester (2.4 g, m.p. 152°–153° C.); δ (360 MHz, DMSO) 2.28 (1H, ddd, J=14.0, 7.1 and 5.4 Hz, $CH_ACH_BH_CCH_D$), 2.80 (1H, dt, J=14.0 and 3.5 Hz, $CH_ACH_BH_CCH_D$), 3.64 (3H, s, CH$_3$), 3.67 (3H, s, CH$_3$), 3.94 (1H, dd, J=7.0 and 3.1 Hz, $CH_ACH_BH_CCH_D$), 4.06 (1H, dd, J=5.4 and 3.6 Hz, $CH_ACH_BH_CCH_D$), 6.63 (1H, d, J=1.8 Hz, 6-H or 8-H), 6.67 (1H, d, J=1.8 Hz, 6-H or 8H); m/e 317 (M$^+$), 198 (100%, M-H, CO$_2$Me, CO$_2$Me); Found: C, 49.05; H, 4.13; N, 4.41. C$_{13}$H$_{13}$Cl$_2$NO$_4$ requires C, 49.08; H, 4.12; N, 4.40%.

EXAMPLE 16

Trans-2-carboxy-5,7-dichloro-4-methoxycarbonyl-1,2,3,4-tetrahydroquinoline a) Trans-5,7-dichloro-2,4-dimethoxycarbonyl-1,2,3,4-tetrahydroquinoline 5,7-Dichloro-2,4-dimethoxycarbonyquinoline (2 g) was dissolved in glacial acetic acid (15 ml) and sodium cyanoborohydride (2.4 g, 6 molar equivalents) was added in portions over a period of 15 minutes. The reaction mixture was heated at 50° C. for 1 h then stirred at room temperature for 14 h. The solution was diluted with dichloromethane (30 ml) and ice-cold 50% sodium hydroxide solution was added until a pH of 14 was attained. The two-phase mixture was stirred vigorously for 2 h then more dichloromethane (50 ml) was added and the two layers were separated. The aqueous layer was extracted with dichloromethane (3×100 ml) and the combined organic layers were washed with brine, dried, (Na$_2$SO$_4$), filtered and concentrated in vacuo. The residue was purified by chromatography on silicas gel using first 70% dichloromethane in hexane then 100% dichloromethane as eluents to give the less polar isomer, trans-5,7-dichloro-2,4-dimethoxycarbonyl-1,2,3,4-tetrahydroquinoline, as a colourless solid (1.3 g, m.p. 113°–114° C.); δ (360 MHz, CDCl$_3$) 1.88 (1H, ddd, J=13.4, 12.2 and 5.9 Hz, $CH_ACH_BH_CCH_D$), 2.67 (1H, dt, J=13.4 and 2.6 Hz, $CH_ACH_BH_CCH_D$), 3.74 (3H, s, CH$_3$), 3.82 (3H, s, CH$_3$), 4.04 (1H, dd, J=12.2 and 3.2 Hz, $CH_ACH_BH_CCH_D$), 4.06 (1H, m, $CH_ACH_BH_CCH_D$), 4.74 (1H, broad s, NH), 6.56 (1H, d, J=2.0 Hz, 6-H or 8-H), 6.73 (1H, d, J=2.0 Hz, 6-H or 8-H); m/e 317 (M$^+$) 198 (100%, M-H, CO$_2$Me, CO$_2$Me); Found: C, 49.13; H, 4.17; N, 4.35. C$_{13}$H$_{13}$Cl$_2$NO$_4$ requires C, 49.08; H, 4.12; N, 4.40%. Also isolated was the cis diester (0.64 g) which was identical with the by-product isolated in Example 15c.

b) Trans-2-carboxy-5,7-dichloro-4-methoxy-carbonyl-1,2,3,4-tetrahydroquinoline

Trans-5,7-dichloro-2,4-dimethoxycarbonyl-1,2,3,4-tetrahydroquinoline (1.13 g) was dissolved in 50% aqueous methanol (80 ml) and sodium hydroxide (0.16 g 1.1 molar equivalents) was added. The solution was stirred at room temperature for 4 h then concentrated in vacuo and redissolved in water (40 ml). The aqueous solution was washed with diethyl ether (2×20 ml) then acidified to pH 1 with 1N hydrochloric acid and extracted into diethyl ether (2×50 ml), dried (Na$_2$SO$_4$), filtered and the solvent evaporated to give an oil. This was purified by chromatography on silica gel with 2.5% methanol, 0.5% acetic acid and 97% dichloromethane as eluent to give, as a colourless solid, trans-2-carboxy-5,7-dichloro-4-methoxycarbonyl-1,2,3,4-tetrahydroquinoline (0.85 g, m.p. 160° C. dec); δ (360 MHz, DMSO), 1.91 (1H, ddd, J=13.4, 11.7 and 6.0 Hz, $CH_ACH_BH_CCH_D$), 2.41 (1H, dm, J=13.4 Hz, $CH_ACH_BH_CCH_D$), 3.65 (3H, s, $CH_3$), 3.79 (1H, dd, J=11.7 and 3.2 Hz, $CH_ACH_BH_CCH_D$), 3.96 (1H, dd, J=6.0 and 2.5 Hz, $CH_ACH_BH_CCH_D$), 6.66 (1H, d, J=2.1 Hz. 6-H or 8-H), 6.83 (1H, d, J=2.1 Hz, 6-H or 8-H); m/e 303 (M+) 198 (M-H, $CO_2H$, $CO_2Me$); Found: C, 47.31; H, 3.70; N. 4.57. $C_{12}H_{11}Cl_2NO_4$ requires C, 47.39; H, 3.65; N, 4.61%.

EXAMPLE 17

Cis-4-benzyloxycarbonyl-2-carboxy-5,7-dichloro-1,2,3,4-tetrahydroquinoline a) Cis-2,4-dicarboxy-5,7-dichloro-1,2,3,4-tetrahydroquinoline Cis-5,7-dichloro-2,4-dimethoxycarbonyl-1,2,3,4-tetrahydroquinoline (0.55 g) (obtained as a by-product described in Examples 15c and 16a) was dissolved in 50% aqueous methanol (60 ml) with sodium hydroxide (1 g) and heated at reflux for 14 h. The solvents were evaporated in vacuo and the residue was redissolved in water (50 ml) and washed with diethyl ether (1×30 ml). The aqueous layer was acidified to pH 1 with 1N hydrochloric acid and extracted with diethyl ether (3×100 ml). The combined organic layers were dried ($Na_2SO_4$), filtered and concentrated in vacuo to leave a residue which was purified by recrystallisation from diethyl ether/hexane to give, as a white solid, cis-2,4-dicarboxy-5,7-dichloro-1,2,3,4-tetrahydroquinoline (0.37 g, m.p. 225°-227° C.); δ (360 MHz, DMSO) 2.19 (1H, m, $CH_ACH_BH_CCH_D$), 2.55 (1H, dm, J=13.8 Hz, $CH_ACH_BH_CCH_D$), 3.76 (1H, dd, J=7.3 and 3.5 Hz, $CH_ACH_BH_CCH_D$), 3.99 (1H, m, $CH_ACH_BH_CCH_D$), 6.64 (1H, d, J=2.1 Hz, 6-H or 8-H), 6.71 (1H, d, J=2.1 Hz, 6-H or 8-H), 6.71 (1H, d, J=2.1 Hz, 6-H or 8-H), 6.81 (1H, br, d, J=2.6 Hz, NH); m/e 289 (M+), 198 (100%, M-H, $CO_2H$, $CO_2H$); Found: C, 45.54; H, 3.20; N. 4.75. $C_{11}H_9Cl_2NO_4$ requires C, 45.54; H, 3.13; N, 4.83%.

b) Cis-2,4-dibenzyloxycarbonyl-5,7-dichloro-1,2,3,4-tetrahydroquinoline and trans-2,4-dibenzyloxycarbonyl-5,7-dichloro-1,2,3,4-tetrahydroquinoline Cis-2,4-dicarboxy-5,7-dichloro-1,2,3,4-tetrahydroquinoline (0.47 g) was dissolved in dry dimethylformamide (30 ml) with potassium carbonate (1.12 g). After 15 minutes rapid stirring at room temperature benzyl bromide (0.43 ml) was added and the reaction mixture was left to stir at ambient temperature for 14 h. The dimethylformamide was removed under high vacuum on the rotary evaporator and the residue partitioned between water (50 ml) and dichloromethane (2×75 ml). the combined organic layers were dried ($Na_2SO_4$), filtered and concentrated in vacuo to leave an oil which was purified by chromatography on silica gel to give, as colourless solids, the more polar isomer cis-2,4-dibenzyloxycarbonyl-5,7-dichloro-1,2,3,4-tetrahydro-quinoline (0.23 g, m.p. 112°-114° C.) and the less polar isomer trans-2,4-dibenzyloxycarbonyl-5,7-dichloro-1,2,3,4-tetrahydroquinoline (0.35 g, m.p. 150°-152° C.).

Data for cis: δ (360 MHz, CDCl₃) 2.43 (1H, ddd, J=13.9, 7.2 and 5.1 Hz, $CH_ACH_BH_CCH_D$), 2.80 (1H, dt, J=13.9 and 4.4 Hz, $CH_ACH_BH_CCH_D$), 4.01 (1H, dd, J=7.2 and 4.4 Hz, $CH_ACH_BH_CCH_D$), 4.05 (1H, m, $CH_ACH_BH_CCH_D$), 4.64 (1H, br, s, NH), 5.04 (4H, m, $PhCH_2$ ×2), 6.56 (1H, d, J=2.0 Hz, 6-H or 8-H), 6.77 (1H, d, J=2.0 Hz, 6-H or 8-H), 7.31 (10H, m, Ph×2); m/e 469 (M+) (91, 100% $PhCH_2$).

Data for trans: δ (360 MHz, CDCl₃) 1.89 (1H, ddd, J=13.5, 11.2 and 5.0 Hz, $CH_ACH_BH_CCH_D$), 2.68 (1H, dm, J=13.5 Hz, $CH_ACH_BH_CCH_D$), 4.02 1H, dd, J=12.2 and 3.1 Hz, $CH_ACH_BH_CCH_D$), 4.09 (1H, dd, J=5.9 and 2.1 Hz, $CH_ACH_BH_CCH_D$), 4.72 (1H, br, s, NH), 5.16 (2H, s, $PhCH_2$), 5.21 (2H, s, $PhCH_2$), 6.54 (1H, d, J=1.9 Hz, 6-H or 8-H), 6.72 (1H, d, J=1.9 Hz, 6-H or 8-H), 7.35 (10H, m, Ph×2); m/e 469) M+).

c) Cis-4-benzyloxycarbonyl-2-carboxy-1,2,3,4-tetrahydroquinoline

Cis-2,4-dibenzyloxycarbonyl-5,7-dichloro-1,2,3,4-tetrahydroquinoline (0.23 g) was dissolved in 50% aqueous methanol (30 ml) and 1N sodium hydroxide (0.54 ml, 1.1 molar equivalents) was added and the reaction mixture was stirred for 14 h at room temperature. The solvents were removed in vacuo to give a residue which was dissolved in water (30 ml) and washed with diethyl ether (2×30 ml). The aqueous layer was acidified to pH 1 with dilute hydrochloric acid and extracted into diethyl ether (2×30 ml) then dried ($Na_2SO_4$), filtered and concentrated in vacuo to leave a residue which was purified by chromatography on silica gel with 2.5% methanol, 0.5% acetic acid and 97% dichloromethane as eluent. The solid obtained on evaporation was recrystallised from diethyl ether/hexane to give, as a colourless solid, cis-4-benzyloxycarbonyl-2-carboxy-1,2,3,4-tetrahydroquinoline (0.027 g, m.p. 144° C. dec). δ (360 MHz, CDCl₃) 2.35 (1H, m, $CH_ACH_BH_CCH_D$), 2.81 (1H, dm, J=13.9 Hz, $CH_ACH_BH_CCH_D$), 4.03 (2H, m, $CH_ACH_BH_CCH_D$), 5.07 (2H, s, $PhCH_2$), 6.57 (1H, d, J=1.5 Hz, 6-H or 8-H), 6.77 (1H, d, J=1.5 Hz, 6-H or 8-H), 7.32 (5H, m, Ph); m/e 379 (M+), 198 (100%); Found: C, 56.53; H, 4.00; N, 3.65. $C_{18}H_{15}Cl_2NO_4$ requires C, 56.86; H, 3.98; N, 3.68%.

EXAMPLE 18

Trans-4-benzyloxycarbonyl-1-2-carboxy-5,7-dichloro-1,2,3,4-tetrahydroquinoline

Trans-2,4-dibenzyloxycarbonyl-5,7-dichloro-1,2,3,4-tetrahydroquinoline (0.35 g) (Example 17b) was treated under the conditions described in Example 17c to give the title compound (0.045 mg, m.p. 124°-126° C. (diethyl ether/hexane); δ (360 MHz, CDCl₃) 1.95 (1H, m, $CH_ACH_BH_CCH_D$), 2.71 (1H. dm, J=12.6 Hz, $CH_ACH_BH_CCH_D$), 4.08 (1H, dd, J=12.3 and 3.1 Hz, $CH_ACH_BH_CCH_D$), 4.13 (1H, dd, J=5.8 and 2.0 Hz, $CH_ACH_BH_CCH_D$), 5.19 (2H, s, $PhCH_2$), 6.56 (1H, d, J=1.8 Hz, 6-H or 8-H), 6.75 (1H, d, J=1.8 Hz, 6-H or 8-H), 7.33 (5H, m, Ph); m/e (CI+) 380 (M+1), 91 (100%, $PhCH_2$); Found: C, 56.12; H, 4.07; N, 3.56. $C_{18}H_{15}Cl_2NO_4.0.2H_2O$ requires C, 56.33; H, 4.04; N, 3.65%.

EXAMPLE 19

(Cis/trans)-2-carboxy-5,7-dichloro-4-(3-methyl-1,2,4-oxadiazol-5-yl)-1,2,3,4-tetrahydroquinoline Cis-2-carboxy-5,7-dichloro-4-ethoxycarbonyl-1,2,3,4-tetrahydroquinoline (Example 13) (0.317 g, 0.001 mol) was added to a preformed solution of acetamide oxime (0.148, 0.002 mol) and sodium hydride (0.075 g of 80% dispersion in oil, 0.0025 m) in dry THF (30 ml) at room temperature. The reaction mixture was heated at 60° C. for 2 h, cooled and poured into dilute hydrochloric acid (20 ml). The solution was extracted with diethyl ether (3×50 ml), dried ($Na_2SO_4$), filtered and concentrated in vacuo to leave a residue which was purified by chromatography on silica gel with 5% methanol and 1% acetic acid in dichloromethane to give (as a colourless foam) a 1:1 mixture of the title compounds (0.105 g); δ (360 MHz, CDCl$_3$) 2.07-2.91 (2H, m, 2×CH$_A$CH$_B$H$_C$CH$_D$), 2.30 and 2.38 (3H, 2s, 2×CH$_3$), 4.12 (1H, m, 2×CH$_A$CH$_B$H$_C$CH$_D$), 4.68 (1H, dd, J=6.8 and 3.2 Hz, CH$_A$CH$_B$H$_C$CH$_D$), 4.77 (1H, dd, J=5.6 and 2.1 Hz, CH$_A$CH$_B$H$_C$CH$_D$), 6.62 (1H, d, J=1.9 Hz, 6-H or 8-H), 6.65 (1H, d, J=1.9 Hz, 6-H or 8-H), 6.75 (1H, d, J=1.9 Hz, 6-H or 8-H), 6.79 (1H, d, J=1.9 Hz, 6-H or 8-H); m/e (CI$^+$) 328 (M+1) 198 (100%, M-H, CO$_2$H, oxadiazolyl); Found: C, 47.40; H, 3.48; N, 12.66; C$_{13}$H$_{11}$Cl$_2$N$_3$O$_3$ requires C, 47.58; H, 3.38; N, 12.81%.

EXAMPLE 20

Cis-4-aminocarbonyl-2-carboxy-5,7-dichloro-1,2,3,4-tetrahydroquinoline a) 2,4-Dicarboxy-5,7-dichloroquinoline 5,7-Dichloro-2,4-dimethoxycarbonylquinoline (Example 15a) (28 g) was dissolved in 50% aqueous methanol (700ml) with sodium hydroxide (35.8 g) and the solution was heated at reflux for 18 h. After cooling, the methanol was removed by evaporation and the residue was diluted with water to a volume of approximately 700 ml. Concentrated hydrochloric acid was added to the aqueous solution at 90° C. and the white solid produced was filtered while the filtrate was still hot. The solid was dried in a vacuum oven at 100° C. (20 mmHg) for 48 h to give the title compound (19.5 g, m.p. 246° C.); δ (360 MHz, DMSO) 8.09 (1H, s, 3-H), 8.13 (1H, d, J=2.2 Hz, 6-H or 8-H), 8.32 (1H, d, J=2.2 Hz, 6-H or 8H); m/e 354 (M$^+$); Found: C, 43.48; H, 2.45; N, 4.58% C$_{11}$H$_5$Cl$_2$NO$_4$.H$_2$O requires C, 43.45; H, 2.32; N, 4.61% b) 4-Carboxy-5,7-dichloro-2-methoxycarbonylquinoline 2,4-Dicarboxy-5,7-dichloroquinoline was added to methanol (presaturated with dry hydrogen chloride) (500 ml) and the solution left at room temperature for 1 h. After this time the volume of solvent was reduced to approximately 100 ml and the white solid that precipitated was collected by filtration and dried in a vacuum oven at 100° C. (20 mm Hg) for 2 h to give the title compound (18.5 g, m.p. 260°-262° C.); δ (250 MHz, DMSO) 3.98 (3H, s, CH$_3$), 8.11 (1H, s, 3-H), 8.15 (1H, d, J=2.1 Hz, 6-H or 8-H), 8.36 (1H, d, J=2.1 Hz, 6-H or 8-H); m/e 299 (M$^+$) 241 (100%, M-CO$_2$CH$_3$+H); Found: C, 47.58; H, 2.42; N, 4.62. C$_{12}$H$_7$Cl$_2$NO$_4$. 0.2 H$_2$O requires C, 47.46; H, 2.46; N, 4.61%.

c) 4-Chlorocarbonyl-5,7-dichloro-2-methoxycarbonylquinoline

4-Carboxy-5,7-dichloro-4-methoxycarbonylquinoline (15.2 g) was dissolved in thionyl chloride (300 ml) and the solution was heated at 60° C. for 3 h. The solvent was removed in vacuo and the residue dried under high vacuum for 14 h to leave, as a white solid, the title compound (16.5 g) which was pure by nmr; δ (360 MHz, CDCl$_3$) 4.12 (3H, s, CH$_3$), 7.83 (1H, d, J=1.9 Hz, 6-H or 8-H), 8.25 (1H, s, 3-H), 8.35 (1H, d, J=1.9 Hz, 6-H or 8-H); m/e 317 (M$^+$), 282 (100%, M-Cl).

d) Cis-4-aminocarbonyl-5,7-dichloro-2-methoxycarbonyl-1,2,3,4-tetrahydroquinoline and trans-4-aminocarbonyl-5,7-dichloro-2-methoxycarbonyl-1,2,3,4-tetrahydroquinoline 4-Chlorocarbonyl-5,7-dichloro-2-methoxycarbonylquinoline (1.5 g) was dissolved in dry tetrahydrofuran (20 ml) at 0° C. and an ice-cool solution of tetrahydrofuran (150 ml), presaturated with ammonia gas, was added in one portion. After stirring at room temperature for 30 minutes the white solid which precipitated was collected by filtration and dried (1.4 g). A portion of this solid (1 g) was suspended in glacial acetic acid (20 ml) and sodium cyanoborohydride (1.3 g) was added in portions. When the addition was complete the reaction mixture was heated at 50° C. for 2 h, cooled and stirred at room temperature for 14 h. The solution was diluted with dichloromethane (to a volume of 100 ml) and ice cold 50% sodium hydroxide solution added cautiously until a pH of 14 was attained. The organic layer was separated and the aqueous layer was re-extracted with dichloromethane (2×100 ml). The combined organic fractions were washed with brine (1×150 ml), dried (Na$_2$SO$_4$), filtered and concentrated in vacuo to give a residue which was purified by chromatography on silica gel with 2% methanol in dichloromethane as eluent to give, as the less polar isomer, trans-4-aminocarbonyl-5,7-dichloro-2-methoxycarbonyl-1,2,3,4-tetrahydroquinoline (0.15 g, m.p. 217°-229° C. [recrystallised from methanol]); δ (360 MHz, DMSO) 1.83 (1H, m, CH$_A$CH$_B$H$_C$CH$_D$), 2.32 (1H, dm, J=13.2 Hz, CH$_A$CH$_B$H$_C$CH$_D$), 3.72 (3H, s, CH$_3$), 3.78 (1H, dd, J=5.8 and 2.0 Hz, CH$_A$CH$_B$H$_C$CH$_D$), 4.01 (1H, dd, J=12.2 and 2.1 Hz, CH$_A$CH$_B$H$_C$CH$_D$), 6.63 (1H, d, J=2.1 Hz, 6-H or 8-H), 6.66 (1H, br, s, NH), 6.78 (1H, d, J=2.1 Hz, 6-H or 8-H), 7.02 (1H, br, s, NH), 7.51 (1H, br, s, NH); m/e 302 (M$^+$), 198 (100%, M-H, CONH$_2$ and CO$_2$CH$_3$); Found: C, 47.46; H, 3.95; N, 9.18 C$_{12}$H$_{12}$Cl$_2$N$_2$O$_3$ requires C, 47.55; H, 3.99; N, 9.24%; and as the more polar isomer, cis-4-aminocarbonyl-5,7-dichloro-2-methoxycarbonyl-1,2,3,4-tetrahydroquinoline (0.14 g, m.p. 203°-204° C.); δ (360 MHz, DMSO), 2.05 (1H, m, CH$_A$CH$_B$H$_C$CH$_D$), 2.52 (1H, m, CH$_A$CH$_B$H$_C$CH$_D$), 3.54 (3H, s, CH$_3$), 3.71 (1H, dd, J=7.2 and 3.4 Hz, CH$_A$CH$_B$H$_C$CH$_D$), 4.11 (1H, dd, J=5.2 and 3.2 Hz, CH$_A$CH$_B$H$_C$CH$_D$), 6.61 (1H, d, J=2.1 Hz, 6-H or 8-H), 6.70 (1H, d, J=2.1 Hz, 6-H or 8-H), 6.84 (2H, br, s, CONH$_2$), 7.20 (1H, br, s, NH); m/e (CI$^+$) 303 (M+1); Found: C, 47.38; H, 3.98; N, 9.14. C$_{12}$H$_{12}$Cl$_2$N$_2$O$_3$ requires C, 47.55; H, 3.99; N, 9.24%.

e) Cis-4-aminocarbonyl-2-carboxy-5,7-dichloro-1,2,3,4-tetrahydroquinoline

Cis-4-aminocarbonyl-5,7-dichloro-2-methoxycarbonyl-1,2,3,4-tetrahydroquinoline (0.12 g) was dissolved in 50% aqueous methanol (20 ml) and 1N sodium hydroxide solution (0.6 ml) was added. The reaction mixture was stirred at room temperature for 14 h then the solvents were evaporated in vacuo to leave a residue which was redissolved in water (20 ml) and acidified to pH 1 with concentrated hydrochloric acid. The aqueous solution was extracted with ethyl acetate (3×40 ml), dried (Na$_2$SO$_4$), filtered and concentrated under vacuum to give an off white solid which was triturated with diethyl ether and collected by filtration to give the title compound (0.082 g, m.p. 220°-222° C.); δ (360 MHz, DMSO) 2.28 (2H, m, CH$_A$CH$_B$H$_C$CH$_D$), 3.71 (1H, m, CH$_A$CH$_B$H$_C$CH$_D$), 3.89 (1H, m, CH$_A$CH$_B$H$_C$CH$_D$), 6.62 (1H, d, J=2.1 Hz, 6-H or 8-H), 6.64 (1H, br, s, NH), 6.74 (1H, d, J=2.1 Hz, 6-H or 8-H), 6.81 (1H, s, br, NH), 7.26 (1H, s, br, NH); m/e (FAB) 289 (M+1); Found: C, 44.84; H, 3.67; N, 8.95. C$_{11}$H$_{10}$Cl$_2$N$_2$O$_3$.0.4H$_2$O requires C, 44.59; H, 3.67; N, 9.45%.

EXAMPLE 21

Trans-4-aminocarbonyl-2-carboxy-5,7-dichloro-1,2,3,4-tetrahydroquinoline

Trans-4-aminocarbonyl-5,7-dichloro-2-methoxy-carbonyl-1,2,3,4-tetrahydroquinoline (Example 20d) (0.12 g) was subjected to the conditions described in Example 20e to give the title compound (0.104 g, m.p. 168°–170° C., diethyl ether/hexane); δ (360 MHz, DMSO) 1.79 (1H, m, $CH_ACH_BH_CCH_D$), 2.35 (1H, dm, J=13.4 Hz, $CH_ACH_BH_CCH_D$), 3.78 (1H, m, $CH_ACH_BH_CCH_D$), 3.89 (1H, dm, J=11.8 Hz, $CH_ACH_BH_CCH_D$), 6.55 (1H, br, s, NH), 6.61 (1H, d, J=2.0 Hz, 6-H or 8-H), 6.81 (1H, d, J=2.0 Hz, 6-H or 8-H), 7.02 (1H, s, NH), 7.49 (1H, s, NH); m/e (FAB) 289 (M+1); Found: C, 44.83; H, 3.43; N, 9.29. $C_{11}H_{10}Cl_2N_2O_3.0.4H_2O$ requires C, 44.59; H, 3.67; N, 9.45%.

EXAMPLE 22

Cis-2-carboxy-4-methoxycarbonyl-5,7-dimethyl-1,2,3,4-tetrahydroquinoline

This compound was prepared by the route outline in Example 13 using 3,5-dimethylaniline as the starting material (m.p. 173° C., diethyl ether/hexane); δ (360 MHz, DMSO) 1.95 (3H, s, $CH_3$), 2.10 (3H, s, $CH_3$), 2.14 (1H, m, $CH_ACH_BH_CCH_D$), 2.56 (1H, d, J=13.6 Hz, $CH_ACH_BH_CCH_D$), 3.51 (3H, s, $CH_3OCO$), 3.76 (1H, m, $CH_ACH_BH_CCH_D$), 3.87 (1H, dd, $CH_ACH_BH_CCH_D$), 5.93 (1H, br, s, NH), 6.19 (1H, s, 6-H, or 8-H), 6.29 (1H, s, 6-H or 8H); m/e 263 (M+), 158 (100% M-H,$CO_2H$,$CO_2Me$); Found: 263.1147. $C_{14}H_{17}NO_4$ requires 263.1158; Found: C, 63.61; H, 6.69; N, 5.27. $C_{14}H_{17}NO_2.0.1H_2O$ requires C, 63.43; H, 6.54; N, 5.28%.

EXAMPLE 23

Cis-2-carboxy-4-methoxycarbonyl-5,6,7-trichloro-1,2,3,4-tetrahydroquinoline

This compound was prepared by the route outlined in Example 13 using 3,4,5-trichloroaniline as starting material (m.p. 210° C., diethyl ether); δ (360 MHz, DMSO) 2.17 (1H, m, $CH_ACH_BH_CCH_D$), 2.61 (1H, dm, J=14.1 Hz, $CH_ACH_BH_CCH_D$), 3.54 (3H, s, $CH_3$), 3.95 (1H, dd, J=7.0 and 2.7 Hz, $CH_ACH_BH_CCH_D$), 6.94 (1H, s, 8-H), 7.01 (1H, br, s, NH); m/e 337 and 339 (M+) 232 and 234 (100% M-H, $CO_2H$, $CO_2Me$); Found: C, 41.93; H, 3.03; N, 4.02. $C_{12}H_{10}Cl_3NO_4. 0.25H_2O$ requires C, 42.01; H, 3.08; N. 4.08%.

EXAMPLE 24

Cis-2-carboxy-7-chloro-5-iodo-4-methoxycarbonyl-1,2,3,4-tetrahydroquinoline

This compound was prepared by the route outlined in Example 15 using 3-chloro-5-iodoaniline as starting material (m.p. 188° C. dec., dichlormethane/hexane); δ (360 MHz, $CDCl_3$) 2.29 (1H, m, $CH_ACH_BH_CCH_D$), 2.92 (1H, dm, J=14.2 Hz, $CH_ACH_BH_CCH_D$), 3.65 (3H, s, $CH_3$), 3.91 (1H, dd, J=6.4 and 3.4 Hz, $CH_ACH_BH_CCH_D$), 4.10 (1H, dd, J=6.1 and 3.3 Hz, $CH_ACH_BH_CCH_D$), 6.66 (1H, d, J=2.0 Hz, 6-H or 8-H), 7.26 (1H, d, J=2.0 Hz, 6-H or 8-H); m/e 395 (M+), 290 (100%, M-H, $CO_2H$, $CO_2Me$); Found: C, 35.71; H, 2.80; N. 3.40. $C_{12}H_{11}ClINO_4.0.4H_2O$ requires C, 35.78; H, 2.95; N, 3.48%.

EXAMPLE 25

Trans-2-carboxy-7-chloro-5-iodo-4-methoxycarbonyl-1,2,3,4-tetrahydroquinoline

This compound was prepared by the route outlined in Example 15 and 16 using 3-chloro-5-iodoaniline as starting material (colourless foam); δ (360 MHz, $CDCl_3$), 1.95 (1H, ddd, J=14.4, 12.2 and 5.6 Hz, $CH_ACH_BH_CCH_D$), 2.72 (1H, dm, J=14.4 Hz, $CH_ACH_BH_CCH_D$), 3.76 (3H, s, $CH_3$), 3.98 (1H, dd, J=5.6 and 2.1 Hz, $CH_ACH_BH_CCH_D$), 4.09 (1H, dd, J=12.2 and 3.4 Hz, $CH_ACH_BH_CCH_D$), 6.64 (1H, d, J=1.9 Hz, 6-H or 8-H), 7.20 (1H, d, J=1.9 Hz, 6-H and 8-H); m/e 395 (M+), 290 (100%, M-H, $CO_2H$, $CO_2Me$); Found: C, 36.88; H, 3.00; N, 3.38. $C_{12}H_{11}ClINO_4$ requires C, 36.44; H, 2.80; N, 3.54%.

EXAMPLE 26

Cis-2-carboxy-4-methoxycarbonyl-7-chloro-1,2,3,4-tetrahydroquinoline

This compound was prepared by the route outlined in Example 15 using 3-chloroaniline as starting material (m.p. 176°–178° C., diethyl ether/hexane); δ (360 MHz, DMSO) 2.44 (2H, m, $CH_ACH_BH_CCH_D$), 3.62 (3H, s, $CH_3$), 3.87 (1H, dd, J=7.0 and 6.8 Hz, $CH_ACH_BH_CCH_D$), 3.97 (1H, m, $CH_ACH_BH_CCH_D$), 6.34 (1H, br, s, NH), 6.48 (1H, dd, J=8.2 and 2.2 Hz, 6-H), 6.72 (1H, d, J=2.2 Hz, 8-H), 6.85 (1H, d, J=8.2 Hz, 5-H); m/e 269 (M+), 164 (100% M-H, $CO_2H$, $CO_2Me$); Found: 269.0447. $C_{12}H_{12}ClNO_4$ requires 269.0455; Found: C, 53.74; H, 4.59; N, 5.18. $C_{12}H_{12}ClNO_4$ requires C, 53.44; H, 4.49; N, 5.19%.

EXAMPLE 27

Trans-2-carboxy-4-methoxycarbonyl-7-chloro-1,2,3,4-tetrahydroquinoline

This compound was prepared by the route outlined in Examples 15 and 16 using 3-chloroaniline as starting material (m.p. 122°–124° C., diethyl ether): δ (360 MHz, DMSO) 1.88 (1H, m, $CH_ACH_BH_CCH_D$), 2.33 (1H, dm, J=13.5 Hz, $CH_ACH_BH_CCH_D$), 3.65 (3H, s, $CH_3$), 3.75 (1H, t, J=5.0 Hz, $CH_ACH_BH_CCH_D$), 3.99 (1H, dd, J=9.5 and 3.8 Hz, $CH_ACH_BH_CCH_D$), 6.37 (1H, br, s, NH), 6.49 (1H, dd, J=8.2 and 2.2 Hz, 6-H), 6.74 (1H, d, J=2.2 Hz, 8-H), 6.94 (1H, d, J=8.2 Hz, 5-H); m/e 269 (M+), 164 (100% M-H, $CO_2H$, $CO_2Me$); Found: 269.0464. $C_{12}H_{12}ClNO_4$ requires 269.0455; Found: C, 53.37; H, 4.49; N, 5.06. $C_{12}H_{12}ClNO_4$ requires C, 53.44; H, 4.49; N, 5.19%.

EXAMPLE 28

Trans-2-carboxy-4-methoxycarbonyl-5-chloro-1,2,3,4-tetrahydroquinoline

This compound was prepared by the route outlined in Examples 15 and 16 using 3-chloroaniline as starting material (m.p. 159°–161° C, diethyl ether); δ (360 MHz, DMSO) 1.93 (1H, m, $CH_ACH_BH_CCH_D$), 2.39 (1Hm dm, J=13.4 Hz, $CH_ACH_BH_CCH_D$), 3.65 (3H, s, $CH_3$), 3.74 (1H, dd, J=11.6 and 3.1 Hz, $CH_ACH_BH_CCH_D$), 3.96 (1H, dd, J=6.1 and 2.7 Hz, $CH_ACH_BH_CCH_D$), 6.30 (1H, br, s, NH), 6.59 (1H, d, J=7.7 Hz, 6-H or 8-H), 6.72 (1H, d, J=8.2 Hz, 6-H or 8-H), 6.99 (1H, t, J=8.0 Hz, 7-H); m/e 269 (M+), 164 (100% M-H, $CO_2H$, $CO_2Me$); Found: C, 53.30; H, 4.55; N, 5.10. $C_{12}H_{12}ClNO_4$ requires C, 53.44; H, 4.49; N, 5.19%.

EXAMPLE 29

Trans-2-carboxy-4-methoxycarbonyl-5,7-dibromo-1,2,3,4-tetrahydroquinoline

This compound was prepared by the route outlined in Examples 15 and 16 using 3,5-dibromoaniline as starting material (m.p. 175°-176° C., diethyl ether); δ (360 MHz, DMSO) 1.90 (1H, dt, J=13.4 and 5.7 Hz, $CH_ACH_BH_CCH_D$), 2.41 (1H, dm, J=13.4 Hz, $CH_ACH_BH_CCH_D$), 3.66 (3H, s, $CH_3$), 3.76 (1H, dd, J=11.9 and 3.1 Hz, $CH_ACH_BH_CCH_D$), 3.92 (1H, dd, J=4.5 and 1 Hz, $CH_ACH_BH_CCH_D$), 6.65 (1H, br, s, NH), 6.91 (1H, d, J=1.8 Hz, 6-H or 8-H), 7.02 (1H, d, J=1.8 Hz, 6-H or 8-H); m/e 393 (M+), 288 (100% M-H, $CO_2H$, $CO_2Me$); Found: 392.9041 and 394.9028. $C_{12}H_{11}Br_2NO_4$ requires 392.9034 and 394.9014; Found; C, 36.73; H, 2.82; N, 3.55. $C_{12}H_{11}Br_2NO_4$ requires C, 36.67; H, 2.82; N, 3.56%.

EXAMPLE 30

Cis-2-carboxy-4-methoxycarbonyl-5,7-dibromo-1,2,3,4-tetrahydroquinoline

This compound was prepared by the route outlined in Example 15 using 3,5-dibromoaniline as starting material (m.p. 171°-173° C., diethyl ether); δ (360 MHz, DMSO) 2.15 (1H, m, $CH_ACH_BH_CCH_D$), 2.59 (1H, dm, J=13.9 Hz, $CH_ACH_BH_CCH_D$), 3.53 (3H, s, $CH_3$), 3.82 (1H, m, $CH_ACH_BH_CCH_D$), 4.00 (1H, m, $CH_ACH_BH_CCH_D$), 6.89 (3H, br, m, 6-H, 8-H and NH); m/e 393 (M+), 288 (100% M-1, $CO_2H$, $CO_2Me$); Found: 390.9055. $C_{12}H_{11}Br_2NO_4$ requires 390.9055; Found: C, 36.43; H, 2.80; N, 3.55. $C_{12}H_{11}Br_2NO_4$ requires C, 36.67; H, 2.82; N, 3.56%.

EXAMPLE 31

Cis-2-carboxy-4-methoxycarbonyl-5-chloro-1,2,3,4-tetrahydroquinoline

This compound was prepared by the route outlined in Example 15 using 3-chloroaniline as starting material (m.p. 190°-193° C., diethyl ether); δ (360 MHz, DMSO) 2.20 (1H, m, $CH_ACH_BH_CCH_D$), 2.56 (1H, dm, J=13.8 Hz, $CH_ACH_BH_CCH_D$), 3.55 (3H, s, $CH_3$), 3.91 (1H, dd, J=7.1 and 3.3 Hz, $CH_ACH_BH_CCH_D$), 3.98 (1H, m, $CH_ACH_BH_CCH_D$), 6.53 (1H, br, s, NH), 6.58 (1H, d, J=7.8 Hz, 6-H or 8-H), 6.64 (1H, d, J=8.3 Hz, 6-H or 8-H), 6.98 (1H, t, J=8.0 Hz, 7-H); Found: C, 53.41; H, 4.53; N, 5.20. $C_{12}H_{12}ClNO_4$ requires C, 53.44; H, 4.49; N, 5.19%.

EXAMPLE 32

Trans-2-carboxy-5,7-dichloro-4-methylsulphonylamino-1,2,3,4-tetrahydroquinoline a) Trans-5,7-dichloro-2-methoxycarbonyl-4-methylsulphonylamino-1,2,3,4-tetrahydroquinoline To a suspension of trans-4-amino-5,7-dichloro-2-methoxycarbonyl-1,2,3,4-tetrahydroquinoline hydrochloride (0.15 g, 0.482 mmol) in dichloromethane (15 ml) was added triethylamine (0.14 ml, 1.01 mmol) and the mixture was stirred under an atmosphere of nitrogen at room temperature until dissolution was complete. To this solution was added methanesulphonyl chloride (0.039 ml, 0.50 mmol) and the resulting mixture was stirred at room temperature under an atmosphere of nitrogen for 2.5 h. A further portion of methanesulphonyl chloride (0.039 ml, 0.50 mmol) was added and stirring was continued for 2 h after which time more triethylamine (0.07 ml, 0.50 mmol) was added and the mixture was stirred for a further 18 hours. The solvent was removed in vacuo and the residue obtained was partitioned between dilute citric acid solution (50 ml) and ethyl acetate (100 ml). The organic layer was washed with saturated sodium hydrogen carbonate (2×50 ml), brine (1×50 ml), dried ($MgSO_4$) and evaporated to give the title compound as colourless crystals (0.14 g, m.p. 143°-146° C.); δ (250 MHz, $CDCl_3$) 1.69 (1H, m, $CH_ACH_BH_CCH_D$), 2.90 (1H, dm, J=13.6 Hz, $CH_ACH_BH_CCH_D$), 3.17 (3H, s, $-SO_2CH_3$), 3.83 3H, s, $CO_2CH_3$), 4.26 (2H, m, $CH_ACH_BH_CCH_D$) and $CHNHSO_2CH_3$), 4.84 (1H, m, $CH_ACH_BH_CCH_D$), 6.57 (1H, d, J=1.9 Hz, 6-H or 8-H), 6.73 (1H, d, J=1.9 Hz, 6-H or 8-H); m/e 353 (M+), 198 (100% M-$NHSO_2CH_3$, $CO_2CH_3$ and H).

b) Trans-2-Carboxy-5,7-dichloro-4-methylsulphonylamino-1,2,3,4-tetrahydroquinoline To a solution of trans-5,7-dichloro-2-methoxy-carbony-4-methylsulphonylamino-1,2,3,4-tetrahydro-quinoline (0.127 g, 0.36 mmol) in tetrahydrofuran (10 ml) was added water (5 ml) and aqueous lithium hydroxide (0.80 ml of a 0.5 M solution, 0.40 mmol) and the resulting mixture was stirred at room temperature for 1.5 hours. The organic solvent was removed in vacuo and to the aqueous residue was added dilute sodium hydrogen carbonate solution (40 ml). The mixture was washed with ethyl acetate (30 ml), the pH of the aqueous layer was adjusted to 1 with dilute hydrochloric acid and extracted with ethyl acetate (2×40 ml). The combined organic extracts were washed with brine (40 ml), dried ($Na_2SO_4$) and evaporated to give the crude product which was triturated with diethyl ether to give the title compound as colourless crystals (0.08 g, m.p. 194°-195° C.); δ (360 MHz, DMSO) 1.60 (1H, m, $CH_ACH_BH_CCH_D$), 2.47 (1H, m, $CH_ACH_BH_CCH_D$), 3.04 (3H, s, $CH_3$), 4.00 (1H, m, $CH_ACH_BH_CCH_D$), 4.65 (1H, m, $CH_ACH_BH_CCH_D$), 6.64 (1H, d, J=1.9 Hz, 6-H or 8-H), 6.76 (1H, br, s, ArNH), 6.84 (1H, d, J=1.9 Hz, 6-H or 8-H), 7.43 (1H, d, J=5.8 Hz, $CHNHSO_2CH_3$); m/e (FAB) 337 (M-1); Found: C, 39.13; H, 3.60; N, 8.02; $C_{11}H_{12}Cl_2N_2O_4S$ requires C, 38.95; H, 3.57; N, 8.26%.

EXAMPLE 33

Trans-2-carboxy-4-cyclohexylcarbonylamino-5,7-dichloro-1,2,3,4-tetrahydroquinoline a) Trans-4-cyclohexylcarbonylamino-5,7-dichloro-2-methoxycarbonyl-1,2,3,4-tetrahydroquinoline This material was prepared by the same method as described in Example 32a using cyclohexane carboxylic acid to give the title compound (m.p. 280°-282° C. dec); δ (360MHz, DMSOS), 1.11-1.44 (5H, m,5×aliphatic H), 1.54-1.75 (6H, m, $CH_ACH_BH_CCH_D$ and 5×aliphatic H), 2.00-2.14 (2H, m, $CH_ACH_BH_CCH_D$ and 1×aliphatic H), 3.72 (3H, s, $SO_2CH_3$), 3.92 (1H, dd, J=12.4 and 2.6 Hz, $CH_ACH_BH_CCH_D$), 4.98 (1H, m, $CH_ACH_BH_CCH_D$), 6.67 (1H, d, J=1.9 Hz, 6-H or 8-H), 6.85 (2H, m, 6-H or 8-H and ArNH), 8.00 (1H, d, J=7.0 Hz, $SO_2NH$); m/e 384($M^{30}$).

b) Trans-2-carboxy-4-cyclohexylcarbonylamino-5,7-dichloro-1,2,3,4-tetrahydroquinoline This material was prepared using the same method as described in Example 32b to give the title compound ($Et_2O$, m.p. 190°-195° C.); δ 1.05-1.44 (5H, m, 5×aliphatic H), 1.50-1.75 (6H, m, $CH_ACH_BH_CCH_D$ and 5×aliphatic H), 2.02-2.15 (2H, m, $CH_ACH_BH_CCH_D$ and 1×aliphatic H), 3.80 (1H, dd, H=12.6 and 2.9 Hz $CH_ACH_BH_CCH_D$), 4.98 (1H, m, $CH_ACH_BH_CCH_D$), 6.63 (1H, d, J=2.0 Hz, 6-H or 8-H), 6.73 (1H, br, s, ArNH), 6.86 (1H, d, J=2.0 Hz, 6-H or 8-H), 7.98 (1H, d, J=7.2 Hz, SO$_2$NH); m/e (FAB$^+$) 399 (M+1); Found: C, 54.63; H, 5.47; N. 7.27; C$_{17}$H$_{20}$Cl$_2$N$_2$O$_3$. 0.2H$_2$O requires C, 54.47; H, 5.49; N, 7.47%.

EXAMPLE 34

Trans-2-carboxy-5,7-dichloro-4-phenylmethylcarbonylamino-1,2,3,4-tetrahydroquinoline a) Trans-5,7-dichloro-2-methoxycarbonyl-4-phenylmethylcarbonylamino-1,2,3,4-tetrahydroquinoline This material was prepared by the same method as described in Example 32a using phenylacetyl chloride to give the title compound as colourless crystals (m.p. 226°-228° C.); δ (360 MHz, DMSO) 1.65 (1H, ddd, J=12.9, 12.6 and 3.9 Hz, CH$_A$CH$_B$H$_C$CH$_D$), 2.15 (1H, dm, J=12.9 Hz, CH$_A$CH$_B$H$_C$CH$_D$), 3.41 (2H, s, CH$_2$Ph), 3.72 (3H, s, CO$_2$CH$_3$), 3.95 (1H, dd, J=12.6 and 2.8 Hz, CH$_A$CH$_B$H$_C$CH$_D$), 5.00 (1H, m, CH$_A$CH$_B$H$_C$CH$_D$), 6.69 (1H, d, J=2.0 Hz, 6-H or 8-H), 6.87 (1H, d, J=2.0 Hz, 6-H or 8-H), 6.90 (1H, s, ArNH), 7.18-7.30 (5H, m, 5×ArH), 8.45 (1H, d, J=7.1 Hz, CHNHCOPh); m/e (CI$^+$) 393 (M+1).

b) Trans-2-carboxy-5,7-dichloro-4-phenylmethylcarbonylamino-1,2,3,4-tetrahydroquinoline This material was prepared by the same method as described in Example 32b to give the title compound as colourless crystals (m.p. 186°-188° C. dec) δ 1.60 (1H, ddd, J=13.2, 12.5 and 3.8 Hz, CH$_A$CH$_B$H$_C$CH$_D$), 2.16 (1H, dm, J=13.2 Hz, CH$_A$CH$_B$H$_C$CH$_D$), 3.41 (2H, s, CH$_2$Ph), 3.84 (1H, dd, J=12.5 and 2.7 Hz, CH$_A$CH$_B$H$_C$CH$_D$), 5.00 (1H, m, CH$_A$CH$_B$H$_C$CH$_D$), 6.66 (1H, d, J=1.9 Hz, 6-H or 8-H), 6.79 (1H, s, ArNH), 6.88 (1H, d, J=1.9 Hz, 6-H or 8-H), 7.19-7.30 (5H, m, ArH), 8.43 (1H, d, J=7.1 Hz, CHNHCOPh); m/e 378 (M$^+$), 91 (100%, PhCH$_2$$^+$); Found C, 56.98; H, 4.29; N, 7.38; C$_{18}$H$_{16}$Cl$_2$N$_2$O$_3$ requires C, 57.01; H, 4.25; N, 7.39%.

EXAMPLE 35

Trans-2-carboxy-5,7-dichloro-4-(4-pyridyl)carbonyl amino-1,2,3,4-tetrahydroquinoline a) Trans-5,7-dichloro-2-methoxycarbonyl-4(4-pyridyl)carbonyl-amino-1,2,3,4-tetrahydroquinoline To a suspension of trans-4-amino-5,7-dichloro-2-methoxycarbonyl-1,2,3,4-tetrahydroquinoline hydrochloride (example 9a) (0.200 g, 0.642 mmol) and isonicotinoyl chloride hydrochloride (0.124 g, 0.706 mmol) in anhydrous dichloromethane (20 ml) under an atmosphere of nitrogen was added dry triethylamine (0.307 ml, 2.2 mmol) and the resulting mixture was stirred at room temperature for 1 h. The mixture was then evaporated to dryness in vacuo and the residue was partitioned between water (100 ml) and ethyl acetate (250 ml). The organic layer was separated, washed successively with water (3×100 ml), saturated sodium bicarbonate solution (1×100 ml), brine (1×100 ml), dried (MgSO$_4$) and evaporated. The resulting solid was triturated with ethyl acetate and collected by filtration to give the title compound as colourless crystals (0.200 g) mp 200° C. (dec) δ (DMSO, 360 MHz) 1.82 (1H, ddd, J=13.2, 12.6 and 4.1 Hz, CH$_A$CH$_B$H$_C$CH$_D$), 2.27 (1H, dm, J=13.2 Hz, CH$_A$CH$_B$H$_C$CH$_D$), 3.72 (3H, s, CO$_2$CH$_3$), 4.07 (1H, dd, J=12.6 and 2.9 Hz, CH$_A$CH$_B$H$_C$CH$_D$), 5.27 (1H, m, CH$_A$CH$_B$H$_C$CH$_D$NHCO-), 6.70 (1H, d, J=2.0 Hz, 6-H or 8-H), 6.91 (1H, d, J=2.0 Hz, 6-H or 8-H), 6.97 (1H, s, ArNH), 7.77 (2H, dd, J=4.5 and 1.6 Hz, ArH), 8.70 (2H, dd, J=4.5 and 1.6 Hz, ArH), 9.02 (1H, d, J=7.1 Hz, -CH$_D$NHCO-); m/e (CI$^+$) 380 (M+1)$^+$, 123 (100%).

b) Trans-2-carboxy-5,7-dichloro-4(4-pydridyl)carbonylamino-1,2,3,4-tetrahydroquinoline To a suspension of trans-5,7-dichloro-2-methoxycarbonyl-4(4-pyridyl)-carbonylamino-1,2,3,4-tetrahydroquinoline (0.18 g, 0.47 mmol) in a mixture of tetrahydrofuran (15 ml) and water (5 ml) was added aqueous lithium hydroxide (1.04 ml of a 0.50M solution, 0.521 mmol) and the resulting mixture was stirred at room temperature for 3 h. The organic solvent was removed in vacuo then the aqueous residue was diluted with dilute sodium bicarbonate solution (100 ml) and washed with ethyl acetate (2×75 ml). The aqueous layer was then acidified to pH 6 with dilute hydrochloric acid and extracted with ethyl acetate (4×75 ml). The combined extracts were washed with brine (1×100 ml), dried (Na$_2$SO$_4$) and evaporated to give the title compound as colourless crystals (0.116 g), m.p. 270°-275° C. [dec]. δ (DMSO, 360 MHz) 1.76 (1H, ddd, J=13.3, 12.7 and 4.0 Hz, CH$_A$CH$_B$H$_C$CH$_D$), 2.27 (1H, dm, J=13.3 Hz, CH$_A$CH$_B$H$_C$CH$_D$), 3.95 (1H, dd, J=12.7 and 2.7 Hz, CH$_A$CH$_B$H$_C$CH$_D$), 5.26 (1H, m, CH$_A$CH$_B$H$_C$CH$_D$NH-CO-); 6.66 (1H, d, J=1.9 Hz, 6-H or 8-H), 6.84 (1H, s, ArNH), 6.92 (1H, d, J=1.9 Hz, 6-H or 8-H), 7.78 (2H, dd, J=4.4 and 1.6 Hz, ArH), 8.71 (2H, dd, J=4.4 and 1.6 Hz, ArH), 8.99 (1H, d, J=7.1 Hz, CH$_D$NHCO-); m/e (CI$^+$) 366 (M+1)$^+$, 123 (100%); Found C, 52.05; H, 3.64; N, 11.25; C$_{16}$H$_{13}$Cl$_2$N$_3$O$_3$.0.2H$_2$O requires C, 51.97; H, 3.65; N, 11.365%.

EXAMPLE 36

Trans-2-carboxy-5,7-dichloro-4-n-propylcarbonylamino-1,2,3,4-tetrahydroquinoline a) Trans-5,7-dichloro-2-methoxycarbonyl-4-n-propylcarbonylamino-1,2,3,4-tetrahydroquinoline To a suspension of trans-4-amino-5,7-dichloro-2-methoxycarbonyl-1,2,3,4-tetrahydroquinoline hydrochloride (example 9a) (0.200 g, 0.642 mmol) in anhydrous dichloromethane (15 ml) under an atmosphere of nitrogen was added dry triethylamine (0.197 ml, 1.41 mmol) and the mixture was stirred until dissolution was complete. To this solution was then added butyryl chloride (0.073 ml, 0.706 mmol) and the reaction was stirred at room temperature for 4 h. The mixture was then evaporated to dryness in vacuo and the residue was partitioned between ethyl acetate (50 ml) and 0.5M aqueous citric acid (30 ml). The organic layer was separated, washed successively with saturated sodium bicarbonate solution (1×30 ml) and brine (1×30 ml), then dried (MgSO$_4$) and evaporated to give a solid which was triturated with diethyl ether. The solid was collected by filtration to give the pure title compound as colourless crystals (0.187 g), m.p. 205°-206° C. δ (CDCl$_3$, 360 MHz) 0.96 (3H, t, J=7.4 Hz, COCH$_2$CH$_2$CH$_3$). 1.64-1.72 (3H, m, CH$_A$CH$_B$H$_C$CH$_D$ and COCH$_2$CH$_2$CH$_3$), 2.17 (2H, t, J=7.4 Hz, COCH$_2$CH$_2$CH$_3$), 2.68 (1H, dm, J=14.0 Hz, CH$_A$CH$_B$H$_C$CH$_D$), 3.81 (3H, s, CO$_2$CH$_3$), 3.94 (1H, dd, J=12.6 and 2.9 Hz, CH$_A$CH$_B$H$_C$CH$_D$), 4.85 (1H, br.s, ArNH), 5.26 (1H, m, CH$_A$CH$_B$H$_C$CH$_D$NHCO), 5.37 (1H, br.d, J=18 7 Hz, CH$_D$NHCO), 6.56 (1H, d, J=2.0 Hz, 6-H or 8-H), 6.73 (1H, d, J=2.0 Hz, 6-H or 8-H). m/e (CI$^+$) 345 (100%, (M+I)$^+$).

b) Trans-2-carboxy-5,7-dichloro-4-n-propylcarbonylamino-1,2,3,4-tetrahydroquinoline To a solution of trans-5,7-dichloro-2-methoxycarbonyl-4-n-propylcarbonyl-amino-1,2,3,4-tetrahydroquinoline (0.70 g, 0.493 mmol) in a mixture of tetrahydrofuran (15 ml) and water (5 ml) was added aqueous lithium hydroxide (1.1 ml of a 0.50M solution, 0.55 mmol) and the resulting mixture was stirred at room temperature for 20 h. The organic solvent was then removed under vacuum and the aqueous residue was diluted with dilute sodium bicarbonate solution (50 ml) then washed with ethyl acetate (1×30 ml). The aqueous phase was separated, acidified with dilute hydrochloric acid and extracted with ethylacetate (2×50 ml). The combined extracts were washed with brine (1×50 ml), dried ($MgSO_4$) and evaporated to give a solid which was triturated with diethyl ether to give the title compound as colourless crystals (0.123 g) m.p. 174°–176° C. (dec). δ (DMSO, 360 MHz) δ 0.85 (3H, t, J=7.4 Hz, $COCH_2CH_2CH_3$), 1.48–1.64 (3H, m, $CH_ACH_BH_CCH_D$) and $COCH_2CH_2CH_3$), 2.04 (2H, t, J=7.2 Hz, $COCH_2CH_2CH_3$), 2.16 (1H, dm, J=13.1 Hz, $CH_ACH_BH_CCH_D$), 3.82 (1H, dd, J=12.6 and 2.8 Hz, $CH_ACH_BH_CCH_D$), 5.01 (1H, m, $CH_ACH_BH_CCH_DNHCO$) 6.64 (1H, d, J=2.1 Hz, 6-H or 8-H), 6.76 (1H, s, ArNH), 6.87 (1H, d, J=2.1 Hz, 6-H or 8-H), 8.10 (1H, d, J=7.2 Hz, —$CH_DNHCO$—); m/e 330 ($M^+$), 198 (100%, M-$NHCOCH_2CH_2CH_3$, $CO_2H$ and H); Found C, 50.09; H, 4.78; N, 8.41; $C_{14}H_{16}Cl_2N_2O_3.0.2H_2O$ requires C, 50.22; H, 4.94; N, 8.37%.

EXAMPLE 37

Trans-2-carboxy-5,7-dichloro-4-phenylmethylcarbonylamino-1,2,3,4-tetrahydroquinoline a) Trans-5,7-dichloro-2-methoxycarbonyl-4-phenylmethylcarbonylamino-1,2,3,4-tetrahydroquinoline To a suspension of 4-amino-5,7-dichloro-2-methoxycarbonyl-1,2,3,4-tetrahydroquinoline hydrochloride (example 9a) (3.0 g, 9.63 mmol) in anhydrous tetrahydrofuran (300 ml) under an atmosphere of nitrogen was added dry triethylamine (2.95 ml, 21.2 mmol) and the resulting mixture was stirred at room temperature for 0.5 h. To this suspension was added phenlyacetic acid (1.44 g, 10.6 mmol), 1-hydroxybenzotriazole (1.43 g, 10.6 mmol) and 1-(3-dimethylaminopropyl)-3-ethylcarbodiimide hydrochloride (2.03 g, 10.6 mmol) and stirring was continued for 65 h. The reaction mixture was concentrated in vacuo and the residue obtained was partitioned between ethyl acetate (1000 ml) and 1M aqueous citric acid (300 ml). The organic layer was collected, washed successively with 1M aqueous citric acid (1×300 ml), saturated sodium bicarbonate solution (2×300 ml) and brine (200 ml) then dried ($MgSO_4$) and evaporated. The resulting crude product was recrystallised from methanol to give the title compound as colourless needles (2 crops, 3.26 g) identical in physical properties to the material obtained in example 34 step a.

b) Trans-2-carboxy-5,7-dichloro-4-phenylmethylcarbonylamino-1,2,3,4-tetrahydroquinoline To a suspension of trans-5,7-dichloro-2-methoxy-carbonyl-4-phenylmethylcarbonylamino-1,2,3,4-tetrahydroquinoline (3.11 g, 7.89 mmol) in a mixture of tetrahydrofuran (100 ml) and water (50 ml) was added aqueous lithium hydroxide (17.4 ml of a 0.5M solution, 8.70 mmol) and the resulting mixture was stirred at room temperture for 3 h. The organic solvent was removed in vacuo and the aqueous residue was acidified with concentrated hydrochloric acid and extracted with ethyl acetate (2×100 ml). The combined extracts were washed with saturated brine (1×100 ml), dried ($MgSO_4$) and evaporated to give the crude product which was recrystallised from ethyl acetate/petroleum ether 60-80 to give the title compound as colourless crystals (2 crops, 2.65 g) identical in physical properties to example 34 step b.

EXAMPLE 38

Trans-2-carboxy-5,7-dichloro-4-phenylaminocarbonylamino-1,2,3,4-tetrahydroquinoline a) Trans-5,7-dichloro-2-methoxycarbonyl-4-phenylaminocarbonylamino-1,2,3,4-tetrahydroquinoline To a suspension of trans-4-amino-5,7-dichloro-2-methoxycarbonyl-1,2,3,4-tetrahydroquinoline hydrochloride (0.200 g, 0.642 mmol) in anhydrous dichloromethane (20 ml) under an atmosphere of nitrogen was added dry triethylamine (0.098 ml, 0.706 mmol) and the mixture was stirred until dissolution was complete. To this solution was then added phenyl isocyanate (0.077 ml, 0.706 mmol) and the resulting mixture was stirred at room temperature for 2 h. The solvent was removed under vacuum and the residue was partitioned between ethyl acetate (150 ml) and 1M aqueous citric acid (75 ml). The organic layer was successively washed with 1M aqueous citric acid (1×75 ml), saturated sodium bicarbonate solution (2×75 ml) and saturated brine (1×75 ml), then dried ($MgSO_4$) and evaporated. The crude product was recrystallised from methanol to give the title compound as colourless crystals (0.185 g), m.p. 228°–229° C. (dec). δ (DMSO, 360 MHz) 1.67 (1H, ddd, J=12.7, 12.4 and 3.5 Hz, $CH_ACH_BH_CCH_D$), 2.34 (1H, dm, J=12.7 Hz, $CH_ACH_BH_CCH_D$), 3.73 (3H, s, $CO_2CH_3$), 4.00 (1H, dd, J=12.4 and 2.9 Hz, $CH_ACH_BH_CCH_D$), 4.94 (1H, m, $CH_ACH_BH_CCH_DNHCO$), 6.53 (1H, d, J=6.4 Hz, $CH_DNHCONAr$), 6.72 (1H, d, J=2.0 Hz, 6-H or 8-H), 6.88–6.93 (3H, m, 6-H or 8-H, ArH and ArNH), 7.20–7.25 (2H, m, ArH) 7.39 (2H, d, J=8.0 Hz, ArH), 8.15 (1H, s, $CH_DNHCONHAr$); m/e 393 ($M^+$), 198 (100%, M-NHCONHPh, $CO_2CH_3$ and H); Found C, 54.76; H, 4.39; N, 10.48; $C_{18}H_{17}Cl_2N_3O_3$ requires C, 54.84; H, 4.35; N, 10.66%.

b) Trans-2-carboxy-5,7-dichloro-4-phenylaminocarbonylamino-1,2,3,4-tetrahydroquinoline.

To a suspension of trans-5,7-dichloro-2-methoxycarbonyl-4-phenylaminocarbonylamino-1,2,3,4-tetrahydroquinoline (0.185 g, 0.47 mmol) in a mixture of tetrahydrofuran (10 ml) and water (5 ml) was added aqueous lithium hydroxide (1.04 ml of a 0.5M solution, 0.52 mmol) and the resulting mixture was stirred at room temperature for 2 h. The reaction mixture was concentrated in vacuo and the aqueous residue was dissolved in dilute sodium bicarbonate solution (100 ml) then washed with diethyl ether (100 ml). The aqueous phase was separated, acidified with concentrated hydrochloric acid and extracted with ethyl acetate (2×100 ml). The combined extracts were washed with brine (100 ml), dried ($MgSO_4$) and evaporated to give the crude product which was redissolved in methanol and evaporated to give an oil which was crystallised with diethyl ether. The title compound was collected by filtration to give colourless crystals (0.110 g), m.p. 148°–150° C. (starts to decompose above 120° C.). δ (DMSO, 360 MHz) 1.63 (1H, ddd, J=13.2, 12.6 and 3.7 Hz, $CH_ACH_BH_CCH_D$), 2.33 (1H, dm, J=13.2 Hz, $CH_ACH_BH_CCH_D$), 3.89 (1H, dd, J=12.6 and 2.8 Hz, $CH_ACH_BH_CCH_D$), 4.94 (1H, m, CH$_A$CH$_B$H$_C$CH$_D$NHCO), 6.51 (1H, d, J=6.5 Hz, CH$_D$NHCONAr), 6.69 (1H, d, J=2.0 Hz, 6-H or 8-H), 6.79 (1H, s, ArNH), 6.88-6.92 (2H, m, 6-H or 8-H and ArH), 7.20-7.25 (2H, m, ArH), 7.37-7.40 (2H, m, ArH), 8.15 (1H, s, CH$_D$NHCONHAr); m/e (FAB$^+$) 380 (M+1)$^+$.

EXAMPLE 39

Trans-2-carboxy-4(4-chlorophenyl)carbonylamino-5,7-dichloro-1,2,3,4-tetrahydroquinoline This compound was prepared by the same method given for example 36 using 4-chlorobenzoyl chloride in place of butyryl chloride to give the title compound as colourless crystals m.p. 228°-229° C. (dec). δ (DMSO, 360 MHz) 1.75 (1H, ddd, J=13.2, 12.5 and 4.2 Hz, CH$_A$CH$_B$H$_C$CH$_D$), 2.26 (1H, dm, J=13.2 Hz, CH$_A$CH$_B$H$_C$CH$_D$), 3.95 (1H, dd, J=12.5 and 2.5 Hz, CH$_A$CH$_B$H$_C$CH$_D$), 5.25 (1H, m, CH$_A$CH$_B$H$_C$CH$_D$NHCO), 6.66 (1H, d, J=2.0 Hz, 6-H or 8-H), 6.82 (1H, s, ArNH), 6.91 (1H, d, J=2.0 Hz, 6-H or 8-H), 7.51 (2H, d, J=8.6 Hz, ArH), 7.90 (2H, d, J=8.6 Hz, ArH), 8.78 (1H, d, J=6.5 Hz, CH$_D$NHCO); m/e 399 (M+1), 198 (100%, M-NHCOC$_6$H$_4$Cl, CO$_2$H and H); Found C, 51.21; H, 3.38; N, 7.01; C$_{17}$H$_{13}$Cl$_3$N$_2$O$_3$ requires C, 51.09; H, 3.28; N, 7.01%.

EXAMPLE 40

Trans-2-carboxy-5,7-dichloro-4(4-methoxyphenyl)carbonylamino-1,2,3,4-tetrahydroquinoline This compound was prepared by the same method given for example 36 using para-anisoyl chloride in place of butyryl chloride to give the title compound as colourless crystals, m.p. 209°-210° C. (dec). δ (DMSO, 360 MHz), 1.71 (1H, ddd, J=13.2, 12.5 and 4.0 Hz, CH$_A$CH$_B$H$_C$CH$_D$), 2.26 (1H, dm, J=13.2 Hz, CH$_A$CH$_B$H$_C$CH$_D$), 3.79 (3H, s, ArOCH$_3$), 3.95 (1H, dd, J=12.5 and 2.5 Hz, CH$_A$CH$_B$H$_C$CH$_D$), 5.25 (1H, m, CH$_A$CH$_B$H$_C$CH$_D$NHCO), 6.64 (1H, d, J=2.0 Hz, 6-H or 8-H), 6.79 (1H, brs, ArNH), 6.90 (1H, d, J=2.0 Hz, 6-H or 8-H), 6.96 (2H, d, J=8.9 Hz, ArH), 7.86 (2H, d, J=8.9 Hz, ArH), 8.50 (1H, d, J=7.2 Hz, CH$_D$NHCO), m/e 394 (M+), 135 (100%, CH$_3$OC$_6$H$_4$CO); Found C, 54.47; H, 4.16; N, 7.09; C$_{18}$H$_{16}$Cl$_2$N$_2$O$_4$ requires C, 54.70; H, 4.08; N, 7.09%.

EXAMPLE 41

Trans-2-carboxy-5,7-dichloro-4-phenylmethylaminocarbonylamino-1,2,3,4-tetrahydroquinoline This compound was prepared using the same method given for example 38 using benzyl isocyantate in place of phenyl isocyanate to give the title compound as colourless crystals, m.p. 163°-164° C. (dec). δ (DMSO, 360 MHz), 1.57 (1H, ddd, J=12.9, 12.6 and 3.5 Hz, CH$_A$CH$_B$H$_C$CH$_D$), 2.26 (1H, dm, J=12.9 Hz, CH$_A$CH$_B$H$_C$CH$_D$), 3.84 ((1H, dd, J=12.6 and 2.7 Hz, CH$_A$CH$_B$H$_C$CH$_D$), 4.20 (1H, dd, J=15.5 and 5.7 Hz, PhCH$_E$H$_F$NHCO), 4.29 (1H, dd, J=15.5 and 6.2 Hz. PhCH$_E$H$_F$NHCO), 4.89 (1H, m, CH$_A$CH$_B$H$_C$CH$_D$), 6.08 (1H, m, PhCH$_E$H$_F$NHCO), 6.34 (1H, d, J=6.5 Hz, CH$_D$NHCO), 6.66 (1H, d, J=2.0 Hz, 6-H or 8-H), 6.73 (1H, s, ArNH), 6.85 (1H, d, J=2.0 Hz, 6-H or 8-H), 7.19-7.32 (5H, m, ArH); (FAB$^-$) 392 (M-1)$^-$; Found C, 54.77; H, 4.41; N, 10.57; C$_{18}$H$_{17}$Cl$_2$N$_3$O$_3$ requires C, 54.84; H, 4.35; N, 10.66%.

EXAMPLE 42

Trans-2-carboxy-5,7-dichloro-4-(2-methoxyphenyl)methylcarbonylamino-1,2,3,4-tetrahydroquinoline This compound was prepared using the same method given for example 37 using 2-methoxyphenylacetic acid in place of phenylacetic acid to give the title compound as colourless crystals, m.p. 222°-223° C. (dec) δ (DMSO, 360 MHz) 1.61 (1H, ddd, J=13.1, 12.6 and 3.9 Hz, CH$_A$CH$_B$H$_C$CH$_D$), 2.19 (1H, dm, J=13.1 Hz, CH$_A$CH$_B$H$_C$CH$_D$), 3.37 (2H, s, ArCH$_2$CO), 3.73 (3H, s, ArOCH$_3$), 3.89 (1H, dd, J=12.6 and 2.7 Hz, CH$_A$CH$_B$H$_C$CH$_D$), 5.03 (1H, m, CH$_A$CH$_B$H$_C$CH$_D$NHCO), 6.67 (1H, d, J=2.0 Hz, 6-H or 8-H), 6.82-6.94 (4H, m, 2×ArH, ArNH and 6-H or 8-H), 7.16-7.22 (2H, m, 2×ArH), 8.33 (1H, d, J=7.3 Hz, CH$_D$NHCO); m/e (CI$^+$) 409 (M+1)$^+$, 166 (100%); Found C, 55.72; H, 4.51; N, 6.77; C$_{19}$H$_{18}$Cl$_2$N$_2$O$_4$ requires C, 55.70; H, 4.43; N, 6.85%.

EXAMPLE 43

Trans-2-carboxy-5,7-dichloro-4(2-methylphenyl)methylcarbonylamino-1,2,3,4-tetrahydroquinoline This compound was prepared using the same method given for example 37 using ortho-tolyacetic acid in place of phenylacetic acid to give the title compound as colourless crystals, m.p. 214°-215° C. (dec). δ (DMSO, 360 MHz) 1.62 (1H, ddd, J=13.0, 12.7 and 3.7 Hz, CH$_A$CH$_B$H$_C$CH$_D$), 2.18 (1H, dm, J=13.0 Hz, CH$_A$CH$_B$H$_C$CH$_D$), 2.24 (3H, s, ArCH$_3$), 3.44 (2H, s, ArCH$_2$CO), 3.86 (1H, dd, J=12.7 and 2,7 Hz, CH$_A$CH$_B$H$_C$CH$_D$), 5.02 (1H, m, CH$_A$CH$_B$H$_C$CH$_D$NHCO). 6.67 (1H, d, J=2.0 Hz, 6-H or 8-H), 6.85 (1H, s, ArNH), 6.89 (1H, d, J=2.0 Hz, 6-H or 8-H), 7.07-7.20 (4H, m, 4×ArH), 8.46 (1H, d, J=7.1 Hz, CHDNHCO); m/e 392 (M$^+$), 91 (100%, C$_6$H$_4$CH$_3$$^+$); Found C, 57.97; H, 4.74; N, 7.01: C$_{19}$H$_{18}$Cl$_2$N$_2$O$_3$ requires C, 58.03; H, 4.61; N, 7.12%.

EXAMPLE 44

Trans-2-carboxy-5,7-dichloro-4-phenyl(methoxy)methylcarbonylamino-1,2,3,4-tetrahydroquinoline (Isomer A)

Step a): Trans-5,7-dichloro-2-methoxycarbonyl-4-phenyl(methoxy)methylcarbonylamino-1,2,3,4-tetrahydroquinoline (Isomers A and B)

To a suspension of trans-4-amino-5,7-dichloro-2-methoxycarbonyl-1,2,3,4-tetrahydroquinoline hydrochloride (example 9a) (0.400 g, 1.28 mmol) in anhydrous THF (50 ml) was added dry triethylamine (0.393 ml, 2.82 mmol) and the resulting mixture was stirred at room temperature under an atmosphere of nitrogen for 0.25 h. To this suspension was then added (+)-α-methoxyphenylacetic acid (0.234 g, 1.41 mmol), 1-hydroxybenzotriazole (0.191 g, 1.41 mmol) and 1-(3-dimethylaminopropyl)-3-ethylcarbodiimide hydrochloride (0.270 g, 1.41 mmol) and stirring was continued for 4 h. The solvent was then removed under vacuum and the residue was partitioned between ethyl acetate (100 ml) and 1M aqueous citric acid (100 ml). The organic layer was separated and washed successively with 1M aqueous citric acid (1×75 ml), saturated sodium bicarbonate solution (2×75 ml), saturated brine (1×75 ml) then dried (MgSO$_4$) and evaporated to give a solid. The two diastereoisomers were separated by flash chromatography using 30-40% ethyl acetate in petroleum ether (bp 60°-80°) as eluent to give, after recrystallisation from hot ethyl acetate-petroleum (ether bp 60°-80°), the less polar isomer A (0.234 g, m.p. 182°-184° C.) and the more polar isomer B (0.162 g, m.p. 228°-229° C.). Isomer A: $\delta$ (360 MHz, DMSO) 1.64 (1H, ddd, J=13.5, 12.7 and 3.7 Hz, $CH_ACH_BH_CCH_D$), 2.54 (1H, dm, J=13.5 Hz, $CH_ACH_BH_CCH_D$), 3.36 (3H, s, NHCOCH(OCH$_3$)Ph), 3.75 (3H, s, CO$_2$CH$_3$), 3.84 (1H, dd, J=12.7 and 2.9 Hz), 4.66 (1H, s, NHCOCH(OCH$_3$)Ph), 4.86 (1H, s, ArNH), 5.28 (1H, m, $CH_ACH_BH_CCH_D$NhCO), 6.58 (1H, d, J=1.9 Hz, 6-H or 8-H), 6.67 (1H, d, J=6.2 Hz, $CH_D$NHCO), 6.76 (1H, d, J=1.9 Hz, 6-H or 8-H), 7.30-7.40 (5H, m, ArH); m/e (EI) 422 (M+), 198 (100%, M-NHCOCHOCH$_3$)Ph, CO$_2$CH$_3$ and H). Isomer B $\delta$ (360 MHz, CDCl$_3$) 1.73 (1H, ddd, J=14.1, 12.5 and 3.8 Hz, $CH_ACH_BH_CCH_D$), 2.72 (1H, dm, J=14.1 Hz, $CH_ACH_BH_CCH_D$), 3.29 (3H, s, NHCOCH(OCH$_3$)Ph), 3.82 (3H, s, CO$_2$CH$_3$), 4.01 (1H, dd, J=12.5 and 2.4 Hz, $CH_ACH_BH_CCH_D$), 4.64 (1H, s, NHCOCH(OCH$_3$)Ph), 4.89 (1H, s, ArNH), 5.20 (1H, m, $CH_ACH_BH_CCH_D$HCO), 6.58 (1H, d, J=1.9 Hz, 6-H or 8-H), 6.74 (1H, d, J=1.9 Hz, 6-H or 8-H), 6.77 (1H, d, J=6.6 Hz, $CH_D$NHCO), 7.31-7.41 (5H, m, ArH): m/e (CI+) 423 (M+), 147 (100%).

Step b: Trans-2-carboxy-5,7-dichloro-4-phenyl(methoxy)methylcarbonylamino-1,2,3,4-tetrahydroquinoline (Isomer A)

To a solution of trans-5,7-dichloro-2-methoxycarbonyl-4-phenyl(methoxy)methylcarbonylamino-1,2,3,4-tetrahydroquinoline (Isomer A, 0.180 g, 0.426 mmol) in a mixture of tetrahydrofuran (10 ml) and water (5 ml) was added aqueous lithium hydroxide (0.904 ml of a 0.50M solution, 0.47 mmol), and the resulting mixture was stirred at room temperature for 3 h. The solvent was then removed under vacuum and the residue was diluted with sodium bicarbonate solution (50 ml) and washed with diethyl ether (1×30 ml). The aqueous layer was separated, acidified with concentrated hydrochloric acid and extracted with ethyl acetate (2×40 ml). The combined extracts were washed with saturated brine (1×40 ml), dried (MgSO$_4$) and evaporated to give a solid which was recrystallised from hot ethyl acetate/petroleum ether (bp 60°-80°) to give the title compound as colourless crystals (0.102 g), m.p. 232°-233° C. $\delta$ (360 MHz, DMSO) 1.63 (1H, ddd, J=13.2, 12.6 and 4.1 Hz, $CH_ACH_BH_CCH_D$), 2.11 (1H, dd, J=13.2 Hz, $CH_ACH_BH_CCH_D$), 3.27 (3H, s, NHCOCH(OCH$_3$)Ph), 3.90 (1H, dd, J=12.6 and 7.7 Hz, $CH_ACH_BH_CCH_D$), 4.64 (1H, s, NHCOCH(OCH$_3$)Ph), 5.00 (1H, m, $CH_ACH_BH_CCH_D$NHCO), 6.63 (1H, d, J=2.0 Hz, 6-H or 8-H), 6.78 (1H, s, ArNH), 6.88 (1H, d, J=2.0 Hz, 6-H or 8-H), 7.27-7.41 (5H, m, ArH), 8.48 (1H, d, J=7.4 Hz, $CH_D$NHCO); m/e (CI+) 409 (M+H), 166 (100%); Found C, 55.83; H, 4.46; N, 6.81; $C_{19}H_{18}Cl_2N_2O_4$ requires C, 55.76; H, 4.43; N, 6.85%.

EXAMPLE 45

Trans-2-carboxy-5,7-dichloro-4-phenyl(methoxy)methylcarbonylamino-1,2,3,4-tetrahydroquinoline (Isomer B)

To a solution of trans-5,7-dichloro-2-methoxycarbonyl-4-phenyl(methoxy)methylcarbonylamino-1,2,3,4-tetrahydroquinoline (Isomer B) (0.140 g, 0.331 mmol) (Example 44a) in a mixture of tetrahydrofuran (10 ml) and water (5 ml) was added aqueous lithium hydroxide (0.73 ml of a 0.5M solution, 0.364 mmol) and the resulting mixture was stirred at room temperature for 2 h. The organic solvent was removed under vacuum and the residue was diluted with sodium bicarbonate solution (50 ml) then washed with diethyl ether (1×30 ml). The aqueous layer was separated, acidified with concentrated hydrochloric acid and extracted with ethyl acetate (2×40 ml). The combined extracts were washed with saturated bring (1×40 ml), dried (MgSO$_4$) and evaporated to give the crude product which was recrystallised from hot ethyl acetate/petroleum ether (bp 60°-80°) to give the title compound as colourless crystals (0.070 g), m.p. 238°-239° C. $\delta$ (360 MHz, DMSO) 1.63 (1H, ddd, J=13.2, 12.6 and 4.0 Hz, $CH_ACH_BH_CCH_D$), 2.07 (1H, dm, J=13.2 Hz, $CH_ACH_BH_CCH_D$), 3.28 (3H, s, NHCOCH(OCH$_3$)Ph), 3.83 (1H, dd, J=12.6 and 2.6 Hz, $CH_ACH_BH_CCH_D$), 4.67 (1H, s, NHCOCH(OCH$_3$)Ph), 5.04 (1H, m, $CH_ACH_BH_CCH_D$NHCO), 6.66 (1H, d, J=2.0 Hz, 6-H or 8-H), 6.77 (1H, s, ArNH), 6.88 (1H, d, J=2.0 Hz, 6-H or 8-H), 7.26-7.40 (5H, m, ArH), 8.49 (1H, d, J=7.4 Hz, $CH_D$NHCO); m/e(CI+) 409 (M+H), 166 (100%); Found C, 55.77; H, 4.57; N, 6.64; $C_{19}H_{18}Cl_2N_2O_4$ requires C, 55.76; H, 4.43; N, 6.85%.

EXAMPLE 46

Trans-2-carboxy-5,7-dichloro-4-(2-nitrophenyl)methyl carbonylamino-1,2,3,4-tetrahydroquinoline This compound was prepared using the same method given for example 37 using 2-nitrophenylacetic acid in place of phenylacetic acid to give the title compound as colourless crystals, m.p. 220°-221° C. (dec). $\delta$ (DMSO, 360 MHz), 1.60 (1H, ddd, J=13.1, 12.6 and 3 Hz, $CH_ACH_BH_CCH_D$), 2.17 (1H, dm, J=13.1 Hz, $CH_ACH_BH_CCH_D$), 3.84 (2H, s, Ar CH$_2$CO), 3.90 (1H, dd, J=12.6 and 2.7 Hz, $CH_ACH_BH_CCH_D$), 4.99 (1H, m, $CH_ACH_BH_CCH_D$NHCO), 6.66 (1H, d, J=2.0 Hz, 6-H or 8-H), 6.79 (1H, s, ArNH), 6.88 (1H, d, J=2.0 Hz, 6-H or 8-H), 7.50-7.54 (2H, m, ArH), 7.64-7.68 (1H, m, ArH), 7.99 (1H, d, J=8.1 Hz, ArH), 8.45 (1H, d, J=7.2 Hz, $CH_D$NHCO); m/e (CI+) 424 (M+1)+, 198 (100%,M-NHCOCH$_2$C$_6$H$_4$NO$_2$, (CO$_2$H and H); Found C, 50.92; H, 3.68; N, 9.75; $C_{18}H_{15}Cl_2N_3O_5$ requires C, 50.96; H, 3.56; N, 9.91%.

EXAMPLE 47

Trans-2-carboxy-5,7-dichloro-4-(2-nitrophenyl)amino carbonylamino-1,2,3,4-tetrahydroquinoline This compound was prepared using the same method given for example 38 using 2-nitrophenyl isocyanate in place of phenyl isocyanate to give the title compound as yellow crystals, mp 214°-215° C. (dec). $\delta$ (DMSO, 360 MHz) 1.68 (1H, ddd, J=13.1, 12.7 and 3.7 Hz, $CH_ACH_BH_CCH_D$), 2.30 (1H, dm, $CH_ACH_BH_CCH_D$), 3.89 (1H, dd, J=12.7 and 2.8 Hz, $CH_ACH_BH_CCH_D$), 4.98 (1H, m, $CH_ACH_BH_CCH_D$NHCO), 6.69 (1H, d, J=2.0 Hz, 6-H or 8-H), 6.83 (1H, s,ArNH), 6.90 (1H, d, J=2.0 Hz, 6-H or 8-H), 7.10-7.15 (1H, m, ArH), 7.64-7.70 (1H, m, ArH), 8.03 (1H, d, J=7.0 Hz, $CH_D$NHCO), 8.08 (1H, dd, J=8.4 and 1.5 Hz, ArH), 8.52 (1H, m, ArH), 9.38 (1H, s, $CH_D$NHCONHAr); Found C, 48.04; H, 3.37; N, 13.13; $C_{17}H_{14}Cl_2N_4O_5$ requires C, 48.02; H, 3.32; N, 13.18%.

EXAMPLE 48

Trans-2-carboxy-5,7-dichloro-4-(2-methoxyphenyl)amino carbonylamino-1,2,3,4-tetrahydroquinoline This compound was prepared using the same method given for example 38 using 2-methoxyphenyl isocyanate in place of phenylisocyanate to give the title compound as colourless crystals, m.p. 198°-199° C. (dec). δ (360 MHz, DMSO) 1.62 (1H, ddd, J=13.3, 12.7 and 3.5 Hz, CH$_A$CH$_B$H$_C$CH$_D$), 2.32 (1H, dm, J=13.3 Hz, CH$_A$CH$_B$H$_C$CH$_D$), 3.79 (3H, s, ArOCH$_3$), 3.85 (1H, dd, J=12.7 and 2.9 Hz, CH$_A$CH$_B$H$_C$CH$_D$), 4.94 (1H, m, CH$_A$CH$_B$H$_C$CH$_D$NHCO), 6.69 (1H, d, J=2.0 Hz, 6-H or 8-H), 6.79 (1H, s, ArNH), 6.83-6.96 (4H, m, ArH and 6-H or 8-H), 7.20 (1H, d, J=6.5 Hz, CH$_D$NHCON-HAr), 7.83 (1H, s, CH$_D$NHCONHAr), 8.14 (1H, m, ArH); m/e (FAB) 408 (M-1)$^-$; Found C, 52.90; H, 4.27; N, 10.15; C$_{18}$H$_{17}$Cl$_2$N$_3$O$_4$ requires C, 52.70; H, 4.18; N, 10.24%.

EXAMPLE 49

Trans-2-carboxy-5,7-dichloro-4-(2-methylphenyl)aminocarbonylamino-1,2,3,4-tetrahydroquinoline This compound was prepared using the method given for example 38 using ortho-tolyl isocyanate in place of phenyl isocyanate to give the title compound as colourless crystals, m.p. 196°-197° C. (dec). δ (360 MHz, DMSO) 1.63 (1H, ddd, J=13.2, 12.6 and 3.5 Hz, CH$_A$CH$_B$H$_C$CH$_D$), 2.14 (3H, s, ArCH$_3$), 2.34 (1H, dm, J=13.2 Hz, CH$_A$CH$_B$H$_C$CH$_D$), 3.89 (1H, dd, J=12.6 and 2.8 Hz, CH$_A$CH$_B$H$_C$CH$_D$), 4.95 (1H, m, CH$_A$CH$_B$H$_C$CH$_D$NHCO), 6.70 (1H, d, J=2.0 Hz, 6-H or 8-H), 6.82-6.94 (4H, m, ArNH, ArH, 6-H and 8-H), 7.08 (2H, m, ArH), 7.46 (1H, s, CH$_D$NHCONHAr), 7.96 (1H, d, J=7.9 Hz, CH$_D$NHCONHAr); m/e (FAB$^+$) 394 (M+1)$^+$; Found C, 54.83; H, 4.41; N, 10.53; C$_{18}$H$_{17}$Cl$_2$N$_3$O$_3$ requires C, 54.84; H, 4.35; N, 10.66%.

EXAMPLE 50

Trans-2-carboxy-5,7-dichloro-4(2-chlorophenyl)aminocarbonylamino-1,2,3,4-tetrahydroquinoline This compound was prepared using the method given for example 38 using ortho-chlorophenyl isocyanate in place of phenyl isocyanate to give the title compound as colourless crystals, m.p. 203°-204° C. (dec). δ (360 MHz, DMSO) 1.66 (1H, ddd, J=13.2, 12.6 and 3.5 Hz, CH$_A$CH$_B$H$_C$CH$_D$), 2.33 (1H, dm, J=13.2, CH$_A$CH$_B$H$_C$CH$_D$), 3.87 (1H, dd, J=12.6 and 2.8 Hz, CH$_A$CH$_B$H$_C$CH$_D$), 4.96 (1H, m, CH$_A$CH$_B$H$_C$CH$_D$NHCONH), 6.70 (1H, d,J=2.0 Hz, 6-H or 8-H), 6.83 (1H, s, ArNH), 6.90 (1H, d, J=2.0 Hz, 6-H or 8-H), 6.93-6.97 (2H, m, ArH), 7.23-7.28 (1H, m, ArH), 7.38-7.43 (2H, m, ArH and CH$_D$NHCONHAr), 7.88 (1H, s, CH$_D$NHCONHAr), 8.27 (1H, dd, J=8.3 and 1.3 Hz, ArH); m/e (FAB$^-$) 414 (M-H)$^-$[2×$^{35}$Cl+1×$^{37}$Cl]; Found C, 49.16; H, 3.52: N, 9.90; C$_{17}$H$_{14}$Cl$_3$N$_3$O$_3$ requires C, 49.24; H, 3.40; N, 10.13%.

EXAMPLE 51

Trans-2-carboxy-5,7-dichloro-4(4phenyl)phenylcarbonyl amino-1,2,3,4-tetrahydroquinoline This compound was prepared by the method given for example 36 using 4-phenylbenzoyl chloride in the place of butyryl chloride to give the title compound as colourless crystals m.p. 267° C. δ (DMSO, 360 MHz) 1.74 (1H, ddd, J=13.3, 12.9 and 3.8 Hz, CH$_A$CH$_B$H$_C$CH$_D$) 2.30 (1H, dm, J=13.3 Hz, CH$_A$H$_B$H$_C$CH$_D$). 3.97 (1H, dd J=2.6 Hz, 12.6 Hz, CH$_A$CH$_B$H$_C$CH$_D$), 5.29 (1H, m, CH$_A$(-CH$_A$CH$_B$H$_C$CH$_D$), 6.66 (1H, d, J=2.0 Hz, 6-H or 8-H), 6.81 (1H, br s, NH), 6.92 (1H, d, J=2.0 Hz, 6-H or 8-H), 7.40 (1H, t, J=7.3 Hz, Ar-H), 7.49 (2H, dd, J= 7.3 and 8.3 Hz, Ar-H), 7.71 (2H, d, J=7.6 Hz, Ar-H), 7.73 (2H, d, J=7.6 Hz, Ar-H), 7.98 (2H, d, J=8.3 Hz, Ar-H), 8.74 (1H, d, J=7.2 Hz, NHCO); m/e 440 (M$^+$), 198 (100% M-H, CO$_2$H,NHCOC$_6$H$_4$C$_6$H$_5$); Found C, 61.44; H, 4.12; N, 6.24; C$_{23}$H$_{18}$Cl$_2$N$_3$O$_3$.0.4H$_2$O requires C, 61.59; C, 4.23; N.6.25%.

EXAMPLE 52

Trans-2-carboxy-5,7-dichloro-4-isopropylcarbonylamino-1,2,3,4-tetrahydroquinoline This compound was prepared by the method given for example 36 using isobutyryl chloride in place of butyryl chloride to give the title compound as colourless crystals, m.p. 197°-198° C. δ (DMSO, 360 MHz), 0.99 (3H, d, J=5.2 Hz, CH$_3$), 1.01 (3H, d, J=5.2 Hz, CH$_3$), 1.60 (1H, ddd, J=13.3, 12.9 and 3.8 Hz, CH$_A$CH$_B$H$_C$CH$_D$), 2.12 (1H, dm, J=13.3 Hz, CH$_A$CH$_B$H$_C$CH$_D$), 2.35 (1H,2q, J=6.8 Hz, CH (CH$_3$)$_2$), 3.81 (1H, dd, J=12.6 and 2.71 Hz, CH$_A$CH$_B$H$_C$CH$_D$), 4.99 (1H, m, CH$_A$CH$_B$H$_C$CH$_D$), 6.65 (1H, d, J=2.1 Hz, 6-H or 8-H), 6.75 (1H, br s, NH), 6.87 (1H,d,J=2.1 Hz, 6-H or 8-H), 8.02 (1H, br, d, J=7.2 Hz, NHCO), m/e 330 (M$^+$), 198(100%, M-H, CO$_2$H, NHCOCH (CH$_3$)$_2$).

EXAMPLE 53

Trans-2-carboxy-5,7-dichloro-4-(2-chlorophenyl)carbonylamino-1,2,3,4-tetrahydroquinoline This compound was prepared by the method given for example 36 using 2-chlorobenzoyl chloride in place of butyryl chloride to give the title compound as colourless crystals, m.p. 141°-143° C. δ (DMSO, 360 MHz), 1.74 (1H, dt, J=13.2, 12.8 and 3.7 Hz, CH$_A$CH$_B$H$_C$CH$_D$), 2.37 (1H, dm, J=13.2 Hz, CH$_B$CH$_B$H$_C$CH$_D$), 3.97 (1H, dd, J=12.5 and 2.7 Hz, CH$_A$CH$_B$H$_C$CH$_D$), 5.23 (1H, m, CH$_A$CH$_B$H$_C$CH$_D$), 6.66 (1H, d, J=2.0 Hz, 6-H or 8-H), 6.75 (1H, brs, NH), 6.85 (1H, d, J=2.0 Hz, 6-H or 8-H), 7.35-7.47 (4H, m, Ar-H), 8.82 (1H, d, J=7.4 Hz, NHCO); m/e 398 (M$^+$), 198 (100% M-H, CO$_2$H, NHCOC$_6$H$_4$Cl); Found C, 53.18; H, 4.84; N, 6.02; C$_{17}$H$_{13}$Cl$_3$N$_2$O$_3$.C$_4$H$_{10}$O requires C, 53.24; H, 4.89; N, 5.91%.

EXAMPLE 54

Trans-2-carboxy-5,7-dichloro-4-(1-naphthalenyl)carbonyl amino-1,2,3,4-tetrahydroquinoline This compound was prepared by the method given for example 36 using 1-naphthoyl chloride in place of butyryl chloride to give the title compound as colourless crystals, m.p. 263°-264° C. δ (DMSO, 360 MHz) 1.82 (1H, ddd, J=13.1, 12.6 and 4.0 Hz, CH$_A$CH$_B$H$_C$CH$_D$), 2.46 (1H, dm, J=13.1 Hz, CH$_A$CH$_B$H$_C$CH$_D$), 3.97 (1H, dd, J=12.7 Hz and 2.7 Hz, CH$_A$CH$_B$H$_C$CH$_D$), 5,38 (1H, m, CH$_A$CH$_B$H$_C$CH$_D$), 6.68 (1H, d, J=2.0 Hz, 6-H or 8-H), 6.77 (1H, br s, NH), 6.87 (1H, d, J=2.0 Hz, 6-H or 8-H), 7.50-7.59 (4H, m, 5,6,7,8-naphthoyl), 7.97 (2H, m, 3,4-naphthoyl), 8.26 (1H, d, J=7.3 Hz, 2-naphthoyl), 8.90 (1H, d, J=7.4 Hz, NHCO); m/e 414 (M$^+$), 172 (100%). Found C, 60.21; H, 4.11; N, 6.56; C$_{21}$H$_{16}$Cl$_2$N$_2$O$_3$.0.2-H$_2$O requires C, 60.22; H, 3.95; N, 6.69%.

EXAMPLE 55

Trans-2-carboxy-5,7-dichloro-4-(2-naphthalenyl)carbonylamino-1,2,3,4-tetrahydroquinoline This compound was prepared by the method given for Example 36 using 2-naphthoyl chloride in place of butyryl chloride to give the title compound as colourless crystals, m.p. 193°–194° C. $\delta$ (360 MHz, DMSO) 1.76 (1H, ddd, J=13.2, 12.8 and 3.7 Hz, $CH_ACH_BH_CCH_D$), 2.33 (1H, dm, J=13.2 Hz, $CH_ACH_BH_CCH_D$), 4.01 (1H, dd, J=12.6 Hz and 2.6 Hz, $CH_ACH_BH_CCH_D$), 5.33 (1H, m, $CH_ACH_BH_CCH_D$), 6.67 (1H, d, J=2.0 Hz, 6-H or 8-H), 6.83 (1H, br s, NH), 6.93 (1H, d, J=2.0 Hz, 6-H or 8-H), 7.58 (2H, m, 3,4-naphthoyl), 7.97 (4H, m, 5,6,7,8-naphthoyl), 8.49 (1H, s, 1-naphthoyl), 8.84 (1H, d, J=7.1 Hz, NHCO); m/e 414 (M+) 198 (100% M-H, $CO_2H$, $NHCOC_{10}H_7$) Found C, 60.82; H, 4.35; N, 6.45; $C_{21}H_{16}Cl_2N_2O_3.0.3C_4H_{10}O$ requires C, 60.95; H, 4.38; N, 6.40%.

EXAMPLE 56

Trans-2-carboxy-5,7-dichloro-4-(2-furanylcarbonyl)amino-1,2,3,4-tetrahydroquinoline This compound was prepared by the method given for Example 36 using 2-furoyl chloride in place of butyryl chloride to give the title compound as colourless crystals, m.p. 219°–220° C. $\delta$ (360 MHz, DMSO) 1.72 (1H, ddd, J=13.2, 12.7 and 4.0 Hz, $CH_ACH_BH_CCH_D$), 2.22 (1H, dm, J=13.2 Hz, $CH_ACH_BH_CCH_D$), 3.94 (1H, dd, J=12.3 and 2.2 Hz, $CH_ACH_BH_CCH_D$), 5.21 (1H, m, $CH_ACH_BH_CCH_D$), 6.59 (1H, dd, J=1.5 Hz, 4-furoyl), 6.65 (1H, d, J=2.0 Hz, 6-H or 8-H), 6.79 (1H, br s, NH), 6.90 (1H, d, J=2.0 Hz, 6-H or 8-H), 7.17 (1H, d, J=3.1 Hz, 3-furoyl), 7.79 (1H, d, J=1.5 Hz, 5-furoyl), 8.62 (1H, br d, J=7.2 Hz, NHCO); m/e 355 (M+), 198 (100% M-H, $CO_2H$, $NHCOC_4H_3O$); Found C, 52.85; H, 4.99; N, 6.63; $C_{15}H_{12}Cl_2N_2O_3.0.85\ C_4H_{10}O$ requires C, 52.98: H, 4.98; N, 6.70%.

EXAMPLE 57

Trans-2-carboxy-5,7-dichloro-4-(2-methylphenyl)carbonyl amino-1,2,3,4-tetrahydroquinoline This compound was prepared by the method given for Example 36 using 2-methylbenzoyl chloride in place of butyryl chloride to give the title compound as colourless crystals, m.p. 153°–156° C. $\delta$ (360 MHz, DMSO) 1.74 (1H, ddd, J=13.7, 13.2 and 3.9 Hz, $CH_ACH_BH_CCH_D$), 2.30 (1H, dm, J=13.2 Hz, $CH_ACH_BH_CCH_D$), 2.35 (3H, s, $CH_3$), 3.93 (1H, dd, J=12.6 and 2.7 Hz, $CH_ACH_BH_CCH_D$), 5.23 (1H, m, $CH_ACH_BH_CCH_D$), 6.66 (1H, d, J=2.0 Hz, 6-H or 8-H), 6.74 (1H, br, s, NH), 6.86 (1H, d, J=2.1 Hz, 6-H or 8-H), 7.16–7.31 (4H, m, Ar-H), 8.60 (1H, br d, J=7.2 Hz, NHCO); m/e 378 (M+), 91 (100%, $C_6H_4CH_3^+$); Found C, 56.34; H, 4.30; N, 7.24; $C_{18}H_{16}Cl_2N_2O_3.0.2H_2O$ requires C, 56.47; H, 4.32; N, 7.32%.

EXAMPLE 58

Trans-2-carboxy-5,7-dichloro-4-(phenethylcarbonyl)amino-1,2,3,4-tetrahydroquinoline This compound was prepared by the method given for Example 36 using dihydrocinnamoyl chloride in place of butyryl chloride to give the title compound as colourless crystals, m.p. 188° C. $\delta$ (360 MHz, DMSO) 1.59 (1H, ddd, J=13.2, 13.0 and 3.7 Hz, $CH_ACH_BH_CCH_D$), 2.16 (1H, dm, J=13.2 Hz, $CH_ACH_BH_CCH_D$), 2.37 (2H, t, J=7.6 Hz, $CH_{2E}CH_{2F}$), 2.83 (2H, t, J=7.6 Hz, $CH_{2E}CH_{2F}$), 3.79 (1H, dd, J=12.6 Hz and 2.7 Hz, $CH_ACH_BH_CCH_D$), 5.02 (1H, m, $CH_ACH_BH_CCH_D$), 6.63 (1H, d, J=2.0 Hz, 6-H or 8-H), 6.75 (1H, br s, NH), 6.86 (1H, d, J=2.0 Hz, 6-H or 8-H), 7.13–7.26 (5H, m, Ar-H), 8.16 (1H, br d, J=7.1 Hz, NHCO); m/e 392 (M+), 198 (100%, M-H), $CO_2H$. $NHCOCH_2CH_2C_6H_5$); Found C, 57.72; H, 4.64; N, 7.10; $C_{19}H_{18}Cl_2N_2O_3.0.1H_2O$ requires C, 57.76; H, 4.64; N, 7.09%.

EXAMPLE 59

Trans-2-carboxy-5,7-dichloro-4-(phenethenyl carbonyl)amino-1,2,3,4-tetrahydroquinoline This compound was prepared by the method given for Example 36 using cinnamoyl chloride in place of butyryl chloride to give the title compound as colourless crystals, m.p. 214°–216° C. $\delta$ (360 MHz, DMSO) 1.69 (1H, ddd, J=13.1, 12.9 and 3.6 Hz, $CH_ACH_BH_CCH_D$), 2.25 (1H, dm, J=13.1 Hz, $CH_ACH_BH_CCH_D$), 3.87 (1H, dd, J=12.7 Hz and 2.7 Hz, $CH_ACH_BH_CCH_D$), 5.16 (1H, m, $CH_ACH_BH_CCH_D$), 6.61 (1H, d, J=15.8 Hz, CH=CHPh), 6.68 (1H, d, J=2.0 Hz, 6-H or 8-H), 6.83 (1H, br s, NH), 6.91 (1H, d, J=2.0 Hz, 6-H or 8-H), 7.36–7.55 (6H, m, Ar-H and CH=CHPh), 8.46 (1H, br d, J=7.2 Hz, NHCO); m/e 390 (M+), 198 (100% M-H, $CO_2H$, NHCOCH=CH$C_6H_5$); Found C, 57.82; H, 4.26; N, 7.00; $C_{19}H_{16}Cl_2N_2O_3.0.2H_2O$ requires C, 57.82; H, 4.19; N, 7.09%.

EXAMPLE 60

Trans-2-carboxy-5,7-dichloro-4-(2-thiophenylmethyl carbonyl)amino-1,2,3,4-tetrahydroquinoline This compound was prepared by the method given for Example 36 using thiophene-2-acetyl chloride in place of butyryl chloride to give the title compound as colourless crystals, m.p. 166°–169° C. $\delta$ (360 MHz, DMSO) 1.61 (1H, ddd, J=13.3, 13.0 and 3.71 Hz, $CH_ACH_BH_CCH_D$), 2.17 (1H, dm, J=13.3 Hz, $CH_ACH_BH_CCH_D$), 3.63 (2H, s, $COCH_2$-thiophene), 3.82 (1H, dd, J=12.6 Hz and 2.7 Hz, $CH_ACH_BH_CCH_D$), 5.01 (1H, m, $CH_ACH_BH_CCH_D$), 6.65 (1H, d, J=2.0 Hz, 6-H or 8-H), 6.79 (1H, br, s, NH), 6.88–6.94 (3H, m, 3,4-thiophene and 6-H or 8-H), 7.34 (1H, dd, J=5.0 Hz, 1.2 Hz, 5-thiophene), 8.46 (1H, d, J=7.1 Hz, NHCO); m/e 384 (M+), 97 (100%, $CH_2C_4H_3S^+$); Found C, 49.52; H, 3.69; N, 7.24; $C_{16}H_{14}Cl_2N_2O_3S.0.15H_2O$ requires C, 49.53; H, 3.72; N, 7.22%.

EXAMPLE 61

Trans-2-carboxy-5,7-dichloro-4-(3-chlorophenyl)carbonyl amino-1,2,3,4-tetrahydroquinoline This compound was prepared by the method given for Example 36 using 3-chlorobenzoyl chloride in place of butyryl chloride to give the title compound as colourless crystals, m.p. 262°–263° C. $\delta$ (360 MHz, DMSO) 1.74 (1H, ddd, J=13.2, 12.9 and 3.9 Hz, $CH_ACH_BH_CCH_D$), 2.24 (1H, dm, J=13.2 Hz, $CH_ACH_BH_CCH_D$), 3.99 (1H, dd, J=12.6 Hz and 2.6 Hz, $CH_ACH_BH_CCH_D$), 5.25 (1H, m, $CH_ACH_BH_CCH_D$), 6.66 (1H, d, J=2.0 Hz, 6-H or 8-H), 6.83 (1H, br s, NH), 6.92 (1H, d, J=2.0 Hz, 6-H or 8-H), 7.48 (1H, t, J=7.8 Hz, Ar-H), 7.59 (1H, dd, 1Hz, 7.8 Hz, Ar-H), 7.85 (1H, dd, J=1 Hz, 7.7 Hz, Ar-H), 7.94 (1H, d, J=1 Hz, Ar-H), 8.82 (1H, d. J=7.1 Hz, NHCO); m/e 398 (M+), 198 (100%, M-H, CO$_2$H, NHCOC$_6$H$_4$Cl); Found C, 51.24; H, 3.54; N, 6.85; C$_{17}$H$_{13}$Cl$_3$N$_2$O$_3$ requires C, 51.09; H, 3.28; N, 7.01%.

EXAMPLE 62

Trans-2-carboxy-5,7-dichloro-4-(3-phenylpropyl)carbonylamino-1,2,3,4-tetrahydroquinoline This compound was prepared by the method given for Example 36 using 4-phenylbutyryl chloride in place of butyryl chloride to give the title compound as colourless crystals, m.p. 189°–191° C. δ (360 MHz, DMSO) 1.61 (1H, ddd, J=13.0, 12.8 and 3.7 Hz, CH$_A$CH$_B$H$_C$CH$_D$), 1.80 (2H, qn, J=~7.5 Hz, COCH$_2$CH$_2$CH$_2$Ph), 2.09 (2H, t, J=7.0 Hz, CH$_2$CH$_2$CH$_2$Ph), 2.17 (1H, dm, J=13.0 Hz, CH$_A$CH$_B$H$_C$CH$_D$), 2.56 (2H, t, J=8.0 Hz, COCH$_2$CH$_2$CH$_2$Ph), 3.83 (1H, dd, J=12.6 and 2.7 Hz, CH$_A$CH$_B$H$_C$CH$_D$), 5.03 (1H, m, CH$_A$CH$_B$H$_C$CH$_D$), 6.65 (1H, d, J=2.0 Hz 6-H or 8-H), 6.76 (1H, br s, NH), 6,87 (1H, d, J=2.0 Hz, 6-H or 8-H), 7.14–7.21 (5H, m, Ar-H), 8.16 (1H, d, J=7.2 Hz, NHCO); m/e 406 (M+), 198 (100%, M-H, CO$_2$H,NHCO(CH$_2$)$_3$Ph); Found C, 57.83; H, 4.95; N, 6.73; C$_{20}$H$_{20}$Cl$_2$N$_2$O$_3$.0.45H$_2$O requires C, 57.83; H, 5.07; N, 6.74%.

EXAMPLE 63

Trans-2-carboxy-5,7-dichloro-4-(9-fluorenyl)carbonylamino-1,2,3,4-tetrahydroquinoline This compound was prepared by the method given for Example 36 using 9-fluorenyl chloride in place of butyryl chloride to give the title compound as colourless crystals, m.p. 266°–268° C. δ (DMSO, 360 MHz) 1.68 (1H, ddd, J=13.3, 12.9 and 3.5 Hz, CH$_A$CH$_B$H$_C$CH$_D$), 2.21 (1H, dm, J=13.3 Hz, CH$_A$CH$_B$H$_C$CH$_D$), 4.05 (1H, dd, J=12.5 and 2.6 Hz, CH$_A$CH$_B$H$_C$CH$_D$), 4.79 (1H, s, NHCOCHAr$_2$) 5.07 (1H, m, CH$_A$CH$_B$H$_C$CH$_D$), 6.75 (1H, d, J=2.0 Hz, 6-H or 8-H), 6.89 (1H, br s, NH) 6.94 (1H, d, J=2.0 Hz, 6-H or 8-H), 7.29–7.47 (6H, m, Ar-H), 7.87 (2H, d, J=7.5 Hz, Ar-H), 8.98 (1H, d, J=7.1 Hz, NHCO); m/e 452 (M+), 243 (100%, M-H, NHCOC$_{13}$H$_9$); Found C, 62.63; H, 4.06; N, 6.03; C$_{24}$H$_{18}$Cl$_2$N$_2$O$_3$.0.4H$_2$O requires C, 62.59; H, 4.11; N, 6.08%.

EXAMPLE 64

Trans-2-carboxy-5,7-dichloro-4-(cyclohexylmethylcarbonyl) amino-1,2,3,4-tetrahydroquinoline This compound was prepared by the method given for Example 36 except using cyclohexyl acetyl chloride in place of butyryl chloride to give the title compound as colourless crystals m.p. 197°–200° C. δ (DMSO, 360 MHz) 0.85–0.92 (2H, m, cyclohexyl), 1.07–1.23 (3H, m, cyclohexyl), 1.56–1.65 (7H, m, cyclohexyl and CH$_A$CH$_B$H$_C$CH$_D$), 1.94 (2H, d, J=6.7 Hz, NHCOCH$_2$), 2.16 (1H, dm, J=13.3 Hz, CH$_A$CH$_B$H$_C$CH$_D$), 3.81 (1H, dd, J=12.6 and 2.6 Hz, CH$_A$CH$_B$H$_C$CH$_D$), 5.01 (1H, m, CH$_A$CH$_B$H$_C$CH$_D$), 6.65 (1H, d, J=2.0 Hz, 6-H or 8-H), 6.76 (1H, br s, NH), 6.86 (1H, d, J=2.0 Hz, 6-H or 8-H), 8.11 (1H, d, J=7.1 Hz, NHCO);m/e 384 (M+), 142 (100%); Found C, 55.11; H, 5.64; N, 7.07; C$_{18}$H$_{22}$Cl$_2$N$_2$O$_3$.0.35H$_2$O requires C, 55.21; H, 5.84; N, 7.15%.

EXAMPLE 65

Trans-2-carboxy-5,7-dichloro-4-(2chlorophenyl)methylcarbonylamino-1,2,3,4-tetrahydroquinoline This compound was prepared by the method given for Example 37 using 2-chlorophenylacetic acid in place of phenylacetic acid to give the title compound as colourless crystals, m.p. 244°–245° C. δ (DMSO, 360 MHz) 1.61 (1H, ddd, J=13.2, 12.9 and 3.7 Hz, CH$_A$CH$_B$H$_C$CH$_D$), 2.23 (1H, dm, J=13.2 Hz, CH$_A$CH$_B$H$_C$CH$_D$), 3.58 (2H, s, COCH$_2$Ar), 3.88 (1H, dd, J=12.6 and 2.7 Hz, CH$_A$CH$_B$H$_C$CH$_D$), 5.04 (1H, m, CH$_A$CH$_B$H$_C$CH$_D$), 6.67 (1H, d, J=2.1 Hz, 6-H or 8-H), 6.79 (1H, br s, NH), 6.88 (1H, d, J=2.1 Hz, 6-H or 8-H), 7.24–7.42 (4H, m, Ar-H), 8.48 (1H, d, J=7.1 Hz, NHCO); m/e 412 (M+), 198 (100%, m-NHCOCH$_2$C$_6$H$_4$Cl,CO$_2$H,H); Found C, 52.00; H, 3.70; N, 6.62; C$_{18}$H$_{15}$Cl$_3$N$_2$O$_3$.0.1H$_2$O requires C, 52.03; H, 3.69; N, 6.74%.

EXAMPLE 66

Trans-2-carboxy-5,7-dichloro-4-(3-chlorophenylmethyl carbonyl)-amino-1,2,3,4-tetrahydroquinoline This compound was prepared by the method given for Example 37 using 3-chlorophenylacetic acid in place of phenylacetic acid to give the title compound as colourless crystals, m.p. 193°–194° C. δ (DMSO, 360 MHz) 1.62 (1H, ddd, J=13.3, 13.1 and 4.0 Hz, CH$_A$CH$_B$H$_C$CH$_D$), 2.16 (1H, dm, J=13.3 Hz, CH$_A$CH$_B$H$_C$CH$_D$), 3.44 (2H, s, COCH$_2$Ar), 3.88 (1H, dd, J=12.6 and 2.7 Hz, CH$_A$CH$_B$H$_C$CH$_D$), 4.99 (1H, m, CH$_A$CH$_B$H$_C$CH$_D$), 6.67 (1H, d, J=2.1 Hz, 6-H or 8-H), 6.80 (1H, br s, NH), 6.89 (1H, d, J=2.1 Hz, 6-H or 8-H), 7.19–7.34 (4H, m, Ar-H), 8.48 (1H, d, J=7.1 Hz, NHCO); m/e 412 (M+),198 (100%, M-H, CO$_2$H,NHCOCH$_2$C$_6$H$_4$Cl); Found C, 51.64; H, 3.69; N, 6.64; C$_{18}$H$_{15}$Cl$_3$N$_2$O$_3$.0.25H$_2$O requires C, 51.70; H, 3.74; N, 6.70%.

EXAMPLE 67

Trans-2-carboxy-5,7-dichloro-4-(4-chlorophenylmethyl carbonyl)amino-1,2,3,4-4-tetrahydroquinoline This compound was prepared by the method given for Example 37 using 4-chlorophenylacetic acid in place of phenylacetic acid to give the title compound as colourless crystals, m.p. 244°–245° C. δ (DMSO, 360 MHz) 1.61 (1H, ddd, J=13.1, 12.6 and 3.7 Hz, CH$_A$CH$_B$H$_C$CH$_D$), 2.14 (1H, dm, J=13.1 Hz, CH$_A$CH$_B$H$_C$CH$_D$), 3.41 (2H, s, COCH$_2$ Ar), 3.82 (1H, dd, J=12.7 and 2.8 Hz, CH$_A$CH$_B$H$_C$CH$_D$), 5.00 (1H, m, CH$_A$CH$_B$H$_C$CH$_D$), 6.66 (1H, d, J=2.0 Hz, 6-H or 8-H), 6.79 (1H, br s, NH), 6.88 (1H, d, J=2.0 Hz, 6-H or 8-H), 7.27 (2H, d, J=8.5 Hz, Ar-H), 7.34 (2H, d, J=8.5 Hz, Ar-H), 8.44 (1H, d, J=7.1 Hz, NHCO); m/e 412 (M+), 198 (100%, M-H,CO$_2$H,NHCOCH$_2$C$_6$H$_4$Cl); Found C, 52.36; H, 3.76; N, 6.69; C$_{18}$H$_{15}$Cl$_3$N$_2$O$_3$ requires C, 52.26; H, 3.65; N, 6.77%.

EXAMPLE 68

Trans-2-carboxy-5,7-dichloro-4-(4-methylphenyl methylcarbonyl)amino-1,2,3,4-tetrahydroquinoline This compound was prepared by the method given for Example 37 using 4-methylphenylacetic acid in place of phenylacetic acid to give the title compound as colourless crystals, m.p. 229°–230° C. δ (DMSO, 360 MHz) 1.60 (1H, ddd, J=13.2, 13.0 and 3.6 Hz, $CH_ACH_BH_CCH_D$), 2.14 (1H, dm, J=13.2 Hz, $CH_ACH_BH_CCH_D$), 2.26 (3H, s, ArCH$_3$), 3.35 (2H, s, COCH$_2$Ar), 3.83 (1H, dd, J=12.6 and 2.7 Hz, $CH_ACH_BH_CCH_D$), 5.00 (1H, m, $CH_ACH_BH_CCH_D$), 6.67 (1H, d, J=2.0 Hz, 6-H or 8-H), 6.83 (1H, br s, NH), 6.88 (1H, d, J=2.0 Hz, 6-H or 8-H), 7.07 (2H, d, J=8.0 Hz, Ar-H), 7.13 (2H, d, J=8.0 Hz, Ar-H), 8.43 (1H, d, J=7.1 Hz, NHCO); m/e 392 (M+), 105 (100%; CH$_2$C$_6$H$_4$CH$_3$+); Found C, 58.07; H, 4.74; N, 7.03; C$_{19}$H$_{18}$Cl$_2$N$_2$O$_3$ requires C, 58.02; H, 4.61; N, 7.12%.

EXAMPLE 69

Trans-2-carboxy-5,7-dichloro-4-(4-methoxyphenyl methyl)carbonylamino-1,2,3,4-tetrahydroquinoline This compound was prepared by the method given for Example 37 using 4-methoxyphenylacetyic acid in place of phenylacetic acid to give the title compound as colourless crystals, m.p. 245°–247° C. δ (DMSO, 360 MHz) 1.60 (1H, ddd, J=13.3, 12.7 and 3.7 Hz, $CH_ACH_BH_CCH_D$), 2.13 (1H, dm J=13.3 Hz, $CH_ACH_BH_CCH_D$), 3.33 (2H, s, COCH$_2$Ar), 3.72 (3H, s, ArOCH$_3$), 3.82 (1H, dd, J=12.6 and 2.7 Hz, $CH_ACH_BH_CCH_D$), 4.98 (1H, m, $CH_ACH_BH_CCH_D$), 6.67 (1H, d, J=2.0 Hz, 6-H or 8-H), 6.84 (3H, d, J=8.6 Hz, NH and Ar-H), 6.88 (1H, d, J=2.0 Hz, 6-H or 8-H), 7.15 (2H, d, J=8.6 Hz, Ar-H), 8.41 (1H, d, J=7.1 Hz, NHCO); m/e 408 (M+), 121 (100%; CH$_2$C$_6$H$_4$OCH$_3$+); Found C, 55.62; H, 4.54; N, 6.69; C$_{19}$H$_{18}$Cl$_2$N$_2$O$_4$ requires C, 55.76; H, 4.43; N, 6.84%.

EXAMPLE 70

Trans-2-carboxy-5,7-dichloro-4-(4-nitrophenyl methylcarbonyl)amino-1,2,3,4-hydroquinoline This compound was prepared by the method given for Example 37 using 4-nitrophenylacetic acid in place of phenylacetic acid to give the title compound as yellow crystals m.p. 246°–248° C. δ (DMSO, 360 MHz), 1.62 (1H, ddd, J=13.2, 13.1 and 3.9 Hz, $CH_ACH_BH_CCH_D$), 2.15 (1H, dm, J=13.2 Hz, $CH_ACH_BH_CCH_D$), 3.59 (2H, s, COCH$_2$Ar), 3.82 (1H, dd, J=12.7 and 2.8 Hz, $CH_ACH_BH_CCH_D$), 5.00 (1H, m, $CH_ACH_BH_CCH_D$), 6.66 (1H, d, J=2.0 Hz, 6-H or 8-H), 6.81 (1H, br, s, NH), 6.89 (1H, d, J=2.0 Hz, 6-H or 8-H), 7.53 (2H, d, J=8.7 Hz, Ar-H), 8.17 (2H, d, J=8.7 Hz, Ar-H), 8,55 (1H, d, J=7.1 Hz, NHCO); m/e (CI+,NH$_3$), 424 (M+1), 198 (100%, M-NHCOCH$_2$C$_6$H$_4$NO$_2$,CO$_2$H,H); Found C, 50.86; H, 3.73; N, 9.63; C$_{18}$H$_{15}$Cl$_2$N$_3$O$_5$.O.1H$_2$O requires C, 50.75; H, 3.60; N, 9.86%.

EXAMPLE 71

Trans-2-carboxy-5,7-dichloro-4-(3-cyanophenyl carbonyl)amino-1,2,3,4-tetrahydroquinoline This compound was prepared by the method given for Example 37 using 3-cyanobenzoic acid in place of phenylacetic acid to give the title compound as colourless crystals, m.p. 229°–231° C. δ (DMSO, 360 MHz), 1.76 (1H, dt, J=13.3, 13.1 and 4.0 Hz, $CH_ACH_BH_CCH_D$), 2.30 (1H, dm, J=13.3 Hz, $CH_ACH_BH_CCH_D$), 3.97 (1H, dd, J=12.7 Hz and 2.7 Hz, $CH_ACH_BH_CCH_D$), 5.27 (1H, m, $CH_ACH_BH_CCH_D$), 6.67 (1H, d, J=2.0 Hz, 6-H or 8-H), 6.85 (1H, br s, NH), 6.93 (1H, d, J=2.0 Hz, 6-H or 8-H), 7.68 (1H, t, J=7.9 Hz, Ar-H), 7.99 (1H, dt, J=7.9 and 1.3 Hz, Ar-H), 8.20 (1H, dt, J=7.9 Hz, NHCO); m/e (CI+, NH$_3$), 390 (M+1), 130 (100%, COC$_6$H$_4$CN); Found C, 54.96; H, 3.57; N, 10.43; C$_{18}$H$_{13}$Cl$_2$N$_3$O$_3$.0.2-H$_2$O requires C, 54.90; H, 3.43; N, 10.67%.

EXAMPLE 72

Trans-2-carboxy-5,7-dichloro-4-(4-chlorophenyl)amino carbonylamino-1,2,3,4-tetrahydroquinoline This compound was prepared by the method given for Example 38 using 4-chlorophenyl isocyanate in place of phenyl isocyanate to give the title compound as colourless crystals, m.p. 199°–200° C. δ (DMSO, 360 MHz) 1.62 (1H, ddd, J=13.3, 13.1 and 4.0 Hz, $CH_ACH_BH_CCH_D$), 2.33 (1H, dm, J=13.3 Hz, $CH_ACH_BH_CCH_D$), 3.86 (1H, dd, J=12.9 and 3.0 Hz, $CH_ACH_BH_CCH_D$), 4.92 (1H, m, $CH_ACH_BH_CCH_D$), 6.59 (1H, d, J=6.6 Hz, NHCONHAr), 6.68 (1H, d, J=2.0 Hz, 6-H or 8-H), 6.77 (1H, br s, NH), 6.89 (1H, d, J=2.0 Hz, 6-H or 8-H), 7.26 (2H, d, J=8.9 Hz, Ar-H), 7.42 (2H, d, J=8.9 Hz, Ar-H), 8.31 (1H, s, NHCONHAr); m/e 413 (M+), 93 (100%); Found C, 47.77; H, 3.30; N, 9.81; C$_{17}$H$_{14}$Cl$_3$N$_3$O$_3$. 0.6H$_2$O requires C, 47.99; H, 3.60; N, 9.88%.

EXAMPLE 73

Trans-2-carboxy-5,7-dichloro-4-(4-methylphenyl)-amino carbonylamino-1,2,3,4-tetrahydroquinoline This compound was prepared by the method given for Example 38 using 4-methylphenyl isocyanate in place of phenyl isocyanate to give the title compound as colourless crystals, m.p. 197°–198° C. δ (DMSO, 360 MHz) 1.61 (1H, ddd, J=13.1, 13.1 and 3.3 Hz, $CH_ACH_BH_CCH_D$), 2.22 (3H, s, Ar-CH$_3$), 2.32 (1H, dm, J=13.1 Hz, $CH_ACH_BH_CCH_D$), 3.87 (1H, dd, J=13.1 and 3 Hz, $CH_ACH_BH_CCH_D$), 4.93 (1H, m, $CH_ACH_BH_CCH_D$), 6.44 (1H, d, J=6.5 Hz, NHCONHAr), 6.68 (1H, d, J=2.0 Hz 6-H or 8-H), 6.78 (1H, br, s, NH), 6.88 (1H, d, J=2.0 Hz, 6-H or 8-H), 7.03 (2H, d, J=8.3 Hz, Ar-H), 7.27 (2H, d, J=8.3 Hz, Ar-H), 8.03 (1H, s, NHCONHAr); m/e (FAB-), 392 (M-1), 91 (100%, C$_6$H$_4$CH$_3$), 183 (100%); Found C, 54.27; H, 4.42; N, 10.37; C$_{18}$H$_{17}$Cl$_2$N$_3$O$_3$.0.25H$_2$O requires C, 54.22; H, 4.42; N, 10.54%.

EXAMPLE 74

Trans-2-carboxy-5,7-dichloro-4-(4-methoxyphenyl)amino carbonylamino-1,2,3,4-tetrahydroquinoline This compound was prepared by the method given for example 38 using 4-methoxyphenyl isocyanate in the place of phenyl isocyanate to give the title compound as colourless crystals, m.p. 189°–190° C. δ (DMSO, 360 MHz) 1.61 (1H, ddd, J=13.1, 12.8 and 3.3 Hz, $CH_ACH_BH_CCH_D$), 2.32 (1H, dm J=13.1 Hz, $CH_ACH_BH_CCH_D$), 3.69 (3H, s, Ar-OCH$_3$), 3.88 (1H, dd, J=13.0 and 3.0 Hz, $CH_ACH_BH_CCH_D$), 4.92 (1H, m, $CH_ACH_BH_CCH_D$), 6.39 (1H, d, J=6.5 Hz, NHCONHAr), 6.68 (1H, d, J=2.0 Hz, 6-H or 8-H), 6.77 (1H, br s, NH), 6.82 (2H, d, J=8.9 Hz, Ar-H), 6.88 (1H, d, J=2.0 Hz, 6-H or 8-H), 7.29 (2H, d, J=8.9 Hz, Ar-H), 7.95 (1H, s, NHCONHAr), m/e (FAB+), 410 (M+1), 93 (100%); Found C, 52.30; H, 4.19; N, 10.12; C$_{18}$H$_{17}$Cl$_2$N$_3$O$_4$.0.15H$_2$O requires C, 52.35; H, 4.22; N, 10.18%.

EXAMPLE 75

Trans-2-carboxy-5,7-dichloro-4-(4-nitrophenyl)amino carbonylamino-1,2,3,4-tetrahydroquinoline This compound was prepared by the method given for Example 38 using 4-nitrophenyl isocyanate in place of phenyl isocyanate to give the title compound as yellow crystals, m.p. 185°-186° C. δ (DMSO, 360 MHz) 1.66 (1H, ddd, J=13.3, 12.8 and 3.3 Hz, $CH_ACH_BH_CCH_D$), 2.33 (1H, dm, J=13.3 Hz, $CH_ACH_BH_CCH_D$), 3.88 (1H, dd, J=12.7 and 2.8 Hz, $CH_ACH_BH_CCH_D$), 4.97 (1H, m, $CH_ACH_BH_CCH_D$), 6.68 (1H, d, J=2.0 Hz, 6-H or 8-H), 6.78 (1H, br s, NH), 6.90 (1H, d, J=2.0 Hz, 6-H or 8H), 6.93 (1H, d, J=6.7 Hz, NHCONHAr), 7.63 (2H, d, J=9.3 Hz, Ar-H), 8.15 (2H, d, J=9.3 Hz, Ar-H), 8.97 (1H, s, NHCONHAr); m/e (FAB-), 423 (M-1), 91 (100%, $NHC_6H_4$); Found C, 46.31; H, 3.32; N, 12.55; $C_{17}H_{14}Cl_2N_4O_5.0.8H_2O$ requires C, 46.44; H, 3.58; N, 12.74%.

EXAMPLE 76

Trans-2-carboxy-5,7-dichloro-4-(4-iodophenyl)amino carbonylamino-1,2,3,4-tetrahydroquinoline Step a: 1-Phenyl-3-(4-Iodophenyl)carbamate To a solution of 4-iodoaniline (1.94 g, 8.85 mmol) in anhydrous dichloromethane (40 ml) was added phenylchloroformate (1.11 ml, 8.85 mmol) and triethylamine (1.42 ml, 10.28 mmol). The mixture was stirred under an atmosphere of nitrogen for 18 h. The dichloromethane was removed in vacuo and the solid residue partioned between ethyl acetate (100 ml) and 0.5M citric acid (150 ml). The organic layer was retained and washed succesively with 0.5M citric acid (100 ml) saturated sodium bicarbonate solution (2×150 ml) and brine (100 ml) before drying ($Na_2SO_4$). The solvent was removed by rotary evaporation and the solid residue recrystallised from ethyl acetate/hexane to give the title compound as colourless crystals (2.61 g) m.p. 155°-157° C. δ (DMSO, 250 MHz) 7.21-7.47 (7H, m, Ar-H), 7.67 (2H, d, J=8.7 Hz, Ar-H).

Step b: Trans-2-methoxycarbonyl-5,7-dichloro-4-(4-iodophenyl)aminocarbonylamino-1,2,3,4-tetrahydroquinoline To a solution of 1-phenyl-3-(4-iodophenyl)carbamate (770 mg, 7.61 mmol), in anhydrous toluene (15 ml) was added dry triethylamine (0.670 ml, 4.33 mmol). The solution was heated, with stirring, in an oil bath to 120° C. and then allowed to cool to <90° C. before addition of trimethylsilyl chloride (0.55 ml, 4.33 mmol). The solution was heated at reflux (120° C.) for 2 h. The mixture was cooled below 30° C. and a solution of trans-2-methoxycarbonyl-5,7-dichloro-4-amino-tetrahydroquinolinehydrochloride (example 9a) (750 mg, 2.41 mmol) was added as a solution in anhydrous dichloromethane (10 ml) with triethylamine (0.403 ml, 2.87 mmol). The mixture was stirred under an atmosphere of nitrogen for 18 h. The organic solvents were removed in vacuo and the solid residue partitioned between 0.5M citric acid (100 ml) and ethyl acetate (100 ml). The organic layer was retained and washed succesively with 0.5M citric acid (100 ml), saturated sodium bicarbonate solution (2×100 ml) and brine (100 ml) before drying ($Na_2SO_4$). The solvent was removed and the product recrystallised from ethyl acetate/hexane to give the title compound as colourless crystals (668 mg), m.p. 253°-255° C. δ (DMSO, 250 MHz) 1.68 (1H, ddd, J=13.1, 12.0 and 3.4 Hz, $CH_ACH_BH_CCH_D$), 2.32 (1H, dm, J=13.1 Hz, $CH_ACH_BH_CCH_D$), 3.73 (3H, s, $CH_3$), 4.01 (1H, dd, J=13.0 and 3.0 Hz, $CH_ACH_BH_CCH_D$), 4.93 (1H, m, $CH_ACH_BH_CCH_D$), 6.62 (1H, d, J=6.5 Hz, NHCONHAr), 6.72 (1H, d, J=2.0 Hz, 6-H or 8-H), 6.89 (1H, d, J=2.0 Hz, 6-H or 8-H), 6.92 (1H, s, ArNHCH), 7.25 (2H, d, J=8.7 Hz, Ar-H), 7.54 (2H, d, J=8.7 Hz, Ar-H), 8.27 (1H, s, NHCONHAr).

Step c: Trans-2-carboxy-5,7-dichloro-4-(4-iodophenyl)aminocarbonylamino-1,2,3,4-tetrahydroquinoline This compound was prepared by the method given for Example 38 step b using trans-2-methoxycarbonyl-5,7-dichloro-4(4-iodophenylaminocarbonyl)amino-1,2,3,4-tetrahydroquinoline in place of trans-2-methoxycarbonyl-5,7-dichloro-4(phenylaminocarbonyl)amino-1,2,3,4-tetrahydroquinoline to give the title compound as colourless crystals, m.p. 224°-226° C. δ (DMSO, 360 MHz) 1.62 (1H, ddd, J=13.1, 12.9 and 3.4 Hz, $CH_ACH_BH_CCH_D$), 2.31 (1H, dm, J=13.1 Hz, $CH_ACH_BH_CCH_D$), 3.87 (1H, dd, J=12.7 and 2.7 Hz, $CH_ACH_BH_CCH_D$), 4.92 (1H, m, $CH_ACH_BH_CCH_D$), 6.58 (1H, d, J=6.6 Hz, NHCONHAr), 6.68 (1H, d, J=2.0 Hz, 6-H or 8-H), 6.79 (1H, s, ArNHCH), 6.88 (1H, d, J=2.0 Hz, 6-H or 8-H), 7.25 (2H, d, J=8.7 Hz-Ar-H), 7.54 (2H, d, 8.7 Hz, Ar-H), 8.26 (1H, s, NHCONHAr); m/e (FAB+) 506 (M+1) 93 (100%); Found C, 40.14; H, 2.80; N, 8.20; $C_{17}H_{14}Cl_2N_3IO_3.O.1-H_2O$ requires C, 40.20; H, 2.82; N, 8.24%.

EXAMPLE 77

Trans-2-carboxy-5,7-dichloro-4-(phenyl)aminocarbonyl-N-methylamino)-1,2,3,4-tetrahydroquinoline Step a: Trans-2-methoxycarbonyl-5,7-dichloro-4-N-methylamino-1,2,3,4-tetrahydroquinoline Trans-2-carboxy-5,7-dichloro-4-amino-1,2,3,4-tetrahydroquinoline hydrochloride (Example 9a) (760 mg, 2.44 mmol) was shaken with a solution of potassium carbonate for 5 min. The solid in suspension was extracted into ethyl acetate (2×50 ml). The combined organic extracts were evaporated and the solid residue redissolved in anhydrous tetrahydrofuran (300 ml). This solution was cooled (−5° C.) and a solution of methyl iodide (159 μl, 2.56 mmol) in tetrahydrofuran (50 ml) was added dropwise, under an atmosphere of nitrogen. The mixture was allowed to warm to room temperature and was stirred for 70 h. The THF was removed and the solid residue redissolved in 30 ml of THF. A further quantify of methyl iodide (159 μl, 2.56 mmol) was added as a solution in THF (5 ml) and the mixture stirred for a further 16 h in an atmosphere of nitrogen. The solvent was evaporated and the residue separated by silica chromatography (eluent; methanol/dichloromethane) to yield the title compound as a colourless crystalline solid. δ ($CDCl_3$, 250 MHz) 1.49 (1H, $CH_ACH_BH_CCH_D$, partially masked by $H_2O$), 2.46 (1H, dm, J=13.3 Hz, $CH_ACH_BH_CCH_D$), 2.55 (3H, s, $NH_3$), 3.81-3.87 (4H, m, $CH_ACH_BH_CCH_D$, and $OCH_3$), 4.29 (1H, dd, J=12.3 and 2.2 Hz, $CH_ACH_BH_CCH_D$), 4.80 (1H, br s, NHMe), 6.53 (1H, d, J=2.0 Hz, 6-H or 8-H), 6.69 (1H, d, J=2.0 Hz).

Step b: Trans-2-carboxy-5,7-dichloro-4-(phenyl)aminocarbonyl-N-(methylamino)-1,2,3,4-tetrahydroquinoline This compound was prepared by the method given for Example 38 using trans-2-methoxycarbonyl-5,7-dichloro-4N-methylamino-1,2,3,4-tetrahydroquinoline in place of trans-2-methoxycarbonyl-5,7-dichloro-4- amino-1,2,3,4-tetrahydroquinoline hydrochloride and triethylamine, to give the title compound as colourless crystals, m.p. 139°-140° C. δ (DMSO, 360 MHz) 1.75 (1H, ddd, J=13.4, 12,8 and 3.8 Hz, $CH_ACH_BH_CCH_D$), 2.37 (1H, dm, J=13.4 Hz, $CH_ACH_BH_CCH_D$), 2.65 (3H, s, NCH$_3$), 3.94 (1H, dd, J=12.4 and 3.5 Hz, $CH_ACH_BH_CCH_D$), 5.35 (1H, m, $CH_ACH_BH_CCH_D$), 6.69 (1H, d, J=2.0 Hz, 6-H or 8-H), 6.83 (1H, br s, ArNHCH), 6.93 (1H, d, J=2.0 Hz, 6-H or 8-H), 6.95 (1H, m, Ar-H), 7.24 (2H, t, J=8.5 Hz, Ar-H), 7.54 (2H, dd, J=2.1 Hz, 8.8 Hz, Ar-H), 8.23 (1H, br s, CONHAr); m/e 346 (M-CO$_2$H,H,H), 91 (100%); Found C, 55.08; H, 4.76; N, 10.12; $C_{18}H_{17}Cl_2N_3O_3.0.2C_4H_{10}O$ requires C, 55.20; H, 4.68; N, 10.27%.

EXAMPLE 78

Trans-2-carboxy-5,7-dichloro-4-(-N-methyl)-(N-phenyl)amino-carbonylamino-1,2,3,4-tetrahydroquinoline Step a: Trans-2-methoxycarbonyl-5,7-dichloro-4-(phenyloxy)carbonylamino-1,2,3,4-tetrahydroquinoline This compound was prepared by the method given for Example 36, step a, using phenylchloroformate in the place of butyryl chloride to give the title compound as colourless crystals, m.p. 159°-161° C. δ (360 MHz, CDCl$_3$) 1.73 (1H, m, $CH_ACH_BH_CCH_D$), 2.73 (1H, dm, J=13.5 Hz, $CH_ACH_BH_CCH_D$), 3.84 (3H, s, CO$_2$CH$_3$), 4.07 (1H, dd, J=12.6 and 2.6 Hz, $CH_ACH_BH_CCH_D$), 4.82 (1H, s, ArNH), 5.02-5.16 (2H, m, $CH_ACH_BH_CCH_DNHCO$ and $CH_DNHCO$), 6.57 (1H, d, J=1.9 Hz, 6-H or 8-H), 6.77 (1H, d, J=1.9 Hz, 6-H or 8-H), 7.15-7.30 (3H, m, ArH), 7.35-7.43 (2H, m, ArH); m/e (CI+), 395 (M+H), 258 (100%, M-NHCO$_2$Ph).

Step b: Trans-2-methoxycarbonyl-5,7-dichloro-4(N-methyl)-(N-phenyl)aminocarbonylamino-1,2,3,4-tetrahydroquinoline To a solution of trans-2-methoxycarbonyl-5,7-dichloro-4-(phenyloxy)carbonylamino-1,2,3,4-tetrahydroquinoline (225 mg, 0.587 mmol) in anhydrous toluene (7 ml) was added dry triethylamine (245 μl, 1.76 mmol). The mixture was heated with stirring, in an oil bath to 120° C. and then allowed to cool to <90° C. before the addition of trimethylsilyl chloride (186 μl, 1.47 mmol). The solution was heated at reflux (120° C.) for 2 h. After cooling to <30° C., a further one equivalent of triethylamine was added (81 μl, 0.588 mmol) followed by N-methylaniline (126 mg, 1.174 mmol). The mixture was stirred at room temperature under an atmosphere of nitrogen for 18 h. The organic solvent was removed and the solid residue paritioned between ethyl acetate (75 ml) and 0.5M citric acid (100 ml). The organic layer was retained and washed successively with 0.5M citric acid (100 ml), saturated sodium bicarbonate solution (2×100 ml) and brine (100 ml) before drying (Na$_2$SO$_4$). The solvent was removed in vacuo to yield an orange oil which was isolated by flash chromatography (solvent; ethyl acetate/hexane) to give the title compound as colourless crystals (89 mg) m.p. 185°-189° C. δ (CDCl$_3$, 250 MHz) 1.64 (1H, ddd, J=13.4, 13.1 and 3.6 Hz, $CH_ACH_BH_CCH_D$), 2.73 (1H, dm, J=13.4 Hz, $CH_ACH_BH_CCH_D$), 3.30 (3H, s, NCH$_3$), 3.80 (1H, dd, J=11.7 and 2.8 Hz, $CH_ACH_BH_CCH_D$), 3.81 (3H, s, OCH$_3$), 4.23 (1H, d, J=5.0 Hz, NHCO), 4.77 (1H, s, ArNHCO), 5.11 (1H, m, $CH_ACH_BH_CCH_D$), 6.47 (1H, d, J=1.9 Hz, 6-H or 8-H), 6.68 (1H, d, J=1.9 Hz, 6-H or 8-H), 7.22-7.40 (5H, m, Ar-H).

Step c: Trans-2-carboxy-5,7-dichloro-4-(N-methyl)-)N-phenyl)amino)carbonylamino-1,2,3,4-tetrahydroquinoline This compound was prepared by the method given for Example 38, step b, using trans-2-methoxycarbonyl-5,7-dichloro-4-(N-methyl)-(N-phenyl)aminocarbonylamino-1,2,3,4-tetrahydroquinoline in place of trans-2-methoxycarbonyl-5,7-dichloro-4(phenyl)N-methylaminocarbonylamino-1,2,3,4-tetrahydroquinoline to give the title compound as colourless crystals, m.p. 204°-205° C. δ (DMSO, 360 MHz) 1.58 (1H, ddd, J=13.2, 12.8 and 3.8 Hz, $CH_ACH_BH_CCH_D$), 2.27 (1H, dm J=13.2 Hz, $CH_ACH_BH_CCH_D$), 3.15 (3H, s, NCH$_3$), 3.87 (1H, dd, J=12.6 and 2.7 Hz, $CH_ACH_BH_CCH_D$), 4.93 (1H, m, $CH_ACH_BH_CCH_D$), 6.26 (1H, d, J=6.9 Hz, NHCO), 6.62 (1H, d, J=2.0 Hz, 6-H or 8-H), 6.67 (1H, br s, ArNHCH), 6.82 (1H, d, J=2.0 Hz, 6-H or 8-H), 7.14 (1H, t, J=7.3 Hz, Ar-H), 7.25 (2H, d, J=8.5 Hz, Ar-H), 7.32 (2H, t, J=7.2 Hz, Ar-H); m/e m/e 347 (M-CO$_2$H,H), 107 (100%, $C_6H_5NHCH_3$+); Found C, 53.96; H, 4.37; N, 10.37; $C_{18}H_{17}Cl_2N_3O_3.0.35H_2O$ requires C, 53.95; H, 4.45; N, 10.49%.

EXAMPLE 79

Trans-2-carboxy-5,7-dichloro-4-(2,3-dihydroindole-1-carbonyl)amino-1,2,3,4-tetrahydroquinoline This compound was prepared by the method given for Example 78 using indoline in place of N-methylaniline to give the title compound as colourless crystals, m.p. 251°-252° C. δ (DMSO, 360 MHz) 1.64 (1H, ddd, J=13.2, 13.1 and 3.7 Hz, $CH_ACH_BH_CCH_D$), 2.38 (1H, dm, J=13.2 Hz, $CH_ACH_BH_CCH_D$), 3.08 (2H, t, J=8.7 Hz, $CH_EH_FCH_2$), 3.76 (1H, q, J=9.0 Hz, $CH_EH_FCH_2$), 3.92 (1H, q, J=9.0 Hz, $CH_ECH_FCH_2$), 3.98 (1H, dd, J=12.9 and 2.7 Hz, $CH_ACH_BH_CCH_D$), 5.04 (1H, m, $CH_ACH_BH_CCH_D$), 6.65 (1H, d, J=2.0 Hz, 6-H or 8-H), 6.78-6.85 (3H, m, Ar-H and ArNHCH), 6.89 (1H, d, J=2.0 Hz, 6-H or 8-H), 7.06-7.14 (2H, m, Ar-H), 8.76 (1H, d, J=8.0 Hzm NHCO); m/e 405 (M+), 91 (100%); Found C, 55.66; H, 4.39; N, 10.02; $C_{19}H_{17}Cl_2N_3O_3.0.2H_2O$ requires C, 55.68; H, 4.28; N, 10.25%.

EXAMPLE 80

Trans-2-carboxy-5,7-dichloro-4-(2-carboxyethyl)carbonyl)amino-1,2,3,4-tetrahydroquinoline Step a: trans-2-methoxycarbonyl-5,7-dichloro-4-(2-carboxyethyl)carbonylamino-1,2,3,4-tetrahydroquinoline To a suspension of trans-2-methoxycarbonyl-5,7-dichloro-4-amino-1,2,3,4-tetrahydroquinoline hydrochloride (Example 9a) (225 mg, 0.819 mmol) in ethyl acetate (50 ml) was added a solution of potassium carbonate (50 ml). The mixture was shaken until no solid remained (5 min). The organic layer was retained and washed with brine (50 ml) before drying (Na$_2$SO$_4$). The solvent was removed in vacuo. The residue was redissolved in xylene (20 ml) and succinic anhydride (90 mg, 0.901 mmol) was added. The mixture was heated, with stirring, in an oil bath (80° C.) for 16h. The precipitate was removed by filtration and washed with ether to give the title compound as a colourless crystalline solid. δ (DMSO, 250 MHz), 1.65 (1H, ddd, J=13.0, 12.7 and 3.7 Hz, $CH_ACH_BH_CCH_D$), 2.15 (1H, dm, J=13.0 Hz, $CH_ACH_BH_CCH_D$), 2.18-2.41 (4H, m, CO(CH$_2$)$_2$ CO), 3.73 (3H, s, CH$_3$), 3.94 (1H, dd, J 13.0 and 3.0 Hz, $CH_ACH_BH_CCH_d$), 5.01 (1H, m, $CH_ACH_BH_CCH_D$), 6.69 (1H, J=2.1 Hz, 6-H or 8-H), 6.86 (1H, d, J=2.1 Hz, 6-H or 8-H), 6.91 (1H, s, ArNHCH), 8.23 (1H, d, J=7.2 Hz, NHCO).

Step b: Trans-2-carboxy-5,7-dichloro-4-(2-carboxyethyl)carbonylamino-1,2,3,4-tetrahydroquinoline This compound was prepared by the method given for Example 36, step b, using trans-2-methoxycarbonyl-5,7-dichloro-4(2-carboxyethyl)carbonylamino-1,2,3,4-tetrahydroquinoline in place of trans-2-methoxycarbonyl-5,7-dichloro-4-butylcarbonylamino-1,2,3,4-tetrahydroquinoline to give the title compound as colourless crystals, m.p. 221°-223° C. δ DMSO, 360 MHz) 1.59 (1H, ddd, J=13.2, 12.9 and 3.8 Hz, CH$_A$CH$_B$H$_C$CH$_D$), 2.15 (1H, dm, J=13.2 Hz, CH$_A$CH$_B$H$_C$CH$_D$), 2.31 (2H, t, J=6.7 Hz, COCH$_{E2}$ CH$_{F2}$CO), 2.41-2.45 (2H, m, COCH$_{E2}$CH$_{F2}$), 3.83 (1H, dd, J=12.5 and 2.6 Hz, CH$_A$CH$_B$H$_C$CH$_D$), 5.01 (1H, m, CH$_A$CH$_B$H$_C$CH$_D$), 6.64 (1H, d, J=2.0 Hz, 6-H or 8-H), 6.75 (1H, br s, ArNHCH), 6.87 (1H, d, J=2.0 Hz, 6-H or 8-H), 8.16 (1H, d, J=7.2 Hz, NHCO); m/e 342 (M-H$_2$O), 198 (100% M-NHCO(CH$_2$)$_2$ CO$_2$H, CO$_2$H,H); Found C, 46.59; H, 4.02; N, 7.57; C$_{14}$H$_{14}$Cl$_2$N$_2$O$_5$ requires C, 46.56; H, 3.91; N, 7.76%.

EXAMPLE 81

Trans-2-carboxy-5,7-dichloro-4-(3-aminomethylphenyl)carbonylamino-1,2,3,4-tetrahydroquinoline hydrochloride Step a: 3-(tert-Butyloxycarbonylamino)methyl benzoic acid To a solution of 3-cyanobenzoic acid (1.0 g, 6.79 mmol) in ethanol (150 ml) was added 100 mg of 10% palladium on carbon and the mixture was hydrogenated at 50 psi for approximately 18 h. Di-tert-butyl dicarbonate (1.63 g, 7.47 mmol) was added to the mixture, with a further 110 mg of catalyst and hydrogenation was continued under the same conditions for a further 20 h. After this time all the starting material had been consumed by t.l.c. (solvent: 1% MeOH, 0.5% AcOH, 98.5% CH$_2$Cl$_2$). The catalyst was removed by filtration, and the ethanol was removed by rotary evaporation to give an orange oil which crystallised after drying under high vacuum (1 h). The product was recrystallised for ether/hexane to give the title compound as colourless crystals, m.p. 127°-128° C. δ (CDCl$_3$, 250 MHz) 1.47(9H, s, C(CH$_3$)$_3$), 4.39 (2H, d, J=5.9 Hz, ArCH$_2$NH), 4.95 (1H, br s, NH), 7.44 (1H, t, J=7.8 Hz, Ar-H), 7.56 (1H, m, Ar-H), 8.01 (2H, m, Ar-H).

Step b: Trans-2-methoxycarbonyl-5,7-dichloro-4-(3-tertbutyloxycarbonylaminomethylphenyl)carbonylamino-1,2,3,4-tetrahydroquinoline To a suspension of 2-methoxycarbonyl-5,7-dichloro-4-amino-1,2,3,4-tetrahydroquinoline hydrochloride (Example 9) (300 mg, 0.963 mmol) in anhydrous dichloromethane (15 ml) under an atmosphere of nitrogen was added dry triethylamine (403 µl, 2.89 mol) and the resulting mixture was stirred at room temperature for 5 min. To this was added 3-(tertbutyloxycarbonylamino)methyl benzoic acid (step a) (290 mg, 1.16 mmol), 1-hydroxybenzotriazole (156 mg, 1.16 mol) followed by 1-(3-dimethylaminopropyl)-3-ethylcarbodiimide hydrochloride (222 mg, 1.16 mmol) and stirring was continued for approximately 18 h. The mixture was then concentrated in vacuo and the residue partitioned between ethyl acetate (100 ml) and 0.5M citric acid (150 ml). The organic layer was retained and washed successively with 0.5M citric acid (150 ml), saturated sodium bicarbonate solution (2×150 ml) and brine (100 ml) before drying (Na$_2$SO$_4$). The solvent was removed and the residue was recrystallised from ethyl acetate/hexane to give the title compound as colourless crystals (351 mg), m.p. 222°-223° C. δ (DMSO, 250 MHz) 1.39 (9H, s, C(CH$_3$)$_3$), 1.78 (1H, ddd, J=12.8, 12.6 and 3.9 Hz, CH$_A$CH$_B$H$_C$CH$_D$), 2.26 (1H, dm, J=12.8 Hz, CH$_A$CH$_B$H$_C$CH$_D$), 3.71 (3H, s, COOCH$_3$), 4.05 (1H, dd, J=13.0 and 3.0 Hz, CH$_A$CH$_B$H$_C$CH$_D$), 4.14 (2H, d, J=5.8 Hz, ArCH$_2$NH), 5.26 (1H, m, CH$_A$CH$_B$H$_C$CH$_D$), 6.69 (1H, d, J=2.1 Hz, 6-H or 8-H), 6.90 (1H, d, J=2.1 Hz, 6-H or 8-H), 6.93 (1H, s, ArNHCH), 7.37 (3H, m, Ar-H and CH$_2$NHCO), 7.71-7.76 (2H, m, Ar-H), 8.68 (1H, d, J=7.1 Hz); m/e 507 (M+), 198 (100%, M-H, CO$_2$CH$_2$CH$_3$,NH-COC$_6$H$_4$CH$_2$NHCOOC(CH$_3$)$_3$).

Step c: Trans-2-carboxy-5,7-dichloro-4-(3-tert-butyloxycarbonylaminomethylphenyl)carbonylamino-1,2,3,4-tetrahydroquinoline To a solution of trans-2-methoxycarbonyl-5,7-dichloro-4-(3-tert-butyloxycarbonylaminomethylphenyl)carbonylamino-1,2,3,4-tetrahydroquinoline (step b) (430 mg, 0.846 mmol) in a mixture of tetrahydrofuran (20 ml) and water (10 ml) was added aqueous lithium hydroxide (1.95 ml of a 0.5M solution, 0.973 mmol), and the resulting mixture was stirred at room temperature for 3 h. The organic solvent was removed in vacuo and the aqueous residue was diluted to 50 ml before acidifying to pH 1 with 1N HCl. The white precipitate was extracted into ethyl acetate (150 ml), washed with brine and dried (Na$_2$SO$_4$). The solution was evaporated to give a residue which was washed with diethyl ether and collected by filtration to give the title compound as a colourless crystalline solid, m.p. 192°-193° C. δ (DMSO, 360 MHz) 1.39 (9H, s, C(CH$_3$)$_3$, 1.73 (1H, ddd, 13.2, 13.0 and 3.8 Hz, CH$_A$CH$_B$H$_C$CH$_D$), 2.26 (1H, dm, J=13.2 Hz, CH$_A$CH$_B$H$_C$CH$_D$), 3.96 (1H, dd, J=13.0 and 3.0 Hz, CH$_A$CH$_B$H$_C$CH$_D$), 4.14 (2H, d,J=5.6 Hz, ArCH$_2$NH), 5.26 (1H, m, CH$_A$CH$_B$H$_C$CH$_D$), 6.65 (1H, d, J=2.0 Hz, 6-H or 8-H), 6.82 (1H, br s, ArNHCO), 6.91 (1H, d, J=2.0 Hz, 6-H or 8-H). 7.36-7.37 and 7.72-7.76 (5H, m, Ar-H and CH$_2$NHCO), 8.66 (1H, d, J=7 Hz, NHCOAr); m/e (FAB+), 494 (M+1), 93 (100%); Found C, 55.92; H, 5.22; N, 8.35; C$_{23}$H$_{25}$Cl$_2$N$_3$O$_5$ requires C, 55.88; H, 5.10; N, 8.50%.

Step d: Trans-2-carboxy-5,7-dichloro-4-(3-aminomethylphenyl)carbonylamino-1,2,3,4-tetrahydroquinoline hydrochloride To a solution of trans-2-carboxy-5,7-dichloro-4-(3-tert-butyloxycarbonylaminomethylphenyl)carbonylamino-1,2,3,4-tetrahydroquinoline (85 mg) in ethyl acetate (20 ml) was added 25 ml of ethyl acetate saturated with hydrogen chloride gas and the mixture was stirred in a stoppered flask for 6 h. The ethyl acetate and excess hydrogen chloride were removed in vacuo and the solid residue was recrystallised from ethyl acetate/methanol to give the title compound as colourless crystals (46 mg), m.p. 199°-200° C. δ (DMSO, 360 MHz) 1.76 (1H, ddd, J=13.2, 13.1 and 3.9 Hz, CH$_A$CH$_B$H$_C$CH$_D$), 2.26 (1H, dm J=13.2 Hz, CH$_A$CH$_B$H$_C$CH$_D$), 3.96-4.06 (3H, m, ArCH$_2$NH$_2$ and CH$_A$CH$_B$H$_C$CH$_D$), 5.29 (1H, m, CH$_A$CH$_B$H$_C$CH$_D$), 6.66 (1H, d, J=2.0 Hz, 6-H or 8-H), 6.85 (1H, s, NH), 6.92 (1H, d, J=2.0 Hz, 6-H or 8-H), 7.48 (1H, t, J=7.8 Hz, Ar-H), 7.63 (1H, d, J=7.8 Hz, Ar-H), 7.88 (1H, d, J=7.8 Hz, Ar-H), 8.03 (1H, s, Ar-H), 8.38 (1H, br s, NH$_2$), 8.72 (1H, d, J=7 Hz, NHCO); m/e (FAB+), 394 (M+1), 93 (100%).

EXAMPLE 82

Trans-2-methoxycarbonyl-5,7-dichloro-4-(3-aminomethylphenyl)carbonylamino-1,2,3,4-tetrahydroquinoline hydrochloride A solution of hydrogen chloride in methanol was prepared by the cautious addition of acetyl chloride (6 ml) to ice-cooled methanol (25 ml). Trans-2-carboxy-5,7-dichloro-4-(3-aminomethylphenyl)carbonylamino-1,2,3,4-tetrahydroquinoline hydrochloride (87 mg, 0.202 mmol) (Example 81) was dissolved in the HCl/methanol solution and the resulting mixture was stirred in a stoppered flask for 2 h. The methanol and excess hydrogen chloride were removed in vacuo and the product recrystallised from methanol/ether to give the title compound as a colourless crystalline solid (80 mg) m.p. 173° C. (dec). $\delta$ (DMSO, 360 MHz) 1.94 (1H, ddd, J=13.7, 13.4 and 3.8 Hz, $CH_ACH_BH_CCH_D$), 2.51 (1H, dm J=13.7 Hz, $CH_ACH_BH_CCH_D$), 3.81 (3H, s, $CH_3$), 4.10 (1H, dd, J=12.6 and 2.7 Hz, $CH_ACH_BH_CCH_D$), 4.23 (2H, s, $CH_2NH_2$), 5.36 (1H, m, $CH_ACH_BH_CCH_D$), 6.81 (1H, d, J=2.0 Hz, 6-H or 8-H), 6.91 (1H, d, J=2.0 Hz, 6-H or 8-H), 7.56 (1H, t, J=7.7 Hz, Ar-H), 7.65 (1H, d, J=7.8 Hz, Ar-H), 7.77 (2H, m, Ar-H); m/e (FAB+), 408 (M+1), 93 (100%); Found C, 49.05; H, 4.43; N, 8.94; $C_{19}H_{19}Cl_2N_3O_3$. 1.5HCl requires C, 49.29; H, 4.46; N, 9.08%.

EXAMPLE 83

Trans-2-carboxy-5,7-dichloro-4-(4-aminomethylphenyl)carbonylamino-1,2,3,4-tetrahydroquinoline hydrochloride Step a: 4-(tert-Butyloxycarbonylamino)methyl benzoic acid To a stirred suspension of 4-aminomethyl benzoic acid (5.0 g, 0.0331 mol) in 10% sodium carbonate solution (42 ml, 0.0394 mol) was added a solution of di-tert-butyl dicarbonate (7.43 g, 0.0364 mol) in dioxan (42 ml) and the mixture was stirred at room temperature for 2 h. The mixture was diluted with water to 300 ml and washed with ether (100 ml). The aqueous fraction was retained and acidified to pH3 with 1N citric acid solution. The precipitate was extracted into ethyl acetate, washed with water (2×100 ml), brine (1×100 ml) and dried (Na$_2$SO$_4$). The solvent was removed in vacuo to give a white solid m.p. 170°-171° C. $\delta$ (DMSO, 250 MHz) 1.33 (9H, s, C(CH$_3$)$_3$), 4.12 (2H, d, J=6.0 Hz, ArCH$_2$NH), 7.27 (2H, d, J=8.1 Hz, Ar-H), 7.41 (1H, t, J=6.0 Hz, NH), 7.82 (2H, d, J=8.1 Hz, Ar-H), Step b: Trans-2-carboxy-5,7-dichloro-4-(4-aminomethylphenyl)carbonylamino-1,2,3,4-tetrahydroquinoline hydrochloride This compound was prepared by the method given for Example 81, steps b, c, and d, using 4-(tert-butyloxycarbonylamino)methyl benzoic acid in place of 3-(tert-butyloxycarbonylamino)methyl benzoic acid to give the title compound as colourless crystals, m.p. 219° C. (dec). $\delta$ (DMSO, 360 MHz), 1.74 (1H, ddd, J=13.2, 12.9 and 4.1 Hz, $CH_ACH_BH_CCH_D$), 2.27 (1H, dm, J=13.2 Hz, $CH_ACH_BH_CCH_D$), 3.95 (1H, dd, J=12.5 and 2.5 Hz, $CH_ACH_BH_CCH_D$), 4.06 (2H, s, ArCH$_2$NH$_2$), 5.26 (1H, m, $CH_ACH_BH_CCH_D$), 6.65 (1H, d, J=2.0 Hz, 6-H or 8-H), 6.82 (1H, s, NH), 6.92 (1H, d, J=2.0 Hz, 6-H or 8-H), 7.53 (2H, d, J=8.3 Hz, Ar-H), 7.91 (2H, d, J=8.3 Hz, Ar-H), 8.4 (2H, br s, NH$_2$), 8.70 (1H, d, J=7.2 Hz, NHCO); m/e (FAB+), 394 (M+1), 93 (100%); Found C, 48.18; H, 4.07; N, 9.31; $C_{18}H_{17}Cl_2N_3O_3$. 1.5HCl requires C, 48.16; H, 4.15; N, 9.36%.

EXAMPLE 84

Trans-2-methoxycarbonyl-5,7-dichloro-4-(4-aminomethylphenyl)carbonylamino-1,2,3,4-tetrahydroquinoline hydrochloride This compound was prepared by the method given for Example 82 using trans-2-carboxy-5,7-dichloro-4(4-aminomethylphenyl)carbonylamino-1,2,3,4-tetrahydroquinoline hydrochloride, Example 83, in place of trans-2-carboxy-5,7-dichloro-4(3-aminomethylphenyl)-carbonylamino-1,2,3,4-tetrahydroquinoline hydrochloride to give the title compound as a colourless crystalline solid m.p. 238°-240° C. $\delta$ (DMSO, 360 MHz), 1.80 (1H, ddd, J=13.0, 12.5 and 4.1 Hz, $CH_ACH_BH_CCH_D$), 2.26 (1H, dm, J=13.0 Hz, $CH_ACH_BH_CCH_D$), 3.71 (3H, s, CH$_3$), 4.07 (3H, m, $CH_ACH_BH_CCH_D$ and CH$_2$NH$_2$), 5.26 (1H, m, $CH_ACH_BH_CCH_D$), 6.68 (1H, d, J=2.0 Hz, 6-H or 8-H), 6.91 (1H, d, J=2.0 Hz, 6-H or 8-H), 6.95 (1H, s, NH), 7.53 (2H, d, J=8.2 Hz, Ar-H), 7.91 (2H, d, J=8.2 Hz, Ar-H), 8.38 (2H, br s, NH$_2$), 8.73 (1H, d, J=7.2 Hz, NHCO); m/e (CI+, NH$_3$), 408 (M+1), 15 (100%; Found C, 48.87; H, 4.37; N, 8.95; $C_{19}H_{19}Cl_2N_3O_3$.1.6 HCl requires C, 48.91; H, 4.45; N, 9.10%.

EXAMPLE 85

Trans-2-carboxy-5,7-dichloro-4-(4-aminoethylphenyl)-carbonylamino-1,2,3,4-tetrahydroquinoline hydrochloride Step a: (4-tert-Butyloxycarbonylamino)ethyl benzoic acid To a suspension of 4-aminoethylbenzoic acid hydrochloride (4.32 g, 0.0214 mol), in anhydrous dichloromethance (50 ml) was added triethylamine (8.94 ml, 0.0642 mol) and the mixture was stirred at room temperature for 10 min. To this solution was added di-tert-butyl-dicarbonate (5.14 g, 0.236 mol) and stirring was continued for 18 h. Dimethyl ethylenediamine (2 ml) was added and after stirring for a further 20 min the dichloromethane was removed in vacuo. The residue was partitioned between ethyl acetate (150 ml) and 0.5M citric acid (100 ml). The organic layer was retained and washed successively with 0.5M citric acid (100 ml), water (3×150 ml) and brine (100 ml) before drying (Na$_2$SO$_4$). The solvent was removed in vacuo and the residue recrystallised from ethyl acetate/hexane to give the title compound as a colourless crystalline solid, m.p. 163°-164° C. $\delta$ (DMSO, 250 MHz) 1.35 (9H, s, C(CH$_3$)$_3$ 2.75 (2H, t, J=7.0 Hz, ArCH$_2$CH$_2$NH), 3.17 (2H, m, ArCH$_2$CH$_2$NH), 6.91 (1H, br t, J=8.0 Hz, NH), 7.30 (2H, d, J=8.2 Hz, Ar-H), 7.85 (2H, d, J=8.2 Hz, Ar-H).

Step b: Trans-2-carboxy-5,7-dichloro-4-(4-aminoethylphenyl)carbonylamino-1,2,3,4-tetrahydroquinoline hydrochloride This compound was prepared by the method given for Example 81, steps b, c, and d, using 4-(tert-butyloxycarbonylamino)ethyl benzoic acid as the starting material in the place of 3-(tert-butyloxycarbonylamino)-methyl benzoic acid to give the title compound as colourless crystals, m.p. 204° C.(dec). $\delta$ (DMSO,360 MHz) 1.71 (1H, ddd, J=13.2, 12.9 and 3.9 Hz, $CH_ACH_BH_CCH_D$), 2.25 (1H, dm, J=13.2 Hz, $CH_ACH_BH_CCH_D$), 2.93 (2H, t, J=7.0 Hz, $CH_{E2}CH_{F2}$), 3.04 (2H, t, J=7.0 Hz, $CH_{E2}CH_{F2}$), 3.93 (1H, dd, J=12.5 and 2.5 Hz, $CH_ACH_BH_CCH_D$), 5.25 (1H, m, $CH_ACH_BH_CH_D$), 6.65 (1H, d, J=2.0 Hz, 6-H or 8-H), 6.80 (1H, br s ,NH), 6.91 (1H, d, J=2.0 Hz, 6-H or 8-H), 7.32 (2H, d, J=8.2 Hz, Ar-H), 7.87 (2H, d, J=8.2 Hz, Ar-H), 8.0 (2H, br s, $NH_2$), 8.66 (1H, d, J=7.1 Hz, NHCO); m/e (FAB+), 408 (M+1), 93 (100%); Found C, 47.40; H, 4.30; N, 8.63; $C_{19}H_{19}Cl_2N_3O_3$.2HCl requires C, 47.42; H, 4.40; H, 8.73%.

EXAMPLE 86

Trans-2-methoxycarbonyl-5,7-dichloro-4-(4-aminoethylphenyl)carbonylamino-1,2,3,4-tetrahydroquinoline hydrochloride This compound was prepared by the method given for Example 82 using trans-2-carboxy-5,7-dichloro-4-(4-aminoethylphenyl)carbonylamino-1,2,3,4-tetrahydroquinoline hydrochloride Example 85, in the place of trans-2-carboxy-5,7-dichloro-4(3-aminomethylphenyl)-carbonylamino-1,2,3,4-tetrahydroquinoline hydrochloride to give the title compound as a colourless crystalline solid, m.p. 218° C. (dec). δ (DMSO, 360 MHz) 1.78 (1H, ddd, J=13.2, 12.8 and 4.1 Hz, $CH_ACH_BH_CCH_D$), 2.25 (1H, dm, J=13.2 Hz, $CH_ACH_BH_CCH_D$), 2.92 (2H, t, J=7.0 Hz, $CH_{E2}CH_{F2}$), 3.04 (2H, t, J=7.0 Hz, $CH_{E2}CH_{F2}$), 3.71 (3H, s, $CH_3$), 4.06 (1H, dd, J=12.5 and 2.4 Hz, $CH_ACH_BH_CCH_D$), 5.26 (1H, m, $CH_ACH_BH_CCH_D$), 6.69 (1H, d, J=2.0 Hz, 6-H or 8-H), 6.91 (1H, d, J=2.0 Hz, 6-H or 8-H), 6.94 (1H, s, Ar NHCH), 7.33 (2H, d, J=8.1 Hz, Ar-H), 7.86 (2H, d, J=8.1 Hz, Ar-H), 7.96 (2H, br, s, $NH_2$), 8.70 (1H, d, J=7.1 Hz, NHCO); m/e (CI+, $NH_3$) 422 (M+1); Found C, 48.59; H, 4.55; N, 8.48.$C_{20}H_{21}Cl_2N_3O_3$.2HCl requires C, 48.51; H, 4.68; N, 8.48%.

EXAMPLE 87

Trans-2-carboxy-4-(3-methylphenyl)methylcarbonylamino-5,7-dichloro-1,2,3,4-tetrahydroquinoline This compound was prepared by the method given for Example 37 using 3-methylphenylacetic acid in place of phenylacetic acid to give the title compound as colourless crystals, m.p. 169°-171° C. (δ (360 MHz, DMSO) 1.60 (1H, ddd, J=13.1, 12.5 and 4.0 Hz, $CH_ACH_BH_CCH_D$), 2.16 (1H, dm, J=13.1 Hz, $CH_ACH_BH_CCH_D$), 2.26 (3H, s, s, $CH_3$), 3.37 (2H, s, $CH_2$Ar), 3.84 (1H, dd, J=12.5 and 2.3 Hz, $CH_ACH_BH_CCH_D$), 5.00 (1H, m, $CH_ACH_BH_CCH_DNHCO$), 6.66 (1H, d, J=2.0 Hz, 6-H or 8-H), 6.79 (1H, s, br, ArNH), 6.88 (1H, d, J=2.0 Hz, 6-H or 8-H), 7.00-7.17 (4H, m, ArH), 8.42 (1H, d, J=7.1 Hz, $CH_DNHCO$); m/e 392 (M+), 105 (100%); Found C, 58.39; H, 4.98; N, 6.92. $C_{19}H_{18}Cl_2N_2O_3$ requires C, 58.03; H, 4.61; N, 7.12%.

EXAMPLE 88

Trans-2-carboxy-5,7-dichloro-4-(3-nitrophenyl)methyl carbonylamino-1,2,3,4-tetrahydroquinoline This compound was prepared using the same method given for Example 37 using 3-nitrophenylacetic acid in place of phenylacetic acid to give the title compound as yellow crystals, m.p. 260° C. δ (360 MHz, DMSO), 1.62 (1H, ddd, J=13.1, 12.6 and 3.9 Hz, $CH_ACH_BH_CCH_D$), 2.14 (1H, dm, J=13.1 Hz, $CH_ACH_BH_CCH_D$), 3.59 (2H, s, $ArCH_2CO$), 3.83 (1H, dd, J=12.6 and 2.6 Hz, $CH_ACH_BH_CCH_DNHCO$), 5.01 (1H, m, $CH_ACH_BH_CH_DNHCO$), 6.66 (1H, d, J=1.9 Hz, 6-H or 8-H), 6.82 (1H, s, ArNH), 6.89 (1H, d, J=1.9 Hz, 6-H or 8-H), 7.60 (1H, dd, J=7.9 and 7.8 Hz, ArH), 7.71 (1H, d, J=7.7 Hz, ArH), 8.10 (1H, dd, J=8.2 and 2.0 Hz, ArH), 8.17 (1H, d, J=2.0 Hz, ArH), 8.59 (1H, d, J=7.2 Hz, $CH_DNHCO$); m/e 423 (M+), 197 (100%); Found C, 51.05; H, 3.78; N, 9.69 $C_{18}H_{15}Cl_2N_3O_5$ requires C, 50.96; H, 3.56; N, 9.90%.

EXAMPLE 89

Trans-2-carboxy-5,7-dichloro-4-(3-methoxyphenyl)-methyl carbonylamino-1,2,3,4-tetrahydroquinoline This compound was prepared by the same method given for Example 36 using 3-methoxyphenylacetyl chloride in place of butyryl chloride to give the title compound as colourless crystals, m.p. 242°-244° C., δ (360 MHz, DMSO), 1.61 (1H, ddd, J=13.1, 12.6 and 3.9 Hz, $CH_ACH_BH_CCH_D$), 2.15 (1H, dm, J=13.1 Hz, $CH_ACH_BH_CCH_D$), 3.38 (2H, s, $ArCH_2CO$), 3.72 (3H, s, $CH_3OAr$), 3.85 (1H, dd, J=12.6 and 2.4 Hz, $CH_ACH_BH_CCH_D$), 5.00 (1H, m, $CH_ACH_BH_CCH_D$), 6.66 (1H, d, J=2.0 Hz, 6-H or 8-H), 6.76-6.82 (3H, m, ArH), 6.88 (1H, d, J=2.0 Hz, 6-H or 8-H), 7.18 (1H, dd, J=8.1 and 7.6 Hz, ArH), 8.43 (1H, d, J=7.1 Hz, $CH_DNHCO$); m/e (CI+), 409 (M+1), 166 (100%); Found C, 55.57; H, 4.64; N, 6.47. $C_{19}H_{18}Cl_2N_2O_4$ requires C, 55.76; H, 4.43; N, 6.84%.

EXAMPLE 90

Trans-2-carboxy-4-(1-naphthyl)methylcarbonylamino-5,7-dichloro-1,2,3,4-tetrahydroquinoline This compound was prepared by the method given for Example 37 using 1-naphthylacetic acid in place of phenylacetic acid to give the title compound as colourless crystals, m.p. 257°-258° C. δ (360 MHz, DMSO) 1.61 (1H, ddd, J=13.0, 12.5 and 4.0 OHz, $CH_ACH_BH_CCH_D$), 2.19 (1H, dm, J=13.0 Hz, $CH_ACH_BH_CCH_D$), 3.92 (3H, m, $CH_2Ar$ and $CH_ACH_BH_CCH_D$), 5.04 (1H, m, $CH_ACH_BH_CCH_D$), 6.68 (1H, d, J=1.9 Hz, 6-H or 8-H), 6.83 (1H, s, br, ArNH), 6.90 (1H, d, J=2.0 Hz, 6-H or 8-H), 7.43-8.08 (7H, m, ArH), 8.64 (1H, d, J=7.1 Hz, $CH_DNHCO$); m/e 4.28 (M+), 141 (100%); Found C, 61.25; H, 4.44; N, 6.35. $C_{22}H_{18}Cl_2N_2O_3$ requires C, 61.55; H, 4.23; N, 6.53%.

EXAMPLE 91

Trans-2-carboxy-4-(2-naphthyl)methylcarbonylamino-5,7-dichloro-1,2,3,4-tetrahydroquinoline This compound was prepared by the method given for Example 37 using 2-naphthylacetic acid in place of phenylacetic acid to give the title compound as colourless crystals, m.p. 217°-219° C. δ (360 MHz, DMSO) 1.63 (1H, ddd, J=13.1, 12.5 and 3.9 Hz, $CH_ACH_BH_CCH_D$), 2.19 (1H, dm, J=13.1 Hz, $CH_ACH_BH_CCH_D$), 3.60 (2H, s, $CH_2Ar$), 3.88 (1H, dd, J=12.5 and 2.9 Hz, $CH_ACH_BH_CCH_D$), 5.04 (1H, m, $CH_ACH_BH_CCH_D$), 6.67 (1H, d, J=1.9 Hz, 6-H or 8-H), 6.81 (1H, s, br, ArNH), 6.89 (1H, d, J=1.9 Hz, 6-H or 8-H), 7.40-7.88 (7H, m, ArH), 8.53 (1H, d, J=7.1 Hz, $CH_DNHCO$); m/e (CI+), 429 (M+1), 186 (100%); Found C, 61.93; H, 5.46; N, 5.58. $C_{22}H_{18}Cl_2N_2O_3$.$(C_2H_5)_2O$ requires C, 62.03; H, 5.61; N, 5.56%.

EXAMPLE 92

Trans-2-carboxy-4-(3-thiophenyl)methylcarbonylamino-5,7-dichloro-1,2,3,4-tetrahydroquinoline This compound was prepared by the method given for Example 37 using 3-thiopheneacetic acid in place of phenylacetic acid to give the title compound as colourless crystals, m.p. 198°–200° C.; δ (360 MHz, DMSO) 1.62 (1H, ddd, J=13.0, 12.4 and 4.0 Hz, CH$_A$CH$_B$H$_C$CH$_D$), 2.17 (1H, dm, J=13.0 Hz, CH$_A$CH$_B$H$_C$CH$_D$), 3.42 (2H, s, CH$_2$Ar), 3.84 (1H, dd, J=12.4 and 2.8 Hz, CH$_A$CH$_B$H$_C$CH$_D$), 5.01 (1H, m, CH$_A$CH$_B$H$_C$CH$_D$), 6.66 (1H, d, J=2.0 Hz, 6-H or 8-H), 6.79 (1H, s, br, ArNH), 6.88 (1H, d, J=2.0 Hz, 6-H or 8-H), 7.00 (1H, dd, J=4.9 and 1.1 Hz, thiophene 5-H), 7.21 (1H, dd, J=2.9 and 1.1 Hz, thiophene 2-H), 7.43 (1H, dd, J=4.9 and 2.9 Hz, thiophene 4-H), 8.39 (1H, d, J=7.0 Hz, CH$_D$NHCO); m/e 384 (M+), 97 (100%); Found C, 49.93; H, 3.78; N, 7.19. C$_{16}$H$_{14}$Cl$_2$N$_2$O$_3$ requires C, 49.88, H, 3.66; N, 7.27%.

EXAMPLE 93

Trans-2-carboxy-4-(2,6-dichlorophenyl)methylcarbonyl amino-5,7-dichloro-1,2,3,4-tetrahydroquinoline This compound was prepared by the method given for Example 37 using 2,6-dichlorophenylacetic acid in place of phenylacetic acid to give the title compound as colourless crystals, m.p. 235°–237° C.; δ (360 MHz, DMSO) 1.60 (1H, ddd, J=13.0, 12.5 and 3.9 Hz, CH$_A$CH$_B$H$_C$CH$_D$), 2.22 (1H, dm, J=13.0 Hz, CH$_A$CH$_B$H$_C$CH$_D$), 3.76 (1H, d, J=16.0 Hz, ArCH$_E$H$_F$CO), 3.82 (1H, d, J=16.0 Hz, ArCH$_E$H$_F$CO), 3.87 (1H, dd, J=12.5 and 2.9 Hz, CH$_A$CH$_B$H$_C$CH$_D$), 5.03 (1H, m, CH$_A$CH$_B$H$_C$CH$_D$), 6.67 (1H, d, J=2.0 Hz, 6-H or 8-H), 6.80 (1H, s, br, ArNH), 6.89 (1H, d, J=2.0 Hz, 6-H or 8-H), 7.30 (1H, t, J=7.6 Hz, para H), 7.44 (2H, d, J=7.6 Hz, meta H), 8.51 (1H, d, J=7.1 Hz, CH$_D$NHCO); Found C, 48.36; H, 3.44; N, 5.95. C$_{18}$H$_{14}$Cl$_2$N$_2$O$_3$ requires C, 48.24; H, 3.15; N, 6.25%.

EXAMPLE 94

Trans-2-carboxy-4-(phenylamino)thiocarbonylamino-5,7-dichloro-1,2,3,4-tetrahydroquinoline This compound was prepared by the method given for Example 38 using phenylisothiocyanate in place of phenylisocyanate to give the title compound as colourless crystals, m.p. 186°–187° C.; δ (360 MHz, DMSO) 1.64 (1H, ddd, J=13.0, 12.5 and 3.9 Hz, CH$_A$CH$_B$H$_C$CH$_D$), 2.63 (1H, dm, J=13.0 Hz, CH$_A$CH$_B$H$_C$CH$_D$), 3.86 (1H, dd, J=12.5 and 2.7 Hz, CH$_A$CH$_B$H$_C$CH$_D$), 5.51 (1H, m, CH$_A$CH$_B$H$_C$CH$_D$), 6.69 (1H, d, J=1.9 Hz, 6-H or 8-H), 6.80 (1H, s, br, ArNH), 6.90 (1H, d, J=1.9 Hz, 6-H or 8-H), 7.04–7.49 (5H, m, ArH), 8.09 (1H, d, J=7.1 Hz, CH$_D$NHCO), 9.31 (1H, s, br, ArNHCS); Found C, 51.43; H, 3.88; N, 10.52. C$_{17}$H$_{15}$Cl$_2$N$_3$O$_2$S requires C, 51.52; H, 3.82; N, 10.60%.

EXAMPLE 95

Trans-2-carboxy-4-phenylmethoxycarbonylamino-5,7-dichloro-1,2,3,4-tetrahydroquinoline Trans-4-amino-2-methoxycarbonyl-5,7-dichloro-1,2,3,4-tetrahydroquinoline hydrochloride (Example 9a) (0.3 g, 0.00096 ml) was dissolved in dichloromethane (30 ml) together with triethylamine (0.4 ml, 3 molar equivalents) and dibenzyl dicarbonate (0.33 g, 1.2 molar equivalents). The reaction mixture was stirred at room temperature for 14 h then dimethylethylenediamine (0.3 ml) was added and the reaction stirred for a further 2 h. The solvents were removed by evaporation and the residue redissolved in ethyl acetate (40 ml) and washed with 1 molar citric acid solution (2×30 ml), saturated sodium hydrogen carbonate solution (2×30 ml) and brine (1×30 ml). The organic layer was dried (Na$_2$SO$_4$), filtered and concentrated in vacuo to leave a residue which was purified by chromatography on silica gel using 20% ethyl acetate in hexane as eluent to give a white solid (0.24 g). This was suspended in 50% aqueous methanol (100 ml) and stirred at room temperature for 60 h in the presence of sodium hydroxide (0.2 g). The methanol was removed in vacuo and the aqueous residue acidified to pH 1 with 1M hydrochloric acid. The solid which was precipitated was extracted into ethyl acetate (2×50 ml), washed with brine (1×40 ml), dried (Na$_2$SO$_4$), filtered and concentrated in vacuo. The residue was recrystallised from diethyl ether/hexane to give the title compound as colourless crystals, m.p. 169° C.; δ (360 MHz, DMSO) 1.65 (1H, ddd, J=13.0, 12.4 and 4.0 Hz, CH$_A$CH$_B$H$_C$CH$_D$), 2.17 (1H, dm, J=13.0 Hz, CH$_A$CH$_B$H$_C$CH$_D$), 3.85 (1H, dm, J=12.4 Hz, CH$_A$CH$_B$H$_C$CH$_D$), 4.84 (1H, m, CH$_A$CH$_B$H$_C$CH$_D$), 5.02 (1H, d, J=12.6 Hz, PhCH$_E$H$_F$), 5.11 (1H, d, J=12.6 Hz, PhCH$_E$H$_F$), 6.64 (1H, d, J=2.0 Hz, 6-H or 8-H), 6.74 (1H, s, br, ArNH), 6.85 (1H, d, J=2.0 Hz, 6-H or 8-H), 7.32–7.36 (5H, m, ArH), 7.70 (1H, d, J=7.0 Hz, CH$_D$NHCO); m/e (CI−), 393 (M-1), 243 (100%); Found C, 54.84; H, 4.24; N, 6.85. C$_{18}$H$_{16}$Cl$_2$N$_2$O$_4$ requires C, 54.70; H, 4.08; N, 7.09%.

EXAMPLE 96

Trans-2-carboxy-5,7-dichloro-4-(3-methoxyphenyl)aminocarbonylamino-1,2,3,4-tetrahydroquinoline This compound was prepared by the method given in Example 38 using 3-methoxyphenylisocyanate in place of phenylisocyanate to give the title compound as colourless crystals, m.p. 181°–183° C.; δ (360 MHz, DMSO) 1.62 (1H, ddd, J=13.0, 12.4 and 3.9 Hz, CH$_A$CH$_B$H$_C$CH$_D$), 2.33 (1H, dm, J=13.0 Hz, CH$_A$CH$_B$H$_C$CH$_D$), 3.71 (3H, s, OCH$_3$), 3.88 (1H, dd, J=12.4 and 2.9 Hz, CH$_A$CH$_B$H$_C$CH$_D$), 4.93 (1H, m, CH$_A$CH$_B$H$_C$CH$_D$), 6.47–7.16 (8H, m, 6-H, 8-H, 4×ArH, CH$_D$NHCONHAr and ArNHCH$_A$), 8.16 (1H, s, CH$_D$NHCONHAr); m/e (FAB), 408 (M-1), 91 (100%); Found C, 52.70; H, 4.25; N, 10.11 C$_{18}$H$_{17}$Cl$_2$N$_3$O$_4$ requires C, 52.70; H, 4.18; N, 10.24%.

EXAMPLE 97

Trans-2-carboxy-5,7-dichloro-4-(3-methylphenyl)aminocarbonyl-amino-1,2,3,4-tetrahydroquinoline This compound was prepared by the method given in Example 38 using 3-methylphenylisocyanate instead of phenylisocyanate to give the title compound as colourless crystals, m.p. 172°–174° C.; δ (360 MHz, DMSO) 1.61 (1H, ddd, J=13.0, 12.5 and 3.9 HZ, CH$_A$CH$_B$H$_C$CH$_D$), 2.24 (3H, s, CH$_3$), 2.32 (1H, dm, J=13.0 Hz, CH$_A$CH$_B$H$_C$CH$_D$), 3.85 (1H, dd, J=12.5 and 2.8 Hz, CH$_A$CH$_B$H$_C$CH$_D$), 4.92 (1H, m, CH$_A$CH$_B$H$_C$CH$_D$), 6.49 (1H, d, J=6.5 Hz, CH$_D$NHCONHAr), 6.68 (1H, d, J=1.9 Hz, 6-H or 8-H)), 6.72 (1H, d, J=7.3 Hz, ArH), 6.77 (1H, s, br ArNHCH$_A$), 6.89 (1H, d, J=1.9 Hz, 6-H or 8-H), 7.07–7.23 (3H, m, ArH), 8.06 (1H, s, CH$_D$NHCONHAr),; m/e (FAB), 392 (M-1), 392 (100%); Found C, 54.24; H, 4.53; N, 10.10. C$_{18}$H$_{17}$Cl$_2$N$_3$O$_3$.0.3H$_2$O requires C, 54.10; H, 4.44; N, 10.51%.

EXAMPLE 98

Trans-2-carboxy-5,7-dichloro-4-(3-chlorophenyl)aminocarbonylamino-1,2,3,4-tetrahydroquinoline This compound was prepared by the method outlined in Example 38 using 3-chlorophenylisocyanate instead of phenylisocyanate to give the title compound as colourless crystals, m.p. 173°–175° C.; δ (360 MHz, DMSO) 1.62 (1H, ddd, J=13.0, 12.5 and 4.0 Hz, $CH_ACH_BH_CCH_D$), 2.31 (1H, dm, J=13.0 Hz, $CH_ACH_BH_CCH_D$), 3.86 (1H, dd, J=12.5 and 2.9 Hz, $CH_ACH_BH_CCH_D$), 4.93 (1H, m, $CH_ACH_BH_CCH_D$), 6.66 (2H, m, 6-H and $CH_DNHCONHAr$), 6.77 (1H, s, br, $ArNHCH_A$), 6.89 (1H, d, J=1.9 Hz, 6-H or 8-H), 6.94 (1H, dm, J=7.9 Hz, ArH), 7.16–7.26 (2H, m, 2×ArH), 7.69 (1H, m, ArH), 8.37 (1H, s, $CH_DNHCONHAr$); m/e (FAB), 412 (M-1), 183 (100%); Found C, 48.95; H, 3.44; N, 10.04. $C_{17}H_{14}Cl_3N_3O_3$ requires C, 49.24; H, 3.40; N, 10.13%.

EXAMPLE 99

Trans-2-carboxy-5,7-dichloro-4-(3-nitrophenyl)aminocarbonylamino-1,2,3,4-tetrahydroquinoline This compound was prepared by the method given in Example 38 using 3-nitrophenylisocyanate instead of phenylisocyanate to give the title compound as yellow crystals, m.p. 209°–210° C.; δ (360 MHz, DMSO) 1.66 (1H, ddd, J=13.0, 12.4 and 3.9 Hz, $CH_ACH_BH_CCH_D$), 2.33 (1H, dm, J=13.0 Hz, $CH_ACH_BH_CCH_D$), 3.90 (1H, dd, J=12.4 and 3.0 Hz, $CH_ACH_BH_CCH_D$), 4.97 (1H, m, $CH_ACH_BH_CCH_D$), 6.90 (1H, d, J=1.9 Hz, 6-H or 8-H), 6.80 (2H, m, $ArNHCH_A$ and $CH_DNHCONHAr$), 7.49–7.64 (3H, m, ArH), 8.54 (1H, m, ArH), 8.69 (1H, s, $CH_DNHCONHAr$); m/e (FAB), 423 (M-1), 183 (100%); Found C, 48.27; H, 3.59; N, 12.65. $C_{17}H_{14}Cl_2N_4O_5.0.2$ EtOAc requires C, 48.28; H, 3.55; N, 12.65%.

EXAMPLE 100

Trans-2-carboxy-4-(3-aminopropyl)carbonylamino-5,7-dichloro-1,2,3,4-tetrahydroquinoline hydrochloride a) 4-(Tertiarybutyloxycarbonylamino)butanoic acid 4-Amino butyric acid (2.06 g, 0.02M) was suspended in a solution of tetrahydrofuran (30 ml) and dichloromethane (20 ml) with triethylamine (2.77 ml, 1 molar equivalent) was ditertiarybutyl dicarbonate (4.36 g, 1 molar equivalent) was added. After stirring at room temperature for 14 h the solvents were evaporated and the residue was chromatographed on silica gel using 1% acetic acid, 4% methanol and 95% dichloromethane as eluent to give the required compound (1.9 g) as an oily solid; δ (250 MHz, DMSO) 1.37 (9H, s, $(CH_3)_3C$), 1.58 (2H, m, $HO_2CCH_2CH_2CH_2NHBoc$), 2.19 (2H, t, J=7.4 Hz, $HO_2CCH_2CH_2CH_2NHBoc$), 2.92 (2H, m, $HO_2CCH_2CH_2CH_2NHBoc$), 6.82 (1H, m, NH), 11.8–12.3 (1H, br, s, $CO_2H$); m/e (FAB), 204 (M+1).

b) Trans-2-carboxy-4-(3-aminopropyl)carbonylamino-5,7-dichloro-1,2,3,4-tetrahydroquinoline hydrochloride 4-(Tertiarybutyloxycarbonylamino)butanoic acid (0.3 g, 1.5 molar equivalents), 2-methoxycarbonyl-5,7-dichloro-4-amino-1,2,3,4-tetrahydroquinoline hydrochloride (Example 9a) (0.3 g, 0.000963M), hydroxybenzotriazole (0.156 g, 1.2 molar equivalents) and triethylamine (0.4 ml, 3 molar equivalents) were dissolved in anhydrous tetrahydrofuran (40 ml) followed by 1-(3-dimethylaminopropyl)-3-ethylcarbodiimide hydrochloride (0.22 g, 1.2 molar equivalents). After stirring at room temperature for 14 h the solvents were evaporated, the residue was dissolved in ethyl acetate (100 ml) and washed with 0.5M citric acid solution (2×50 ml), saturated sodium hydrogen carbonate solution (2×50 ml) and brine (1×50 ml). The organic layer was dried ($Na_2SO_4$), filtered and concentrated in vacuo to leave a residue which was dissolved in 50% aqueous methanol and treated with sodium hydroxide (0.5 g). After stirring the solution for 36 h at room temperature the methanol was removed under vacuum and the residual aqueous solution was treated with 1M HCl until a pH of 1 was attained. The precipitated solid was extracted into ethyl acetate (2×20 ml) and the combined organic layers were dried ($Na_2SO_4$), filtered and concentrated in vacuo. The residue obtained was treated with 5 molar HCl in ethyl acetate (30 ml) and stirred at room temperature for 60 h. The solvents were evaporated and the residue recrystallised from methanol/diethyl ether/ethyl acetate to give the title compound as a white crystalline solid, m.p. 238°–240° C.; δ (360 MHz, DMSO) 1.63 (1H, ddd, J=13.0, 12.4 and 3.9 Hz, $CH_ACH_BH_CCH_D$), 1.80 (2H, m, $NHCOCH_2CH_2CH_2NH_3^+$), 2.13–2.21 (3H, m, $CH_ACH_BH_CCH_D$ and $NHCOCH_2CH_2CH_2NH_3^+$), 2.77 (2H, t, J=7.6 Hz, $NHCOCH_2CH_2CH_2NH_3^+$), 3.84 (1H, dd, J=12.4 and 2.7 Hz, $CH_ACH_BH_CCH_D$), 5.02 (1H, m, $CH_ACH_BH_CCH_D$), 6.65 (1H, d, J=1.9 Hz, 6-H or 8-H), 6.83 (1H, s, br, ArNH), 6.88 (1H, d, J=1.9 Hz, 6-H or 8-H), 7.97 (3H, s, br, $NH_3^+$), 8.31 (1H, d, J=7.3 Hz, $CH_DNHCO$); Found C, 44.50; H, 4.95; N, 10.12. $C_{14}H_{17}N_3O_3Cl_2.HCl.0.25EtoAc$ requires C, 44.52; H, 4.98; N, 10.38%.

EXAMPLE 101

Trans-2-carboxy-4-(3-aminoethyl)carbonylamino-5,7-dichloro-1,2,3,4-tetrahydroquinoline hydrochloride This compound was prepared by the method described in Example 100b using 3-(tertiarybutyloxycarbonylamino)propanoic acid instead of 4-(tertiarybutyloxycarbonylamino)butanoic acid to give the title compound as colourless crystals, m.p. 214°–215° C.; δ (360 MHz, DMSO) 1.64 (1H, ddd, J=12.9, 12.5 and 4.0 Hz, $CH_ACH_BH_CCH_D$), 2.19 (1H, dm, J=12.9 Hz, $CH_ACH_BH_CCH_D$), 2.49 (2H, t, J=7.2 Hz, $NHCOCH_2CH_2NH_3^+$), 2.99 (2H, t, J=7.2 Hz, $NHCOCH_2CH_2NH_3^+$), 3.84 (1H, dd, J=12.5 and 2.9 Hz, $CH_ACH_BH_CCH_D$), 5.04 (1H, m, $CH_ACH_BH_CCH_D$), 6.66 (1H, d, J=2.0 Hz, 6-H or 8-H), 6.81 (1H, s, br, ArNH), 6.88 (1H, d, J=2.0 Hz, 6-H or 8-H), 7.92 (3H, s, br, $NH_3^+$), 8.45 (1H, d, J=7.3 Hz, $CH_DNHCO$); m/e (FAB), 332 (M+1); Found C, 42.23; H, 4.28; N, 11.36. $C_{13}H_{15}N_3O_3Cl_2.HCl$ requires C, 42.36; H, 4.37; N, 11.40%.

EXAMPLE 102

Trans-2-carboxy-4-(4-aminobutyl)carbonylamino-5,7-dichloro-1,2,3,4-tetrahydroquinoline hydrochloride This compound was prepared by the method described in Example 100a and 100b using 5-amino valeric acid instead of 4-aminobutyric acid to give the title compound as colourless crystals, m.p. 160° C. (dec); δ (360 MHz, DMSO) 1.56–1.65 (5H, m, $CH_ACH_BH_CCH_D$ and $NHCOCH_2CH_2CH_2CH_2NH_3^+$), 2.08–2.17 (3H, m, $NHCOCH_2CH_2CH_2CH_2NH_3^+$), 2.75 (2H, m, $NhCOCH_2CH_2CH_2CH_2NH_3^+$ and $CH_ACH_BH_CCH_D$), 3.83 (1H, dd, J=12.4 and 2.8 Hz, CH$_A$CH$_B$H$_C$CH$_D$), 5.02 (1H, m, CH$_A$CH$_B$H$_C$CH$_D$), 6.65 (1H, d, J=1.9 Hz, 6-H or 8-H), 6.79 (1H, s, br, ArNH), 6.88 (1H, d, J=1.9 Hz, 6-H or 8-H), 7.94 (3H, s, br, NH$_3^+$), 8.20 (1H, d, J=7.2 Hz, CH$_D$NHCO); Found C, 44.60; H, 5.05; N, 10.10. C$_{15}$H$_{19}$Cl$_2$N$_3$O$_3$. HCl.0.5H$_2$O requires C, 44.41; H, 5.22; N, 10.36%.

EXAMPLE 103

Trans-2-carboxy-4-(4-piperidylmethyl)carbonylamino-5,7-dichloro-1,2,3,4-tetrahydroquinoline hydrochloride This compound was prepared by the method described in Example 100a and 100b using 4-piperidine acetic acid in place of 4-aminobutyric acid to give the title compound as colourless crystals, m.p. 175° C. (dec); δ (360MHz, DMSO) 1.33-3.21 (1H, m, piperidylmethyl protons and CH$_A$CH$_B$H$_C$CH$_D$), 3.81 (1H, dd, J=12.4 and 2.7Hz, CH$_A$CH$_B$H$_C$CH$_D$), 5.02 (1H, m, CH$_A$CH$_B$H$_C$CH$_D$), 6.65 (1H, d, J=2.0 Hz, 6-H or 8-H), 6.80 (1H, br, s, ArNH), 6.88 (1H, d, J=2.0 Hz, 6-H or 8-H), 8.27 (1H, d, J=7.2 Hz, CH$_D$NHCO), 8.8 (2H, s, br, NH$_2^+$); Found C, 46.75; H, 5.17; N, 9.42. C$_{17}$H$_{21}$Cl$_2$N$_3$O$_3$.HCl.0.75H$_2$O requires C, 46.80; H, 5.43; N, 9.63%.

EXAMPLE 104

Trans-2-carboxy-4-(4-aminomethylphenyl)methylcarbonylamino-5,7-dichloro-1,2,3,4-tetrahydroquinoline hydrochloride This compound was prepared by the route outlined in Example 100a and 100b using 4-aminomethylphenylacetic acid in place of 4-aminobutyric acid to give the title compound as colourless crystals, m.p. 248°-250° C.; δ (360 MHz, DMSO) 1.62 (1H, ddd, J=13.0, 12.6 and 4.0 Hz, CH$_A$CH$_B$H$_C$CH$_D$), 2.14 (1H, dm, J=13.0 Hz, CH$_A$CH$_B$H$_C$CH$_D$), 3.44 (2H, d, J=2.3 Hz, COCH$_2$PhCH$_2$NH$_3^+$), 3.86 (1H, dd, J=12.6 and 2.6 Hz, CH$_A$CH$_B$H$_C$CH$_D$), 3.98 (2H, s, COCH$_2$PhCH$_2$NH$_3^+$), 5.00 (1H, m, CH$_A$CH$_B$H$_C$CH$_D$), 6.67 (1H, d, J=1.9 Hz, 6-H or 8-H), 6.82 (1H, s, br, ArnH), 6.89 (1H, d, J=1.9 Hz, 6-H or 8-H), 7.28 (2H, d, J=8.1 Hz, 2×ArH), 7.39 (2H, d, J=8.1 Hz, 2×ArH), 8.34 (3H, br, s, NH$_3^+$), 8.50 (1H, d, J=7.3 Hz, CH$_D$NHCO); Found C, 50.10; H, 4.77; N, 8.98. C$_{19}$H$_{19}$N$_3$O$_3$Cl$_2$.HCl.0.5H$_2$O requires C, 50.29; H, 4.66; N, 9.26%.

EXAMPLE 105

Trans-2-methoxycarbonyl-4-(4-aminomethylphenyl)methylcarbonylamino-5,7-dichloro-1,2,3,4-tetrahydroquinoline hydrochloride This compound was prepared by the method given in Example 82 using trans-2-carboxy-4(-4-aminomethylphenyl)-methylcarbonylamino-5,7-dichloro-1,2,3,4-tetrahydroquinoline hydrochloride (Example 104) in place of trans-2-carboxy-4(3-aminomethylphenyl)carbonylamino-5,7-dichloro-1,2,3,4tetrahydroquinoline hydrochloride to give the title compound as colourless crystals, m.p. 172°-174° C.; δ (360 MHz, DMSO) 1.66 (1H, ddd, J=13.0, 12.5 and 4.0 Hz, CH$_A$CH$_B$H$_C$CH$_D$), 2.14 (1H, dm, J=13.0 Hz, CH$_A$CH$_B$H$_C$CH$_D$), 3.44 (2H, s, COCH$_2$PhCH$_2$NH$_3^+$), 3.73 (3H, s, CH$_3$), 3.98 (3H, m, CH$_A$CH$_B$H$_C$CH$_D$ and COCH$_2$PhCH$_2$NH$_3^+$), 5.00 (1H, m, CH$_A$CH$_B$H$_C$CH$_D$), 6.70 (1H, d, J=2.0 Hz, 6-H or 8-H), 6.88 (1H, d, J=2.0 Hz, 6-H or 8-H), 7.28 (2H, d, J=8.0 Hz, 2×ArH), 7.40 (2H, d, J=8.0 Hz, 2×ArH), 8.36 (3H, br, s, NH$_3^+$), 8.51 (1H, d, J=7.4 Hz, CH$_D$NHCO); m/e (CI+), 422 (M+1), 165 (100%).

EXAMPLE 106

Trans-4-(4-aminoethylphenyl)methylcarbonylamino-2-carboxy-5,7-dichloro-1,2,3,4-tetrahydroquinoline hydrochloride Step a Methyl-4-tertiary-butyloxycarbonylamino ethylphenylacetate To a solution of 4-cyanomethylphenylacetic acid (1.0 g, 5.7 mmol) in a mixture of water (150 ml), 15% aqueous potassium hydroxide (20 ml) and concentrated aqueous ammonia (50 ml) was added a slurry of Raney nickel in water (approx. 0.5 g) and the resulting mixture was hydrogenated at room temperature under 50 psi for 2.25 h. The mixture was then filtered and evaporated to dryness in vacuo. The residue was then dissolved in water (100 ml), acidified with concentrated hydrochloric acid, washed with ethyl acetate (2×75 ml) and the aqueous phase was freeze-dried to give a solid. To a solution of this solid in a mixture of water (40 ml) and 1,4-dioxan (40 ml) was added anhydrous sodium carbonate (2.01 g, 19.9 mmol) and di-tertiarybutyldicarbonate (2.62 g, 12.0 mmol) and the mixture was stirred at room temperature for 2 hours. The organic solvent was then removed under vacuum and the aqueous residue was diluted with water (100 ml) and washed with diethyl ether (2×75 ml). The aqueous phase was acidified with concentrated hydrochloric acid and extracted with ethyl acetate (2×75 ml). The combined extracts were washed with saturated brine solution (1×75 ml), dried (MgSO$_4$) and evaporated to give the crude intermediate as an oil. This preparation was repeated using 1.13 g of 4-cyanomethylphenylacetic acid (6.46 mmol) and the resulting oil was combined with that from above. To a solution of this crude material in diethyl ether (300 ml) was added a solution of diazomethane (16 mmol) in diethyl ether (80 ml) and the mixture was allowed to stand at room temperature for 0.25 h. The reaction was then quenched with glacial acetic acid (0.5 ml) and the mixture was washed with saturated sodium bicarbonate solution (3×100 ml), saturated brine solution (1×100 ml), dried (MgSO$_4$) and evaporated. The resulting solid was purified using flash chromatography (using 30% ethyl acetate in petroleum ether bp 60°-80° as eluent) to give the title compound as colourless crystals (3.00 g), m.p. 77°-78° C. δ (360 MHz, CDCl$_3$) 1.43 (9H, s, C(CH$_3$)$_3$), 2.77 (2H, m, ArCH$_2$CH$_2$NHBoc), 3.36 (2H, m, ArCH$_2$CH$_2$NHBoc), 3.60 (2H, s, ArCH$_2$CO$_2$CH$_3$), 3.69 (3H, s, ArCH$_2$CO$_2$CH$_3$). 4.54 (1H, br, s, ArCH$_2$CH$_2$NHBoc), 7.14 (2H, d, J=8.0 Hz, ArH), 7.21 (2H, d, J=8.0 Hz, ArH); m/e (CI−) 292 (100%, m-H).

Step b
4-Tertiary-butyloxycarbonylaminoethylphenylacetic acid

To a solution of methyl 4-(tertiarybutyloxy carbonylaminoethyl)-phenylacetate (0.500 g, 1.71 mmol) in a mixture of tetrahydrofuran (20 ml) and water (10 ml) was added aqueous lithium hydroxide (3.8 ml of a 0.50M solution, 1.90 mmol) and the resulting mixture was stirred at room temperature for 16 h. The organic solvent was removed under vacuum and the residue was diluted with water (40 ml), acidified with concentrated hydrochloric acid and extracted with ethyl acetate (2×30 ml). The combined extracts were washed with brine (1×30 ml), dried (MgSO4) and evaporated to give the pure title compound as colourless crystals (0.460 g), m.p. 94°–95° C. δ (360 MHz, CDCl3) 1.42 (9H, s, C(CH3)3), 2.77 (2H, br, m, ArCH2CH2NHBoc), 3.35 (2H, br, m, ArCH2CH2NHBoc), 3.61 (2H, s, ArCH2CO2H), 4.57 (1H, br, s, ArCH2CH2NHBoc), 7.14 (2H, d, J=7.7 Hz, ArH), 7.21 (2H, d, J=7.7 Hz, ArH); m/e (CI$^-$) 278 (100%, m-H).

Step c: Trans-(4-(4-tertiary-butyloxycarbonylaminoethylphenyl)methylcarbonylamino-5,7-dichloro-2-methoxycarbonyl-1,2,3,4-tetrahydroquinoline This material was prepared using the method given for Example 37 Step a using 4-(tertiarybutyloxycarbonylaminoethyl) phenylacetic acid in place of phenylacetic acid to give the title compound as colourless crystals, m.p. 219°–221° C. δ (360 MHz, DMSO) 1.37 (9H, s, C(CH3)3), 1.65 (1H, ddd, J=13.0, 12.6 and 3.8 Hz, CH$_A$CH$_B$H$_C$CH$_D$), 2.15 (1H, dm, J=13.0 Hz, CH$_A$CH$_B$H$_C$CH$_D$), 2.66 (2H, m, ArCH2CH2NHBoc), 3.10 (2H, m, ArCH2CH2NHBoc), 3.37 (2H, s, NHCOCH2Ar), 3.72 (3H, s, CO2CH3), 3.95 (1H, dd, J=12.6 and 2.5 Hz, CH$_A$CH$_B$H$_C$CH$_D$), 5.00 (1H, m, CH$_A$CH$_B$H$_C$CH$_D$NHCO), 6.69 (1H, d, J=1.9 Hz, 6-H or 8-H), 6.83 (1H, br, m, ArCH2CH2NHBoc), 6.87 (1H, d, J=1.9 Hz, 6-H or 8-H), 6.91 (1H, s, ArNH), 7.0–9 (2H, d, J=8.0 Hz, ArH), 7.15 (2H, d, J=8.0 Hz, ArH), 8.43 (1H, d, J=7.0 Hz, CH$_D$NHCOCH2Ar); m/e (CI$^+$) 536 (m+H), 179 (100%).

Step d: Trans-4-(4-aminoethylphenyl)methylcarbonylamino-2-carboxy-5,7-dichloro-1,2,3,4-tetrahydroquinoline hydrochloride To a solution of trans-4-(4-tertiary-butyloxycarbonyl aminoethylphenyl)methylcarbonylamino-5,7-dichloro-2-methoxycarbonyl-1,2,3,4-tetrahydroquinoline (0.095 g, 0.177 mmol) in a mixture of tetrahydrofuran (10 ml) and water (5 ml) was added aqueous lithium hydroxide (0.40 ml of a 0.50M solution, 0.20 mmol) and the resulting mixture was stirred at room temperature for 1 h. The organic solvent was then removed under vacuum, and the residue was diluted with sodium bicarbonate solution (40 ml) and washed with diethyl ether (1×30 ml). The aqueous phase was then acidified with concentrated hydrochloric acid and extracted with ethyl acetate (2×40 ml). The combined extracts were washed with brine (1×40 ml), dried (MgSO4) and evaporated to give an oil. To a solution of this oil in ethyl acetate (5 ml) was added a saturated solution of hydrogen chloride in ethyl acetate (5 ml) and the mixture was stirred at room temperature for 35 min. The solid was collected by filtration, washed with ethyl acetate and dried to give the title compound as colourless crystals (0.075 g), m.p. 142°–145° C. δ (360 MHz, DMSO) 1.62 (1H, ddd, J=12.8, 12.5 and 3.9 Hz, CH$_A$CH$_B$H$_C$CH$_D$), 2.15 (1H, dm, J=12.8 Hz, CH$_A$CH$_B$H$_C$CH$_D$), 2.85 (2H, m, ArCH2CH2NH3), 3.01 (2H, m, ArCH2CH2NH3), 3.40 (2H, s, NHCOCH2Ar), 3.86 (1H, dd, J=12.5 and 2.4 Hz, CH$_A$CH$_B$H$_C$CH$_D$), 5.00 (1H, m, CH$_A$CH$_B$H$_C$CH$_D$NHCO), 6.66 (1H, d, J=2.0 Hz, 6-H or 8-H), 6.82 (1H, s, ArNH), 6.89 (1H, d, J=2.0 Hz, 6-H or 8-H), 7.17 (2H, d, J=8.2 Hz, ArH), 7.21 (2H, d, J=8.2 Hz, ArH), 7.98 (3H, br s, NH3), 8.45 (1H, d, J=7.1 Hz, CH$_D$NHCO-); m/e (FAB$^+$) 422 (M+H); Found C, 50.87; H, 5.20; N, 8.55; C20H21Cl2N3O3.HCl.0.8H2O.0.2 EtOAc requires C, 50.70; H, 5.18; N, 8.56.

EXAMPLE 107

Trans-4-(4-aminoethylphenyl)methylcarbonylamino-5,7-dichloro-2-methoxycarbonyl-1,2,3,4-tetrahydroquinoline hydrochloride To a solution of trans-4-(4-tertiary-butyloxycarbonylaminoethylphenyl)methylcarbonylamino-5,7-dichloro-2-methoxycarbonyl-1,2,3,4-tetrahydroquinoline (Example 106c) (0.150 g, 0.28 mmol) in ethyl acetate (5 ml) was added a saturated solution of hydrogen chloride in ethyl acetate (5 ml) and the resulting mixture was stirred at room temperature for 40 minutes. The solvent was then removed under vacuum and the residue was triturated with hot ethyl acetate. A gummy solid was collected by filtration and this was dissolved in water and freeze dried to give the title compound as a colourless solid (0.121 g), m.p. decomposes above 200° C. δ (360 MHz, DMSO 1.65 (1H, ddd, J=13.0, 12.5 and 3.8 Hz, CH$_A$CH$_B$H$_C$CH$_D$), 2.14 (1H, dm, J=13.0 Hz, CH$_A$CH$_B$H$_C$CH$_D$), 2.86 (2H, m, ArCH2CH2NH3), 3.00 (2H, m, ArCH2CH2NH3), 3.36 (2H, s, NHCOCH2Ar), 3.72 (3H, s, CO2CH3), 3.97 (1H, dd, J=12.5 and 2.5 Hz, CH$_A$CH$_B$H$_C$CH$_D$), 5.00 (1H, m, CH$_A$CH$_B$H$_C$CH$_D$NHCO), 6.69 (1H, d, J=2.0 Hz, 6-H or 8-H), 6.88 (1H, d, J=2.0 Hz, 6-H or 8-H), 6.93 (1H, s, ArNH), 7.17 (2H, d, J=8.2 Hz, ArH), 7.21 (2H, d, J=8.2 Hz, ArH), 8.04 (3H, brs, NH3), 8.49 (1H, d, J=7.0 Hz, CH$_D$NHCO); m/e 435 (M$^+$), 198 (100%, M-NHCOCH2C6H4CH2CH2NH2, CO2CH3 and H); Found C, 51.47; H, 5.37; N, 8.60; C21H23Cl2N3O3.HCl.H2O requires C, 51.39; H, 5.34; N, 8.56%.

EXAMPLE 108

Trans-2-carboxy-5,7-dichloro-4-(4-N-methylaminomethylphenyl)methyl-carbonylamino-1,2,3,4-tetrahydroquinoline hydrochloride Step a) 4-N-tertiary-butyloxycarbonyl-N-methylaminomethylphenylacetic acid To a solution of 4-(bromomethyl)phenylacetic acid (8.58 g, 37.5 mmol) in anhydrous N,N-dimethylformamide (200 ml) was added methylamine hydrochloride (25.3 g, 375 mmol) and dry triethylamine (63.0 ml, 450 mmol). The resulting mixture was stirred under an atmosphere of nitrogen at room temperature for 16.5 h. The reaction was then concentrated in vacuo and the resulting residue was partitioned between ethyl acetate (200 ml) and 1M hydrochloric acid (200 ml). The aqueous layer was separated, washed with ethyl acetate (200 ml) and the pH adjusted to 14 by the addition of solid sodium hydroxide. The alkaline solution was washed with diethyl ether (2×100 ml), then re-acidified with concentrated hydrochloric acid and evaporated in vacuo to give the crude amino acid hydrochloride as a mixture with inorganic material. To a solution of this solid in water (100 ml) was added 1,4-dioxan (100 ml), sodium carbonate (13.1 g, 124 mmol) and di-tertiary-butyldicarbonate (18.0 g, 82 mmol) and the reaction was stirred at room temperature for 3 h. The organic solvent was removed under vacuum and the aqueous residue was washed with diethyl ether (2×75 ml), acidified by the addition of concentrated hydrochloric acid and extracted with ethyl acetate (2×75 ml). The combined extracts were washed with brine (1×75 ml), dried (MgSO4) and evaporated in vacuo to give the crude N-protected amino acid as an oil (0.91 g). To a solution of this oil (0.91 g, 3.3 mmol) in ethanol (50 ml) at room temperature was added sufficient of a solution of diazomethane (~5 mmol) in diethyl ether (~90 ml) to allow a yellow colour to persist. The excess diazomethane was then destroyed by the addition of glacial acetic acid (1 ml) and the mixture was concentrated in vacuo. The residue was dissolved in diethyl ether (5 ml), washed with saturated sodium bicarbonate solution (3×25 ml), brine (1×25 ml), dried (MgSO$_4$) and evaporated to give an oil which was purified by flash chromatography on silica gel using a gradient of 10–15% ethyl acetate in petroleum ether bp (60°–80°) as eluent, to give the pure fully protected amino acid as a clear oil (0.549 g). To a solution of this oil (0.532 g, 1.82 mmol) in a mixture of tetrahydrofuran (30 ml) and water (15 ml) was added aqueous lithium hydroxide (4.0 ml of a 0.50M solution) and the reaction was stirred at room temperature for 3 h. The organic solvent was removed under vacuum and the aqueous mixture was diluted with water (40 ml), acidified with concentrated hydrochloric acid and extracted with ethyl acetate (2×25 ml). The combined extracts were washed with brine (1×25 ml), dried (MgSO$_4$) and evaporated in vacuo to give the title compound as colourless crystals (0.50 g), mp 122°–125° C. δ (250 MHz, CDCl$_3$) 1.47 (9H, s, C(CH$_3$)$_3$), 2.80 (3H, brs, N-CH$_3$), 3.63 (2H, s, ArCH$_2$CO$_2$H), 4.40 (2H, s, ArCH$_2$N-), 7.18 (2H, d, J=8.2 Hz, ArH), 7.25 (2H, d, J=8.2 Hz, ArH); m/e (FAB+) 280 (M+1)+.

Step b) Trans-4-(4-N-tertiary-butyloxycarbonyl-N-methylaminomethylphenyl)methylcarbonylamino-5,7-dichloro-2-methoxycarbonyl-1,2,3,4-tetrahydroquinoline This material was prepared using the method given for Example 37, Step a) using 4-N-tertiary-butyloxycarbonyl-N-methyl-aminomethylphenylacetic acid in place of phenylacetic acid, yielding the crude product which was purified by flash chromatography on silica gel, using 45% ethyl acetate in petroleum ether bp (60°–80°). Recrystallisation from ethyl acetate-petroleum ether bp (60°–80°) gave the title compound as colourless crystals, mp 128°–129.5° C. δ (360 MHz, DMSO) 1.41 (9H, s, C(CH$_3$)$_3$), 1.65 (1H, m, CH$_A$CH$_B$H$_C$CH$_D$), 2.15 (1H, dm, J=13.2 Hz, CH$_A$CH$_B$H$_C$CH$_D$), 2.73 (3H, s, N-CH$_3$), 3.39 (2H, s, ArCH$_2$CO), 3.72 (3H, s, CO$_2$CH$_3$), 3.94 (1H, dm, J=12.6 Hz, CH$_A$CH$_B$H$_C$CH$_D$), 4.33 (2H, s, ArCH$_2$N), 5.00 (1H, m, CH$_A$CH$_B$H$_C$CH$_D$), 6.68 (1H, d, J=2.0 Hz, 6-H or 8-H), 6.87 (1H, d, J=2.0 Hz, 6-H or 8-H), 6.91 (1H, s, ArNH), 7.13 (2H, d, J=8.0 Hz, ArH), 7.22 (2H, d, J=8.0 Hz, arH), 8.44 (1H, d, J=7.1 Hz, CH$_D$NHCO); m/e (CI−) 535 (100%, M).

Step c) Trans-2-carboxy-5,7-dichloro-4-(4-N-methylaminomethylphenyl)methylcarbonylamino-1,2,3,4-tetrahydroquinoline hydrochloride This material was prepared using the method given for Example 106, Step d) using trans-4-(4-N-tertiary-butyloxycarbonyl-N-methylaminomethylphenyl)methylcarbonylamino-5,7-dichloro-2-methoxycarbonyl-1,2,3,4-tetrahydroquinoline to give the title compound as colourless crystals, mp 140° C. dec. δ (360 MHz, CD$_3$OH) 1.69 (1H, ddd, J=13.3, 12.7 and 3.9 Hz, CH$_A$CH$_B$H$_C$CH$_D$), 2.37 (1H, dm, J=13.3 Hz, CH$_A$CH$_B$H$_C$CH$_D$), 2.68 (3H, s, NCH$_3$), 3.53 (2H, s, ArCH$_2$CO), 3.90 (1H, dd, J=12.7 and 2.8 Hz, CH$_A$CH$_B$H$_C$CH$_D$), 4.14 (2H, s, ArCH$_2$N), 5.14 (1H, m, CH$_A$CH$_B$H$_C$CH$_D$), 6.62 (1H, d, J=1.9 Hz, 6-H or 8-H), 6.71 (1H, d, J=1.9 Hz, 6-H or 8-H), 7.40 (4H, s, ArH); m/e (FAB−) 420 (M−1)−; Found C, 50.95; H, 5.12; N, 8.61%; C$_{20}$H$_{21}$Cl$_2$N$_3$O$_3$.HCl.0.8H$_2$O. 0.16 CH$_3$CO$_2$Et requires C, 50.88; H, 5.15; N, 8.62%.

EXAMPLE 109

Trans-5,7-dichloro-2-methoxycarbonyl-4(4-N-methylaminomethylphenyl)methylcarbonylamino-1,2,3,4-tetrahydroquinoline hydrochloride This material was prepared using the method given for Example 107 using trans-4-(4-N-tertiary-butyloxycarbonyl-N-methylaminomethylphenyl)methylcarbonylamino-5,7-dichloro-2-methoxycarbonyl-1,2,3,4-tetrahydroquinoline in place of trans-4-(4-tertiary-butyloxycarbonylaminoethylphenyl)methylcarbonylamino-5,7-dichloro-2-methoxycarbonyl-1,2,3,4-tetrahydroquinoline to give the title compound as colourless crystals, m.p. 140° C. dec. δ (360 MHz, DMSO) 1.66 (1H, ddd, J=13.1, 12.7 and 3.9 Hz, CH$_A$CH$_B$H$_C$CH$_D$), 2.14 (1H, dm, J=13.1 Hz, CH$_A$CH$_B$H$_C$CH$_D$), 2.50 (3H, s, NCH$_3$), 3.45 (2H, s, ArCH$_2$CO), 3.73 (3H, s, CO$_2$CH$_3$), 3.98 (1H, dd, J=12.7 and 2.8 Hz, CH$_A$CH$_B$H$_C$CH$_D$), 4.03–4.07 (2H, m, ArCH$_2$N), 5.00 (1H, m, CH$_A$CH$_B$H$_C$CH$_D$), 6.69 (1H, d, J=2.0 Hz, 6-H or 8-H), 6.88 (1H, d, J=2.0 Hz, 6-H or 8-H), 7.29 (2H, d, J=8.0 Hz, ArH), 7.45 (2H, d, J=8.0 Hz, ArH), 8.56 (1H, d, J=7.2 Hz, CH$_D$NHCO), 9.20–9.43 (2H, m, br, −NH$_2$+Me); m/e (FAB+) 436 (M+H)+; Found C, 51.03; H, 5.27; N, 8.37%; C$_{21}$H$_{23}$Cl$_2$N$_3$O$_3$.HCl.1.2 H$_2$O requires C, 51.01; H, 5.38; N, 8.50%.

EXAMPLE 110

Trans-5,7-dichloro-4-(4-N,N-dimethylaminomethylphenyl)methylcarbonylamino-2-methoxycarbonyl-1,2,3,4-tetrahydroquinoline Step a) Ethyl 4-(tertiary-butyloxycarbonylaminomethyl)phenylacetate To a refluxing suspension of 4-(bromomethyl)-phenylacetic acid (20.63 g, 90.1 mmol) in chloroform (160 ml) was slowly added a solution of hexamethylenetetramine (13.4 g, 95.5 mmol) in chloroform (110 ml). The resulting mixture was heated at reflux under an atmosphere of nitrogen for 2.5 h, then cooled to room temperature and the colourless solid which had formed was collected by filtration. A solution of this solid in a mixture of concentrated hydrochloric acid (50 ml) and ethanol (140 ml) was heated at reflux for 1 h, then cooled, filtered and the filtrate was concentrated in vacuo to yield an oily solid. This solid was dissolved in ethanol (300 ml) and the solution was saturated with hydrogen chloride gas with cooling in ice then stirred at room temperature for 18 h. After evaporation of the solvent under vacuum, the residue was dissolved in water (500 ml) and washed with ethyl acetate (2×200 ml). The aqueous phase was separated, basified with solid sodium bicarbonate, extracted with ethyl acetate (3×200 ml), then basified further with solid sodium carbonate and again extracted with ethyl acetate (5× 100 ml). The combined extracts were washed with brine (1×300 ml), dried (MgSO$_4$) and evaporated to give the crude amine ester as an oil (13.5 g). To a solution of this oil (13.5 g) in dichloromethane (350 ml) was added di-tertiary-butyldicarbonate (21.0 g, 96 mmol) and the resulting mixture was stirred at room temperature under an atmosphere of nitrogen for 4 h. To the reaction was then added N,N-dimethylethylenediamine (8.4 ml, 76 mmol) and stirring was continued for 0.5 h. The mixture was then washed successively with 1M aqueous citric acid (2×700 ml), saturated aqueous sodium bicarbonate solution (2×700 ml), brine (1×200 ml) then dried (MgSO4) and evaporated to give a brown oil. This was purified by flash chromatography on silica gel using 20% ethyl acetate in petroleum ether bp (60°-80°) as eluent to yield the title compound as a colourless oil (13.46 g). δ (360 MHz, CDCl3) 1.25 (3H, t, J=7.2 Hz, CH2CH3), 1.46 (9H, s, C(CH3)3), 3.59 (2H, s, ArCH2CO), 4.14 (2H, q, J=7.2 Hz, CH2CH3), 4.29 (2H, br, ArCH2N), 7.24 (4H, s, ArH); m/e (CI−) 292 (M-H)−.

Step b) Ethyl 4-(aminomethyl)phenylacetate hydrochloride

To a solution of ethyl 4-(tertiary-butyloxycarbonylaminomethyl)phenylacetate (1.50 g, 5.1 mmol) in ethyl acetate (10 ml) was added a saturated solution of hydrogen chloride in ethyl acetate (20 ml) and the resulting mixture was stirred at room temperature in a stoppered flask for 2 h. The reaction was then concentrated in vacuo and the solid residue was triturated with hot ethyl acetate and collected by filtration to give the title compound as colourless crystals (1.11 g), mp 184°-186° C. δ (360 MHz, D2O) 1.27 (3H, t, J=7.2 Hz, CH2CH3), 3.79 (2H, s, ArCH2CO), 4.17-4.23 (4H, m, ArCH2N+ and CH2CH3), 7.39 (2H, d, J=8.2 Hz, ArH), 7.46 (2H, d, J=8.2 Hz, ArH); m/e (CI+) 194 (M+H)+.

Step c) Ethyl 4-(N,N-dimethylaminomethyl)phenylacetate

A solution of ethyl 4-(aminomethyl)phenylacetate hydrochloride (2.00 g, 8.71 mmol) in water (100 ml) was basified by the addition of sodium carbonate, then saturated with sodium chloride and extracted with ethyl acetate (3×50 ml). The combined extracts were dried (MgSO4) and evaporated to give an oil. To a solution of this oil in acetonitrile (50 ml) was added aqueous formaldehyde (3.5 ml of a 37% solution, 43 mmol) and sodium cyanoborohydride (approx. 0.9 g, 14 mmol) and the resulting cloudy mixture was stirred at room temperature for 0.5 h. Sufficient glacial acetic acid to give a pH of 5 (when tested on wet indicator paper) was then added and stirring was continued for 1.2 h. The reaction was quenched with dilute aqueous sodium carbonate (50 ml), and the organic solvent was removed under vacuum to give an aqueous residue which was extracted with ethyl acetate (3×20 ml). The combined extracts were concentrated in vacuo and partitioned between 1M hydrochloric acid (75 ml) and diethyl ether (30 ml). The aqueous phase was separated, washed with ethyl acetate (2×30 ml) then basified with sodium carbonate, saturated with sodium chloride and extracted with ethyl acetate (3×20 ml). The combined extracts were washed with saturated brine (30 ml), dried (MgSO4) and evaporated to give the title compound as an oil (0.545 g). δ (360 MHz, CDCl3) 1.25 (3H, t, J=7.1 Hz, CH2CH3), 2.23 (6H, s, N(CH3)2), 3.40 (2H, s, ArCH2CO), 3.59 (2H, s, ArCH2N), 4.14 (2H, q, J=7.1 Hz, CH2CH3), 7.22-7.29 (4H, m, ArH); m/e (EI) 221 (100%, M+).

Step d) 4-(N,N-dimethylaminomethyl)phenylacetic acid

To a solution of ethyl 4-(N,N-dimethylaminomethyl)phenylacetate (0.470 g, 2.13 mmol) in a mixture of tetrahydrofuran (15 ml) and water (5 ml) was added aqueous lithium hydroxide (4.7 ml, 2.34 mmol) and the resulting mixture was stirred at room temperature for 4 h. The organic solvent was removed under vacuum and the aqueous residue was freeze dried to give the crude lithium salt. This material was applied to an ion-exchange resin (Dowex 50W×8), eluted with dilute aqueous ammonia and freeze dried to give the title compound as a non-crystalline solid (0.368 g). δ (360 MHz, DMSO) 2.13 (6H, s, N(CH3)2), 3.36 (2H, s, ArCH2CO), 3.49 (2H, s, ArCH2N), 7.18 (4H, s, ArH); m/e (FAB−) 192 (M-H)−.

Step e) Trans-5,7-dichloro-4-(4-N,N-dimethylaminomethylphenyl)methylcarbonylamino-2-methoxycarbonyl-1,2,3,4-tetrahydroquinoline A solution of trans-4-amino-5,7-dichloro-2-methoxycarbonyl-1,2,3,4-tetrahydroquinoline hydrochloride (0.35 g, 1.12 mmol) in water (50 ml) was basified with sodium carbonate, saturated with sodium chloride and extracted with ethyl acetate (2×30 ml). The combined extracts were washed with brine (1×30 ml), dried (MgSO4) and evaporated to give the free base as a solid (0.28 g). To a solution of this material (0.28 g, 1.02 mmol) in anhydrous tetrahydrofuran (30 ml) were added 4-N,N-dimethylaminomethylphenylacetic acid (0.216 g, 1.12 mmol), 1-hydroxybenzotriazole (0.151 g, 1.12 mmol) and N,N'-dicyclohenxylcarbodiimide (0.231 g, 1.12 mmol) and the resulting mixture was stirred at room temperature under an atmosphere of nitrogen for 18 h. The reaction was concentrated in vacuo and the residue was suspended in ethyl acetate (50 ml) and extracted with 1M hydrochloric acid (4×20 ml). The combined aqueous extracts were washed with ethyl acetate (1×20 ml), filtered, basified with sodium carbonate, saturated with sodium chloride and extracted with ethyl acetate (3×20 ml). The combined extracts were washed with brine (20 ml), dried (MgSO4) and evaporated under vacuum to give the crude product which was purified by flash chromatography on silica gel using dichloromethane containing 8% methanol and 0.1% ammonia as eluent, followed by recrystallisation from ethyl acetate/petroleum ether bp (60°-80°), to give the title compound as colourless crystals (0.261 g), mp 182°-183° C. δ (360 MHz, DMSO) 1.64 (1H, m, CH$_A$CH$_B$H$_C$CH$_D$), 2.10-2.17 (7H, m, CH$_A$CH$_B$H$_C$CH$_D$ and N(CH3)2), 3.34 (2H, s, ArCH2N or ArCH2CO), 3.39 (2H, s, ArCH2N or ArCH2CO), 4.03 (1H, dm, J= 12.2 Hz, CH$_A$CH$_B$H$_C$CH$_D$), 5.00 (1H, m, CH$_A$CH$_B$H$_C$CH$_D$), 6.69 (1H, d, J=2.0 Hz, 6-H or 8-H), 6.87 (1H, d, J=2.0 Hz, 6-H or 8-H), 6.90 (1H, s, ArNH), 7.16-7.21 (4H, m, ArH), 8.43 (1H, d, J=7.1 Hz, CH$_D$NHCO); m/e (FAB+) 450 (M)+; Found C, 58.72; H, 5.65; N, 9.22%. C22H25Cl2N3O3 requires C, 58.67; H, 5.60; N, 9.33%.

EXAMPLE 111

Trans-2-carboxy-5,7-dichloro-4(4-N,N-dimethylaminomethylphenyl)methylcarbonylamino-1,2,3,4-tetrahydroquinoline To a solution of trans-5,7-dichloro-4(4-N,N-dimethylaminomethylphenyl)methylcarbonylamino-2-methoxycarbonyl-1,2,3,4-tetrahydroquinoline (Example 110, 0.120 g, 0.267 mmol) in a mixture of tetrahydrofuran (10 ml) and water (5 ml) was added aqueous lithium hydroxide (0.58 ml of a 0.50M solution, 0.29 mmol) and the resulting mixture was stirred at room temperature for 2 h. The reaction was then evaporated to dryness in vacuo to give a solid which was applied to an ion-exchange resin (Dowex 50 W×8), and eluted with dilute aqueous ammonia. The solution was then freeze dried to give the crude product which was triturated with hot methanol and collected by filtration to yield the title compound as a colourless solid (0.032 g), mp 190°-193° C. δ (360 MHz, DMSO, 320° K.) 1.57 (1H, m, CH$_A$CH$_B$H$_C$CH$_D$) 2.18-2.22 (7H, m, CH$_A$CH$_B$H$_C$CH$_D$ and N(CH3)2), 3.41 (2H, s, ArCH2N or ArCH2CO), 3.43 (2H, s, ArCH2N or ArCH2CO), 3.79 (1H, dd, J=12.6 and 2.0 Hz, CH$_A$CH$_B$H$_C$CH$_D$), 5.01 (1H, m, CH$_A$CH$_B$H$_C$CH$_D$), 6.62 (1H, d, J=2.0 Hz, 6-H or 8-H), 6.87 (1H, d, J=2.0 Hz, 6-H or 8-H), 7.21 (4H, s, br, ArH), 8.27 (1H, d, J=7.0 Hz, CH$_D$NHCO); m/e (FAB+) 436 (M+H)$^{30}$; Found C, 54.54; H, 5.54; N, 9.15%; C$_{21}$H$_{23}$Cl$_2$N$_3$O$_3$. 1.5 H$_2$O requires C, 54.44; H, 5.66; N, 9.07%.

EXAMPLE 112

Trans-2-carboxy-4-(4-(3-aminoprop-2-ynyl)phenyl)methylcarbonylamino-5,7-dichloro-1,2,3,4-tetrahydroquinoline hydrochloride a) 4-(3-Hydroxyprop-2-ynyl)phenylacetic acid methyl ester 4-Bromophenylacetic acid methyl ester (23 g, 0.1 mol) was dissolved in dry triethylamine (80 ml) with propynol (5.82 ml, 0.1 mol). After the addition of cuprous iodide (0.3 g) and bis (triphenylphosphine)palladium (II) chloride (1 g) the reaction mixture was heated at 65° C. under nitrogen for 14 h. The solvent was evaporated under vacuum and the residue was dissolved in ethyl acetate (500 ml) and washed successively with 0.5M citric acid solution (2×200 ml), saturated sodium hydrogen carbonate solution (2×200 ml) and brine (1×150 ml). The organic solution was dried (Na$_2$SO$_4$), filtered and concentrated in vacuo to give an oil which was purified by chromatography on silica gel using 20% ethyl acetate in hexane as eluent to give the required compound (5.6 g) as an oil. δ (360 MHz, CDCl$_3$) 3.62 (2H, s, CH$_2$CO$_2$CH$_3$), 3.69 (3H, s, CH$_2$CO$_2$CH$_3$), 4.48 (1H, s, HOCH$_2$), 7.22 (2H, d, J=8.2 Hz, ArH), 7.39 (2H, d, J=8.2 Hz, ArH); m/e 204 (M+).

b) 4-(3-Chloroprop-2-ynyl)phenylacetic acid methyl ester

To a solution of 4-(3-Hydroxyprop-2-ynyl)phenylacetic acid methyl ester (5.5 g, 0.027M) in tetrahydrofuran (110 ml) and carbon tetrachloride (110 ml) was added triphenylphosphine (7.81 g, 1.1 molar equivalents). The reaction mixture was heated at 60° C. for 3 h. After cooling, the solid obtained was removed by filtration and the mother liquors were concentrated under vacuum. The residue was purified by chromatography on silica gel using 50% diethyl ether in hexane as eluent to give the required product (5.35 g) as a colourless oil. δ (360 MHz, CDCl$_3$) 3.62 (2H, s, CH$_2$CO$_2$CH$_3$), 3.69 (3H, s, CH$_2$CO$_2$CH$_3$), 4.36 (2H, s, CH$_2$Cl), 7.23 (2H, d, J=8.2 Hz, ArH), 7.40 (2H, d, J=8.2 Hz, ArH).

c) 4-(3-Azidoprop-2-ynyl)phenylacetic acid methyl ester 4-(3-Chloroprop-2-ynyl)phenylacetic acid methyl ester (5.3 g, 0.023M) was dissolved in dry dimethylformamide (30 ml) with sodium azide (1.7 g, 1.1 molar equivalents) and stirred at room temperature for 14 h. The reaction mixture was diluted with water (200 ml) and washed with dichloromethane (2×150 ml). The combined organic layers were washed with water (2×100 ml) and brine (1×100 ml) then dried (Na$_2$SO$_4$), filtered and concentrated in vacuo to give a residue which was purified by passage down a silica gel column, using as eluents 20% dichloromethane in hexane and finally neat dichloromethane, to give the required product (5.3 g) as a colourless oil. δ (360 MHz, CDCl$_3$) 3.63 (2H, s, CH$_2$CO$_2$CH$_3$), 3.70 (3H, s, CH$_2$CO$_2$CH$_3$), 4.14 (2H, s, CH$_2$N$_3$), 7.24 (2H, d, J=8.4 Hz, ArH), 7.42 (2H, d, J=8.4 Hz, ArH); m/e 229 (M+).

d) 4-(3-(Tertiary-butyloxycarbonylamino)-prop-2-ynyl)phenylacetic acid methyl ester 4-(3-Azidoprop-2-ynyl)phenylacetic acid methyl ester (2.6 g, 0.0113 mol) was dissolved in methanol (60 ml) in the presence of triethylamine (7.86 ml, 5 molar equivalents) and propane 1,3-dithiol (5.67 ml, 5 molar equivalents). After stirring at room temperature for 14 h the reaction mixture was concentrated under vacuum and the residue was purified by silica gel chromatography, using initially neat dichloromethane then finally 5% methanol in dichloromethane. After evaporation of the solvents the residue obtained was dissolved in dichloromethane (100 ml) and triethylamine (3.13 ml, 2 molar equivalents) and ditertiary-butyldicarbonate (3.0 g, 1.2 molar equivalents) were added. After stirring at room temperature for 14 h the solvent was removed in vacuo and the oil obtained was purified by chromatography on silica gel using dichloromethane as eluent to give the required product as a viscous oil (1.95 g). δ (360 MHz, CDCl$_3$) 1.47 (9H, s, (CH$_3$)$_3$C), 3.61 (2H, s, CH$_2$CO$_2$CH$_3$), 3.69 (3H, s, CH$_2$CO$_2$CH$_3$), 4.13 (2H, br, d, J=4.92 Hz, CH$_2$NH), 4.76 (1H, br, NH), 7.21 (2H, d, J=8.2 Hz, ArH), 7.36 (2H, d, J=8.2 Hz, ArH).

e) 4-(3-(Tertiary-butyloxycarbonylamino)prop-2-ynyl)phenylacetic acid 4-(3-Tertiarybutyloxycarbonylamino)-prop-2-ynyl-phenylacetic acid methyl ester (1.9 g) was dissolved in 50% aqueous methanol (100 ml) with sodium hydroxide (1 g) and the solution stirred at room temperature for 14 h. After this time the methanol was removed under vacuum and the aqueous residue was treated with 1N hydrochloric acid until a pH of 1 was obtained. The precipitate produced was extracted into ethyl acetate (2×200 ml), the organic layer was dried (Na$_2$SO$_4$), filtered and concentrated in vacuo to give the required product (1.7 g) as a white solid. δ (360 MHz, CDCl$_3$) 1.47 (9H, s, (CH$_3$)$_3$C), 3.63 (2H, s, CH$_2$CO$_2$H), 4.13 (2H, br, s, CH$_2$NH), 4.81 (1H, br, s, NH). 7.21 (2H, d, J=8.1 Hz, ArH), 7.35 (2H, d, J=8.1 Hz, ArH).

f) Trans-2-carboxy-4-(4-(3-aminoprop-2-ynyl)-phenyl)methylcarbonylamino-5,7-dichloro-1,2,3,4-tetrahydroquinoline hydrochloride This compound was prepared by the route outlined in Example 100b using 4-(3-(tertiarybutyloxycarbonylamino)prop-2-ynyl)phenylacetic acid in place of 4-(tertiarybutyloxycarbonylamino)butanoic acid to give the title compound as colourless crystals, m.p. 162°-164° C.; δ (360 MHz, DMSO) 1.61 (1H, ddd, J=13.0, 12.6 and 4.0 Hz, CH$_A$CH$_B$H$_C$CH$_D$), 2.14 (1H, dm, J=13.0 Hz, CH$_A$CH$_B$H$_C$CH$_D$), 3.46 (2H, s, CH$_2$CONHCH$_D$), 3.84 (1H, dd, J=12.6 and 2.6 Hz, CH$_A$CH$_B$H$_C$CH$_D$), 4.99 (1H, m, CH$_A$CH$_B$H$_C$CH$_D$), 6.65 (1H, d, J=2.0 Hz, 6-H or 8-H), 6.81 (1H, br, s, ArNH), 6.89 (1H, d, J=2.0 Hz, 6-H or 8-H), 7.29 (2H, d, J=8.2 Hz, ArH), 7.39 (2H, d, J=8.2 Hz, ArH), 8.50 (1H, d, J=7.2 Hz, CH$_D$NHCO); m/e FAB 432 M+1; Found C, 50.32; H, 4.31; N, 8.16. C$_{21}$H$_{19}$N$_3$O$_3$Cl$_2$.2HCl requires C, 49.92; H, 4.19; N, 8.32%.

EXAMPLE 113

Trans-2-methoxycarbonyl-4-(4-(3-aminoprop-2-ynyl)-phenyl)methylcarbonylamino-5,7-dichloro-1,2,3,4-tetrahydroquinoline hydrochloride This compound was prepared by the method given in Example 82 using trans-2-carboxy-4-(4-(3-aminoprop-2-ynyl)phenyl)methylcarbonylamino-5,7-dichloro-1,2,3,4-tetrahydroquinoline hydrochloride (Example 112) in place of trans-2-carboxy-4-(3-aminomethyl-phenyl)carbonylamino-5,7-dichloro-1,2,3,4-tetrahydroquinoline hydrochloride to give the title compound as colourless crystals, m.p. 202° C. dec; δ (360 MHz, DMSO) 1.66 (1H, ddd, J=13.0, 12.4 and 3.9 Hz, CH$_A$CH$_B$H$_C$CH$_D$), 2.13 (1H, dm, J=13.0 Hz, CH$_A$CH$_B$H$_C$CH$_D$), 3.46 (2H, s, CH$_2$CONH), 3.72 (3H, s, CO$_2$CH$_3$), 3.96 (3H, m, CH$_A$CH$_B$H$_C$CH$_D$ and CH$_2$NH$_3^+$), 4.99 (1H, m, CH$_A$CH$_B$H$_C$CH$_D$), 6.69 (1H, d, J=1.9 Hz, 6-H or 8-H), 6.87 (1H, d, J=1.9 Hz, 6-H or 8-H), 7.30 (2H, d, J=8.2 Hz, ArH), 7.39 (2H, d, J=8.2 Hz, ArH), 8.56 (4H, m, ArNH and CH$_2$NH$_3^+$); m/e FAB 446 (M+1); Found C, 48.11; H, 4.41; N, 7.68. C$_{22}$H$_{21}$Cl$_2$N$_3$O$_3$.2.5HCl.0.8H$_2$O requires C, 47.88; H, 4.58; N, 7.61%.

EXAMPLE 114

Trans-2-carboxy-4-(4-(3-aminopropyl)phenyl)methylcarbonylamino-5,7-dichloro-1,2,3,4-tetrahydroquinoline hydrochloride a) 4-(3-(Tertiary-butyloxycarbonylamino)propyl)-phenylacetic acid methyl ester 4-(3-Azidoprop-2-ynyl)phenylacetic acid methyl ester (Example 112c) (2.6 g, 0.0113 m) was dissolved in ethyl acetate (100 ml) with ditertiarybutyl dicarbonate (5.9 g, 2.4 molar equivalents) and after the addition of 10% palladium on carbon catalyst (0.25 g) the reaction mixture was shaken under a 50 p.s.i. pressure of hydrogen for 14 h. The catalyst was removed by filtration and the organic solution was concentrated in vacuo to leave a residue which was purified by chromatography on silica gel, using 10% ethyl acetate in dichloromethane as eluent, to give the required product (2.07 g) as an oil; δ (360 MHz, CDCl$_3$) 1.44 (9H, s, COC(CH$_3$)$_3$), 1.79 (2H, m, CH$_2$CH$_2$CH$_2$NH), 2.61 (2H, t, J=7.6 Hz, CH$_2$CH$_2$CH$_2$NH), 3.14 (2H, m, CH$_2$CH$_2$CH$_2$NH), 3.58 (2H, s, CH$_2$CO$_2$CH$_3$), 3.68 (3H, s, CH$_2$CO$_2$CH$_3$), 4.52 (1H, br, s, NH), 7.12 (2H, d, J=8.1 Hz, ArH), 7.19 (2H, d, J=8.1 Hz, ArH); m/e (CI) 308 (M+1).

b) 4-(3-(Tertiarybutyloxycarbonylamino)propyl)-phenylacetic acid 4-(3-(Tertiarybutoxycarbonylamino)propyl)phenylacetic acid methyl ester (2.0 g) was dissolved in 50% aqueous methanol (100 ml) with sodium hydroxide (1 g) and stirred at room temperature for 14 h. The methanol was removed under vacuum and the residual aqueous solution was acidified to pH1 using 1N hydrochloric acid, and the resulting precipitate extracted into ethyl acetate (2×100 ml). The combined organic extracts were dried (Na$_2$SO$_4$), filtered and concentrated under vacuum to give the required product as a white solid (1.82 g). δ (360 MHz, CDCl$_3$) 1.44 (9H, s, COC(CH$_3$)$_3$, 1.78 (2H, m, CH$_2$CH$_2$CH$_2$NH), 2.60 (2H, t, J=7.5 Hz, CH$_2$CH$_2$CH$_2$NH), 3.13 (2H, m, CH$_2$CH$_2$CH$_2$NH), 3.60 (2H, s, CH$_2$CO$_2$H), 4.57 (1H, br, s, NH), 7.12 (2H, d, J=8.0 Hz, ArH), 7.19 (2H, d, J=8.0 Hz, ArH); m/e (CI) 294 (M+1).

c) Trans-2-carboxy-4-(4-(3-aminopropyl)phenyl)methylcarbonylamino-5,7-dichloro-1,2,3,4-tetrahydroquinoline hydrochloride This compound was prepared by the route outlined in Example 100b using 4-(3-(tertiarybutyloxycarbonylamino)propyl)phenylacetic acid in place of 4-(tertiarybutyloxycarbonylamino)butanoic acid to give the title compound as colourless crystals, m.p. 161°-164° C.; δ (360 MHz, DMSO) 1.62 (1H, ddd, J=13.0, 12.4 and 4.0 Hz, CH$_A$CH$_B$H$_C$CH$_D$), 1.85 (2H, m, CH$_2$CH$_2$CH$_2$NH$_3^+$), 2.15 (1H, dm, J=13.0 Hz, CH$_A$CH$_B$H$_C$CH$_D$), 2.61 (2H, t, J=7.5 Hz, CH$_2$CH$_2$CH$_2$NH$_3^+$), 2.75 (2H, m, CH$_2$CH$_2$CH$_2$NH$_3^+$), 3.37 (2H, s, NHCOCH$_2$), 3.86 (1H, dd, J=12.4 and 2.8 Hz, CH$_A$CH$_B$H$_C$CH$_D$), 4.99 (1H, m, CH$_A$CH$_B$H$_C$CH$_D$), 6.66 (1H, d, J=1.9 Hz, 6-H or 8-H), 6.70 (1H, br, s, ArNH), 6.89 (1H, d, J=1.9 Hz, 6-H or 8-H), 7.12 (2H, d, J=7.6 Hz, ArH), 7.18 (2H, d, J=7.6 Hz, ArH), 7.94 (3H, br, s, NH$_3^+$), 8.44 (1H, d, J=7.2 Hz, NHCOCH$_2$); m/e (FAB) 436 (M+1); Found C, 52.42; H, 5.48; N, 8.39. C$_{21}$H$_{23}$Cl$_2$N$_3$O$_3$.HCl.0.6H$_2$O requires C, 52.16; H, 5.25; N, 8.69%.

EXAMPLE 115

Trans-4-methoxycarbonyl-4-(4-(3-aminopropyl)-phenyl)methylcarbonylamino-5,7-dichloro-1,2,3,4-tetrahydroquinoline hydrochloride This compound was prepared by the method described in Example 82 using trans-2-carboxy-4-(4-(3-aminopropyl)phenyl)methylcarbonylamino-1,2,3,4-tetrahydroquinoline hydrochloride in place of trans-2-carboxy-4-(3-aminomethylphenyl)carbonylamino-5,7-dichloro-1,2,3,4-tetrahydroquinoline hydrochloride to give the title compound a colourless crystals, m.p. 140° C. dec; δ (360 MHz, DMSO) 1.65 (1H, ddd, J=13.0, 12.5 and 3.9 Hz, CH$_A$CH$_B$H$_C$CH$_D$), 1.85 (2H, m, CH$_2$CH$_2$CH$_2$NH$_3^+$), 2.14 (1H, dm, J=13.0 Hz, CH$_A$CH$_B$H$_C$CH$_D$), 2.61 (2H, t, J=7.6 Hz, CH$_2$CH$_2$CH$_2$NH$_3^+$), 2.76 (2H, m, CH$_2$CH$_2$CH$_2$NH$_3^+$), 3.38 (2H, s, NHCOCH$_2$), 3.72 (3H, s, CO$_2$CH$_3$), 3.96 (1H, dd, J=12.5 and 2.7 Hz, CH$_A$CH$_B$H$_C$CH$_D$), 5.00 (1H, m, CH$_A$CH$_B$H$_C$CH$_D$), 6.69 (1H, d, J=1.9 Hz, 6-H or 8-H), 6.88 (1H, d, J=1.9 Hz, 6-H or 8-H), 7.14 (4H, m, ArH), 8.01 (3H, br, s, NH$_3^+$), 8.49 (1H, d, J=7.2 Hz, NHCOCH$_2$); m/e (FAB) 450 (M+1); Found C, 49.82; H, 5.10; N, 7.83. C$_{22}$H$_{25}$Cl$_2$N$_3$O$_3$.2HCl.0.5H$_2$O requires C, 49.64; N, 5.30; N, 7.89%.

EXAMPLE 116

Trans-2-carboxy-4(4-(4-aminobut-2-ynyl)phenyl)methylcarbonylamino-5,7-dichloro-1,2,3,4-tetrahydroquinoline hydrochloride This compound was prepared by the methods given in Example 112a), b), c), d), and e) and Example 100b) using but-3-yn-1-ol in place of propynol (in Example 112a) to give the title compound as colourless crystals, m.p. 162° C. dec; δ (360 MHz, DMSO) 1.61 (1H, ddd, J=13.0, 12.4 and 4.0 Hz, CH$_A$CH$_B$H$_C$CH$_D$), 2.16 (1H, dm, J=13.0 Hz, CH$_A$CH$_B$H$_C$CH$_D$), 2.79 (2H, t, J=7.1 Hz, CH$_2$CH$_2$NH$_3^+$), 3.03 (2H, t, J=7 Hz, CH$_2$CH$_2$NH$_3^+$), 3.44 (2H, s, NHCOCH$_2$), 3.86 (1H, dd, J=12.4 and 2.7 Hz, CH$_A$CH$_B$H$_C$CH$_D$), 5.00 (1H, m, CH$_A$CH$_B$H$_C$CH$_D$), 6.65 (1H, d, J=1.9 Hz, 6-H or 8-H), 6.75 (1H, br, s, ArNH), 6.89 (1H, d, J=1.9 Hz, 6-H or 8-H), 7.25 (2H, d, J=8.2 Hz, ArH), 7.37 (2H, d, J=8.2 Hz, ArH), 8.14 (3H, br, s, NH$_3^+$), 8.42 (1H, d, J=7.1 Hz, CH$_D$NHCO); m/e (FAB) 444 (M-1); Found C, 52.92; H, 4.76; N, 8.08. C$_{22}$H$_{21}$Cl$_2$N$_3$O$_3$.HCl.H$_2$O requires C, 52.76; H, 4.83; N, 8.39%.

EXAMPLE 117

Trans-2-methoxycarbonyl-4(4-(4-aminobut-2-ynyl)-phenyl)methylcarbonylamino-5,7-dichloro-1,2,3,4-tetrahydroquinoline hydrochloride This compound was prepared by the method given in Example 82 using trans-2-carboxy-4-(4(4-aminobut-2-ynyl)phenyl)methylcarbonylamino-5,7-dichloro-1,2,3,4-tetrahydroquinoline hydrochloride in place of trans-2-carboxy-4-(3-aminomethylphenyl)carbonylamino-5,7-dichloro-1,2,3,4-tetrahydroquinoline hydrochloride to give the title compound as colourless crystals, m.p. 162° C. dec; δ (360 MHz, DMSO) 1.66 (1H, ddd, J=12.9, 12.4 and 3.9 Hz, $CH_ACH_BH_CCH_D$), 2.14 (1H, dm, J=12.9 Hz, $CH_ACH_BH_CCH_D$), 2.79 (2H, t, J=7.1 Hz, $CH_2CH_2NH_3^+$), 3.03 (2H, m, $CH_2CH_2NH_3^+$), 3.44 (2H, s, $NHCOCH_2$), 3.73 (3H, s, $CO_2CH_3$), 3.95 (1H, m, $CH_ACH_BH_CCH_D$), 5.00 (1H, m, $CH_ACH_BH_CCH_D$), 6.70 (1H, d, J=2.0 Hz, 6-H or 8-H), 6.89 (1H, d, J=2.0 Hz, 6-H or 8-H), 7.25 (2H, d, J=8.2 Hz, ArH), 7.39 (2H, d, J=8.2 Hz, ArH), 8.15 (3H, br, s, $NH_3^+$), 8.51 (1H, d, J=7.2 Hz, $NHCOCH_2$); m/e 459 (M+); Found C, 50.41; H, 4.66; N, 7.62. $C_{23}H_{23}Cl_2N_3O_3.2HCl.H_2O$ requires C, 50.11; H, 4.94; N, 7.62%.

EXAMPLE 118

Trans-2-carboxy-4(4-(4-aminobutyl)phenyl)methylcarbonylamino-5,7-dichloro-1,2,3,4-tetrahydroquinoline hydrochloride This compound was prepared by the methods given in Examples 112a), b), c), 114a), b) and 100b) using but-3-yn-1-ol in place of propynol (in Example 112a) to give the title compound as colourless crystals, m.p. 110° C. dec; δ (360 MHz, DMSO) 1.60 (5H, m, $CH_ACH_BH_CCH_D$ and $CH_2CH_2CH_2CH_2NH_3^+$), 2.16 (1H, dm, J=12.9 Hz, $CH_ACH_BH_CCH_D$), 2.57 (2H, t, J=6.8 Hz, $CH_2CH_2CH_2CH_2NH_3^+$), 2.78 (2H, t, J=7.2 Hz, $CH_2CH_2CH_2CH_2NH_3^+$), 3.38 (2H, s, $NHCOCH_2$), 3.86 (1H, dd, J=12.4 and 2.7 Hz, $CH_ACH_BH_CCH_D$), 5.01 (1H, m, $CH_ACH_BH_CCH_D$), 6.66 (1H, d, J=1.9 Hz, 6-H or 8-H), 6.74 (1H, br, s, ArNH), 6.89 (1H, d, J=1.9 Hz, 6-H or 8-H), 7.11 (2H, d, J=8.1 Hz, ArH), 7.17 (2H, d, J=8.1 Hz, ArH), 7.86 (3H, br, s, $NH_3^+$), 8.37 (1H, d, J=7.2 Hz, $CH_DNHCO$); m/e (FAB) 450 (M+1); Found C, 52.73; H, 5.58; N, 7.87. $C_{22}H_{25}Cl_2N_3O_3.HCl.H_2O$ requires C, 52.34; H, 5.59; N, 8.32%.

EXAMPLE 119

Trans-2-methoxycarbonyl-4(4-(4-aminobutyl)phenyl)methylcarbonylamino-5,7-dichloro-1,2,3,4-tetrahydroquinoline hydrochloride This compound was prepared by the method given in Example 82 using trans-2-carboxy-4(4-(4-aminobutyl)phenyl)methylcarbonylamino-5,7-dichloro-1,2,3,4-tetrahydroquinoline hydrochloride in place of trans-2-carboxy-4-(3-aminomethylphenyl)carbonylamino-5,7-dichloro-1,2,3,4-tetrahydroquinoline hydrochloride to give the title compound as colourless crystals, m.p. 138°–140° C.; δ (360 MHz, DMSO) 1.64 (5H, m, $CH_ACH_BH_CCH_D$ and $CH_2CH_2CH_2CH_2NH_3^+$), 2.15 (1H, dm, J=13.0 Hz, $CH_ACH_BH_CCH_D$), 2.57 (2H, t, J=7.1 Hz, $CH_2CH_2CH_2CH_2NH_3^+$), 2.79 (2H, m, $CH_2CH_2CH_2CH_2NH_3^+$), 3.39 (2H, s, $NHCOCH_2$), 3.74 (3H, s, $CO_2CH_3$), 3.98 (1H, dd, J=12.4 and 2.8 Hz, $CH_ACH_BH_CCH_D$), 5.01 (1H, m, $CH_ACH_BH_CCH_D$), 6.70 (1H, d, J =1.9 Hz, 6-H or 8-H), 6.89 (1H, d, J=1.9 Hz, 6-H or 8-H), 7.15 (4H, m, ArH), 7.92 (3H, br, s, $NH_3^+$), 8.48 (1H, d, J=7.2 Hz, $CH_DNHCO$); m/e (FAB) 464 (M+1); Found C, 50.04; H, 5.32; N, 7.51. $C_{23}H_{27}Cl_2N_3O_3.2HCl.H_2O$ requires C, 49.75; H, 5.62; N, 7.57%.

EXAMPLE 120

Trans-4-(3-aminomethylphenyl)methylcarbonylamino-2-carboxy-5,7-dichloro-1,2,3,4-tetrahydroquinoline hydrochloride Step a) 3-Bromomethylphenyl acetic acid methyl ester A solution of 3-tolyacetic acid (5 g, 33 mmol) and N-bromosuccinimide (5.9 g, 33 mmol) in carbon tetrachloride (100 ml) was refluxed for 3 hours then cooled and filtered. The solvent was removed under vacuum to yield a crude product to which was added methanol (250 ml) which had been saturated with hydrogen chloride (250 ml) and this mixture was stirred at room temperature for 4 hours. The solvent was removed under vacuum and the crude residue was purified using flash chromatography (using ethyl acetate in hexane as eluent) to yield the title compound (7.3 g) as a yellow oil. δ (250 MHz, $CDCl_3$) 3.58 (2H, s, $CH_2CO_2CH_3$), 3.69 (3H, s, $CO_2CH_3$), 4.47 (2H, s, $CH_2Br$), 7.24 (4H, m, ArH).

Step b) 3-Azidomethylphenyl acetic acid methyl ester

To a solution of 3-bromomethylphenyl acetic acid methyl ester (7.3 g, 30 mmol) in N,N-dimethylformamide (100 ml) was added sodium azide (2.53, 33 mmol) and the solution was stirred at room temperature for 18 hours. The reaction mixture was poured into water (600 ml), extracted into ethyl acetate (3×100 ml) and the combined extracts were washed with water (2×100 ml) and brine solution (2×100 ml), dried ($MgSO_4$) and evaporated to give a crude product, which was purified by flash chromatography (using ethyl acetate in hexane as eluent) to give the title compound as an oil (4.2g); δ (360 MHz, $CDCl_3$) 3.64 (2H, s, $CH_2CO_2CH_3$), 3.69 (3H, s, $CO_2CH_3$), 4.33 (2H, s, $CH_2N_3$), 7.31 (4H, m, ArH).

Step c) 3-(Tertiarybutyloxycarbonylaminomethyl)phenyl acid methyl ester

This material was prepared using the method given for Example 114 step a) using 3-azidomethylphenyl acetic acid methyl ester in place of 4-(3-azidoprop-2-ynyl)phenylacetic acid methyl ester to give the title compound as an oil; δ (360 MHz, DMSO) 1.39 (9H, s, $C(CH_3)_3$), 3.60 (3H, s, $CO_2CH_3$), 3.65 (2H, s, $CH_2CO_2CH_3$), 4.10 (2H, d, J=6.2 Hz, $CH_2NH$), 7.22 (5H, m, ArH, $ArCH_2NH$).

Step d) 3-(Tertiarybutyloxycarbonylaminomethyl)phenyl acetic acid

This material was prepared using the method given for Example 106 step b) using methyl 3-(tertiarybutyloxycarbonylaminomethyl)phenylacetate in place of methyl 4-(tertiarybutyloxocarbonylaminoethyl)phenylacetate to give the title compound as a colourless oil; δ (360 MHz, DMSO) 1.39 (9H, s, $C(CH_3)_3$), 3.52 (2H, s, $CH_2CO_2H$), 4.10 (2H, d, J=6.2 Hz, $ArCH_2NH$), 7.22 (5H, m, ArH, $ArCH_2NH$), 12.10 (1H, vbs, $CO_2H$).

Step e) Trans-4-(3-tertiary-butyloxycarbonylaminomethyl)phenylmethylcarbonylamino-5,7-dichloro-2-methoxycarbonyl-1,2,3,4-tetrahydroquinoline This material was prepared using the method given for Example 37 step a) using 3-(tertiarybutyloxycarbonylaminomethyl)phenyl acetic acid in place of phenylacetic acid to give the title compound as colourless crystals, m.p. 162°–163.4° C.; δ (360 MHz, DMSO) 1.39 (9H, s, $C(CH_3)_3$), 1.65 (1H, ddd, J=13.3, 12.9 and 3.9

Hz, $CH_ACH_BH_CCH_D$), 2.15 (1H, dm, J=13.3 Hz, $CH_ACH_BH_CCH_D$), 3.39 (2H, s, NHCOCH$_2$Ar), 3.72 (3H, s, CO$_2$CH$_3$), 3.96 (1H, dd, J=12.9 Hz, $CH_ACH_BH_CCH_D$), 4.09 (2H, d, J=5.9 Hz, ArCH$_2$NH), 5.00 (1H, m, $CH_ACH_BH_CCH_D$), 6.68 (1H, d, J=2.0 Hz, 6-H or 8-H), 6.87 (1H, d, J=2.0 Hz, 6-H or 8-H), 6.90 (1H, s, ArNH), 7.22 (5H, m, ArH and ArCH$_2$NH), 8.45 (1H, d, J=7.1 Hz, $CH_D$NHCOCH$_2$); m/e (CI$^-$) 521 (M).

Step f) Trans-4-(3-aminomethylphenyl)methylcarbonylamino-2-carboxy-5,7-dichloro-1,2,3,4-tetrahydroquinoline hydrochloride This material was prepared using the method given in Example 106 step d) using trans-4-(3-tertiary-butyloxycarbonylaminomethyl)phenylmethylcarbonylamino-5,7-dichloro-2-methoxycarbonyl-1,2,3,4-tetrahydroquinoline in place of trans-4-(4-tertiary-butyloxycarbonylaminoethylphenyl)methylcarbonylamino-5,7-dichloro-2-methoxycarbonyl-1,2,3,4-tetrahydroquinoline to give the title compound as colourless crystals, m.p. 163.7°–165° C. dec; m/e CI$^+$ 409 (M+1); δ (360 MHz, DMSO) 1.63 (1H, ddd, J=13.2, 12.7 and 3.9 Hz, $CH_ACH_BH_CCH_D$), 2.17 (1H, dm, J=13.2 Hz, $CH_ACH_BH_CCH_D$), 3.88 (1H, dd, J=12.7 Hz, $CH_ACH_BH_CCH_D$), 3.98 (2H, m, CH$_2$NH$_3^+$), 5.00 (1H, m, $CH_ACH_BH_CCH_D$), 6.65 (1H, d, J=2.0 Hz, 6-H or 8-H), 6.68 (1H, d, J=2.0 Hz, 6-H or 8-H), 7.37 (4H, m, ArH), 8.35 (3H, bs, NH$_3^+$), 8.52 (1H, d, J=7.0 Hz, CHNHCOCH$_2$); Found C, 46.28; H, 4.45; N, 8.09; C$_{19}$H$_{19}$Cl$_2$N$_3$O$_3$.2HCl. 0.5H$_2$O.0.1 CH$_3$CO$_2$C$_2$H$_5$ requires C, 46.68; H, 4.61; N, 8.42%.

EXAMPLE 121

Trans-4-(3-aminomethylphenyl)methylcarbonylamino-5,7-dichloro-2-methoxycarbonyl-1,2,3,4-tetrahydroquinoline hydrochloride This compound was prepared by the method given in Example 107 using trans-4-(3-tertiary-butyloxycarbonylaminomethyl)phenylmethylcarbonylamino-5,7-dichloro-2-methoxycarbonyl-1,2,3,4-tetrahydroquinoline (Example 120e) in place of trans-4(4-tertiarybutyloxycarbonylaminoethylphenyl)methylcarbonylamino-5,7-dichloro-2-methoxycarbonyl-1,2,3,4-tetrahydroquinoline to give the title compound as a colourless solid; m.p. 161°–162° C.; m/e (CI+) 422 (M=1); δ (360 MHz, DMSO) 1.66 (1H, ddd, J=13.3, 12.7 and 3.8 Hz, $CH_ACH_BH_CCH_D$), 2.15 (1H, dm, J=13.3 Hz, $CH_ACH_BH_CCH_D$), 3.72 (3H, s, CO$_2$CH$_3$), 3.98 (3H, m, $CH_ACH_BH_CCH_D$ and ArCH$_2$NH$_3^+$), 5.00 (1H, m, $CH_ACH_BH_CCH_D$), 6.69 (1H, d, J=2 Hz, 6-H or 8-H), 6.88 (1H, d, J=2 Hz, 6-H or 8-H), 7.34 (5H, m, 4×ArH and ArNH), 8.40 (3H, bs, NH$_3^+$), 8.48 (1H, d, J=7.0 Hz, $CH_D$NHCOCH$_2$); Found C, 47.67; H, 4.80; N, 8.33; C$_{20}$H$_{21}$Cl$_2$N$_3$O$_3$.2HCl.0.5H$_2$O requires C, 47.64; H, 4.80; N, 8.33%.

EXAMPLE 122

Trans-4-(2-aminomethylphenyl)methylcarbonylamino-2-carboxy-5,7-dichloro-1,2,3,4-tetrahydroquinoline hydrochloride Step a) 2-(Azidomethyl)phenyl acetic acid
This material was prepared using the method given for Example 120 steps a), b) and d) using 2-tolyacetic acid in place of 3-tolyacetic acid to give the title compound as a colourless oil; δ (360 MHz, DMSO) 3.67 (2H, s, CH$_2$CO$_2$H$_3$), 4.46 (2H, s, CH$_2$N$_3$), 7.30 (4H, m, ArH).

Step b) Trans-4-(2-azidomethylphenyl)methylcarbonylamino-5,7-dichloro-2-methoxycarbonyl-1,2,3,4-tetrahydroquinoline This material was prepared using the method given for Example 37 step a) using 2-(azidomethyl)phenylacetic acid in place of phenylacetic acid to give the title compound as colourless crystals, m.p. 216°–217° C.; δ (360 MHz, DMSO) 1.65 (1H, ddd, J=13.2, 12.6 and 3.8 Hz, $CH_ACH_BH_CCH_D$), 2.19 (1H, dm, J=13.2 Hz, $CH_ACH_BH_CCH_D$), 3.53 (2H, s, NHCOCH$_2$Ar), 3.72 (3H, s, CO$_2$CH$_3$), 3.97 (1H, dd, J=12.6 and 2.9 Hz, $CH_ACH_BH_CCH_D$), 4.45 (2H, dd, J=13.7 Hz, COCH$_2$Ar), 5.00 (1H, m, $CH_ACH_BH_CCH_D$), 6.71 (1H, d, J=2.0 Hz, 6-H or 8-H), 6.86 (1H, d, J=2.0 Hz, 6-H or 8-H), 7.3 (5H, m, ArNH and ArH); m/e (CI+) 448 (M+1).

Step c) Trans-4-(2-tertiary-butyloxycarbonylaminomethyl)phenylmethylcarbonylamino-5,7-dichloro-2-methoxycarbonyl-1,2,3,4-tetrahydroquinoline To a solution of trans-4-(2-azidomethylphenyl)methylcarbonylamino-5,7-dichloro-2-methoxycarbonyl-1,2,3,4-tetrahydroquinoline (0.3 g, 0.67 mmol) in ethyl acetate (30 ml) was added ditertiary-butyldicarbonate (0.22 g, 1.0 mmol) and 10% palladium on carbon and this mixture was hydrogenated under 50 psi pressure for 18 hours. The mixture was filtered and the solvent was removed under vacuum to yield the crude product, which was purified by flash chromatography (using ethyl acetate in hexane as eluent) followed by recrystalisation from ethyl acetate/hexane to give the title compound, m.p. 224°–225° C.; δ (360 MHz, DMSO) 1.38 (1H, ddd, J=13.2, 12.6 and 3.8 Hz, $CH_ACH_BH_CCH_D$), 2.18 (1H, dm, J=13.2 Hz, $CH_ACH_BH_CCH_D$), 3.50 (2H, s, NHCOCH$_2$Ar), 3.73 (3H, s, CO$_2$CH$_3$), 3.95 (1H, dd, J=12.6 Hz, $CH_ACH_BH_CCH_D$), 4.17 (2H, d, J=5.7 Hz, ArCH$_2$NH), 5.00 (1H, m, $CH_ACH_BH_CCH_D$), 6.70 (1H, d, J=2.0 Hz, 6-H or 8-H), 6.87 (1H, d, J=2.0 Hz, 6-H or 8-H), 6.92 (1H, s, ArNH), 7.19 (4H, m, ArH), 8.50 (1H, d, J=6.9 Hz, $CH_D$NHCOCH$_2$); m/e (EI+) 522 (M+1).

Step d) Trans-4-(2-aminomethylphenyl)methylcarbonylamino-2-carboxy-5,7-dichloro-1,2,3,4-tetrahydroquinoline hydrochloride This material was prepared using the method given for Example 106 step d) using trans-4-(2-tertiarybutyloxycarbonylaminomethyl)phenylmethylcarbonylamino-5,7-dichloro-2-methoxycarbonyl-1,2,3,4-tetrahydroquinoline in place of trans-4-(4-tertiarybutoxycarbonylaminoethylphenyl)methylcarbonylamino-5,7-dichloro-2-methoxycarbonyl-1,2,3,4-tetrahydroquinoline to give the title compound as colourless crystals, m.p. 182°–185° C. dec; δ (360 MHz, DMSO) 1.42 (1H, ddd, J=13.2, 12.6 and 3.8 Hz, $CH_ACH_BH_CCH_D$), 2.21 (1H, dm, J=13.2 Hz, $CH_ACH_BH_CCH_D$), 3.65 (2H, m, ArCH$_2$NH$_3^+$), 4.00 (3H, m, $CH_ACH_BH_CCH_D$ and NHCOCH$_2$Ar), 4.94 (1H, m, $CH_ACH_BH_CCH_D$), 6.65 (1H, s, ArNH), 6.59 (1H, d, J=2.0 Hz, 6-H or 8-H), 6.92 (1H, d, J=2.0 Hz, 6-H or 8-H), 7.31 (4H, m, ArH), 7.47 (1H, d, J=6.9 Hz, $CH_D$NHCOCH$_2$), 7.9 (3H, vbs, NH$_3^+$); m/e (FAB+) 408 (M+1).

EXAMPLE 123

Trans-4-(2-aminomethylphenyl)methylcarbonylamino-5,7-dichloro-2-methoxycarbonyl-1,2,3,4-tetrahydroquinoline hydrochloride This material was prepared by the method given in Example 107 using trans-4-(2-tertiarybutyloxycarbonylaminomethyl)phenylmethylcarbonylamino-5,7-dichloro-2-methoxycarbonyl-1,2,3,4-tetrahydroquinoline in place of trans-4-(4-tertiary-butyloxycarbonylaminoethylphenyl)methylcarbonylamino-5,7-dichloro-2-methoxycarbonyl-1,2,3,4-tetrahydroquinoline to give the title compound as a colourless solid, m.p. 169°–172° C. dec; δ (360 MHz, DMSO) 1.68 (1H, ddd, J=13.2, 12.6 and 3.8 Hz, $CH_ACH_BH_CCH_D$), 2.09 (1H, dm, J=13.2 Hz, $CH_ACH_BH_CCH_D$), 3.67 (2H, s, NHCOCH$_2$Ar), 3.71 (3H, s, CO$_2$CH$_3$), 4.00 (1H, dd, J=12.6 AND 2.9 Hz, $CH_ACH_BH_CCH_D$), 4.14 (2H, m, ArCH$_2$NH$_3$), 4.98 (1H, m, $CH_ACH_BH_CCH_D$), 6.72 (1H, d, J=2.0 Hz, 6-H or 8-H), 6.91 (1H, d, J=2.0 Hz, 6-H or 8-H), 6.98 (1H, s, ArNH), 7.34 (4H, m, ArH), 8.03 (3H, bs, NH$_3^+$), 9.05 (1H, d, J=7.1 Hz, $CH_D$NHCOCH$_2$); m/e (CI$^+$) 422 (M+1).

EXAMPLE 124

Trans-4-(2-(4-aminomethylphenyl)ethyl)carbonylamino-2-carboxy-5,7-dichloro-1,2,3,4-tetrahydroquinoline hydrochloride Step a) 3-(4-Cyanophenyl)propenoic acid methyl ester To a solution of 4-cyanobenzaldehyde (10 g) in toluene (100 ml) was added methyl(triphenylphosphoranylidine)-acetate (30.6 g) and the solution was heated to reflux for four hours, then cooled to room temperature. The solvent was removed under vacuum and the crude product was purified by flash chromatography (using ethyl acetate in hexane as eluent) to yield the title compound (11.5 g). δ (360 MHz, DMSO) 3.74 (3H, s, CO$_2$CH$_3$), 6.80 (1H, d, J=16.2 Hz, ArCHCHCO$_2$CH$_3$), 7.70 (1H, d, J=16.2 Hz, ArCHCHCO$_2$CH$_3$), 7.95 (4H, m, ArH).

Step b) Methyl-4-tertiarybutyloxycarbonylaminomethylphenylproponate

To a solution of 3-(4-cyanophenyl)propenoic acid methyl ester (10 g) in ethanol (300 ml) was added 1M hydrochloric acid (30 ml) followed by 10% palladium on carbon (2 g) and the resulting mixture was hydrogenated at room temperature under 50 psi for 18 hr. The mixture was filtered and the solvent was removed under vacuum. To the crude residue was added dichloromethane (300 ml) and ditertiarybutyldicarbonate (17.3 g, 80.5 mmol), followed by the dropwise addition of triethylamine (15 ml, 204 mmol) and the mixture was stirred at room temperature for 4 hours. The reaction mixture was washed with water (2×100 ml), aqueous citric acid (2×100 ml, 1M), saturated sodium bicarbonate solution (3×100 ml) and brine solution (1×100 ml), dried (MgSO$_4$) and evaporated. The crude residue was purified by flash chromatography (using ethyl acetate in hexane as eluent to give the title compound (2.5 g); δ (360 MHz, DMSO) 1.38 (9H, s, C(CH$_3$)$_3$), 2.59 (2H, t, J=7.5 Hz, ArCH$_2$CH$_2$CO$_2$CH$_3$), 2.81 (2H, t, J=7.5 Hz, ArCH$_2$CH$_2$CO$_2$CH$_3$), 3.29 (3H, s, CO$_2$CH$_3$), 4.07 (2H, d, J=6.2 Hz, ArCH$_2$NH), 7.13 (4H, m, ArH), 7.31 (1H, m, ArCH$_2$NH).

Step c) 4-Tertiarybutyloxycarbonylaminomethylphenyl propionic acid

This material was prepared using the method given for Example 106 step b) using methyl-4-tertiarybutyloxocarbonylaminomethylphenylpropionate in place of methyl 4-(tertiarybutyloxycarbonylaminoethyl)-phenylacetate to give the title compound as colourless crystals, m.p. 140°–141.5° C.; δ (360 MHz, DMSO) 1.36 (9H, s, C(CH$_3$)$_3$), 2.50 (2H, t, J=7.5 Hz, ArCH$_2$CH$_2$CO$_2$H), 2.79 (2H, t, J=7.5 Hz, ArCH$_2$CH$_2$CO$_2$H), 4.07 (2H, d, J=6.0 Hz, ArCH$_2$NH), 7.13 (4H, m, ArH), 7.30 (1H, m, ArCH$_2$NH).

Step d) Trans-4-(2-(4-tertiarybutyloxycarbonylaminomethylphenyl)ethyl)carbonylamino-5,7-dichloro-2-methoxycarbonyl-1,2,3,4-tetrahydroquinoline This material was prepared using the method given for Example 37 step a) using 4-tertiarybutyloxycarbonylaminomethylphenylpropionic acid in place of phenylacetic acid to give the title compound as colourless crystals, m.p. 193°–194° C. δ (360 MHz, DMSO) 1.38 (9H, s, C(CH$_3$)$_3$), 1.64 (1H, ddd, J=13.1, 12.4 and 3.9 Hz, $CH_ACH_BH_CCH_D$), 2.14 (1H, dm, J= 13.1 Hz, $CH_ACH_BH_CCH_D$), 2.34 (2H, t, J=8.0 Hz, NHCOCH$_2$CH$_2$Ar), 2.80 (2H, t, J=8.0 Hz, NHCOCH$_2$CH$_2$Ar), 3.73 (3H, s, CO$_2$CH$_3$), 3.86 (1H, dd, J=12.4 Hz, $CH_ACH_BH_CCH_D$), 4.06 (2H, d, J=5.7 Hz, ArCH$_2$NH), 5.01 (1H, m, $CH_ACH_BH_CCH_D$), 6.66 (1H, d, J=1.8 Hz, 6-H or 8-H), 6.85 (2H, m, 6-H or 8-H and ArNH), 7.11 (4H, m, ArH), 7.27 (1H, m, ArCH$_2$NHC(CH$_3$)$_3$), 8.18 (1H, d, J=7.1 Hz, CHNHCOCH$_2$CH$_2$Ar); m/e CI$^+$ 536 (M+1).

Step e) Trans-4-(2-(4-aminomethylphenyl)ethyl)carbonylamino-2-carboxy-5,7-dichloro-1,2,3,4-tetrahydroquinoline hydrochloride This compound was prepared by the method given in Example 106 step d) using trans-4-(2-(4-tertiarybutyloxycarbonylaminomethylphenyl)ethyl)carbonylamino-5,7-dichloro-2-methoxycarbonyl-1,2,3,4-tetrahydroquinoline in place of trans-4-(4-tertiarybutyloxycarbonylaminoethylphenyl)methylcarbonylamino-5,7-dichloro-2-methoxycarbonyl-1,2,3,4-tetrahydroquinoline to give the title compound as colourless crystals, m.p. 156°–159° C. dec; δ (360 MHz, DMSO) 1.59 (1H, ddd, J=12.6, 10.7 and 3.9 Hz, $CH_ACH_BH_CCH_D$), 2.15 (1H, dm, J=12.6 Hz, $CH_ACH_BH_CCH_D$), 2.38 (2H, t, J=8.3 Hz, NHCOCH$_2$CH$_2$Ar), 2.84 (2H, t, J=8.3 Hz, NHCOCH$_2$CH$_2$Ar), 3.78 (1H, dd, J=10.7 and 2.9 Hz, $CH_ACH_BH_CCH_D$), 3.94 (2H, m, ArCH$_2$NH$_3^+$), 5.02 (1H, m, $CH_ACH_BH_CCH_D$), 6.64 (1H, d, J=2.0 Hz, 6-H or 8-H), 6.87 (1H, d, J=2.0 Hz, 6-H or 8-H), 7.25 (2H, d, J=7.9 Hz, 2× ArH), 7.36 (2H, d, J=7.9 Hz, 2×ArH), 8.13 (1H, d, J=7.0 Hz, CHNHCOCH$_2$CH$_2$Ar), 8.30 (3H, bs, NH$_3^+$); m/e (FAB$^-$) 520 (M-1); Found C, 48.92; H, 4.71; N, 8.25; C$_{20}$H$_{21}$Cl$_2$N$_3$O$_3$.1.9 HCl requires C, 48.87; H, 4.70; N, 8.55%.

EXAMPLE 125

Trans-4-(2-(4-aminomethylphenyl)ethyl)carbonylamino-5,7-dichloro-2-methoxycarbonyl-1,2,3,4-tetrahydroquinoline hydrochloride This compound was prepared by the method given in Example 82 using trans-4-(2-(4-aminomethylphenyl)ethylcarbonylamino-2-carboxy-5,7-dichloro-1,2,3,4-tetrahydroquinoline hydrochloride in place of trans-2-carboxy-5,7-dichloro-4-(3-aminomethylphenyl)carbonylamino-1,2,3,4-tetrahydroquinoline hydrochloride to give the title compound as colourless crystals, m.p. 172°–173.2° C.; δ (360 MHz, DMSO) 1.62 (1H, ddd, J=13.2, 10.1 and 3.7 Hz, CH$_A$CH$_B$CH$_C$CH$_D$), 2.16 (1H, dm, J=13.2 Hz, CH$_A$CH$_B$CH$_C$CH$_D$), 2.36 (2H, t, J=8.2 Hz, NHCOCH$_2$CH$_2$Ar), 2.84 (2H, t, J=8.2 Hz, NHCOCH$_2$CH$_2$Ar), 3.74 (3H, s, CO$_2$CH$_3$), 3.95 (3H, m, CH$_A$CH$_B$CH$_C$CH$_D$ and ArCH$_2$NH$_3$+), 5.02 (1H, m, CH$_A$CH$_B$CH$_C$CH$_D$), 6.68 (1H, d, J=1.8 Hz, 6-H or 8-H), 6.80 (2H, m, 6-H or 8-H and ArNH), 7.24 (2H, d, J=8.0 Hz, 2×ArH), 7.36 (2H, d, J=8.0 Hz, 2×ArH), 8.10 (1H, d, J=7.1 Hz, CHNHCOCH$_2$CH$_2$), 8.34 (3H, bs, NH$_3$+); Found C, 49.69; H, 4.83; N, 8.35; C$_{21}$H$_{23}$Cl$_2$N$_3$O$_3$.2 HCl requires C, 49.53; H, 4.95; N, 8.25%.

EXAMPLE 126

Trans-4-(4-aminophenylmethylcarbonylamino-5,7-dichloro-2-carboxy-1,2,3,4-tetrahydroquinoline hydrochloride Step a) Trans-4-(4-tertiarybutyloxycarbonylaminophenyl)methylcarbonylamino-5,7-dichloro-2-methoxycarbonyl-1,2,3,4-tetrahydroquinoline This material was prepared using the method given for Example 37 step a) using 4-tertiarybutyloxycarbonylaminophenylacetic acid in place of phenylacetic acid to give title compound as colourless crystals, m.p. 236°-239° C. δ (360 MHz, DMSO) 1.47 (9H, s, C(CH$_3$)$_3$), 1.64 (1H, ddd, J=13.2, 12.4 and 3.9 Hz, CH$_A$CH$_B$H$_C$CH$_D$), 2.13 (1H, dm, J=13.2 Hz, CH$_A$CH$_B$H$_C$CH$_D$), 3.29 (2H, s, NHCOCH$_2$), 3.72 (3H, s, CO$_2$CH$_3$), 3.93 (1H, dd, J=12.4 Hz, CH$_A$CH$_B$H$_C$CH$_D$), 4.99 (1H, m, CH$_A$CH$_B$H$_C$CH$_D$), 6.69 (1H, d, J=2.0 Hz, 6-H or 8-H), 6.87 (1H, d, J=2.0 Hz, 6-H or 8-H), 6.90 (1H, s, ArNH), 7.11 (2H, d, J=8.4 Hz, ArH), 7.34 (2H, d, J=8.2 Hz, ArH), 8.40 (1H, d, J=7.1 Hz, NHCOCH$_2$).

Step b) Trans-4-(4-aminophenyl)methylcarbonylamino-5,7-dichloro-2-carboxy-1,2,3,4-tetrahydroquinoline hydrochloride This compound was prepared by the method given in Example 106 step d) using trans-4-(4-tertiarybutyloxycarbonylaminophenyl)methylcarbonylamino-5,7-dichloro-2-methoxycarbonyl-1,2,3,4-tetrahydroquinoline in place of trans-4-(4-tertiarybutyloxycarbonylaminoethylphenyl)-methylcarbonylamino-5,7-dichloro-2-methoxycarbonyl-1,2,3,4-tetrahydroquinoline to give the title compound as colourless crystals, m.p. 165°-167° C. δ (360 MHz, DMSO), 1.62 (1H, ddd, J=13.2, 12.6, 3.8 Hz, CH$_A$CH$_B$H$_C$CH$_D$), 2.14 (1H, dm, J=13.2 Hz, CH$_A$CH$_B$H$_C$CH$_D$), 3.46 (2H, s, NHCOCH$_2$), 3.86 (1H, dd, J=12.6 Hz, CH$_A$CH$_B$H$_C$CH$_D$), 5.00 (1H, m, CH$_A$CH$_B$H$_C$CH$_D$), 6.66 (1H, d, J=2.1 Hz, 6-H or 8-H), 6.89 (1H, d, J=2.1 Hz, 6-H or 8-H), 7.33 (4H, 2d, J=8.6 Hz, ArH); 8.51 (1H, d, J=7.1 Hz, NHCOCH$_2$); m/e (FAB+) 394 (M+); Found C, 46.28; H, 4.10; N, 8.99. C$_{18}$H$_{17}$Cl$_2$N$_3$O$_3$.2HCl requires C, 46.28; H, 4.10; N, 8.99%.

EXAMPLE 127

Trans-2-carboxy-5,7-dichloro-4-(1,2,3,4-tetrahydroisoquinol-3-yl)carbonylamino-1,2,3,4-tetrahydroquinoline hydrochloride Step a) Trans-5,7-dichloro-2-methoxycarbonyl-4-(3-(N-tertiarybutyloxycarbonyl)-1,2,3,4-tetrahydroisoquinoline) carbonylamino-1,2,3,4-tetrahydroquinoline This material was prepared using the method given for Example 37 step a) using 3-(N-tertiarybutyloxycarbonyl)-1,2,3,4-tetrahydroisoquinoline carboxylic acid in place of phenylacetic acid to give the title compound as colourless crystals; m.p. 244°- 246° C.; δ (360 MHz, DMSO) 1.38 (9H, s, C(CH$_3$)$_3$), 1.49 (1H, m, CH$_A$CH$_B$H$_C$CH$_D$), 1.90 (1H, m, CH$_A$CH$_B$H$_C$CH$_D$), 3.01 (2H, m, ArCH$_2$N), 3.70 (3H, s, CO$_2$CH$_3$), 3.93 (1H, m, ArCH$_2$CHCO), 4.45 (2H, m, ArCH$_2$CHCO), 4.90 (1H, m, CH$_A$CH$_B$H$_C$CH$_D$), 6.64 (1H, d, J=2.0 Hz, 6-H or 8-H), 6.85 (1H, d, J=2 Hz, 6-H or 8-H), 6.88 (1H, s, ArNH), 7.16 (4H, m, ArH), 8.30 (1H, m, CH$_D$NHCO).

Step b) Trans-2-carboxy-5,7-dichloro-4-(3-(N-tertiarybutyloxycarbonyl)1,2,3,4-tetrahydroisoquinoline)-carbonylamino-1,2,3,4-tetrahydroquinoline This material was prepared using the method given for Example 106 step d) using trans-5,7-dichloro-2-methoxycarbonyl-4-(3-N-tertiarybutyloxycarbonyl)-1,2,3,4-tetrahydroisoquinoline)carbonyamino-1,2,3,4-tetrahydroquinoline in place of trans-4-(4-tertiarybutyloxycarbonylaminoethylphenyl)methylcarbonylamino-5,7-dichloro-2-methoxycarbonyl-1,2,3,4-tetrahydroquinoline to give the title compound as colourless crystals; m.p. 212°-214° C. dec; δ (360 MHz, DMSO) 1.72 (1H, ddd, J=13.3, 12.6 and 13.3 Hz, CH$_A$CH$_B$H$_C$CH$_D$), 2.23 (1H, dm, J=13.3 Hz, CH$_A$CH$_B$H$_C$CH$_D$), 3.05 (1H, dd, J=16.6 and 11.2 Hz, ArCH$_E$H$_F$CHCO), 3.36 (1H, dd, J=16.6 and 4.8 Hz, ArCH$_E$CH$_F$CHCO), 3.93 (1H, dd, J=3.9 Hz, CH$_A$CH$_B$H$_C$CH$_D$), 4.14 (1H, m, CH$_D$NHCOCHNH$_2$), 4.33 (2H, m, NHCOCHNH$_2$CH$_2$Ar), 5.14 (1H, m, CH$_A$CH$_B$H$_C$CH$_D$), 6.66 (1H, d, J=2.0 Hz, 6-H or 8-H), 6.91 (1H, d, J=2.0 Hz, 6-H or 8-H), 7.23 (4H, m, ArH), 8.98 (1H, d, J=6.8 Hz, CH$_D$NHCO), 9.7 (2H, bm, NH$_2$); m/e (CI+) 420 (M+1); Found C, 49.88; H, 4.38; N, 8.61; C$_{20}$H$_{19}$Cl$_2$N$_3$O$_3$.1.7HCl requires C, 49.81; H, 4.33; N 8.71%.

EXAMPLE 128

Trans-4-(2-carboxyphenyl)carbonylamino-2-carboxy-5,7-dichloro-1,2,3,4-tetrahydroquinoline Step a) Trans-4-(2-carboxyphenyl)carbonylamino-5,7-dichloro-2-methoxycarbonyl-1,2,3,4-tetrahydroquinoline To a suspension of trans-4-amino-5,7-dichloro-2-methoxycarbonyl-1,2,3,4-tetrahydroquinoline (0.5 g, 1.6 mmol) in anhydrous tetrahydrofuran (50 ml) under an atmosphere of nitrogen was added dry triethylamine (0.49 ml, 3.5 mmol) and the mixture stirred until dissolution was complete. To this solution was added phthalic anhydride (0.28 g, 1.9 mmol) and 4-dimethylaminopyridine (5 mg) and the reaction mixture was stirred at room temperature for 3 hours. The mixture was then evaporated to dryness in vacuo and the residue was partitioned between ethyl acetate (100 ml) and water (200 ml). The organic layer was separated and washed successively with dilute hydrochloric acid (2×50 ml, 1M), water (1×50 ml) and brine (1×50 ml), then dried (MgSO$_4$) and evaporated to give a solid which was recrystallised from ethyl acetate/hexane to give the title compound as colourless crystals (0.45 g), m.p. 241°-243° C.; δ (360 MHz, DMSO) 1.71 (1H, ddd, J=13.0, 12.5 and 4.1 Hz, CH$_A$CH$_B$H$_C$CH$_D$), 2.45 (1H, dm, J=13.0 Hz, CH$_A$CH$_B$H$_C$CH$_D$), 3.74 (3H, dd, J=12.6 and 4.1 Hz, CH$_A$CH$_B$H$_C$CH$_D$), 5.19 (1H, m, CH$_A$CH$_B$H$_C$CH$_D$), 6.68 (1H, d, J=2.0 Hz, 6-H or 8-H), 6.82 (1H, s, ArNH), 6.84 (1H, d, J=2.0 Hz, 6-H or 8-H), 7.54 (4H, m, ArH), 8.64 (1H, d, J=7.0 Hz, CH$_D$NHCOCH$_2$), 12.86 (1H, bs, CO$_2$H); m/e (FAB+) 423 (M+1).

Step b) Trans-4-(2-carboxyphenyl)carbonylamino-2-carboxy-5,7-dichloro-1,2,3,4-tetrahydroquinoline This material was prepared by the method given for Example 37 step b) using trans-4-(2-carboxyphenyl)carbonylamino-5,7-dichloro-2-methoxycarbonyl-1,2,3,4-tetrahydroquinoline in place of trans-5,7-dichloro-2-methoxycarbonyl-4-phenylmethylcarbonylamino-1,2,3,4-tetrahydroquinoline to give the title compound as colourless crystals, m.p. 195°-197° C. dec; δ (360 MHz, DMSO) 1.66 (1H, ddd, J=13.0, 12.6 and 4.1 Hz, CH$_A$CH$_B$H$_C$CH$_D$), 2.49 (1H, dm, J=12.6 Hz, CH$_A$CH$_B$H$_C$CH$_D$), 3.94 (1H, dd, J=12.6 and 4.0 Hz, CH$_A$CH$_B$H$_C$CH$_D$), 5.19 (1H, m, CH$_A$CH$_B$H$_C$CH$_D$), 6.64 (1H, d, J=2.0 Hz, 6-H or 8-H), 6.71 (1H, s, ArNH), 6.85 (1H, d, J=2.0 Hz, 6-H or 8-H), 7.51 (4H, m, ArH), 8.62 (1H, d, J=7.1 Hz, CH$_D$NHCO); m/e (FAB+) 409 (M+1); Found C, 52.71; H, 4.01; N, 6.19; C$_{18}$H$_{14}$Cl$_2$N$_2$O$_2$.0.3CH$_3$CO$_2$CH$_2$CH$_3$ requires C, 52.93; H, 3.80; N, 6.43%.

EXAMPLE 129

Trans-2-carboxy-5,7-dichloro-4-(4-chloro-3-nitrophenyl)methylcarbonylamino-1,2,3,4-tetrahydroquinoline This compound was prepared by the method given in Example 37 using 4-chloro-3-nitrophenylacetic acid in place of phenylacetic acid to give the title compound as colourless crystals, m.p. 233°-235° C. δ (360 MHz, DMSO) 1.62 (1H, ddd, J=13.3, 12.6 and 3.7 Hz, CH$_A$CH$_B$H$_C$CH$_D$), 2.15 (1H, dm, J=13.3 Hz, CH$_A$CH$_B$H$_C$CH$_D$), 3.56 (2H, d, NHCOCH$_2$), 3.81 (1H, dd, J=12.6 Hz, CH$_A$CH$_B$H$_C$CH$_D$), 4.99 (1H, m, CH$_A$CH$_B$H$_C$CH$_D$), 6.66 (1H, d, J=2.1 Hz, 6-H or 8-H), 6.81 (1H, s, ArNH), 6.89 (1H, d, J=2 Hz, 6-H or 8-H), 7.58 (1H, dd, J=8.3 and 2.0 Hz, 6-ArH), 7.71 (1H, d, J=8.3 Hz, 5-ArH), 7.95 (1H, d, J=2.0 Hz, 2-ArH), 8.57 (1H, d, J=7 Hz, NHCOCH$_2$); m/e (CI−) 456 (M-1); Found C, 47.21; H, 3.23; N, 9.02. C$_{18}$H$_{14}$Cl$_3$N$_3$O$_5$ requires C, 47.13; H, 3.08; N, 9.16%.

EXAMPLE 130

Trans-2-carboxy-5,7-dichloro-4-(4-hydroxy-3-nitrophenyl)methylcarbonylamino-1,2,3,4-tetrahydroquinoline This compound was prepared by the method given in Example 37 using 4-hydroxy-3-nitrophenylacetic acid in place of phenylacetic acid to give the title compound as yellow crystals, m.p. 245°-247° C. δ (360 MHz, DMSO) 1.61 (1H, ddd, J=13.1, 12.7 and 3.8 Hz, CH$_A$CH$_B$H$_C$CH$_D$), 2.14 (1H, dm, J=13.1 Hz, CH$_A$CH$_B$H$_C$CH$_D$), 3.40 (2H, s, NHCOCH$_2$), 3.81 (1H, dd, J=12.7 and 2.9 Hz, CH$_A$CH$_B$H$_C$CH$_D$), 4.98 (1H, m, CH$_A$CH$_B$H$_C$CH$_D$), 6.66 (1H, d, J=2.0 Hz, 6-H or 8-H), 6.81 (1H, s, ArNH), 6.88 (1H, d, J=2.1 Hz, 6-H or 8-H), 7.06 (1H, d, J=8.5 Hz, ArH), 7.42 (1H, dd, J=8.5 and 2.1 Hz, ArH), 7.80 (1H, d, J=2.1 Hz, ArH), 8.46 (1H, d, J=7.1 Hz, NHCOCH$_2$); m/e (CI+) 440 (M+1); Found C, 49.24; H, 3.58; N, 9.35. C$_{18}$H$_{15}$Cl$_2$N$_3$O$_6$ requires C, 49.11; H, 3.43; N, 9.55%.

EXAMPLE 131

Trans-2-carboxy-5,7-dichloro-4-(diphenylmethylcarbonyl)amino-1,2,3,4-tetrahydroquinoline This compound was prepared by the method given in Example 37 using diphenylacetic acid in place of phenylacetic acid to give the title compound as colourless crystals, m.p. 238°-238° C. δ (360 MHz, DMSO) 1.63 (1H, ddd, J=13.2, 12.6 and 3.8 Hz, CH$_A$CH$_B$H$_C$CH$_D$), 2.16 (1H, dm, J=13.2 Hz, CH$_A$CH$_B$H$_C$CH$_D$), 3.76 (1H, dd, J=12.6 and 2.9 Hz, CH$_A$CH$_B$H$_C$CH$_D$), 4.92 (1H, s, NHCOCHPh$_2$), 5.06 (1H, m, CH$_A$CH$_B$H$_C$CH$_D$), 6.62 (1H, d, J=2.0 Hz, 6-H or 8-H), 6.78 (1H, s, ArNH), 6.86 (1H, d, J=2.0 Hz, 6-H or 8-H), 7.23 (10H, m, ArH), 8.62 (1H, d, J=7.1 Hz, CHNHCOCHPh$_2$); m/e (FAB+) 455 (M+1); Found C, 61.52; H, 5.07; N, 5.24; C$_{24}$H$_{20}$Cl$_2$N$_2$O$_3$. CH$_3$CO$_2$C$_2$H$_5$ requires C, 61.88; H, 5.19; N, 5.15%.

EXAMPLE 132

Trans-2-carboxy-5,7-dichloro-4-(1-phenylethylcarbonyl)amino-1,2,3,4-tetrahydroquinoline (isomer A)

This compound was prepared by the method given in Example 37 using (±) 2-phenylpropionic acid in place of phenylacetic acid. The two diastereoisomers were separated by flash chromatography followed by recrystallisation as their methyl esters. The less polar isomer gave on treatment with lithium hydroxide, the title compound (isomer A) as colourless crystals, m.p. 210°-212° C. δ (360 MHz, DMSO) 1.33 (3H, d, J=7.0 Hz, CHCH$_3$Ph), 1.54 (1H, ddd, J=13.4, 12.9 and 3.8 Hz, CH$_A$CH$_B$H$_C$CH$_D$), 2.03 (1H, dm, J=13.4 Hz, CH$_A$CH$_B$H$_C$CH$_D$), 3.61 (2H, m, CH$_A$CH$_B$H$_C$CH$_D$ and CHCH$_3$Ph), 5.00 (1H, m, CH$_A$CH$_B$H$_C$CH$_D$), 6.60 (1H, d, J=2.0 Hz, 6-H or 8-H), 6.73 (1H, s, ArNH), 6.86 (1H, d, J=2.0 Hz, 6-H or 8-H), 7.20 (5H, m, ArH), 8.29 (1H, d, J=7.0 Hz, CHNHCOCHMePh); m/e (CI+) 393 (M+1); Found C, 57.13; H, 4.72; N, 6.71; C$_{19}$H$_{18}$Cl$_2$N$_2$O$_3$.0.3H$_2$O requires C, 57.24; H, 4.70; N, 7.02%.

EXAMPLE 133

Trans-2-carboxy-5,7-dichloro-4-(1-phenylethylcarbonyl)amino-1,2,3,4-tetrahydroquinoline (isomer B)

The more polar isomer from Example 132 on treatment with lithium hydroxide gave the title compound as colourless crystals, m.p. 248°-249° C. δ (360 MHz, DMSO) 1.32 (3H, d, J=7.0 Hz, CHCH$_3$Ph), 1.61 (1H, ddd, J=13.2, 12.6 and 3.8 Hz, CH$_A$CH$_B$H$_C$CH$_D$), 2.18 (1H, dm, J=13.2 Hz, CH$_A$CH$_B$H$_C$CH$_D$), 3.57 (1H, q, J=7.0 Hz, NHCOCHCH$_3$), 3.86 (1H, dd, J=12.6 Hz, CH$_A$CH$_B$H$_C$CH$_D$), 4.97 (1H, m, CH$_A$CH$_B$H$_C$CH$_D$), 6.56 (1H, d, J=2.1 Hz, 6-H or 8-H), 6.76 (1H, s, ArNH), 6.84 (1H, d, J=2.1 Hz, 6-H or 8-H), 7.23 (5H, m, ArH), 8.26 (1H, d, J=7.2 Hz, CHNHCOCHMePh); m/e (EI+) 243 (M+); Found C, 57.83; H, 4.62; N, 7.14 C$_{19}$H$_{18}$Cl$_2$N$_2$O$_3$ requires C, 58.03; H, 4.61; N, 7.12%.

EXAMPLE 134

Trans-2-carboxy-5,7-dichloro-4-(4-acetylphenylmethylcarbonyl)amino-1,2,3,4-tetrahydroquinoline This compound was prepared by the method given in Example 37 using 4-acetylphenylacetic acid in place of phenylacetic acid to give the title compound as colourless crystals, m.p. 292°-294° C. dec; δ (360 MHz, DMSO) 1.61 (1H, ddd, J=13.2 m 12.7 and 3.8 Hz, CH$_A$CH$_B$H$_C$CH$_D$), 2.15 (1H, dm, J=13.2 Hz, CH$_A$CH$_B$H$_C$CH$_D$), 2.56 (3H, s, COCH$_3$), 3.51 (2H, s, NHCOCH$_2$Ph), 3.83 (1H, dd, J=12.7 and 2.8 Hz, CH$_A$CH$_B$H$_C$CH$_D$), 5.00 (1H, m, CH$_A$CH$_B$H$_C$CH$_D$), 6.66 (1H, d, J=1.7 Hz, 6-H or 8-H), 6.81 (1H, s, ArNH), 6.88 (1H, d, J=1.7 Hz, 6-H or 8-H), 7.39 (2H, d, J=8.2

Hz, ArH), 7.88 (1H, d, J=8.2 Hz, ArH), 8.50 (1H, d, J=7.1 Hz, CHNHCOCH$_2$); m/e (CI$^+$) 422 (M+1); Found C, 56.70; H, 4.33; N, 6.55; C$_{20}$H$_{18}$Cl$_2$O$_4$ requires C, 57.02; H, 4.31; N, 6.66%.

EXAMPLE 135

Trans-2-carboxy-5,7-dichloro-4-(phenyloxymethylcarbonyl)amino-1,2,3,4-tetrahydroquinoline This compound was prepared by the method given in Example 37 using phenoxyacetic acid in place of phenylacetic acid to give the title compound as colourless crystals, m.p. 254°–256° C. δ (360 MHz, DMSO) 1.66 (1H, ddd, J=13.2, 12.6 and 4.0 Hz, CH$_A$CH$_B$H$_C$CH$_D$), 2.18 (1H, dm, J=13.2 Hz, CH$_A$CH$_B$H$_C$CH$_D$), 3.87 (1H, dd, J=12.6 Hz, CH$_A$CH$_B$H$_C$CH$_D$), 4.50 (2H, 2d, J=14.7 Hz, NHCOCH$_2$O), 5.10 (1H, m, CH$_A$CH$_B$H$_C$CH$_D$), 6.66 (1H, d, J=2.1 Hz, 6-H or 8-H), 6.80 (1H, s, ArNH), 6.91 (4H, m, 6-H or 8-H and 3× ArH), 7.25 (2H, m, ArH), 8.49 (1H, d, J=7.1 Hz, CHNHCOCH$_2$OPh); m/e (CI$^-$) 394 (M-1); Found C, 54.38; H, 4.22; N, 6.82. C$_{18}$H$_{16}$Cl$_2$N$_2$O$_4$ requires C, 54.70; H, 4.08; N, 7.09%.

EXAMPLE 136

Trans-2-carboxy-5,7-dichloro-4-(4-ethylphenylmethylcarbonyl)amino-1,2,3,4-tetrahydroquinoline This compound was prepared by the method given in Example 37 using 4-ethylphenylacetic acid in place of phenylacetic acid to give the title compound as colourless crystals, m.p. 218°–220° C. δ (360 MHz, DMSO) 1.16 (3H, t, J=7.6 Hz, CH$_2$PhCH$_2$CH$_3$), 1.60 (1H, ddd, J=13.1, 12.6 and 3.70 Hz, CH$_A$CH$_B$H$_C$CH$_D$), 2.18 (1H, dm, J=13.1 Hz, CH$_A$CH$_B$H$_C$CH$_D$), 2.56 (2H, q, J=7.6 Hz, CH$_2$PhCH$_2$CH$_3$), 3.36 (2H, s, COCH$_2$PhCH$_2$CH$_3$), 3.83 (1H, dd, J=12.6 Hz, CH$_A$CH$_B$H$_C$CH$_D$), 5.00 (1H, m, CH$_A$CH$_B$H$_C$CH$_D$), 6.66 (1H, d, J=2.1 Hz, 6-H or 8-H), 6.79 (1H, s, ArNH), 6.88 (1H, d, J=2.0 Hz, 6-H or 8-H), 7.12 (4H, 2d, ArH), 8.40 (1H, d, J=7.1 Hz, CHNHCOCH$_2$PhCH$_2$CH$_3$); m/e (CI$^-$) 406 (M-1); Found C, 58.77; H, 5.04; N, 6.76. C$_{20}$H$_{20}$Cl$_2$N$_2$O$_3$ requires C, 58.98; H, 4.95; N, 6.88%.

EXAMPLE 137

Trans-2-carboxy-5,7-dichloro-4-(4-hydroxyphenylmethylcarbonyl)amino-1,2,3,4-tetrahydroquinoline This compound was prepared by the method given in Example 37 using 4-hydroxyphenylacetic acid in place of phenylacetic acid to give the title compound as colourless crystals, m.p. 259°–261° C. dec; δ (360 MHz, DMSO) 1.59 (1H, ddd, J=12.6, 12.4 and 3.8 Hz, CH$_A$CH$_B$H$_C$CH$_D$), 2.14 (1H, dm, J=12.6 Hz, CH$_A$CH$_B$H$_C$CH$_D$), 3.22 (2H, s, COCH$_2$Ar), 3.81 (1H, dd, J=12.4 and 2.8 Hz, CH$_A$CH$_B$H$_C$CH$_D$), 4.98 (1H, m, CH$_A$CH$_B$H$_C$CH$_D$), 6.64 (3H, m, 6-H or 8-H, 2×ArH), 6.79 (1H, s, ArNH), 6.67 (1H, d, J=2.0 Hz, 6-H or 8-H), 7.02 (2H, d, J=8.5 Hz, ArH), 8.32 (1H, d, J=7.1 Hz, CHNHCOCH$_2$Ar), 9.16 (1H, bs, ArOH); m/e (CI$^+$) 395 (M+1); Found C, 54.38; H, 4.20; N, 6.91; C$_{18}$H$_{16}$Cl$_2$N$_2$O$_4$ requires C, 54.70; H, 4.08; N, 7.08%.

EXAMPLE 138

Trans-2-carboxy-5,7-dichloro-4-(4-acetamidophenylmethyl carbonyl)amino-1,2,3,4-tetrahydroquinoline This compound was prepared by the method given in Example 37 using 4-acetylaminophenylacetic acid in place of phenylacetic acid to give the title compound as colourless crystals, m.p. 279°–281° C. δ (360 MHz, DMSO) 1.60 (1H, ddd, J=13.2, 12.5 and 3.7 Hz, CH$_A$CH$_B$H$_C$CH$_D$), 2.15 (1H, dm, J=13.2 Hz, CH$_A$CH$_B$H$_C$CH$_D$), 3.34 (2H, s, COCH$_2$PhNHCOCH$_3$), 3.83 (1H, dd, J=12.5 Hz, CH$_A$CH$_B$H$_C$CH$_D$), 5.00 (1H, m, CH$_A$CH$_B$H$_C$CH$_D$), 6.65 (1H, d, J=2.0 Hz, 6-H or 8-H), 6.78 (1H, s, ArNH), 6.88 (1H, d, J=2.0 Hz, 6-H or 8-H), 7.14 (2H, d, J=8.5 Hz, ArH), 7.46 (2H, d, J=8.5 Hz, ArH), 8.38 (1H, d, J=7.1 Hz, CHNHCOCH$_2$PhNHCOCH$_3$); m/e (FAB$^-$) 434 (M-1); Found C, 54.64; H, 4.48; N, 9.30. C$_{20}$H$_{19}$Cl$_2$N$_3$O$_4$.0.25H$_2$O requires C, 54.50; H, 4.46; N, 9.53%.

EXAMPLE 139

Trans-2-carboxy-5,7-dichloro-4-(1-naphthylamino)carbonylamino-1,2,3,4-tetrahydroquinoline This compound was prepared by the method given in Example 38 using 1-naphthyl isocyanate in place of phenyl isocyanate to give the title compound as colourless crystals, m.p. 241°–242° C. δ (360 MHz, DMSO) 1.67 (1H, ddd, J=13.0, 12.7 and 3.3 Hz, CH$_A$CH$_B$H$_C$CH$_D$), 2.38 (1H, dm, J=13.0 Hz, CH$_A$CH$_B$H$_C$CH$_D$), 3.94 (1H, dd, J=12.7 and 2.9 Hz, CH$_A$CH$_B$H$_C$CH$_D$), 5.00 (1H, m, CH$_A$CH$_B$H$_C$CH$_D$), 6.72 (1H, d, J=2.0 Hz, 6-H or 8-H), 6.85 (1H, s, ArNH.), 6.92 (1H, d, J=2.0 Hz, 6-H or 8-H), 6.96 (1H, d, J=6.4 Hz, CH$_D$NHCO), 7.50 (4H, m, ArH), 7.88 (1H, m, ArH), 8.01 (1H, m, ArH), 8.12 (1H, m, ArH), 8.35 (1H, s, NHCONH); m/e (FAB$^+$) 429 (M$^+$); Found C, 58.34; H, 4.07; N, 9.63. C$_{21}$H$_{17}$Cl$_2$N$_3$O$_3$ requires C, 58.62; H, 3.97; N, 9.77%.

EXAMPLE 140

Trans-2-carboxy-5,7-dichloro-4-(cyclohexyl)aminocarbonylamino-1,2,3,4-tetrahydroquinoline This compound was prepared by the method given in Example 38 using cyclohexylisocyanate in place of phenyl isocyanate to give the title compound as colourless crystals, m.p. 217°–219° C. δ (360 MHz, DMSO) 1.18 (5H, m, 5×C$_6$H$_{11}$), 1.53 (1H, ddd, J=13.0, 12.6 and 3.5 Hz, CH$_A$CH$_B$H$_C$CH$_D$), 1.59 (3H, m, 3×C$_6$H$_{11}$), 1.74 (2H, m, 2×C$_6$H$_{11}$), 2.22 (1H, dm, J=13.0 Hz, CH$_A$CH$_B$H$_C$CH$_D$), 3.38 (1H, m, CH$_D$NHCONH-CH), 3.78 (1H, dd, J=12.6 and 2.9 Hz, CH$_A$CH$_B$H$_C$CH$_D$), 4.84 (1H, m, CH$_A$CH$_B$H$_C$CH$_D$), 5.51 (1H, d, J=8.11 Hz, CH$_D$NHCONH), 6.00 (1H, d, J=6.5 Hz, CH$_D$NHCONH), 6.64 (1H, d, J=2.1 Hz, 6-H or 8-H), 6.72 (1H, s, ArNH), 6.84 (1H, d, J=2.1 Hz, 6-H or 8-H); m/e (FAB$^+$) 386 (M+1); Found C, 52.75; H, 5.56; N, 10.49. C$_{17}$H$_{21}$Cl$_2$N$_3$O$_3$ requires C, 52.86; H, 5.48; N, 10.88%.

EXAMPLE 141

Trans-2-carboxy-5,7-dichloro-4-((N-methyl-N-4-methylphenylamino)carbonylamino-1,2,3,4-tetrahydroquinoline The material was prepared using the method given for Example 78 step b) and c) using N-methyl-4-methyl aniline in place of N-methylaniline to give the title compound as colourless crystals, m.p. 210°–212° C.; δ (360 MHz, DMSO) 1.56 (1H, ddd, J=13.3, 12.5 and 3.9 Hz, CH$_A$CH$_B$H$_C$C$_D$), 2.25 (4H, m, ArCH$_3$ and CH$_A$CH$_B$H$_C$CH$_D$), 3.12 (3H, s, NCH$_3$), 3.84 (1H, dd, J=12.5 and 3.9 Hz, CH$_A$CH$_B$H$_C$CH$_D$), 4.90 (1H, m, CH$_A$CH$_B$H$_C$CH$_D$), 6.00 (1H, d, J=6.8 Hz, CH$_D$NHCONCH$_3$), 6.61 (1H, d, J=2.0 Hz, 6-H or 8-H), 6.64 (1H, s, ArNH), 6.81 (1H, d, J=2.0 Hz, 6-H or 8-H), 7.08 (4H, s, ArH); m/e (CI+) 408 (M+). Found C, 55.68; H, 4.75; N, 10.18; $C_{19}H_{19}Cl_2N_3O_3$ requires C, 55.89; H, 4.69; N, 10.29%.

EXAMPLE 142

Trans-2-carboxy-5,7-dichloro-4-(N,N-diphenylamino)-carbonylamino-1,2,3,4-tetrahydroquinoline Step a) Trans-2-methoxycarboxyl-5,7-dichloro-4-(N,N-diphenylamino)carbonylamino-1,2,3,4-tetrahydroquinoline This compound was prepared by the method given in Example 78 step b using N,N-diphenylamine in place of N-methylaniline to give the title compound as colourless crystals. δ (360 MHz, DMSO) 1.67 (1H, ddd, J=13.0, 12.2 and 4.0 Hz, $CH_ACH_BH_CCH_D$), 2.32 (1H, dm, J=13.0 Hz, $CH_ACH_BH_CCH_D$), 3.76 (3H, s, $CO_2CH_3$), 4.00 (1H, dd, J=12.2 and 2.8 Hz, $CH_ACH_BH_CCH_D$), 4.99 (1H, m, $CH_ACH_BH_CCH_D$), 6.66 (1H, d, J=2.0 Hz, 6-H or 8-H), 6.68 (1H, d, J=7.2 Hz, NHCO), 6.79 (1H, d, J=2.1 Hz, 6-H or 8-H), 7.12 (5H, m, ArH), 7.16 (1H, s, ArNH), 7.31 (5H, m, ArH); m/e (CI+) 470 (M+1).

Step b) Trans-2-carboxy-5,7-dichloro-4-(N,N-diphenylamino)carbonylamino-1,2,3,4-tetrahydroquinoline This compound was prepared by the method given in Example 37 step b) using trans-2-methoxycarbonyl-5,7-dichloro-4-(N,N-diphenylamino)carbonylamino-1,2,3,4-tetrahydroquinoline in place of trans-5,7-dichloro-2-methoxycarbonyl-4-phenylmethylcarbonylamino-1,2,3,4-tetrahydroquinoline to give the title compound as colourless crystals, m.p. 214°-216° C. δ (360 MHz, DMSO), 1.63 (1H, ddd, 13.0, 12.1 and 3.9 Hz, $CH_ACH_BH_CCH_D$), 2.33 (1H, dm, J=13.0 Hz, $CH_ACH_BH_CCH_D$), 3.88 (1H, dm, J=12.1 and 2.8 Hz, $CH_ACH_BH_CCH_D$), 4.99 (1H, m, $CH_ACH_BH_CCH_D$), 6.63 (1H, d, J=2.0 Hz, 6-H or 8-H), 6.65 (1H, d, J=7.2 Hz, NHCO), 6.80 (1H, d, J=2.0 Hz, 6-H or 8-H), 7.12 (5H, m, ArH), 7.16 (1H, s, ArNH), 7.31 (5H, m, ArH); m/e (CI+) 456 (M+1); Found C, 59.63; H, 4.36; N, 8.89. $C_{23}H_{19}Cl_2N_3O_3.0.5H_2O$ requires C, 59.37; H, 4.33; N, 9.03%.

EXAMPLE 143

Trans-2-carboxy-5,7-dichloro-4-(4-ethylphenyl)aminocarbonylamino-1,2,3,4-tetrahydroquinoline This compound was prepared by the methods given in Example 78 steps a-c) using 4-ethylaniline in place of 4-iodoaniline to give the title compound as colourless crystals, m.p. 195°-197° C. δ (360 MHz, DMSO), 1.14 (3H, t, J=7.6 Hz, $NHPhCH_2CH_3$), 1.55 (1H, ddd, J=13.2, 12.6 and 3.7 Hz, $CH_ACH_BH_CCH_D$), 2.32 (1H, dm, J=13.2 Hz, $CH_ACH_BH_CCH_D$), 2.50 (2H, q, J=7.6 Hz, $CH_2CH_3$), 3.79 (1H, dd, J=12.6 Hz, $CH_ACH_BH_CCH_D$), 4.93 (1H, m, $CH_ACH_BH_CCH_D$), 6.46 (1H, d, J=6.6 Hz, CHNHCONH), 6.65 (1H, d, J=2.0 Hz, 6-H or 8-H), 6.68 (1H, s, ArNH), 6.87 (1H, d, J=2.0 Hz, 6-H or 8-H), 7.05 (2H, d, J=8.4 Hz, ArH), 7.28 (2H, d, J=8.4 Hz, ArH), 8.09 (1H, s, CHNHCONH); m/e (CI+) 408 (M+1), Found C, 55.24; H, 4.74; N, 9.93. $C_{19}H_{19}Cl_2N_3O_3.0.175H_2O$ requires C, 55.47; H, 4.74; N, 10.21%.

EXAMPLE 144

Trans-2-carboxy-5,7-dichloro-4-((N-ethyl-N-phenyl)amino)carbonylamino-1,2,3,4-tetrahydroquinoline This material was prepared using the method given in Example 78 step b and c) using N-ethylaniline in place of N-methylaniline to give the title compound as colourless crystals, m.p. 227°-229° C.; δ (360 MHz, DMSO) 0.99 (3H, t, J=7.0 Hz, $CH_2CH_3$), 1.56 (1H, ddd, J=13.1, 12.6 and 4.0 Hz, $CH_ACH_BH_CCH_D$), 2.28 (1H, dm, J=13.1 Hz, $CH_ACH_BH_CCH_D$), 3.63 (2H, m, $CH_2CH_3$), 3.84 (1H, dd, J=12.6 and 4.0 Hz, $CH_ACH_BH_CCH_D$), 4.92 (1H, m, $CH_ACH_BH_CCH_D$), 5.96 (1H, d, J=6.9 Hz, $CH_DNHCON$), 6.61 (1H, d, J=2.0 Hz, 6-H or 8-H), 6.64 (1H, s, ArNH), 6.80 (1H, d, J=2.0 Hz, 6-H or 8-H), 7.20 (4H, m, ArH); m/e (CI+) 408 (M+1) Found C, 55.82; H, 4.76; N, 10.0. $C_{19}H_{19}Cl_2N_3O_3$ requires C, 55.89; H, 4.69; N, 10.29%.

EXAMPLE 145

Trans-4-benzylamino-2-carboxy-5,7-dichloro-1,2,3,4-tetrahydroquinoline

Step a) Trans-4-benzylamino-5,7-dichloro-2-methoxycarbonyl-1,2,3,4-tetrahydroquinoline To a solution of trans-4-amino-5,7-dichloro-2-methoxycarbonyl-1,2,3,4-tetrahydroquinoline hydrochloride (0.300 g, 0.96 mmol) in anhydrous DMF (10 ml) was added triethylamine (0.403 ml, 2.89 mmol), benzyl bromide (0.230 ml, 1.92 mmol) and a catalytic quantity of sodium iodide. This mixture was stirred under an atmosphere of nitrogen at room temperature for 90 hours. The solvent was removed in vacuo and the residue obtained was partitioned between distilled water (100 ml) and ethyl acetate (200 ml). The organic layer was washed with saturated sodium hydrogen carbonate (2×100 ml), brine (2×100 ml) and distilled water (2×100 ml), dried (MgSO4) and concentrated in vacuo. The residue was purified by chromatrography on silica gel (using from 10% ethyl acetate in hexane to 50% ethyl acetate in hexane as eluents) to give the title compound as colourless crystals, m.p. 112°-114° C. δ (360 MHz, DMSO), 1.41 (1H, ddd, J=13.4, 12.3 and 3.1 Hz, $CH_ACH_BH_CCH_D$), 2.33 (1H, dm, J=13.4 Hz, $CH_ACH_BH_CCH_D$), 3.73 (3H, s, $CO_2CH_3$), 3.84 (2H, 2 d, J=13.5 Hz, $CH_2C_6H_5$), 4.13 (1H, m, $CH_ACH_BH_CCH_D$), 4.27 (1H, dd, J=12.3 and 2.8 Hz, $CH_ACH_BH_CCH_D$), 6.60 (1H, d, J=2.1 Hz, 6-H or 8-H), 6.73 (1H, s, ArNH, 6.78 (1H, d, J=7.69 (1H, d, 2.1 Hz, 6-H or 8-H), 7.28 (3H, m, ArH), 7.37 (2H, m, ArH), 7.69 (1H, m, $CHNHCH_2$); m/e (CI+) 365 (M+1).

Step b) Trans-4-benzylamino-2-carboxy-5,7-dichloro-1,2,3,4-tetrahydroquinoline

This compound was prepared by the method given in Example 37 step b) using trans-4-benzylamino-5,7-dichloro-2-methoxycarbonyl-1,2,3,4-tetrahydroquinoline in place of trans-5,7-dichloro-2-methoxycarbonyl-4-phenylmethylcarbonylamino-1,2,3,4-tetrahydroquinoline to give the title compound as colourless crystals, m.p. 140°-143° C. δ (360 MHz, DMSO) 1.85 (1H, ddd, J=13.3, 12.4 and 3.0 Hz, $CH_ACH_BH_CCH_D$), 2.73 (1H, dm, J=13.3 Hz, $CH_ACH_BH_CCH_D$), 4.32 (2H, 2d, J=13.4 Hz, $CH_2C_6H_5$), 4.46 (1H, m, $CH_ACH_BH_CCH_D$), 4.48 (1H, m, $CH_ACH_BH_CCH_D$), 6.70 (1H, d, J=2.1 Hz, 6-H or 8-H), 6.90 (1H, d, J=2.1 Hz, 6-H or 8-H), 7.12 (1H, s, ArNH), 7.43 (3H, m, ArH), 7.63 (2H, m, ArH); m/e (FAB−) 349 (M-1); Found C, 50.17; H, 6.22; N, 5.01. $C_{17}H_{16}Cl_2N_2O_2 \cdot 1.8HCl \cdot 0.2 C_6H_{14}$ requires C, 50.06; H, 4.78; N, 6.45%.

EXAMPLE 146

Trans-2-carboxy-5,7-dichloro-4-(phenylaminocarbonylmethylamino)-1,2,3,4-tetrahydroquinoline hydrochloride This material was prepared by the method given in Example 145 step a and b) using phenylaminocarbonylmethyliodide in place of benzyl bromide to yield the title compound as colourless crystals, m.p. 163°-164.2° C. dec.; δ (360 MHz, DMSO) 1.93 (1H, ddd, J=13.3, 12.2 and 3.8 Hz, $CH_ACH_BH_CCH_D$), 2.73 (1H, dm, J=13.3 Hz, $CH_ACH_BH_CCH_D$), 4.00 (2H, 2d, J=16.2 Hz, NHCH$_2$CONHPh), 4.32 (1H, dd, J=12.2 and 3.8 Hz, $CH_ACH_BH_CCH_D$), 4.78 (1H, bs, $CH_ACH_BH_CCH_D$), 6.73 (1H, d, J=2.0 Hz, 6-H or 8-H), 6.92 (1H, d, J=2.0 Hz, 6-H or 8-H), 7.10 (1H, m, ArH), 7.18 (1H, s, ArNH), 7.35 (2H, m, 2 ArH), 7.60 (2H, m, 2 ArH), 9.5 (2H, bm, NH$_2$), 10.72 (1H, m, $CH_DNHCH_2$). m/e (FAB+) 394 (M+1). Found C, 46.73; H, 4.28; N, 8.75; $C_{18}H_{17}Cl_2N_3O_3 \cdot 1.9HCl$ requires C, 46.50; H, 4.32; N, 9.05%.

EXAMPLE 147

Trans-2-[(tertiary-butylcarbonyloxy)methyloxycarbonyl]-5,7-dichloro-4-phenylmethylcarbonylamino-1,2,3,4-tetrahydroquinoline To a solution of trans-2-carboxy-5,7-dichloro-4-phenylmethylcarbonylamino-1,2,3,4-tetrahydroquinoline (0.06 g, 0.16 mmol, Example 34) in tetrahydrofuran (5 ml) was added triethylamine (0.027 ml, 0.19 mmol) followed by a solution of iodomethylpivalate (0.06 g, 0.24 mmol) in tetrahydrofuran (2 ml). This mixture was stirred at room temperature for 4 hours. The solvent was removed under vacuum and the residue obtained was purified by flash chromatography (using ethyl acetate in hexane as eluent) to give the title compound (0.044 g), m.p. 162.4°-163° C. δ (360 MHz, DMSO) 1.41 (9H, s, C(CH$_3$)$_3$, 1.66 (1H, ddd, J=13.4, 12.6 and 3.8 Hz, $CH_ACH_BH_CCH_D$), 2.12 (1H, dm, J=13.4 Hz, $CH_ACH_BH_CCH_D$), 3.41 (2H, NHCOCH$_2$Ph), 3.97 (1H, dd, J=12.6 and 3.8 Hz, $CH_ACH_BH_CCH_D$), 5.02 (1H, m, $CH_ACH_BH_CCH_D$), 5.81 (2H, 2d, J=5.9 Hz, CO$_2$CH$_2$CO), 6.71 (1H, d, J=2.0 Hz, 6-H or 8-H), 6.86 (1H, d, J=2.0 Hz, 6-H or 8-H), 6.97 (1H, bs, ArNH), 7.26 (5H, m, ArH), 8.45 (1H, d, J=7.1 Hz, $CH_DNHCO$); m/e (CI+) 493 (M+1). Found C, 58.37; H, 5.33; N, 5.69; $C_{24}H_{26}Cl_2N_2O_5$ requires C, 58.43; H, 5.31; N, 5.68%.

EXAMPLE 148

Trans-5,7-dichloro-2-[-methylaminocarbonylmethyl)oxycarbonyl]-4-phenylmethylcarbonylamino-1,2,3,4-tetrahydroquinoline To a solution of trans-2-carboxy-5,7-dichloro-4-phenylmethylcarbonylamino-1,2,3,4-tetrahydroquinoline (0.05 g, 0.13 mmol, Example 34) in a tetrahydroquinoline (5 ml) was added triethylamine (0.055 ml, 0.4 mmol), 1-hydroxy-N-methylacetamide (0.018 g, 0.2 mmol), 4-dimethylaminopyridine (0.019 g, 0.16 mmol) and 1-(3-dimethylaminopropyl)-3-ethylcarbodiimide hydrochloride (0.03 g, 0.16 mmol). This mixture was stirred at room temperature for 18 hours. The solvent was removed under vacuum and the residue was partitioned between ethyl acetate (50 ml) and citric acid solution (1M, 100 ml). The organic layer was separated and washed successively with citric acid solution (1M, 1×75 ml), saturated sodium bicarbonate solution (2×75 ml), saturated brine (1×75 ml) then dried (MgSO$_4$) and evaporated and the residue purified by flash chromatography (using ethyl acetate in hexane as eluent) to give the title compound (0.037 g), m.p. 229°-231° C.; m/e (CI+) 450 (M+1); δ (250 MHz, DMSO) 1.65 (1H, ddd, J=13.4, 12.6 and 3.8 Hz, $CH_ACH_BH_CCH_D$), 2.26 (1H, dm, J=13.4 Hz, $CH_ACH_BCH_CCH_D$), 2.63 (3H, d, J=4.6 Hz, NHCH$_3$), 3.42 (2H, s, COCH$_2$Ph), 4.07 (1H, dd, J=12.6 Hz, $CH_ACH_BH_CCH_D$), 4.56 (2H, s, CO$_2$CH$_2$CO), 5.02 (1H, m, $CH_ACH_BH_CCH_D$), 6.71 (1H, d, J=2.1 Hz, 6-H or 8-H), 6.87 (1H, d, J=2.1 Hz, 6-H or 8-H), 6.96 (1H, s, ArNH), 7.23 (5H, m, ArH), 8.00 (1H, m, NHCH$_3$), 8.50 (1H, d, J=7.1 Hz, $CH_DNHCO$). Found C, 55.11; H, 4.75; N, 9.09, $C_{21}H_{21}Cl_2N_3O_4 \cdot 0.5H_2O$ requires C, 54.91; H, 4.83; N, 9.15%.

EXAMPLE 149

Trans-5,7-dichloro-2-[(N,N-dimethylamino)ethylaminocarbonylmethyl)oxycarbonyl]-4-phenylmethylcarbonylamino-1,2,3,4-tetrahydroquinoline hydrochloride To a solution of trans-2-carboxy-5,7-dichloro-4-phenylmethylcarbonylamino-1,2,3,4-tetrahydroquinoline (0.1 g, 0.26 mmol, Example 34) in tetrahydrofuran (20 ml) was added 1,1-carbonyldiimidazole (0.064 g, 0.4 mmol) and this mixture heated to reflux under an atmosphere of nitrogen for 3 hours. The reaction mixture was cooled to −78° C. and a preformed solution of the lithium salt of 1-hydroxy-N,N-dimethylaminoethylacetamide [formed from addition of n-butyllithium (0.63 ml of 1.6M solution in hexane) to a solution of 1-hydroxy-N,N-dimethylaminoethylacetamide (0.170 g, 1.1 mmol) in tetrahydrofuran (10 ml) at −78° C. and warmed to room temperature then recooled back to −78° C.], was added and after stirring for 3 minutes acetic acid (0.3 ml, 5 mmol) was added and the mixture left to warm to room temperature. The solvent was removed under vacuum and the residue was partitioned between ethyl acetate (50 ml) and saturated sodium bicarbonate (100 ml). The organic layer was separated and washed successively with saturated sodium bicarbonate (1×75 ml), saturated brine (1×75 ml), then dried (MgSO$_4$) and evaporated. To the residue was added hydrogen chloride in ethyl acetate (1 ml, 5M), this solution was extracted with water (2×50 ml) and the aqueous layer freeze dried to yield the title compound as a white solid (0.036 g). δ (360 MHz, DMSO) 1.65 (1H, ddd, J=13.4, 12.6 and 3.8 Hz, $CH_ACH_BH_CCH_D$), 2.26 (1H, dm, J=13.4 Hz, $CH_ACH_BH_CCH_D$), 2.76 (6H, s, N(CH$_3$)$_2$), 3.10 (2H, m, CH$_2$N(CH$_3$)$_2$), 3.46 (4H, m, CONHCH$_2$CH$_2$N(CH$_3$)$_2$ and NHCOCH$_2$Ph), 4.06 (1H, dd, J=12.6 and 3.8 Hz, $CH_ACH_BH_CCH_D$), 4.62 (2H, 2d, J=5 Hz, CO$_2$CH$_2$CONH), 5.02 (1H, m, $CH_ACH_BH_CCH_D$), 6.70 (1H, d, J=2.0 Hz, 6-H or 8-H), 6.92 (1H, d, J=2.0 Hz, 6-H or 8-H), 7.60 (1H, s, ArNH), 7.24 (5H, m, ArH), 8.40 (1H, m, CH$_2$CONHCH$_2$), 8.50 (1H, d, J=7.1 Hz, $CH_DNHCO$). Found C, 47.15; H, 5.39; N, 9.12; $C_{24}H_{29}Cl_3N_4O_4 \cdot 2HCl \cdot 1.5H_2O$ requires C, 47.46; H, 5.48; N, 9.22%.

EXAMPLE 150

Trans-5,7-dichloro-2(2-N,N-diethylaminoethyl)oxycarbonyl-4-phenylmethyl-cabonylamino-1,2,3,4-tetrahydroquinoline hydrochloride Step a) N,N-diethylethanolamine lithium salt To a solution of N,N-diethylethanolamine (0.265 ml, 2.0 mmol) in anhydrous tetrahydrofuran (10 ml) cooled to −78° C. under an atmosphere of nitrogen was slowly added a 1.6M solution of n-butyllithium in hexane (1.25 ml, 2.0 mmol). The mixture was then allowed to warm to room temperature and was used as such for step b).

Step b) Trans-5,7-dichloro-2(2-N,N-diethylaminoethyl)oxycarbonyl-4-phenylmethylcarbonylamino-1,2,3,4-tetrahydroquinoline hydrochloride To a solution of trans-2-carboxy-5,7-dichloro-4-phenylmethylcarbonylamino-1,2,3,4-tetrahydroquinoline (0.100 g, 0.264 mmol) in anhydrous tetrahydrofuran (20 ml) was added carbonyldiimidazole (0.065 g, 0.40 mmol) and the resulting mixture was heated at reflux under an atmosphere of nitrogen for 3 h. The reaction was then cooled to −78° C. and a solution of N,N-diethylethanolamine lithium salt in tetrahydrofuran (from step a), 4.60 ml, 0.80 mmol) was added slowly. The resulting mixture was stirred at −78° C. for 5 mins then quenched with glacial acetic acid (0.1 ml), allowed to warm to room temperature and concentrated in vacuo. The residue was suspended in ethyl acetate (50 ml), washed with saturated sodium bicarbonate (2×20 ml), saturated brine (1×20 ml), dried (MgSO4) and evaporated under vacuum to give a solid which was purified by flash chromatography on silica gel, using 5% methanol in dichloromethane as eluent. To a solution of the purified material in ethyl acetate (5 ml) was added a saturated solution of hydrogen chloride in ethyl acetate (1 ml) and the resulting mixture was stirred at room temperature for 5 min. The solvent was removed under vacuum to give the crude hydrochloride salt as an oil which was dissolved in water (10 ml), filtered and freeze dried to give the title compound as a colourless foam (0.072 g). δ (360 MHz, CD3OD) 1.21 (6H, t, J=7.2 Hz, N(CH2CH3)2), 1.68 (1H, ddd, J=13.3, 12.6 and 4.0 Hz, CH$_A$CH$_B$H$_C$CH$_D$), 2.32 (1H, dm, J=13.3 Hz, CH$_A$CH$_B$H$_C$CH$_D$), 3.15 (4H, q, J=7.2 Hz, N(CH2CH3)2), 3.37–4.43 (4H, m, CO2CH2CH2N+ and ArCH2CO), 3.96 (1H, dd, J=12.6 and 2.8 Hz, CH$_A$CH$_B$H$_C$CH$_D$), 4.42 (2H, t, J=5.0 Hz, CO2CH2CH2N), 5.07 (1H, m, CH$_A$CH$_B$H$_C$CH$_D$), 6.59 (1H, d, J=1.9 Hz, 6-H or 8-H), 6.68 (1H, d, J=1.9 Hz, 6-H or 8-H), 7.12–7.21 (5H, m, ArH), 8.45 (1H, d, J=6.6 Hz, CH$_D$NHCO); m/e (FAB+) 478 (M+H)+.

EXAMPLE 151

Trans-5,7-dichloro-2-(3-N,N-dimethylaminopropyl)oxycarbonyl-4-phenylmethylcarbonylamino-1,2,3,4-tetrahydroquinoline hydrochloride This material was prepared in the same way as Example 150 but using 3-dimethylamino-1-propanol in place of N,N-diethylethanolamine (step a) to give the title compound as a colourless foam. δ (360 MHz, CD3OD) 1.76 (1H, ddd, J=13.3, 12.6 and 4.0 Hz, CH$_A$CH$_B$H$_C$CH$_D$), 2.08–2.17 (2H, m, CO2CH2CH2CH2N), 2.39 (1H, dm, J=13.3 Hz, CH$_A$CH$_B$H$_C$CH$_D$), 2.88 (6H, s, N(CH3)2), 3.18–3.25 (2H, m, CO2CH2CH2CH2N), 3.50 (2H, s, CH2Ph), 4.01 (1H, dd, J=12.6 and 3.0 Hz, CH$_A$CH$_B$H$_C$CH$_D$), 4.22–4.36 (2H, m, CO2CH2CH2CH2N), 5.16 (1H, m, CH$_A$CH$_B$H$_C$CH$_D$), 6.68 (1H, d, J=2.0 Hz, 6-H or 8-H), 6.76 (1H, d, J=2.0 Hz, 6-H or 8-H), 7.20–7.31 (5H, m, ArH), 8.55 (1H, d, J=6.5 Hz, CH$_D$NHCO); m/e (EI) 463 (M+), 198 (100%, M-PhCH2CONH, CO2CH2CH2CH2N(CH3)2and H).

EXAMPLE 152

Trans 2-(2-(N,N-dimethylamino)ethyl)aminocarbonyl-4-phenylmethylcarbonylamino-5,7-dichloro-1,2,3,4-tetrahydroquinoline Trans 5,7-dichloro-2-methoxycarbonyl-4-phenylmethylcarbonylamino-1,2,3,4-tetrahydroquinoline (Example 37a) (0.3 g) was dissolved in N,N-dimethylethylenediamine (30 ml) and allowed to stand at room temperature for 6 h. After this time the reaction mixture was filtered and the solvent was removed under vacuum. The residue was dissolved in ethyl acetate (100 ml) and washed with water (100 ml) then brine (100 ml). The organic solution was dried (MgSO4), filtered and concentrated in vacuo to give a solid which was triturated with diethyl ether and collected by filtration to give the title compound (0.19 g) as a colourless solid, m.p. 158°–159° C.; δ (360 MHz, DMSO) 1.54 (1H, ddd, J=13.0, 12.5 and 4.0 Hz, CH$_A$CH$_B$H$_C$CH$_D$), 2.08 (1H, dm, J=13.0 Hz, CH$_A$CH$_B$H$_C$CH$_D$), 2.16 (6H, s, N(CH3)2), 2.33 (2H, t, J=6.7 Hz, CH2CH2N(CH3)2, 3.21 (2H, m, CH2CH2N(CH3)2), 3.37 (1H, d, J=14.0 Hz, CH$_E$H$_F$Ph), 3.47 (1H, d, J=14.0 Hz, CH$_E$H$_F$Ph), 3.74 (1H, dm, J=12.5 Hz, CH$_A$CH$_B$H$_C$CH$_D$), 4.99 (1H, m, CH$_A$CH$_B$H$_C$CH$_D$), 6.66 (1H, d, J=1.9 Hz, 6-H or 8-H), 6.79 (2H, m, 6-H or 8-H and ArNH), 7.26 (5H, m, ArH), 8.01 (1H, br, s, CONHCH2CH2N(CH3)2), 8.44 (1H, d, J=7.2 Hz, CH$_D$NHCO); m/e 488 (M+); Found C, 58.47; H, 5.84; N, 12.39 C22H26Cl2N4O2 requires C, 58.80; H, 5.83; N, 12.47%.

EXAMPLE 153

Trans-2-(2-(N,N-dimethylamino)ethyl)aminocarbonyl-4-phenylaminocarbonylamino-5,7-dichloro-1,2,3,4-tetrahydroquinoline This compound was prepared by the route outlined in Example 152 using trans 5,7-dichloro-2-methoxycarbonyl-4-phenylaminocarbonylamino-1,2,3,4-tetrahydroquinoline (example 38a) in place of trans-5,7-dichloro-2-4-methoxycarbonyl-phenylmethylcarbonylamino-1,2,3,4-tetrahydroquinoline to give the title compound as colourless crystals m.p. 223°–224° C.; δ (360 MHz, DMSO) 1.55 (1H, ddd, J=13.0, 12.4 and 3.0 Hz, CH$_A$CH$_B$H$_C$CH$_D$), 2.14 (6H, s, N(CH3)2), 2.21 (1H, dm, J=13.0 Hz, CH$_A$CH$_B$H$_C$CH$_D$), 2.31 (2H, t, J=6.7 Hz, CH2CH2N(CH3)2), 3.22 (2H, m, CH2CH2N(CH3)2), 3.77 (1H, dd, J=12.4 and 2.7 Hz, CH$_A$CH$_B$H$_C$CH$_D$), 4.94 (1H, m, CH$_A$CH$_B$H$_C$CH$_D$), 6.44 (1H, d, J=6.8 Hz, CH$_D$NHCONHPh). 6.68 (1H, d, J=1.9 Hz, 6-H or 8-H), 6.73 (1H, br, s, ArNHCH$_A$), 6.79 (1H, d, J=1.9 Hz, 6-H or 8-H), 6.89 (1H, t, J=7.3 Hz, para proton), 7.22 (2H, t, J=7.3 Hz, meta protons), 7.39 (2H, d, J=7.3 Hz, ortho protons), 8.05 (1H, m, NHCH2CH2N(CH3)2), 8.14 (1H, s, CH$_D$NHCONHPh); m/e 449 (M+); Found C, 53.74; H, 5.37; N, 14.87 C21H25Cl2N5O5.0.9H2O requires C, 54.06; H, 5.79; N, 15.01%.

EXAMPLE 154

Trans-4-(4-aminomethylphenyl)methylcarbonylamino-5,7-dichloro-2-(N-methylaminocarbonylmethyl)oxycarbonyl-1,2,3,4-tetrahydroquinoline hydrochloride Step a) Trans-4-(4-tertiary-butyloxycarbonylaminophenyl)methylcarbonylamino-5,7-dichloro-2-(N-methylaminocarbonylmethyl)oxycarbonyl-1,2,3,4-tetrahydroquinoline This compound was prepared by the method given in Example 148 using trans-4-(4-tertiary-butyloxycarbonylaminophenyl)methylcarbonylamino-2-carboxy-5,7-dichloro-1,2,3,4-tetrahydroquinoline (Example 104) in place of trans-2-carboxy-5,7-dichloro-4-phenylmethylcarbonylamino-1,2,3,4-tetrahydroquinoline to give the title compound.

Step b) Trans-4-(4-aminomethylphenyl)methylcarbonylamino-5,7-dichloro-2-(N-methylaminocarbonylmethyl)oxycarbonyl-1,2,3,4-tetrahydroquinoline hydrochloride This compound was prepared by the method given in Example 107 using trans-4-(4-tertiary-butyloxycarbonylaminophenylmethylcarbonylamino-5,7-dichloro-2-(N-methylaminocarbonylmethyl)oxycarbonyl-1,2,3,4-tetrahydroquinoline in place of trans-4-(4-tertiary-butyloxycarbonylaminoethylphenyl)methylcarbonylamino-5,7-dichloro-2-methoxycarbonyl-1,2,3,4-tetrahydroquinoline to give the title compound, m.p. 195°–197° C. dec. δ 1.69 (1H, ddd, J=13.0, 12.6 and 3.9 Hz, $CH_ACH_BH_CCH_D$), 2.22 (1H, dm, J=13.0, $CH_ACH_BH_CCH_D$), 2.62 (3H, d, J=4.5 Hz, CONHCH$_3$), 3.44 (2H, q, J=14.0 Hz, PhCH$_2$NH$_3^+$), 3.98 (2H, bs, NHCOCH$_2$Ph), 4.08 (1H, dd, J=12.6 and 3.9 Hz, $CH_ACH_BH_CCH_D$), 4.57 (2H, s, CO$_2$CH$_2$CONHCH$_2$), 5.01 (1H, m, $CH_ACH_BH_CCH_D$), 6.70 (1H, d, J=2.0 Hz), 6.90 (1H, d, J=2.0 Hz), 7.00 (1H, s, ArNH) 7.33 (4H, m, ArH), 8.07 (4H, bm, ArCH$_2$NH$_3^+$ and CH$_2$CONHCH$_3$), 8.21 (1H, d, J=7.1 Hz, CH$_D$NHCO). Found C, 45.86; H, 4.56; N, 9.78; C$_{22}$H$_{24}$Cl$_2$N$_4$O$_4$.2HCl.1.1H$_2$O requires C, 46.19; H, 4.95; N, 9.79%.

EXAMPLE 155

Trans-4-(4-aminomethylphenyl)methylcarbonylamino-5,7-dichloro-2-hexyloxycarbonyl-1,2,3,4-tetrahydroquinoline hydrochloride This compound was prepared by the methods given for Example 148 followed by Example 107 using n-hexanol in place of 1-hydroxy-N-methylacetamide to give the title compound as colourless solid, m.p. 249°–251° C., δ 0.86 (3H, t, J=6.5 Hz, CO$_2$CH$_2$CH$_2$(CH$_2$)$_3$CH$_3$), 1.28 (6H, m, CO$_2$CH$_2$(CH$_2$)$_3$CH$_3$), 1.62 (3H, m, CO$_2$CH$_2$CH$_2$(CH$_2$)$_3$CH$_3$ and $CH_ACH_BH_CCH_D$), 2.16 (1H, dm, J=13.2 Hz, $CH_ACH_BH_CCH_D$), 3.45 (2H, q, J= 14.1 Hz, PhCH$_2$NH$_3^+$), 3.94 (3H, m, $CH_ACH_BH_CCH_D$ and NHCOCH$_2$Ph), 4.15 (2H, m, CO$_2$CH$_2$(CH$_2$)$_3$CH$_3$), 5.01 (1H, m, $CH_ACH_BH_CCH_D$), 6.69 (1H, d, J=2.1 Hz, 6-H or 8-H), 6.88 (2H, m, 6-H or 8-H and ArNH), 7.28 (2H, d, J=8.1 Hz, 2×ArH), 7.38 (2H, d, J=8.1 Hz, 2×ArH), 8.29 (3H, bs, PhCH$_2$NH$_3^+$), 8.49 (1H, d, J=7.3 Hz, CH$_D$NHCO). m/e (CI$^+$) 492 (M+1);

EXAMPLE 156

Trans-2-carboxy-4-methoxycarbonylmethyl-5,7-dichloro-1,2,3,4-tetrahydroquinoline a) Trans-2-methoxycarbonyl-4-methoxycarbonylmethyl-5,7-dichloro-1,2,3,4-tetrahydroquinoline Trimethylphosphonoacetate (32.4 ml, 0.2 mol) was dissolved in dry THF (700 ml) and sodamide (7.8 g, 0.2 mol) added. The mixture was heated at 60° C. under nitrogen for 1.5 h then cooled to 0° C. 1-Acetyl-2-carboxy-5,7-dichloro-4-oxo-1,2,3,4-tetrahydroquinoline (Example 1d) (16 g) was added and the reaction was allowed to warm slowly to room temperature and stirred for 14 h. After this time the reaction mixture was quenched with glacial acetic acid (10 ml) and the solvents were removed under vacuum. The residue was dissolved in saturated sodium hydrogen carbonate solution (800 ml) and washed with ethyl acetate (4×500 ml). The aqueous solution was acidified to pH1 with 1N hydrochloric acid and extracted with ethyl acetate (2×500 ml). The combined organic layers were washed with water (4×300 ml), dried (Na$_2$SO$_4$), filtered and concentrated in vacuo. This crude residue (~16 g) was dissolved in methanol (1400 ml) and platinum oxide (10 g) added. The reaction mixture was stirred under one atmosphere pressure of hydrogen for 60 h then filtered and concentrated under vacuum. The oily residue was dissolved in methanol (1000 ml) which had been saturated with dry hydrogen chloride, and left at room temperature for 8 days. The solvent was removed under vacuum and the oil obtained was purified by chromatography on silica gel using 20% hexane in dichloromethane as eluent to give the required product as a white solid (6.53 g, m.p. 131° C.); δ (360 MHz, DMSO) 1.69 (1H, ddd, J=13.4, 12.3 and 4.0 Hz, $CH_ACH_BH_CCH_D$), 2.16 (1H, dm, J=13.4 Hz, $CH_ACH_BH_CCH_D$), 2.52 (2H, m, CH$_2$CO$_2$CH$_3$), 3.46 (1H, m, $CH_ACH_BH_CCH_D$), 3.65 (3H, s, CH$_3$), 3.72 (3H, s, CH$_3$), 4.11 (1H, dd, J=12.3 and 2.9 Hz, $CH_ACH_BH_CCH_D$), 6.64 (1H, d, J=1.9 Hz, 6-H or 8-H); 6.71 (1H, br, s, NH), 6.80 (1H, d, J=1.9 Hz, 6-H or 8-H); m/e 331 (M$^+$); Found C, 50.52; H, 4.50; N, 4.31. C$_{14}$H$_{15}$Cl$_2$NO$_4$ requires C, 50.62; H, 4.55; N, 4.22%.

b) Trans-2-carboxy-4-methoxycarbonylmethyl-5,7-dichloro-1,2,3,4-tetrahydroquinoline Trans-2-methoxycarbonyl-4-methoxycarbonylmethyl-5,7-dichloro-1,2,3,4-tetrahydroquinoline (0.4 g, 0.0012 mol) was dissolved in 50% aqueous acetone and cooled to 0° C. whereupon 0.5N sodium hydroxide solution (2.42 ml, 1 molar equivalent) was added. The reaction mixture was allowed to warm slowly to room temperature and stirred for 14 h. The acetone was removed under vacuum and the aqueous residue acidified to pH 1 with 1N hydrochloric acid and extracted into ethyl acetate (2×50 ml). The combined organic layers were dried (Na$_2$SO$_4$), filtered and concentrated in vacuo to leave a residue which was purified by chromatography on silica gel using 4% methanol/1% acetic acid in dichloromethane as eluent to give the title compound (0.26 g, m.p. 181°–182° C.) as a colourless solid; δ (250 MHz, CDCl$_3$) 1.72 (1H, ddd, J=13.3, 12.5 and 4.0 Hz, $CH_ACH_BH_CCH_D$), 2.36 (1H, dm, J=13.3 Hz, $CH_ACH_BH_CCH_D$), 2.39 (1H, dd, J=16.0 and 11.2 Hz, $CH_EH_FCO_2CH_3$), 2.72 (1H, dd, J=16.0 and 3.5 Hz, $CH_EH_FCO_2CH_3$), 3.66 (1H, m, $CH_ACH_BH_CCH_DCH_2CH_3$), 3.73 (3H, s, CO$_2$CH$_3$), 3.99 (1H, dd, J=12.5 and 5.1 Hz, $CH_ACH_BH_CCH_DCH$-

2CO$_2$Me), 5.15 (1H, br, s, NH), 6.56 (1H, d, J=2.0 Hz, 6-H or 8-H), 6.62 (1H, d, J=2.0 Hz, 6-H or 8-H); m/e 317 (M+); Found C, 49.17; H, 4.13; N, 4.42. C$_{13}$H$_{13}$Cl$_2$NO$_4$ requires C, 49.08; H, 4.12; N, 4.40%.

EXAMPLE 157

Trans-2-carboxy-4-carboxymethyl-5,7-dichloro-1,2,3,4-tetrahydroquinoline

Trans-2-methoxycarbonyl-4-methoxycarbonylmethyl-5,7-dichloro-1,2,3,4-tetrahydroquinoline (Example 156a) (0.4 g, 0.0012 mol) was dissolved in 50% aqueous methanol (80 ml) with sodium hydroxide (1 g). The reaction mixture was heated at 70° C. for 14 h and the solvents removed under vacuum. The residue was dissolved in water (50 ml), acidified to pH 1 with 1 normal hydrochloric acid and extracted into ethyl acetate (2×50 ml). The combined organic layers were dried (Na$_2$SO$_4$), filtered and concentrated in vacuo to give a residue which was purified by recrystallisation from diethyl ether/hexane to give the title compound as a colourless solid (0.24 g, m.p. 229°–231° C.); δ (250 MHz, DMSO) 1.63 (1H, ddd, J=13.3, 12.4 and 4.0 Hz, CH$_A$CH$_B$H$_C$CH$_D$), 2.20 (1H, dm, J=13.3 Hz, CH$_A$CH$_B$H$_C$CH$_D$), 2.40 (2H, m, CH$_E$H$_F$CO$_2$H), 3.39 (1H, m, CH$_A$CH$_B$H$_C$CH$_D$CH$_E$H$_F$CO$_2$H), 3.98 (1H, dd, J=12.4 and 3.3 Hz, CH$_A$CH$_B$H$_C$CH$_D$), 6.57 (1H, br, s, NH), 6.61 (1H, d, J=2.0 Hz, 6-H or 8-H), 6.80 (1H, d, J=2.0 Hz, 6-H or 8-H); m/e (FAB) 304 (M+1); Found C, 47.56; H, 3.70; N, 4.57 C$_{12}$H$_{11}$Cl$_2$NO$_4$ requires C, 47.39; H, 3.65; N, 4.61%.

EXAMPLE 158

Trans-2-carboxy-4-phenylaminocarbonylmethyl-5,7-dichloro-1,2,3,4-tetrahydroquinoline a) Trans-4-methoxycarbonylmethyl-2-tertiarybutyloxycarbonyl-5,7-dichloro-1,2,3,4-tetrahydroquinoline Trans-2-carboxy-4-methoxycarbonylmethyl-5,7-dichloro-1,2,3,4-tetrahydroquinoline (Example 156) (4 g) was suspended in dichloromethane (50 ml) and isobutylene (50 ml) was condensed at 0° C. Concentrated sulphuric acid (10 drops) was added and the reaction mixture was shaken for 3 days under a nitrogen atmosphere of 30 p.s.i. The solution was poured into saturated sodium hydrogen carbonate solution and diluted with a further amount of dichloromethane (100 ml). The organic layer was separated and the aqueous solution was washed with diethyl ether (100 ml). The combined organic layers were dried (Na$_2$SO$_4$), filtered and concentrated under vacuum. The residue obtained was purified by chromatography on silica gel with 20% hexane in dichloromethane as eluent to give the title compound as a colourless oil (4.07 g); δ (250 MHz, DMSO) 1.45 (9H, s, (CH$_3$)$_3$C), 1.64 (1H, ddd, J=13.0, 12.4 and 4.0 Hz, CH$_A$CH$_B$H$_C$CH$_D$), 2.10 (1H, dm, J=13.0 Hz, CH$_A$CH$_B$H$_C$CH$_D$), 2.49 (2H, m, CH$_E$CH$_F$CO$_2$CH$_3$), 3.44 (1H, m, CH$_A$CH$_B$H$_C$CH$_D$CH$_E$H$_F$CO$_2$CH$_3$), 3.65 (3H, s, CO$_2$CH$_3$), 3.97 (1H, dd, J=12.4 and 3.4 Hz, CH$_A$CH$_B$H$_C$CH$_D$), 6.63 (2H, m, 6-H or 8-H and NH), 6.79 (1H, d, J=2.0 Hz, 6-H or 8-H); m/e (FAB) 374 (M+1); Found C, 54.93; H, 5.67; N, 3.69. C$_{17}$H$_{21}$Cl$_2$NO$_4$ requires C, 54.56; H, 5.66; N, 3.74%.

b) Trans-carboxymethyl-2-tertiarybutyloxycarbonyl-5,7-dichloro-1,2,3,4-tetrahydroquinoline Trans-4-methoxycarbonylmethyl-2-tertiarybutyloxycarbonyl-5,7-dichloro-1,2,3,4-tetrahydroquinoline (4.0 g, 0.01072 mol) was dissolved in 50% aqueous acetone (300 ml) and cooled to 0° C. whereupon 0.5 normal sodium hydroxide solution (21.5 ml, 1 molar equivalent) was added. The reaction mixture was stirred at room temperature for 3 h and the acetone was then removed under vacuum. The aqueous residue was acidified to pH 1 with 1 normal hydrochloric acid and extracted into ethyl acetate (2×200 ml). The organic layer was dried (Na$_2$SO$_4$), filtered and concentrated in vacuo. Chromatography on silica gel using 4% methanol, 1% acetic acid in dichloromethane gave recovered starting material (2.5 g) as well as the title compound as a colourless solid (0.82 g, m.p. 160°–162° C.); δ (360 MHz, DMSO) 1.45 (9H, s, (CH$_3$)$_3$C), 1.62 (1H, ddd, J=13.0, 12.4 and 4.0 Hz, CH$_A$CH$_B$H$_C$CH$_D$), 2.16 (1H, dm, J=13.0 Hz, CH$_A$CH$_B$H$_C$CH$_D$), 2.35 (1H, dd, J=16.5 and 10.9 Hz, CH$_E$H$_F$CO$_2$H), 2.45 (1H, dd, J=16.5 and 2.9 Hz, CH$_E$H$_F$CO$_2$H), 3.43 (1H, m, CH$_A$CH$_B$H$_C$CH$_D$CH$_E$H$_F$CO$_2$H), 3.95 (1H, dd, J=12.4 and 3.4 Hz, CH$_A$CH$_B$H$_C$CH$_D$CH$_E$H$_F$CO$_2$H), 6.56 (1H, s, br, NH), 6.62 (1H, d, J=2.0 Hz, 6-H or 8-H), 6.78 (1H, d, J=2.0 Hz, 6-H or 8-H); m/e (CI+) 360 (M+1); Found C, 53.55; H, 5.30; N, 3.88. C$_{16}$H$_{19}$Cl$_2$NO$_4$ requires C, 53.35; H, 5.32N, 3.89%.

c) Trans-4-phenylaminocarbonylmethyl-2-tertiarybutyloxycarbonyl-5,7-dichloro-1,2,3,4-tetrahydroquinoline Trans-4-carboxymethyl-2-tertiarybutyloxycarbonyl-5,7-dichloro-1,2,3,4-tetrahydroquinoline (0.25 g, 0.000696M) was dissolved in dry THF with dry triethylamine (0.29 ml, 3 molar equivalents), hydroxybenzotriazole (0.141 g, 1.5 molar equivalents), aniline (0.0925 ml, 1.5 molar equivalents) and 1-(3-dimethylaminopropyl)-3-ethyl-carbodiimide hydrochloride (0.2 g, 1.5 molar equivalents) and the reaction mixture was stirred at room temperature for 14 h. The solvents were removed in vacuo and the residue was dissolved in ethyl acetate (100 ml) and washed successively with 0.5 normal citric acid solution (3×50 ml), saturated sodium hydrogen carbonate solution (3×50 ml) and brine (1×50 ml), dried (Na$_2$SO$_4$), filtered and evaporated under vacuum. The residue obtained was purified by chromatography on silica gel using 10% ethyl acetate in hexane as eluent to give the title compound (0.14 g) as a colourless oil; δ (250 MHz, DMSO) 1.48 (9H, s, (CH$_3$)$_3$C), 1.69 (1H, ddd, J=13.0, 12.4 and 4.0 Hz, CH$_A$CH$_B$H$_C$CH$_D$), 2.47 (2H, m, CH$_A$CH$_B$H$_C$CH$_D$CH$_E$H$_F$CONHPh), 2.73 (1H, dd, J=16.5 and 2.5 Hz, CH$_A$CH$_B$H$_C$CH$_D$CH$_E$H$_F$CONHPh), 3.73 (1H, m, CH$_A$CH$_B$H$_C$CH$_D$CH$_E$H$_F$CONHPh), 3.98 (1H, dd, J=12.4 and 3.3 Hz, CH$_A$CH$_B$H$_C$CH$_D$CH$_E$H$_F$CONHPh), 4.72 (1H, br, s, ArNHCH$_A$), 6.50 (1H, d, J=2.0 Hz, 6-H or 8-H), 6.70 (1H, d, J=2.0 Hz, 6-H or 8-H), 7.15 (2H, m, p-proton and PhNH), 7.33 (2H, t, J=7.5 Hz, m protons), 7.50 (2H, d, J=7.5 Hz, o protons); m/e (FAB) 379 (M+1).

d) Trans-2-carboxy-4-phenylaminocarbonylmethyl-5,7-dichloro-1,2,3,4-tetrahydroquinoline Trans-4-phenylaminocarbonylmethyl-2-tertiarybutyloxycarbonyl-5,7-dichloro-1,2,3,4-tetrahydroquinoline (0.12 g) was dissolved in 10% aqueous trifluoroacetic acid (30 ml) and stood at room temperature for 30 mins. The solvents were removed under vacuum and the residue chromatographed on silica gel using 3% methanol, 1% acetic acid, 96% dichloromethane to give a solid which was recrystallised from diethyl ether/hexane to give the title compound as a colourless solid (0.035 g, m.p. 208° C. dec); δ (360 MHz, DMSO) 1.62 (1H, ddd, J=13.0, 12.4 and 3.9 Hz, CH$_A$CH$_B$H$_C$CH$_D$), 2.19 (1H, d, J=13.0 Hz, CH$_A$CH$_B$H$_C$CH$_D$), 2.49 (2H, m, CH$_E$H$_F$CONHPh), 3.58 (1H, m, CH$_A$CH$_B$H$_C$CH$_D$), 4.08 (1H, dd, J=12.4 and 3.4 Hz, CH$_A$CH$_B$H$_C$CH$_D$), 6.62 (2H, m, 6-H or 8-H and NH), 6.80 (1H, d, J=2.0 Hz, 6-H or 8-H), 7.04 (1H, t, J=7.4 Hz, p proton), 7.31 (2H, t, J=7.4 Hz, m protons), 7.59 (2H, d, J=7.4 Hz, o protons); m/e (FAB) 379 (M+1); Found C, 57.18; H, 4.31; N, 7.22. C$_{18}$H$_{16}$Cl$_2$N$_2$O$_3$ requires C, 57.01; H, 4.25; N, 7.39%.

EXAMPLE 162

Tablet Preparation

Tablets containing 1.0, 2.0, 25.0, 26.0, 50.0 and 100.0 mg, respectively, of:

Trans-2-carboxy-5,7-dichloro-4-phenylmethylcarbonylamino-1,2,3,4-tetrahydroquinoline Trans-2-carboxy-5,7-dichloro-4-benzoylamino-1,2,3,4-tetrahydroquinoline Trans-2-carboxy-5,7-dichloro-4-phenylaminocarbonylamino-1,2,3,4-tetrahydroquinoline Trans-2-methoxycarbonyl-4-(4-aminomethylphenyl)-methylcarbonylamino-5,7-dichloro-1,2,3,4-tetrahydroquinoline hydrochloride Trans-2-carboxy-4-phenylaminocarbonylmethyl-5,7-dichloro-1,2,3,4-tetrahydroquinoline

| TABLE FOR DOSES CONTAINING FROM 1-25 MG OF THE ACTIVE COMPOUND | | | |
|---|---|---|---|
| | Amount-mg. | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 50.0 mg, and 100 mg of active ingredient per tablet.

What is claimed is:

1. A compound represented by formula IIC:

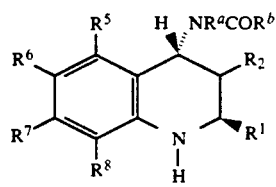

or pharmaceutically acceptable salts thereof, wherein
R$^1$ represents an acidic group or a group which is convertible thereto in vivo;
R$^2$ represents hydrogen, hydrocarbon having up to 18 carbon atoms or a heterocyclic group being of C$_{3-7}$ heterocycloalkyl, selected from the group consisting of piperidyl, piperazinyl and morpholinyl; C$_{3-7}$ heterocycloalkyl C$_{1-6}$ alkyl wherein C$_{3-7}$ heterocycloalkyl is as defined above; heteroaryl, selected from the group consisting of pyridyl, quinolyl, isoquinolyl, pyridazinyl, pyrimidinyl, pyrazinyl, pyranyl, furyl, benzofuryl, thienyl, benzthienyl, indolinyl, imidazolyl, oxadiazolyl, thiadiazolyl and tetrazolyl; and heteroaryl (C$_{1-6}$) alkyl wherein hetero aryl is as defined above, which groups are optionally substituted with a substituent selected from the group consisting of C$_{1-6}$ alkyl, adamantyl, phenyl, halogen, C$_{1-6}$ haloalkyl, amino (C$_{1-6}$) alkyl, mono-or di(C$_{1-6}$) alkyl, arylamino (C$_{1-6}$) alkyl, amino (C$_{2-6}$) alkenyl, amino (C$_{2-6}$) alkynyl, trifluoromethyl, hydroxy, C$_{1-6}$ alkoxy, aryloxy, keto, C$_{1-3}$ alkylenedioxy, nitro, cyano, carboxy, C$_{1-6}$ alkoxycarbonyl, C$_{1-6}$ alkoxycarbonyl (C$_{1-6}$) alkyl, C$_{1-6}$ alkylcarbonyloxy, arylcarbonyloxy, C$_{1-6}$ alkylcarbonyl, arylcarbonyl, C$_{1-6}$ alkylthio, C$_{1-6}$ alkylsulphinyl, C$_{1-6}$ alkylsulphonyl, amino, arylamino, C$_{1-6}$ alkylcarbonylamino, C$_{1-6}$ alkoxycarbonylamino and mono- or di (C$_{1-6}$) alkylamino;

R$^5$, R$^6$, R$^7$ and R$^8$ are independently selected from the group consisting of hydrogen, hydrocarbon having up to 18 carbon atoms; heterocyclic, selected from the group consisting of C$_{3-7}$ heterocycloalkyl, C$_{3-7}$ heterocycloalkyl (C$_{1-6}$) alkyl, heteroaryl and heteroaryl (C$_{1-6}$) alkyl, said groups being as defined above; halogen, cyano, trifluoromethyl, nitro, —OR$^a$, —SR$^a$, —NR$^a$R$^b$ and —CO$_2$R$^a$; and R$^a$ and R$^b$ are independently selected from the group consisting of hydrogen, C$_{1-6}$ alkyl, C$_{2-6}$ alkenyl, C$_{3-7}$ cycloalkyl(C$_{1-6}$) alkyl, aryl, aryl (C$_{1-6}$) alkyl, C$_{3-7}$ heterocycloalkyl, C$_{3-7}$ heterocycloalkyl C$_{1-6}$ alkyl, heteroaryl, and heteroaryl (C$_{1-6}$) alkyl, all of which are optionally substituted with a substituent as defined above.

2. A compound represented by formula IID:

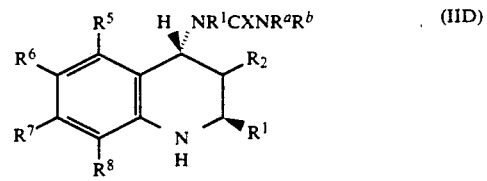

or pharmaceutically acceptable salts thereof, wherein
R$^1$ represents an acidic group or a group which is convertible thereto in vivo;
R$^2$ represents hydrogen, hydrocarbon containing up to 18 carbon atoms or a heterocyclic group selected from the group consisting of C$_{3-7}$ heterocycloalkyl, selected from the group consisting of piperidyl, piperazinyl and morpholinyl; C$_{3-7}$ heterocycloalkyl C$_{1-6}$ alkyl, heteroaryl, selected from the group consisting of pyridyl, quinolyl, isoquinolyl, pyridazinyl, pyrimidinyl, pyrazinyl, pyranyl, furyl, benzofuryl, thienyl, benzthienyl, indolinyl, imidazolyl, oxadiazolyl, thiadiazolyl and tetrazolyl, and heteroaryl (C$_{1-6}$) alkyl, which groups can be substituted with a substituent selected from the group consisting of C$_{1-6}$ alkyl, adamantyl, phenyl, halogen, C$_{1-6}$ haloalkyl, amino (C$_{1-6}$) alkyl, mono-or di(C$_{1-6}$) alkyl, arylamino (C$_{1-6}$) alkyl, amino (C$_{2-6}$) alkenyl, amino (C$_{2-6}$)

alkynyl, trifluoromethyl, hydroxy, $C_{1-6}$ alkoxy, aryloxy, keto, $C_{1-3}$ alkylenedioxy, nitro, cyano, carboxy, $C_{1-6}$ alkoxycarbonyl, $C_{1-6}$ alkoxycarbonyl ($C_{1-6}$) alkyl, $C_{1-6}$ alkylcarbonyloxy, arylcarbonyloxy, $C_{1-6}$ alkylcarbonyl, arylcarbonyl, $C_{1-6}$ alkylthio, $C_{1-6}$ alkylsulphinyl, $C_{1-6}$ alkylsulphonyl, amino, arylamino, $C_{1-6}$ alkylcarbonylamino, $C_{1-6}$ alkoxycarbonylamino and mono- or di ($C_{1-6}$) alkylamino;

$R^5$, $R^6$, $R^7$ and $R^8$ are independently selected from the group consisting of hydrogen, hydrocarbon containing up to 18 carbon atoms; heterocyclic, selected from the group consisting of $C_{3-7}$ heterocycloalkyl, $C_{3-7}$ heterocycloalkyl ($C_{1-6}$) alkyl, heteroaryl and heteroaryl ($C_{1-6}$) alkyl, heteroaryl and heteroaryl ($C_{1-6}$) alkyl, said groups being defined above; halogen, cyano, trifluoromethyl, nitro, —$OR^a$, —$SR^a$, —$NR^aR^b$ and —$CO_2R^a$; and $R^a$ and $R^i$ are independently selected from the group consisting of hydrogen, $C_{1-6}$ alkyl, and aryl; $R^b$ is selected from the group consisting of $C_{3-4}$ cycloalkyl, aryl and aryl ($C_{1-6}$) alkyl, which groups can be substituted with a substituent defined above, and X represents oxygen or sulphur.

3. A compound selected from the group consisting of:
4-benzoylamino-2-carboxy-5,7-dichloro-1,2,3,4-tetrahydroquinoline;
4-acetylamino-2-carboxy-5,7-dichloro-1,2,3,4-tetrahydroquinoline;
2-carboxy-5,7-dichloro-4-cyclohexylcarbonylamino-1,2,3,4-tetrahydroquinoline;
4-benzylcarbonylamino-2-carboxy-5,7-dichloro-1,2,3,4-tetrahydroquinoline;
2-carboxy-4-(4-chlorophenylcarbonylamino)-5,7-dichloro-1,2,3,4-tetrahydroquinoline;
2-carboxy-5,7-dichloro-4-(4-pyridylcarbonylamino)-1,2,3,4-tetrahydroquinoline;
2-carboxy-5,7-dichloro-4-[2-(2-aminophenethyl)]-carbonylamino-1,2,3,4-tetrahydroquinoline;
2-carboxy-5,7-dichloro-4-n-propylcarbonylamino-1,2,3,4-tetrahydroquinoline;
2-carboxy-5,7-dichloro-4-phenylaminocarbonylamino-1,2,3,4-tetrahydroquinoline;
2-carboxy-5,7-dichloro-4-(4-methoxyphenylcarbonylamino)-1,2,3,4-tetrahydroquinoline;
4-benzylaminocarbonylamino-2-carboxy-5,7-dichloro-1,2,3,4-tetrahydroquinoline;
2-carboxy-5,7-dichloro-4-(2-methoxybenzylcarbonylamino)-1,2,3,4-tetrahydroquinoline;
2-carboxy-5,7-dichloro-4-(2-methylbenzylcarbonylamino)-1,2,3,4-tetrahydroquinoline;
2-carboxy-5,7-dichloro-4-(α-methoxybenzylcarbonylamino)-1,2,3,4-tetrahydroquinoline;
2-carboxy-5,7-dichloro-4-(2-nitrobenzylcarbonylamino)-1,2,3,4-tetrahydroquinoline;
2-carboxy-5,7-dichloro-4-(2-nitrophenylaminocarbonylamino)-1,2,3,4-tetrahydroquinoline;
2-carboxy-5,7-dichloro-4-(2-methoxyphenylaminocarbonylamino)-1,2,3,4-tetrahydroquinoline;
2-carboxy-5,7-dichloro-4-(2-methylphenylaminocarbonylamino)-1,2,3,4-tetrahydroquinoline;
2-carboxy-4-(2-chlorophenylaminocarbonylamino)-5,7-dichloro-1,2,3,4-tetrahydroquinoline;
4-(4'-biphenylcarbonylamino)-2-carboxy-5,7-dichloro-1,2,3,4-tetrahydroquinoline;
2-carboxy-5,7-dichloro-4-isopropylcarbonylamino-1,2,3,4-tetrahydroquinoline;
2-carboxy-4-(2-chlorophenylcarbonylamino)-5,7-dichloro-1,2,3,4-tetrahydroquinoline;
2-carboxy-5,7-dichloro-4-(1-naphthylcarbonylamino)-1,2,3,4-tetrahydroquinoline;
2-carboxy-5,7-dichloro-4-(2-naphthylcarbonylamino)-1,2,3,4-tetrahydroquinoline;
2-carboxy-5,7-dichloro-4-(2-furylcarbonylamino)-1,2,3,4-tetrahydroquinoline;
2-carboxy-5,7-dichloro-4-(2-methylphenylcarbonylamino)-1,2,3,4-tetrahydroquinoline;
2-carboxy-5,7-dichloro-4-(2-phenethylcarbonylamino)-1,2,3,4-tetrahydroquinoline;
2-carboxy-5,7-dichloro-4-(2-phenylethenylcarbonylamino)-1,2,3,4-tetrahydroquinoline;
2-carboxy-5,7-dichloro-4-(2-thienylmethylcarbonylamino)-1,2,3,4-tetrahydroquinoline;
2-carboxy-4-(3-chlorophenylcarbonylamino)-5,7-dichloro-1,2,3,4-tetrahydroquinoline;
2-carboxy-5,7-dichloro-4-(3-phenylpropylcarbonylamino)-1,2,3,4-tetrahydroquinoline;
2-carboxy-5,7-dichloro-4-(9-fluorenylcarbonylamino)-1,2,3,4-tetrahydroquinoline;
2-carboxy-4-cyclohexylmethylcarbonylamino-5,7-dichloro-1,2,3,4-tetrahydroquinoline;
2-carboxy-4-(2-chlorobenzylcarbonylamino)-5,7-dichloro-1,2,3,4-tetrahydroquinoline;
2-carboxy-4-(3-chlorobenzylcarbonylamino)-5,7-dichloro-1,2,3,4-tetrahydroquinoline;
2-carboxy-4-(4-chlorobenzylcarbonylamino)-5,7-dichloro-1,2,3,4-tetrahydroquinoline;
2-carboxy-5,7-dichloro-4-(4-methylbenzylcarbonylamino)-1,2,3,4-tetrahydroquinoline;
2-carboxy-5,7-dichloro-4-(4-methoxybenzylcarbonylamino)-1,2,3,4-tetrahydroquinoline;
2-carboxy-5,7-dichloro-4-(4-nitrobenzylcarbonylamino)-1,2,3,4-tetrahydroquinoline;
2-carboxy-4-(3-cyanophenylcarbonylamino)-5,7-dichloro-1,2,3,4-tetrahydroquinoline;
2-carboxy-4-(4-chlorophenylaminocarbonylamino)-5,7-dichloro-1,2,3,4-tetrahydroquinoline;
2-carboxy-5,7-dichloro-4-(4-methylphenylaminocarbonylamino)-1,2,3,4-tetrahydroquinoline;
2-carboxy-5,7-dichloro-4-(4-methoxyphenylaminocarbonylamino)-1,2,3,4-tetrahydroquinoline;
2-carboxy-5,7-dichloro-4-(4-nitrophenylaminocarbonylamino)-1,2,3,4-tetrahydroquinoline;
2-carboxy-5,7-dichloro-4-(4-iodophenylaminocarbonylamino)-1,2,3,4-tetrahydroquinoline;
2-carboxy-5,7-dichloro-4-[phenylaminocarbonyl(N-methyl)amino]-1,2,3,4-tetrahydroquinoline;
2-carboxy-5,7-dichloro-4-[(N-methyl-N-phenyl)aminocarbonylamino]-1,2,3,4-tetrahydroquinoline;
2-carboxy-5,7-dichloro-4-(2,3-dihydroindol-1-ylcarbonylamino)-1,2,3,4-tetrahydroquinoline;
2-carboxy-4-[2-(carboxyethyl)carbonylamino]-5,7-dichloro-1,2,3,4-tetrahydroquinoline;
4-[3-(aminomethyl)phenylcarbonylamino]-2-carboxy-5,7-dichloro-1,2,3,4-tetrahydroquinoline;
4-[3-(aminomethyl)phenylcarbonylamino]-5,7-dichloro-2-methoxycarbonyl-1,2,3,4-tetrahydroquinoline;
4-[4-(aminomethyl)phenylcarbonylamino]-2-carboxy-5,7-dichloro-1,2,3,4-tetrahydroquinoline;
4-[4-(aminomethyl)phenylcarbonylamino]-5,7-dichloro-2-methoxycarbonyl-1,2,3,4-tetrahydroquinoline;
4-[4-(2-aminoethyl)phenylcarbonylamino]-2-carboxy-5,7-dichloro-1,2,3,4-tetrahydroquinoline;
4-[4-(2-aminoethyl)phenylcarbonylamino]-5,7-dichloro-2-methoxycarbonyl-1,2,3,4-tetrahydroquinoline;

2-carboxy-5,7-dichloro-4-(3-methylbenzylcarbonylamino)-1,2,3,4-tetrahydroquinoline;
2-carboxy-5,7-dichloro-4-(3-nitrobenzylcarbonylamino)-1,2,3,4-tetrahydroquinoline;
2-carboxy-5,7-dichloro-4-(3-methoxybenzylcarbonylamino)-1,2,3,4-tetrahydroquinoline;
2-carboxy-5,7-dichloro-4-(1-naphthylmethylcarbonylamino)-1,2,3,4-tetrahydroquinoline;
2-carboxy-5,7-dichloro-4-(2-naphthylmethylcarbonylamino)-1,2,3,4-tetrahydroquinoline;
2-carboxy-5,7-dichloro-4-(3-thienylmethylcarbonylamino)-1,2,3,4-tetrahydroquinoline;
2-carboxy-5,7-dichloro-4-(2,6-dichlorobenzylcarbonylamino)-1,2,3,4-tetrahydroquinoline;
2-carboxy-5,7-dichloro-4-phenylaminothiocarbonylamino-1,2,3,4-tetrahydroquinoline;
4-benzyloxycarbonylamino-2-carboxy-5,7-dichloro-1,2,3,4-tetrahydroquinoline;
2-carboxy-5,7-dichloro-4-(3-methoxyphenylaminocarbonylamino)-1,2,3,4-tetrahydroquinoline;
2-carboxy-5,7-dichloro-4-(3-methylphenylaminocarbonylamino)-1,2,3,4-tetrahydroquinoline;
2-carboxy-4-(3-chlorophenylaminocarbonylamino)-5,7-dichloro-1,2,3,4-tetrahydroquinoline;
2-carboxy-5,7-dichloro-4-(3-nitrophenylaminocarbonylamino)-1,2,3,4-tetrahydroquinoline;
4-(3-aminopropyl)carbonylamino-2-carboxy-5,7-dichloro-1,2,3,4-tetrahydroquinoline;
4-(2-aminoethyl)carbonylamino-2-carboxy-5,7-dichloro-1,2,3,4-tetrahydroquinoline;
4-(4-aminobutyl)carbonylamino-2-carboxy-5,7-dichloro-1,2,3,4-tetrahydroquinoline;
2-carboxy-5,7-dichloro-4-(4-piperidylmethylcarbonylamino)-1,2,3,4-tetrahydroquinoline;
4-[(aminomethyl)benzylcarbonylamino]-2-carboxy-5,7-dichloro-1,2,3,4-tetrahydroquinoline;
4-[(aminomethyl)benzylcarbonylamino]-5,7-dichloro-2-methoxycarbonyl-1,2,3,4-tetrahydroquinoline;
4-[4-(2-aminoethyl)benzylcarbonylamino]-2-carboxy-5,7-dichloro-1,2,3,4-tetrahydroquinoline;
4-[4-(2-aminoethyl)benzylcarbonylamino]-5,7-dichloro-2-methoxycarbonyl-1,2,3,4-tetrahydroquinoline;
2-carboxy-5,7-dichloro-4-[4-(N-methylaminomethyl)benzylcarbonylamino]-1,2,3,4-tetrahydroquinoline;
5,7-dichloro-2-methoxycarbonyl-4-[4-(N-methylaminomethyl)benzylcarbonylamino]-1,2,3,4-tetrahydroquinoline;
5,7-dichloro-4-[4-(N,N-dimethylaminomethyl)benzylcarbonylamino]-2-methoxycarbonyl-1,2,3,4-tetrahydroquinoline;
2-carboxy-5,7-dichloro-4-[4-(N,N-dimethylaminomethyl)benzylcarbonylamino]-1,2,3,4-tetrahydroquinoline;
4-[4-(3-aminoprop-2-ynyl)benzylcarbonylamino]-2-carboxy-5,7-dichloro-1,2,3,4-tetrahydroquinoline;
4-[4-(3-aminoprop-2-ynyl)benzylcarbonylamino]-5,7-dichloro-2-methoxycarbonyl-1,2,3,4-tetrahydroquinoline;
4-[4-(3-aminopropyl)benzylcarbonylamino]-2-carboxy-5,7-dichloro-1,2,3,4-tetrahydroquinoline;
4-[4-(3-aminopropyl)benzylcarbonylamino]-5,7-dichloro-2-methoxycarbonyl-1,2,3,4-tetrahydroquinoline;
4-[4-(4-aminobut-2-ynyl)benzylcarbonylamino]-2-carboxy-5,7-dichloro-1,2,3,4-tetrahydroquinoline;
4-[4-(4-aminobut-2-ynyl)benzylcarbonylamino]-5,7-dichloro-2-methoxycarbonyl-1,2,3,4-tetrahydroquinoline;
4-[4-(4-aminobutyl)benzylcarbonylamino]-2-carboxy-5,7-dichloro-1,2,3,4-tetrahydroquinoline;
4-[4-(4-aminobutyl)benzylcarbonylamino]-5,7-dichloro-2-methoxycarbonyl-1,2,3,4-tetrahydroquinoline;
4-[3-(aminomethyl)benzylcarbonylamino]-2-carboxy-5,7-dichloro-1,2,3,4-tetrahydroquinoline;
4-[3-(aminomethyl)benzylcarbonylamino]-5,7-dichloro-2-methoxycarbonyl-1,2,3,4-tetrahydroquinoline;
4-[2-(aminomethyl)benzylcarbonylamino]-2-carboxy-5,7-dichloro-1,2,3,4-tetrahydroquinoline;
4-[2-(aminomethyl)benzylcarbonylamino]-5,7-dichloro-2-methoxycarbonyl-1,2,3,4-tetrahydroquinoline;
4-[2-(4-(aminomethyl)phenyl)ethylcarbonylamino]-2-carboxy-5,7-dichloro-1,2,3,4-tetrahydroquinoline;
4-[2-(4-(aminomethyl)phenyl)ethylcarbonylamino]-5,7-dichloro-2-methoxycarbonyl-1,2,3,4-tetrahydroquinoline;
4-(4-aminobenzylcarbonylamino)-2-carboxy-5,7-dichloro-1,2,3,4-tetrahydroquinoline;
2-carboxy-5,7-dichloro-4-(1,2,3,4-tetrahydroisoquinol-3-ylcarbonylamino)-1,2,3,4-tetrahydroquinoline;
2-carboxy-4-(2-carboxyphenylcarbonylamino)-5,7-dichloro-1,2,3,4-tetrahydroquinoline;
2-carboxy-4-(4-chloro-3-nitrobenzylcarbonylamino)-5,7-dichloro-1,2,3,4-tetrahydroquinoline;
2-carboxy-5,7-dichloro-4(4-hydroxy-3-nitrobenzylcarbonylamino)-1,2,3,4-tetrahydroquinoline;
2-carboxy-5,7-dichloro-4-(diphenylmethylcarbonylamino)-1,2,3,4-tetrahydroquinoline;
2-carboxy-5,7-dichloro-4-(1-phenylethyl)carbonylamino-1,2,3,4-tetrahydroquinoline;
4-(4-acetylbenzylcarbonylamino)-2-carboxy-5,7-dichloro-1,2,3,4-tetrahydroquinoline;
2-carboxy-5,7-dichloro-4-phenoxymethylcarbonylamino-1,2,3,4-tetrahydroquinoline;
2-carboxy-5,7-dichloro-4-(4-ethylbenzylcarbonylamino)-1,2,3,4-tetrahydroquinoline;
2-carboxy-5,7-dichloro-4-(4-hydroxybenzylcarbonylamino)-1,2,3,4-tetrahydroquinoline;
4-(4-acetamidobenzylcarbonylamino)-2-carboxy-5,7-dichloro-1,2,3,4-tetrahydroquinoline;
2-carboxy-5,7-dichloro-4-(1-naphthylaminocarbonylamino)-1,2,3,4-tetrahydroquinoline;
2-carboxy-4-cyclohexylaminocarbonylamino-5,7-dichloro-1,2,3,4-tetrahydroquinoline;
2-carboxy-5,7-dichloro-4-[N-methyl-N-(4-methylphenyl)amino]carbonylamino-1,2,3,4-tetrahydroquinoline;
2-carboxy-5,7-dichloro-4-(N,N-diphenylamino)carbonylamino-1,2,3,4-tetrahydroquinoline;
2-carboxy-5,7-dichloro-4-(4-ethylphenyl)aminocarbonylamino-1,2,3,4-tetrahydroquinoline;
2-carboxy-5,7-dichloro-4-(N-ethyl-N-phenyl)aminocarbonylamino-1,2,3,4-tetrahydroquinoline;
4-benzylcarbonylamino-2-(t-butylcarbonyloxy)methoxycarbonyl-5,7-dichloro-1,2,3,4-tetrahydroquinoline;
4-benzylcarbonylamino-5,7-dichloro-2-(methylaminocarbonyl)methoxycarbonyl-1,2,3,4-tetrahydroquinoline;
4-benzylcarbonylamino-5,7-dichloro-2-[2-(N,N-dimethylamino)ethylaminocarbonyl]methoxycarbonyl-1,2,3,4-tetrahydroquinoline;
4-benzylcarbonylamino-5,7-dichloro-2-[2-[2-(N,N-dimethylamino)ethoxycarbonyl]-1,2,3,4-tetrahydroquinoline;
4-benzylcarbonylamino-5,7-dichloro-2-[3-(N,N-dimethylamino)propoxycarbonyl]-1,2,3,4-tetrahydroquinoline;

4-benzylcarbonylamino-5,7-dichloro-2-[2-(N,N-dimethylamino)ethylaminocarbonyl]-1,2,3,4-tetrahydroquinoline;

4-benzylcarbonylamino-5,7-dichloro-2-[2-(N,N-dimethylamino)ethylaminocarbonyl]-1,2,3,4-tetrahydroquinoline;

5,7-dichloro-2-[2-(N,N-dimethylamino)ethylaminocarbonyl]-4-phenylaminocarbonylamino-1,2,3,4-tetrahydroquinoline;

4-[4-(aminomethyl)benzylcarbonylamino]-5,7-dichloro-2-(methylaminocarbonyl)methoxycarbonyl-1,2,3,4-tetrahydroquinoline;

4-[4-(aminomethyl)benzylcarbonylamino]-5,7-dichloro-2-hexyloxycarbonyl-1,2,3,4-tetrahydroquinoline;

and pharmaceutically acceptable salts thereof.

4. A pharmaceutical composition comprising an effective neuroprotective amount of a compound according to claim 1 in association with a pharmaceutically acceptable carrier.

5. A method for the treatment of neurodegenerative disorders, said method comprising administering to a patient in need of such treatment an effective neuroprotective amount of a compound according to claim 1.

6. A pharmaceutical composition comprising an effective neuroprotective amount of a compound according to claim 2 in association with a pharmaceutically acceptable carrier.

7. A method for the treatment of neurodegenerative disorders, said method comprising administering to a patient in need of such treatment an effective neuroprotective amount of a compound according to claim 2.

8. A pharmaceutical composition comprising an effective neuroprotective amount of a compound according to claim 3 in association with a pharmaceutically acceptable carrier.

9. A method for the treatment of neurodegenerative disorders, said method comprising administering to a patient in need of such treatment an effective neuroprotective amount of a compound according to claim 3.

* * * * *